(12) United States Patent
Shankar et al.

(10) Patent No.: US 8,859,529 B2
(45) Date of Patent: *Oct. 14, 2014

(54) COMPOUNDS FOR THE TREATMENT OF INFLAMMATORY DISORDERS

(75) Inventors: Bandarpalle B. Shankar, Branchburg, NJ (US); Seong Heon Kim, Livington, NJ (US); Wensheng Yu, Edison, NJ (US); Ling Tong, Warren, NJ (US); Michael K. C. Wong, Somerset, NJ (US); Brian J. Lavey, New Providence, NJ (US); Joseph A. Kozlowski, Princeton, NJ (US); Lei Chen, Roselle Park, NJ (US); Razia K. Rizvi, Bloomfield, NJ (US); Aneta Maria Kosinski, South Amboy, NJ (US); De-Yi Yang, Morris Plains, NJ (US); Guowei Zhou, Somerset, NJ (US); Kristen E. Rosner, Watertown, NJ (US); Luke Fire, Cambridge, MA (US); Judson E. Richard, Kittery, ME (US); Dansu Li, Reading, MA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 756 days.

This patent is subject to a terminal disclaimer.

(21) Appl. No.: 13/120,728

(22) PCT Filed: Sep. 22, 2009

(86) PCT No.: PCT/US2009/057798
§ 371 (c)(1),
(2), (4) Date: Aug. 12, 2011

(87) PCT Pub. No.: WO2010/036638
PCT Pub. Date: Apr. 1, 2010

(65) Prior Publication Data
US 2011/0288054 A1 Nov. 24, 2011

Related U.S. Application Data

(60) Provisional application No. 61/099,686, filed on Sep. 24, 2008.

(51) Int. Cl.
| | |
|---|---|
| *C07D 205/06* | (2006.01) |
| *C07D 413/14* | (2006.01) |
| *C07D 239/02* | (2006.01) |
| *C07D 401/14* | (2006.01) |
| *C07F 9/02* | (2006.01) |
| *C07D 491/04* | (2006.01) |
| *C07D 471/02* | (2006.01) |
| *C07D 233/54* | (2006.01) |
| *C07D 403/14* | (2006.01) |
| *A61K 31/675* | (2006.01) |
| *A61K 31/397* | (2006.01) |
| *A61K 31/5377* | (2006.01) |
| *A61K 31/497* | (2006.01) |
| *A61K 31/505* | (2006.01) |
| *A61K 31/4427* | (2006.01) |
| *A61K 31/4155* | (2006.01) |
| *C07D 405/14* | (2006.01) |
| *C07D 403/06* | (2006.01) |
| *C07D 491/048* | (2006.01) |

(52) U.S. Cl.
CPC ............ *C07D 403/14* (2013.01); *C07D 405/14* (2013.01); *C07D 403/06* (2013.01); *C07D 491/048* (2013.01)
USPC .............. 514/81; 540/362; 544/127; 544/316; 544/321; 544/362; 546/23; 546/89; 546/115; 546/274.4; 548/311.7; 548/312.1; 514/210.02; 514/233.8; 514/253.04; 514/272; 514/274; 514/291; 514/302; 514/339; 514/389

(58) Field of Classification Search
USPC .............. 514/81, 210.02, 233.8, 253.04, 272, 514/274, 291, 302, 339, 389; 544/127, 316, 544/321, 362; 546/23, 89, 115, 274.4; 548/311.7, 312.1; 540/362
See application file for complete search history.

(56) References Cited

U.S. PATENT DOCUMENTS 6,495,565 B2   12/2002   Duan et al.
6,534,491 B2   3/2003    Levin et al.
(Continued)

FOREIGN PATENT DOCUMENTS

WO   WO02/074750 A1   9/2002
WO   WO02/096426 A1   12/2002
(Continued)

OTHER PUBLICATIONS

Ito, Nobuyuki. Cancer Science 94(1), (2003) 3-8.*
(Continued)

*Primary Examiner* — Samantha Shterengarts
(74) *Attorney, Agent, or Firm* — Eric A. Meade; Valerie J. Camara

(57) ABSTRACT

This invention relates to compounds of the Formula (I) as described herein, or a pharmaceutically acceptable salt, solvate or ester thereof, which can be useful for the treatment of diseases or conditions mediated by MMPs, ADAMs, TACE, aggrecanase, TNF- or combinations thereof.

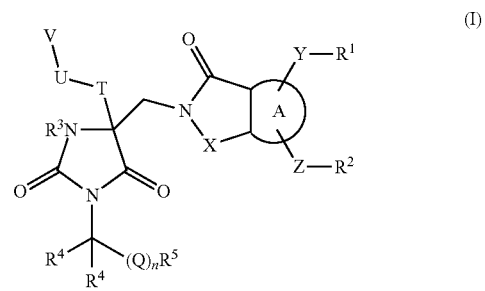

16 Claims, No Drawings

(56) References Cited

U.S. PATENT DOCUMENTS

| | | |
|---|---|---|
| 6,677,355 B1 | 1/2004 | Conrad et al. |
| 7,041,693 B2 | 5/2006 | Sheppeck |
| 7,482,370 B2 | 1/2009 | Yu et al. |
| 7,488,745 B2 | 2/2009 | Yu et al. |
| 7,504,424 B2 | 3/2009 | Yu et al. |
| 7,524,842 B2 | 4/2009 | Lavey et al. |
| 7,683,085 B2 | 3/2010 | Yu et al. |
| 7,687,527 B2 | 3/2010 | Yu et al. |
| 7,772,263 B2 | 8/2010 | Lavey et al. |
| 7,879,890 B2 | 2/2011 | Yu et al. |
| 7,998,961 B2 | 8/2011 | Mansoor et al. |
| 8,178,553 B2 | 5/2012 | Lavey et al. |
| 8,541,572 B2 | 9/2013 | Kozlowski et al. |
| 8,569,336 B2 | 10/2013 | Tong et al. |
| 2012/0010181 A1 | 1/2012 | Kozlowski et al. |
| 2012/0015926 A1 | 1/2012 | Tong et al. |

FOREIGN PATENT DOCUMENTS

| | | |
|---|---|---|
| WO | WO03/053940 A1 | 7/2003 |
| WO | WO03/053941 A2 | 7/2003 |
| WO | WO2004/012663 A2 | 2/2004 |
| WO | WO2004/024698 A1 | 3/2004 |
| WO | WO2004/024715 A1 | 3/2004 |
| WO | WO2004/024721 A1 | 3/2004 |
| WO | WO2004/056766 A1 | 7/2004 |
| WO | WO2006019768 A1 | 2/2006 |

OTHER PUBLICATIONS

PCT International Search Report dated Apr. 10, 2010 for corresponding PCT Application No. PCT/US2009/057798.

Knaggs, A., et al., "Biotransformation of Alosetron: Mechanism of Hydantoin Formation", Tetrahedron Letters, vol. 36, No. 3, pp. 477-480 (1995).

* cited by examiner

COMPOUNDS FOR THE TREATMENT OF INFLAMMATORY DISORDERS

CROSS-REFERENCE TO RELATED APPLICATIONS

This application claims the priority of U.S. Provisional Application No. 61/099,686, filed Sep. 24, 2008, which is herein incorporated by reference in its entirety.

BACKGROUND OF THE INVENTION

1. Field of the Invention

This invention relates generally to novel hydantoin derivatives that can inhibit matrix metalloproteinases (MMPs), a disintegrin and metalloproteases (ADAMs) and/or tumor necrosis factor alpha-converting enzyme (TACE) and in so doing prevent the release of tumor necrosis factor alpha (TNF-α), pharmaceutical compositions comprising such compounds, and methods of treatment using such compounds.

2. Description

Osteo- and rheumatoid arthritis (OA and RA, respectively) are destructive diseases of articular cartilage characterized by localized erosion of the cartilage surface. Findings have shown that articular cartilage from the femoral heads of patients with OA, for example, had a reduced incorporation of radiolabeled sulfate over controls, suggesting that there must be an enhanced rate of cartilage degradation in OA (Mankin at al. J. Bone Joint Surg. 52A (1970) 424434). There are four classes of protein degradative enzymes in mammalian cells: serine, cysteine, aspartic and metalloproteases. The available evidence supports the belief that it is the metalloproteases that are responsible for the degradation of the extracellular matrix of articullar cartilage in OA and RA. Increased activities of collagenases and stromelysin have been found in OA cartilage and the activity correlates with severity of the lesion (Mankin at al. Arthritis Rheum. 21, 1978, 761-766, Woessner at al, Arthritis Rheum. 26, 1983, 63-68 and Ibid. 27, 1984, 305-312). In addition, aggrecanase (a newly identified metalloprotease) has been identified that provides the specific cleavage product of proteoglycan, found in RA and OA patients (Lohmander L. S. et al. Arthritis Rheum. 36, 1993, 1214-22).

Metalloproteases (MPs) have been implicated as the key enzymes in the destruction of mammalian cartilage and bone. It can be expected that the pathogenesis of such diseases can be modified in a beneficial manner by the administration of MP inhibitors (see Wahl et al. Ann. Rep. Med. Chem. 25, 175-184, AP, San Diego, 1990).

MMPs are a family of over 20 different enzymes that are involved in a variety of biological processes important in the uncontrolled breakdown of connective tissue, including proteoglycan and collagen, leading to resorption of the extracellular matrix. This is a feature of many pathological conditions, such as RA and OA, corneal, epidermal or gastric ulceration; tumor metastasis or invasion; periodontal disease and bone disease. Normally these catabolic enzymes are tightly regulated at the level of their synthesis as well as at their level of extracellular activity through the action of specific inhibitors, such as alpha-2-macroglobulins and TIMPs (tissue inhibitor of MPs), which form inactive complexes with the MMP's.

Tumor necrosis factor alpha (TNF-α) is a cell-associated cytokine that is processed from a 26 kDa precursor form to a 17 kd active form. See Black R. A. "Tumor necrosis factor-alpha converting enzyme" int J Biochem Cell Biol. 2002 January; 34(1):1-5 and Moss M L, White J M, Lambert M H, Andrews R C. "TACE and other ADAM proteases as targets for drug discovery" Drug Discov Today. 2001 Apr. 1; 6(8): 417-426, each of which is incorporated by reference herein.

TNF-α has been shown to play a pivotal role in immune and inflammatory responses. Inappropriate or over-expression of TNF-α is a hallmark of a number of diseases, including RA, Crohn's disease, multiple sclerosis, psoriasis and sepsis inhibition of TNF-α production has been shown to be beneficial in many preclinical models of inflammatory disease, making inhibition of TNF-α production or signaling an appealing target for the development of novel anti-inflammatory drugs.

TNF-α is a primary mediator in humans and animals of inflammation, fever and acute phase responses, similar to those observed during acute infection and shock. Excess TNF-α has been shown to be lethal. Blocking the effects of TNF-α with specific antibodies can be beneficial in a variety of conditions, including autoimmune diseases such as RA (Feldman et al, Lancet, (1994) 344, 1105), non-insulin dependent diabetes mellitus (Lohmander L. S. et al., Arthritis Rheum. 36 (1993) 1214-22) and Crohn's disease (Macdonald T. et al., Clin. Exp. Immunol. 81 (1990) 301).

Compounds that inhibit the production of TNF-α are therefore of therapeutic importance for the treatment of inflammatory disorders. Recently it has been shown that metalloproteases, such as TACE, are capable of converting TNF-α from its inactive to active form (Gearing et al Nature, 1994, 370, 555). Since excessive TNF-α production has been noted in several disease conditions also characterized by MMP-mediated tissue degradation, compounds which inhibit both MMPs and TNF-α production may also have a particular advantage in diseases where both mechanisms are involved.

One approach to inhibiting the harmful effects of TNF-α is to inhibit the enzyme, TACE before it can process TNF-α to its soluble form. TACE is a member of the ADAM family of type I membrane proteins and mediates the ectodomain shedding of various membrane-anchored signaling and adhesion proteins. TACE has become increasingly important in the study of several diseases, including inflammatory disease, because of its role in cleaving TNF-α from its "stalk" sequence and thus releasing the soluble form of the TNF-α protein (Black R. A. Int J Biochem Cell Biol. 2002 34, 1-5).

There are numerous patents and publications which disclose hydroxamate, sulphonamide, hydantoin, carboxylate and/or lactam based MMP inhibitors.

U.S. Pat. No. 6,677,355 and U.S. Pat. No. 6,534,491(B2), describe compounds that are hydroxamic acid derivatives and MMP inhibitors.

U.S. Pat. No. 6,495,565 discloses lactam derivatives that are potential inhibitors of MMPs and/or TNF-α.

PCT Publications WO2002/074750, WO2002/096426, WO20040067996, WO2004012663, WO200274750 and WO2004024721 disclose hydantoin derivatives that are potential inhibitors of MMPs.

PCT Publications WO2004024698 and WO2004024715 disclose sulphonamide derivatives that are potential inhibitors of MMPs.

PCT Publications WO2004056766, WO2003053940 and WO2003053941 also describe potential inhibitors of TACE and MMPs.

PCT Publications WO 2006/019768, WO 2007/084415, WO 2007/084451, and WO 2007/084455 refer to hydantoin derivatives that are TACE inhibitors.

There is a need in the art for inhibitors of MMPs, ADAMs, TACE, and TNF-α, which can be useful as anti-inflammatory compounds and cartilage protecting therapeutics. The inhibition of TNF-α, TACE and or other MMPs can prevent the degradation of cartilage by these enzymes, thereby alleviating the pathological conditions of OA and RA as well as many other auto-immune diseases.

SUMMARY OF THE INVENTION

In its many embodiments, the present invention provides a novel class of compounds as inhibitors of TACE, the production of TNF-α, MMPs, ADAMs, aggrecanase, or any combination thereof, methods of preparing such compounds, pharmaceutical compositions comprising one or more such compounds, methods of preparing pharmaceutical formulations comprising one or more such compounds, and methods of treatment, prevention, inhibition or amelioration of one or more diseases associated with TACE, aggrecanase, TNF-α, MMPs, ADAMS or any combination thereof using such compounds or pharmaceutical compositions.

In one embodiment, the present application discloses a compound represented by Formula (I):

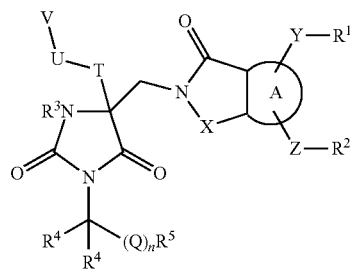

or a pharmaceutically acceptable salt, solvate, ester or isomer thereof, wherein:

ring A is selected from the group consisting of aryl and heteroaryl, each of which is substituted with —Y—$R^1$ and —Z—$R^2$ as shown;

Q is selected from the group consisting of —$NR^7$—, —O—, —S—, —S(O)—, and —S(O)$_2$—;

X is selected from the group consisting of —S—, —O—, —S(O)$_2$—, —S(O)—, —(CR$_2$)$_p$— and —N(R')—;

T is absent or present, and if present, T is selected from the group consisting of alkyl, alkenyl, alkynyl, cycloalkyl, cycloalkenyl, heterocyclyl, heterocyclenyl, aryl, and heteroaryl, wherein when each of said T cycloalkyl, cycloalkenyl, heterocyclyl, heterocyclenyl, aryl and heteroaryl contains two radicals on adjacent carbon atoms, said radicals may optionally be taken together with the carbon atoms to which they are attached to form a second five- or six-membered cycloalkyl, cycloalkenyl, heterocyclyl, heterocycienyl, aryl or heteroaryl ring, wherein when each of said optional second five- or six-membered cycloalkyl, cycloalkenyl, heterocyclyl, heterocyclenyl, aryl or heteroaryl further contains two radicals on adjacent carbon atoms, said radicals may optionally be taken together with the carbon atoms to which they are attached to form a further third five- or six-membered cycloalkyl, cycloalkenyl, heterocyclyl, heterocyclenyl, aryl or heteroaryl ring wherein each of the aforementioned T ary, and heteroaryl, optionally with said first and/or second five- to six-membered cycloalkyl, cycloalkenyl, heterocyclyl, heterocyclenyl, aryl or heteroaryl is independently unsubstituted or substituted with one to four $R^{10}$ moieties which can be the same or different;

U is absent or present or absent, and if present, U is selected from the group consisting of —N($R^6$)—, —N($R^5$)C($R^6$)$_2$—, —N($R^6$)C(O)—, —N($R^6$)S(O)—, —N($R^6$)S(O)$_2$—, —N($R^6$)C(O)N($R^6$)—, —N($R^6$)C(S)N($R^6$)—, —O—, —O—C(O)NH—, —OC(O)N(alkyl)-, —O(O)—, —C(O)O—, —C(O)NH—, —C(O)N(alkyl)-, —C(=N—OH)-alkyl-, and —C(=N—O-alkyl)-alkyl-;

V is absent or present, and if present V is selected from the group consisting of alkyl, alkenyl, alkynyl, cycloalkyl, cycloalkenyl, heterocyclyl, heterocyclenyl, aryl, and heteroaryl, wherein when each of said V cycloalkyl, cycloalkenyl, heterocyclyl, heterocyclenyl, aryl, and heteroaryl contains two radicals on adjacent carbon atoms, said radicals may optionally be taken together with the carbon atoms to which they are attached to form a five- or six-membered cycloalkyl, aryl, heterocyclyl or heteroaryl ring; wherein each of said V alkyl, alkynyl, cycloalkyl, heterocyclyl, aryl, and heteroaryl heterocyclyl, optionally with said five- or six-membered cycloalkyl, aryl, heterocyclyl, or heteroaryl is independently unsubstituted or substituted with one to four $R^{10}$ moieties which can be the same or different;

Y is selected from the group consisting of a covalent bond, —(C($R^6$)$_2$)$_q$—, —N($R^6$)—, —C(O)N($R^6$)—, —N($R^6$)C(O)—, —N($R^6$)C(O)N($R^6$)—, —S(O)$_2$N($R^6$)—, —N($R^6$)—S(O)$_2$, —O—, —S—, —O(O)—, —S(O)—, and —S(O)$_2$—;

Z is selected from the group consisting of a covalent bond, —(C($R^6$)$_2$)$_q$—, —N($R^6$)—, —C(O)N($R^6$)—, —N($R^6$)C(O)—, —N($R^6$)C(O)N($R^6$)—, —S(O)$_2$N($R^6$)—, —N(R)—S(O)$_2$—, —O—, —S—, —C(O)—, —S(O)—, and —S(O)$_2$—;

n is 0 or 1 p is 1 to 3;

q is 1 to 3;

each R independently is selected from the group consisting of H, alkyl, and aryl;

R' is selected from the group consisting of H, alkyl, and aryl;

$R^1$ is selected from the group consisting of H, cyano, —C(O)OH, —C(O)O-alkyl, —C(O)NH$_2$, —C(O)NH(alkyl), —C(O)N(alkyl)$_2$, alkynyl, halogen, alkyl, cycloalkyl, haloalkyl, aryl, heteroaryl, and heterocyclyl, wherein when each of said cycloalkyl, heterocyclyl, aryl and heteroaryl contains two radicals on adjacent carbon atoms, said radicals may optionally be taken together with the carbon atoms to which they are attached to form a five- or six-membered cycloalkyl, aryl, heterocyclyl or heteroaryl ring; wherein each of the $R^1$ alkyl, alkynyl, aryl, heteroaryl, and heterocyclyl, optionally with the five or six-membered cycloalkyl, aryl, heterocyclyl or heteroaryl ring is unsubstituted or optionally independently substituted with one to four $R^{20}$ moieties which can be the same or different; with the proviso that when Y is —N($R^{15}$)—, —S— or —O—, then $R^1$ is not halogen or cyano;

$R^2$ is selected from the group consisting of H, cyano, —C(O)OH, —C(O)O-alkyl, —C(O)NH$_2$, —C(O)NH(alkyl), —C(O)N(alkyl)$_2$, alkynyl, halogen, alkyl, cycloalkyl, cycloalkenyl, haloalkyl, aryl, heteroaryl, heterocyclenyl, and heterocyclyl, wherein when each of said cycloalkyl, cycloalkenyl, heterocyclyl, heterocyclenyl, aryl and heteroaryl contains two radicals on adjacent carbon atoms, said radicals may optionally be taken together with the carbon atoms to which they are attached to form a five- or six-membered cycloalkyl, cyclalkenyl, aryl, heterocyclyl, heterocyclenyl, or heteroaryl ring; wherein each of the $R^2$ alkyl, cycloalkyl, cycloalkenyl, aryl, heteroaryl, heterocyclenyl, and heterocyclyl, optionally with the five or six-membered cycloalkyl, cycloalkenyl, aryl, heterocyclyl, heterocyclenyl, or heteroaryl ring is unsubstituted or optionally independently substituted with one to four $R^{20}$ moieties which can be the same or different; with the proviso that when Y is —N($R^{15}$)—, —S— or —O—, then $R^2$ is not halogen or cyano;

$R^3$ is selected from the group consisting of H, alkyl, alkyl substituted with —O—C(=O)alky, cycloalkyl, cycloalkenyl, heterocyclyl, heterocyclenyl, aryl, heteroaryl, —C(=O)alkyl, —C(=O)cycloalkyl, —C(=O)heterocyclyl, —C(=O)aryl, —C(=O)heteroaryl, —C(=O)O-alkyl, —C(=O)O-alkyl substituted on the alkyl with alkoxy, —C(=O)O-alkyl substituted on alkyl with —N(alkyl)-C(=O)—O-alkyl-aryl, —C(=O)β-cycloalkyl, —C(=O)O-heterocyclyl, —C(=O)O-aryl, and —C(=O)O-heteroaryl;

each $R^4$ is the same or different and is independently selected from the group consisting of H, deuterium, alkyl, and aryl; or the two $R^4$ taken together with the carbon atom to which they are shown attached is —C(=O)—;

$R^5$ is selected from the group consisting of H, alkyl, alkyl substituted with —O-alkyl-O-alkyl-O-alkyl, alkyl substituted with heterocyclyl, alkyl substituted with aryl, heterocyclyl, aryl, heteroaryl, —C(=O)N($R^7$)$_2$, —C(=O)-alkyl, —C(=O)-alkyl substituted on the alkyl with —O-alkyl-O-alkyl, —C(=O)-cycloalkyl, —C(=O)-heterocyclyl, —C(=O)-aryl, —C(=O)-heteroaryl, —C(=O)—O-alkyl, —C(=O)—O-alkyl substituted on the alkyl with —N($R^7$)$_2$, —C(=O)—O-alkyl substituted on the alkyl with —C(=O)—O-alkyl, —C(=O)—O-alkyl substituted on the alkyl with —N($R^7$)—C(=O)-alkyl-aryl, —C(=O)—O-alkyl substituted on the alkyl with heterocyclyl, —C(=O)-β-cycloalkyl, —C(=O)—O-heterocyclyl, —C(=O)—O-aryl, —C(=O)—O-heteroaryl, —P(=O)(—OH)$_2$, —P(=O)(—O-alkyl)$_2$, wherein when each of said "cycloalkyl", "heterocyclyl", "aryl", or "heteroaryl" in any of the aforementioned $R^5$ groups contains two radicals on adjacent carbon atoms, said radicals may optionally be taken together with the carbon atoms to which they are attached to form a five- or six-membered cycloalkyl, aryl, heterocyclyl or heteroaryl ring;

each $R^6$ is the same or different and is independently selected from the group consisting of H, alkyl, cycloalkyl, cycloalkenyl, haloalkyl, hydroxy, -alkylcycloalkyl, -alkyl-N(alkyl)$_2$, heterocyclyl, heterocyclenyl, aryl, and heteroaryl, wherein when each of said cycloalkyl, cycloalkenyl, heterocyclyl, heterocyclenyi, aryl, and heteroaryl contains two radicals on adjacent carbon atoms, said radicals may optionally be taken together with the carbon atoms to which they are attached to form a five- or six-membered cycloalkyl, cycloalkenyl, aryl, heterocyclyl, heterocyclenyl or heteroaryl ring;

each $R^7$ is the same or different and is independently H or alkyl;

$R^{10}$ is selected from the group consisting of hydrogen, cyano, nitro, —OC(O)$R^{15}$, —C($R^{15}$)=N—O$R^{15}$, —O$R^{15}$, —S$R^{15}$, —N($R^{15}$)$_2$, —S(O)$R^{15}$, —S(O)$_2$$R^{15}$, —N($R^{15}$)S(O)$_2$$R^{15}$, —N($R^{15}$)—C(O)—$R^{15}$, —N($R^{15}$)—C(O)—N($R^{15}$)$_2$, —N($r^{15}$)—C(O)—O$R^{15}$, —OC(O)N($R^{15}$)$_2$, —C(O)N($R^{15}$)—S(O)$_2$$R^{15}$, —S(O)$_2$N($R^{15}$)—C(O)—$R^{15}$, —C(O)N($R^{15}$)C(O)$R^{15}$, —C(O)N($R^{15}$)C(O)N$R^{15}$, —S(O)$_2$N($R^{15}$)$_2$, —N($R^{15}$)—C(=N$R^{15}$)—N($R^{15}$)$_2$, —N($R^{15}$)—C(=N—CN)—N($R^{15}$)$_2$, -haloalkoxy, —C(O)O$R^{15}$, —C(O)$R^{15}$, —C(O)N($R^{15}$)$_2$, halogen, alkyl, haloalkyl, aryl, heteroaryl, heterocyclyl, heterocyclenyl, cycloalkenyl, and cycloalkyl, wherein each of the $R^{10}$ alkyl, aryl, heteroaryl, heterocyclyl, heterocyclenyl, cycloalkenyl, and cycloalkyl is unsubstituted or optionally independently substituted with one to four $R^{30}$ moieties which can be the same or different;

or wherein two $R^{10}$ moieties, when attached to the same or adjacent carbon atoms may optionally be taken together with the carbon atom(s) to which they are attached to form a cycloalkyl, cycloalkenyl, heterocyclyl, heterocyclenyl, aryl, or heteroaryl ring;

each $R^{15}$ is the same or different and is independently selected from the group consisting of H, alkyl, cycloalkyl, haloalkyl, hydroxy, heterocyclyl, aryl, and heteroaryl, wherein when each of said cycloalkyl, heterocyclyl, ayl, and heteroaryl contains two radicals on adjacent carbon atoms, said radicals may optionally be taken together with the carbon atoms to which they are attached to form a five- or six-membered cycioalkyl, aryl, heterocyclyl or heteroaryl ring;

$R^{20}$ is selected from the group consisting of hydrogen, cyano, nitro, OC(O)$R^{15}$, —C($R^{15}$)=N—O$R^{15}$, —O$E^{15}$, —S$R^{15}$, —N($R^{15}$)$_2$, —S(O)$R^{/5}$, —S(O)$_2$$R^{15}$, N($R^{15}$)S(O)$_2$$R^{15}$, —N($R^{15}$)—C(O)—$R^{15}$, —N($R^{15}$)—C(O)—N($R^{15}$)$_2$, —N($R^{15}$)—C(O)—O$R^{15}$, —OC(O)N($R^{15}$)$_2$, —C(O)N($R^{15}$)—S(O)$_2$$R^{15}$, —S(O)$_2$N($R^{15}$)—C(O)—$R^{15}$, —C(O)N($R^{15}$)C(O)$R^{15}$, —C(O)N($R^{15}$)C(O)N$R^{15}$, —S(O)$_2$N($R^{15}$)$_2$, —N($R^{15}$)—C(=N$R^{15}$)—N($R^{15}$)$_2$, —N($R^{15}$)—C(=N—CN)—N($R^{15}$)$_2$, -haloalkoxy, —C(O)O$R^{15}$, —C(O)$R^{15}$, —C(O)N($R^{15}$)$_2$, halogen, alkyl, haloalkyl, aryl, heteroaryl, heterocyclyl, heterocyclenyl, cycloalkenyl, and cycloalkyl, wherein when each of said $R^{20}$ aryl, heteroaryl, heterocyclyl, heterocyclenyl, cycloalkenyl, and cycloalkyl contains two radicals on adjacent carbon atoms, said radicals may optionally be taken together with the carbon atoms to which they are attached to form a five- or six-membered cycloalkyl, cycloalkenyl, aryl, heterocyclyl, heterocyclenyl, or heteroaryl ring; wherein each of said $R^{20}$ alkyl, aryl, heteroaryl, heterocyclyl, heterocyclenyl, cycloalkenyl, and cycloalkyl, optionally with said five- or six-membered cycloalkyl, cycloalkenyl, aryl, heterocyclyl, heterocyclenyl, or heteroaryl ring is unsubstituted or substituted with one to four moieties selected independently from the group consisting of alkyl, halo, haloalkyl, hydroxy, alkoxy, haloalkoxy, hydroxyalkyl, cyano, nitro, —NH$_2$, —NH(alkyl), and —N(alkyl)$_2$;

or when two $R^{20}$ moieties when attached to the same or adjacent carbon atoms may optionally be taken together with the carbon atom(s) to which they are attached to form a cycloalkyl, cycloalkenyl, heterocyclyl, aryl, or heteroaryl ring;

$R^{30}$ is selected from the group consisting of hydrogen, cyano, nitro, —OC(O)$R^{15}$, —C($R^{15}$)=N—O$R^{15}$, —O$R^{15}$, —S$R^{15}$, —N($R^{15}$)$_2$, —S(O)$R^{15}$, —S(O)$_2$$R^{15}$, —N($R^{15}$)S(O)$_2$$R^{15}$, —N($R^{15}$)—C(O)—$R^{15}$, —N($R^{15}$)—C(O)—N($R^{15}$)$_2$, —N($R^{15}$)—C(O)—O$R^{15}$, —OC(O)N($R^{15}$)$_2$, —C(O)N($R^{15}$)—S(O)$_2$$R^{15}$, —S(O)$_2$N($R^{15}$)—C(O)—$R^{15}$, —C(O)N($R^{15}$)C(O)$R^{15}$, —C(O)N($R^{15}$)C(O)N$R^{15}$, —S(O)$_2$N($R^{15}$)$_2$, —N($R^{15}$)—C(=N$R^{15}$)—N($R^{15}$)$_2$, —N($R^{15}$)—C(=N—CN)—N($R^{15}$)$_2$, -haloalkoxy, —C(O)O$R^{15}$, —C(O)$R^{15}$, —C(O)N($R^{15}$)$_2$, halogen, alkyl, haloalkyl, aryl, heteroaryl, heterocyclyl, heterocyclenyl, cycloalkenyl, and cycloalkyl, wherein when each of said $R^{30}$ aryl, heteroaryl, heterocyclyl, heterocyclenyl, cycloalkenyl, and cycloalkyl contains two radicals on adjacent carbon atoms, said radicals may optionally be taken together with the carbon atoms to which they are attached to form a five- or six-membered cycloalkyl, cycloalkenyl, aryl, heterocyclyl, heterocyclenyl, heteroaryl ring; wherein each of said $R^{30}$ alkyl, aryl, heteroaryl, heterocyclyl, heterocyclenyl, cycloalkenyl and cycloalkyl, optionally with said five- or six-membered cycloalkyl, cycloalkenyl aryl, heterocyclyl, heterocycfenyl, or heteroaryl ring is unsubstituted or substituted with one to four moieties selected independently from the group consisting of alkyl, halo, haloalkyl, hydroxy, alkoxy, haloalkoxy, cyano, nitro, —NH$_2$, —NH(alkyl), and —N(alkyl)$_2$;

or when two R$^{30}$ moieties when attached to the same or adjacent carbon atoms may optionally be taken together with the carbon atom(s) to which they are attached to form a cycloalkyl, cycloalkenyl, heterocyclyl, aryl, or heteroaryl ring;

with the proviso that at least one of T, U, and V must be present.

In another embodiment, the present application discloses a compound represented by Formula (I):

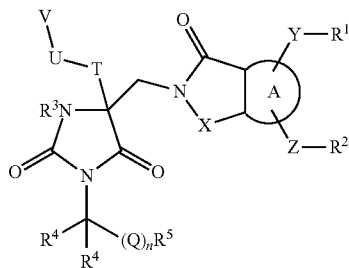

or a pharmaceutically acceptable salt, solvate, ester or isomer thereof, wherein;

ring A is selected from the group consisting of aryl and heteroaryl, each of which is substituted with —Y—R$^1$ and —Z—R$^2$ as shown;

Q is selected from the group consisting of —NR$^7$—, —O—, —S—, —S(O)—, and —S(O)$_2$—;

X is selected from the group consisting of —S—, —O—, —S(O)$_2$—, —S(O)—, —(CR$_2$)$_p$— and —N(R')—:

T is absent or present, and if present, T is selected from the group consisting of alkyl, alkenyl, alkynyl, cycloalkyl, cycloalkenyl, heterocyclyl, heterocyclenyl, aryl, and heteroaryl, wherein when each of said T cycloalkyl, cycloalkenyl, heterocyclyl, heterocyclenyl, aryl and heteroaryl contains two radicals on adjacent carbon atoms, said radicals may optionally be taken together with the carbon atoms to which they are attached to form a second five- or six-membered cycloalkyl, cycloalkenyl, heterocyclyl, heterocyclenyl, aryl or heteroaryl ring, wherein when each of said optional second five- or six-membered cycloalkyl, cycloalkenyl, heterocyclyl, heterocyclenyl, aryl or heteroaryl further contains two radicals on adjacent carbon atoms, said radicals may optionally be taken together with the carbon atoms to which they are attached to form a further third five- or six-membered cycloalkyl, cycloalkenyl, heterocyclyl, heterocyclenyl, aryl or heteroaryl ring wherein each of the aforementioned T aryl, and heteroaryl, optionally with said first and/or second five- to six-membered cycloalkyl, cycloalkenyl, heterocyclyl, heterocyclenyl, aryl or heteroaryl is independently unsubstituted or substituted with one to four R$^{10}$ moieties which can be the same or different;

U is absent or present or absent, and if present, U is selected from the group consisting of —N(R$^6$)—, —N(R$^6$)C(R$^6$)$_2$—, —N(R$^6$)C(O)—, —N(R$^6$)S(O)—, —N(R$^6$)S(O)$_2$—, —N(R$^6$)C(O)N(R$^6$)—, —N(R$^6$)C(S)N(R$^6$)—, —O—, —O—C(O)NH—, —OC(O)N(alkyl)-, —C(O)—, —C(O)O—, —C(O)NH—, —C(O)N(alkyl)-, —C(=N—OH)-alkyl-, and —C(=N—O-alkyl)-alkyl-;

V is absent or present, and if present V is selected from the group consisting of alkyl, alkenyl, alkynyl, cycloalkyl, cycloalkenyl, heterocyclyl, heterocyclenyl, aryl, and heteroaryl, wherein when each of said V cycloalkyl, cycloalkenyl, heterocyclyl, heterocyclenyl, aryl, and heteroaryl contains two radicals on adjacent carbon atoms, said radicals may optionally be taken together with the carbon atoms to which they are attached to form a five- or six-membered cycloalkyl, aryl, heterocyclyl or heteroaryl ring; wherein each of said V alkyl, alkynyl, cycloalkyl, heterocyclyl, aryl, and heteroaryl heterocyclyl, optionally with said five- or six-membered cycloalkyl, aryl, heterocyclyl, or heteroaryl is independently unsubstituted or substituted with one to four R$^{10}$ moieties which can be the same or different;

Y is selected from the group consisting of a covalent bond, —(C(R$^6$)$_2$)$_q$—, —C(O)N(R$^6$)—, —N(R$^6$)C(O)—, —N(R$^5$)C(O)N(R$^6$)—, —S(O)$_2$N(R$^6$)—, —N(R$^6$)—S(O)$_2$, —O—, —S—, —S(O)—, and —S(O)$_2$—;

Z is selected from the group consisting of a covalent bond, —(C(R$^6$)$_2$)$_q$—, —N(R$^6$)—, —C(O)N(R$^6$)—, —N(R$^6$)C(O)—, —N(R$^6$)C(O)N(R$^6$)—, —S(O)$_2$N(R$^6$)—, —N(R$^6$)—S(O)$_2$—, —O—, —S—, —C(O)—, —S(O)—, and —S(O)$_2$—;

n is 0 or 1 p is 1 to 3;

q is 1 to 3;

each R independently is selected from the group consisting of H, alkyl, and aryl;

R' is selected from the group consisting of H, alkyl, and aryl;

R$^1$ is selected from the group consisting of H, cyano, —C(O)OH, —C(O)O-alkyl, —C(O)NH$_2$, —C(O)NH(alkyl), —C(O)N(alkyl)$_2$, alkynyl, halogen, alkyl, cycloalkyl, haloalkyl, aryl, heteroaryl, and heterocyclyl, wherein when each of said cycloalkyl, heterocyclyl, aryl and heteroaryl contains two radicals on adjacent carbon atoms, said radicals may optionally be taken together with the carbon atoms to which they are attached to form a five- or six-membered cycloalkyl, aryl, heterocyclyl or heteroaryl ring; wherein each of the R$^1$ alkyl, alkynyl, aryl, heteroaryl, and heterocyclyl, optionally with the five or six-membered cycloalkyl, aryl, heterocyclyl or heteroaryl ring is unsubstituted or optionally independently substituted with one to four R$^{20}$ moieties which can be the same or different; with the proviso that when Y is —N(R$^{15}$)—, —S— or —O—, then R$^1$ is not halogen or cyano;

R$^2$ is selected from the group consisting of H, cyano, —C(O)OH, —C(O)O-alkyl, —C(O)NH$_2$, —C(O)NH(alkyl), —C(O)N(alkyl)$_2$, alkynyl, halogen, alkyl, cycloalkyl, cycloalkenyl, haloalkyl, aryl, heteroaryl, heterocyclenyl, and heterocyclyl, wherein when each of said cycloalkyl, cycloalkenyl, heterocycyl, heterocyclenyl, aryl and heteroaryl contains two radicals on adjacent carbon atoms, said radicals may optionally be taken together with the carbon atoms to which they are attached to form a five- or six-membered cycloalkyl, cyclalkenyl, aryl, heterocyclyl, heterocyclenyl, or heteroaryl ring; wherein each of the R$^2$ alkyl, cycloalkyl, cycloalkenyl, aryl, heteroaryl, heterocyclenyl, and heterocyclyl, optionally with the five or six-membered cycloalkyl, cycloalkenyl, aryl, heterocyclyl, heterocyclenyl, or heteroaryl ring is unsubstituted or optionally independently substituted with one to four R$^{20}$ moieties which can be the same or different; with the proviso that when Y is —N(R$^{15}$)—, —S— or —O—, then R$^2$ is not halogen or cyano;

R$^3$ is selected from the group consisting of H, alkyl, cycloalkyl, cycloalkenyl, heterocyclyl, heterocyclenyl, aryl, heteroaryl, —C(=O)alkyl, —C(=O)cycloalkyl, —C(=O)heterocyclyl, —C(=O)aryl, —C(=O)heteroaryl, —C(=O)O-alkyl, —C(=O)O-cycloalkyl, —C(=O)O-heterocyclyl, —C(=O)O-aryl, and —C(=O)O-heteroaryl.

each $R^4$ is the same or different and is independently selected from the group consisting of H, alkyl, and aryl; or the two $R^4$ taken together with the carbon atom to which they are shown attached is —C(=O)—;

$R^5$ is selected from the group consisting of H, alkyl, heterocyclyl, aryl, heteroaryl, —C(=O)N($R^7$)$_2$, —C(=O)-alkyl, C(=O)-cycloalkyl, C(=O)-heterocyclyl, —C(=O)-aryl, —C(=O)-heteroaryl, —C(=O)—O-alkyl, —C(=O)—O-cycloalkyl, —C(=O)—O-heterocyclyl, —C(=O)—O-aryl, —C(=O)—O-heteroaryl, —P(=O)(—OH)$_2$, —P(=O)(—O-alkyl)$_2$, wherein when each of said "cycloalkyl", "heterocyclyl", "aryl", or "heteroaryl" in any of the aforementioned $R^5$ groups contains two radicals on adjacent carbon atoms, said radicals may optionally be taken together with the carbon atoms to which they are attached to form a five- or six-membered cycloalkyl, aryl, heterocyclyl or heteroaryl ring;

each $R^6$ is the same or different and is independently selected from the group consisting of H, alkyl, cycloalkyl, cycloalkenyl, haloalkyl, hydroxy,-alkylcycloalkyl, -alkyl-N(alkyl)$_2$, heterocyclyl, heterocyclenyl, aryl, and heteroaryl, wherein when each of said cycloalkyl, cycloalkenyl, heterocyclyl, heterocyclenyl, aryl, and heteroaryl contains two radicals on adjacent carbon atoms, said radicals may optionally be taken together with the carbon atoms to which they are attached to form a five- or six-membered cycloalkyl, cycloalkenyl, aryl, heterocyclyl or heterocyclenyl or heteroaryl ring;

each $R^7$ is the same or different and is independently H or alkyl;

$R^{10}$ is selected from the group consisting of hydrogen, cyano, nitro, —OC(O)$R^{15}$, —C($R^{15}$)=N—O$R^{15}$, —S$R^{15}$, —N($R^{15}$)$_2$, —S(O)$R^{15}$, —S(O)$_2R^{15}$, N($R^{15}$)S(O)$_2R^{15}$, —N($R^{15}$)—C(O)—$R^{15}$, —N($R^{15}$)—C(O)—N($R^{15}$)$_2$, —N($R^{15}$)—C(O)—O$R^{15}$, —OC(O)N($R^{15}$)$_2$, —C(O)N($R^{15}$)—S(O)$_2R^{15}$, —S(O)$_2$N($R^{15}$)—C(O)—$R^{15}$, —C(O)N($R^{15}$)C(O)$R^{15}$, —C(O)N($R^{15}$)C(O)N$R^{15}$, —S(O)$_2$N($R^{15}$)$_2$, —N($R^{15}$)—C(=N$R^{15}$)—N($R^{15}$)$_2$, —N($R^{15}$)—C(=N—CN)—N($R^{15}$)$_2$, -haloalkoxy, —C(O)O$R^{15}$, —C(O)$R^{15}$, —C(O)N($R^{15}$)$_2$, halogen, alkyl, haloalkyl, aryl, heteroaryl, heterocyclyl, heterocyclenyl, cycloalkenyl, and cycloalkyl, wherein each of the $R^{10}$ alkyl, aryl, heteroaryl, heterocyclyl, heterocyclenyl, cycloalkenyl, and cycloalkyl is unsubstituted or optionally independently substituted with one to four $R^{30}$ moieties which can be the same or different;

or wherein two $R^{10}$ moieties, when attached to the same or adjacent carbon atoms may optionally be taken together with the carbon atom(s) to which they are attached to form a cycloalkyl, cycloalkenyl, heterocyclyl, heterocyclenyl, aryl, or heteroaryl ring;

each $R^{15}$ is the same or different and is independently selected from the group consisting of H, alkyl, cycloalkyl, haloalkyl, hydroxy, heterocyclyl, aryl, and heteroaryl, wherein when each of said cycloalkyl, heterocyclyl, ayl, and heteroaryl contains two radicals on adjacent carbon atoms, said radicals may optionally be taken together with the carbon atoms to which they are attached to form a five- or six-membered cycloalkyl, aryl, heterocyclyl or heteroaryl ring;

$R^{20}$ is selected from the group consisting of hydrogen, cyano, nitro, —OC(O)$R^{15}$, —C($R^{15}$)=N—O$R^{15}$, —O$R^{15}$, —S$R^{15}$, —N($R^{15}$)$_2$, —S(O)$R^{15}$, —S(O)$_2R^{15}$, —N($R^{15}$)S(O)$_2R^{15}$, —N($R^{15}$)—C(O)—$R^{15}$, —N($R^{15}$)—C(O)—N($R^{15}$)$_2$, —N($R^{15}$)—C(O)—O$R^{15}$, —OC(O)N($R^{15}$)$_2$, —C(O)N($R^{15}$)—S(O)$_2$R—S(O)$_2$N($R^{15}$)C(O)—$R^{15}$, —C(O)N($R^{15}$)C(O)$R^{15}$, —C(O)N($R^{15}$)C(O)N$R^{15}$, —S(O)$_2$N($R^{15}$)$_2$, —N($R^{15}$)—C(=N$R^{15}$)—N($R^{15}$)$_2$, —N($R^{15}$)—C(=N—CN)—N($R^{15}$)$_2$, -haloalkoxy, —C(O)O$R^{15}$, —C(O)$R^{15}$, —C(O)N($R^{15}$)$_2$, halogen, alkyl, haloalkyl, aryl, heteroaryl, heterocyclyl, heterocyclenyl, cycloalkenyl, and cycloalkyl, wherein when each of said $R^{20}$ aryl, heteroaryl, heterocyclyl, heterocyclenyl, cycloalkenyl, and cycloalkyl contains two radicals on adjacent carbon atoms, said radicals may optionally be taken together with the carbon atoms to which they are attached to form a five- or six-membered cycloalkyl, cycloalkenyl, aryl, heterocyclyl, heterocyclenyl, or heteroaryl ring; wherein each of said $R^{20}$ alkyl, aryl, heteroaryl, heterocyclyl, heterocyclenyl, cycloalkenyl, and cycloalkyl, optionally with said five- or six-membered cycloalkyl, cycloalkenyl, aryl, heterocyclyl, heterocyclenyl, or heteroaryl ring is unsubstituted or substituted with one to four moieties selected independently from the group consisting of alkyl, halo, haloalkyl, hydroxy, alkoxy, haloalkoxy, hydroxyalkyl, cyano, nitro, —NH$_2$, —NH(alkyl), and —N(alkyl)$_2$;

or when two $R^{20}$ moieties when attached to the same or adjacent carbon atoms may optionally be taken together with the carbon atom(s) to which they are attached to form a cycloalkyl, cycloalkenyl, heterocyclyl, aryl, or heteroaryl ring;

$R^{30}$ is selected from the group consisting of hydrogen, cyano, nitro, —OC(O)$R^{15}$, —C($R^{15}$)=N—O$R^{15}$, —S$R^{15}$, —N($R^{15}$)$_2$—S(O)$R^{15}$, —S(O)$_2R^{15}$, —N($R^{15}$)S(O)$_2R^{15}$, —N($R^{15}$)—C(O)—$R^{15}$, —N($R^{15}$)—C(O)—N($R^{15}$)$_2$, —N($R^{15}$)—C(O)—O$R^{15}$, —OC(O)N($R^{15}$)$_2$, —C(O)N($R^{15}$)—S(O)$_2R^{15}$, —S(O)$_2$N($R^{15}$)—C(O)—$R^{15}$, —C(O)N($R^{15}$)C(O)$R^{15}$, —C(O)N($R^{15}$)C(O)N$R^{15}$, —S(O)$_2$N($R^{15}$)$_2$, —N($R^{15}$)—C(=N$R^{15}$)—N($R^{15}$)$_2$, —N($R^{15}$)—C(=N—CN)—N($R^{15}$)$_2$, -haloalkoxy, —C(O)O$R^{15}$, —C(O)$R^{15}$, —C(O)N($R^{15}$)$_2$, halogen, alkyl, haloalkyl, aryl, heteroaryl, heterocyclyl, heterocyclenyl, cycloalkenyl, and cycloalkyl, wherein when each of said $R^{30}$ aryl, heteroaryl, heterocyclyl, heterocyclenyl, cycloalkenyl, and cycloalkyl contains two radicals on adjacent carbon atoms, said radicals may optionally be taken together with the carbon atoms to which they are attached to form a five- or six-membered cycloalkyl, cycloalkenyl, aryl, heterocyclyl, heterocyclenyl, or heteroaryl ring; wherein each of said $R^{30}$ alkyl, aryl, heteroaryl, heterocyclyl, heterocyclenyl, cycloalkenyl and cycloalkyl, optionally with said five- or six-membered cycloalkyl, cycloalkenyl aryl, heterocyclyl, heterocyclenyl, or heteroaryl ring is unsubstituted or substituted with one to four moieties selected independently from the group consisting of alkyl, halo, haloalkyl, hydroxy, alkoxy, haloalkoxy, cyano, nitro, —NH$_2$, —NH(alkyl), and —N(alkyl)$_2$;

or when two $R^{30}$ moieties when attached to the same or adjacent carbon atoms may optionally be taken together with the carbon atom(s) to which they are attached to form a cycloalkyl, cycloalkenyl, heterocyclyl, aryl, or heteroaryl ring;

with the proviso that at least one of T, U, and V must be present.

The compounds of Formula I can be useful as inhibitors of TACE and may be useful in the treatment and prevention of diseases associated with TACE, TNF-α, MMPs, ADAMs or any combination thereof.

DETAILED DESCRIPTION OF THE INVENTION

In its several embodiments, the present invention provides a novel class of inhibitors of TACE, aggrecanase, the production of TNF-α, MMPs, ADAMs or any combination thereof, pharmaceutical compositions containing one or more of the compounds, methods of preparing pharmaceutical formulations comprising one or more such compounds, and methods of treatment, prevention or amelioration of one or more of the symptoms of inflammation.

In one embodiment, the present invention provides compounds which are represented by structural Formula (I) above or a pharmaceutically acceptable salt, solvate, ester or isomer thereof, wherein the various moieties are as described above.

In another embodiment, the isomer referred to the in the preceding paragraph is a stereoisomer, In another embodiment, in formula (I), X is —(C(R)$_2$)$_p$—, wherein p is 1 or 2.

In another embodiment, in formula (I), X is —(C(R)$_2$)$_p$—, wherein p is 2.

In another embodiment, in formula (I), R$^3$ is selected from the group consisting of alkyl, —C(=O)alkyl, —C(=O)aryl, —C(=O)cycloalkyl, —C(=O))O-heterocyclyl, and —C(=O))O-alkyl.

In another embodiment, in formula (I), R$^3$ is alkyl wherein said alkyl of R$^3$ is optionally substituted with —O—C(=O) alkyl.

In another embodiment, in formula (I), R$^3$ is alkyl, wherein said alkyl is optionally substituted with —O—C(=OC) alkyl, wherein the "alkyl" of said R$^3$—C(=O))O-alkyl is optionally substituted with —N(alkyl)-C(=O)—O-alkyl-aryl.

In another embodiment, in formula (I), R$^3$ is —C(=O))O-alkyl, wherein the alkyl is optionally substituted with alkoxy or —N(alkyl)-C(=O)—O-alkyl-aryl.

In another embodiment, in formula (I), T is selected from the group consisting of aryl, heteroaryl and alkynyl, wherein when any of said T heteroaryl or aryl contains two radicals on adjacent carbon atoms, said radicals may optionally be taken together with the carbon atoms to which they are attached to form a second five- or six-membered heterocyclyl, aryl or heteroaryl ring, wherein when each of said optional second five- or six-membered heterocyclyl, aryl or heteroaryl further contains two radicals on adjacent carbon atoms, said radicals may optionally be taken together with the carbon atoms to which they are attached to form a further third five- or six-membered heterocyclyl, aryl or heteroaryl ring, wherein the aforementioned T heteroaryl or aryl, optionally with said second and/or third five- to six-membered heterocyclyl, aryl or heteroaryl is independently unsubstituted or substituted with one to four R$^{10}$ moieties which can be the same or different.

In another embodiment, in formula (I), T is alkynyl.

In another embodiment, in formula (I), said T alkynyl is

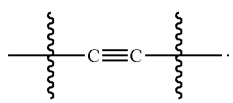

In another embodiment, in formula (I), T is heteroaryl, wherein said heteroaryl optionally with said second and/or third five- to six-membered heterocyclyl, aryl or heteroaryl is selected from the group consisting of:

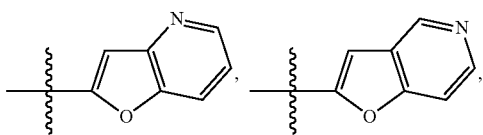

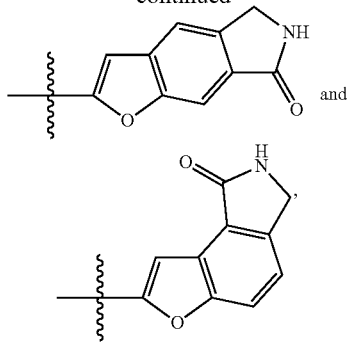

each of which is optionally substituted.

In another embodiment, in formula (I), T is aryl.

In another embodiment, in formula (I), said T aryl is phenyl.

In another embodiment, in formula (I), U is selected from the group consisting of —N(H)C(O)—, —N(H)—S(=O)$_2$—, and —N(H)—.

In another embodiment, in formula (I), V is selected from the group consisting of heterocyclyl, aryl, heteroaryl, wherein when each of said V heterocyclyl, aryl, and heteroaryl contains two radicals on adjacent carbon atoms, said radicals may optionally be taken together with the carbon atoms to which they are attached to form a five- or six-membered aryl, heterocyclyl or heteroaryl ring; wherein each of said V heterocyclyl, aryl, and heteroaryl optionally with said five- or six-membered aryl, heterocyclyl, or heteroaryl is independently unsubstituted or substituted with one to four R$^{10}$ moieties which can be the same or different.

In another embodiment, in formula (I), V is selected from the group consisting of heterocyclyl and heteroaryl, wherein said heterocyclyl and heteroaryl are selected from the group consisting of pyridinyl, piperazinyl, azetidin-2-one-1-yl, 2-pyrrolidinone-1-yl, pyrazolyl, benzopyrazolyl, pyrrolyl,

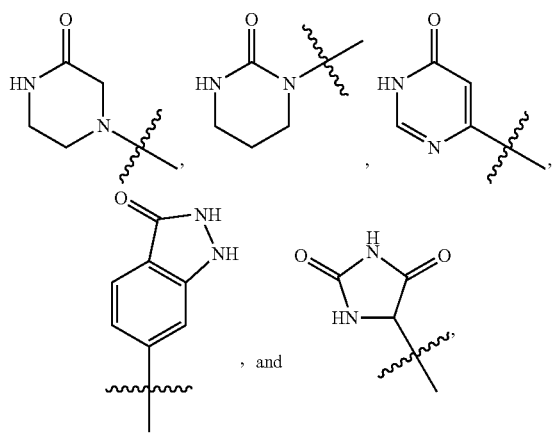

each of which is optionally substituted.

In another embodiment, in formula (I), V is aryl, wherein said aryl is phenyl.

In another embodiment, in formula (I), each of T and V is unsubstituted or substituted with at least R$^{10}$ selected from the group consisting of alkyl, —C(O)N(R$^4$)$_2$, aryl, heterocyclyl, heteroaryl, —N(R$^4$)S(O)$_2$R$^4$, —N(R$^4$)$_2$, —OR$^4$, halo, and —OC(O)R$^4$.

In another embodiment, in formula (I), ring A is selected from the group consisting of phenyl, thiophenyl, pyridyl, pyrimidyl, and

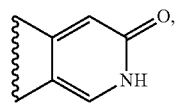

each of which is substituted with —Y—R$^1$ and —Z—R$^2$ as shown.

In another embodiment, in formula (I), ring A is phenyl.

In another embodiment, in formula (I), each of Y and Z is independently selected from the group consisting of a covalent bond and —O—.

In another embodiment, in formula (I), each of Y and Z is independently selected from the group consisting of a covalent bond and —O—, wherein Y is —O— and Z is a covalent bond.

In another embodiment, in formula (I), each of Y and Z is independently selected from the group consisting of a covalent bond and —O—, wherein Y is —O— and Z is a covalent bond, wherein each of R$^1$ and R$^2$ is independently selected form the group consisting of H and alkyl.

In another embodiment, in formula (I), each of Y and Z is independently selected from the group consisting of a covalent bond and —O—, wherein Y is —O— and Z is a covalent bond, wherein R$^1$ is alkyl and R$^2$ is H or halo.

In another embodiment, in formula (I), each of Y and Z is independently selected from the group consisting of a covalent bond and —O—, wherein Y is —O— and Z is a covalent bond, wherein R$^1$ is methyl and R$^2$ is H or halo.

In another embodiment, in formula (I), R$^3$ is selected from the group consisting of H, alkyl, —C(=O)alkyl, —C(=O)cycloalkyl, —C(=O)aryl, —C(=O)O-alkyl, and —C(=O)O-heterocyclyl.

In another embodiment, in formula (I), R$^3$ is selected from the group consisting of H, alkyl, —C(=O)alkyls —C(=O)cycloalkyl, —C(=O)aryl, —C(=O)O-alkyl, -and —C(=O)O-heterocyclyl, wherein the "alkyl" of said R$^3$ alkyl is unsubstituted or substituted with at least one —O—C(=O)-alkyl.

In another embodiment, in formula (I), R is selected from the group consisting of H, alkyl, —C(=O)alkyl, —C(=O)cycloalkyl, —C(=O)aryl, —C(=O)O-alkyl, -and —C(=O)O-heterocyclyl, wherein the "alkyl" of said R$^3$—C(=O)O-alkyl is unsubstituted or substituted with at least substituent selected from the group consisting of heterocyclyl and —N(R$^6$)—C(=O)—O-alkyl-aryl.

In another embodiment, in formula (I), each R$^4$ is the same or different and is independently selected from the group consisting of H, alkyl, and aryl.

In another embodiment, in formula (I), each R$^4$ is H.

In another embodiment, in formula (I), Q is O and n is 1.

In another embodiment, in formula (I), n is 0.

In another embodiment, in formula (I), R$^5$ is selected from the group consisting of H, alkyl, aryl, heteroaryl, —C(=O)-alkyl, —C(=O)-aryl, —C(=O)-heteroaryl, —C(=O)—O-alkyl, —C(=O)-cycloalkyl, and —C(=O)—O-heterocyclyl, wherein when each of said "cycloalkyl", "heterocyclyl", "aryl", or "heteroaryl" in any of the aforementioned R$^5$ groups contains two radicals on adjacent carbon atoms, said radicals may optionally be taken together with the carbon atoms to which they are attached to form a five- or six-membered cycloalkyl, aryl, heterocyclyl or heteroaryl ring.

In another embodiment, in formula (I), said R$^5$ alkyl is unsubstituted or substituted with at least one substituent selected from the group consisting of —O-alkyl-O-alkyl-O-alkyl, heterocyclyl, and aryl.

In another embodiment, in formula (I), the "alkyl" of said R$^5$—C(=O)—O-alkyl is unsubstituted or substituted with at least one substituent selected from the group consisting of —N(R$^7$)$_2$, C(=O)—O-alkyl, —N(R$^7$)—C(=O)O-alkyl-aryl, and heterocyclyl.

In another embodiment, in formula (I), the "alkyl" of said R$^5$—C(=O)-alkyl is unsubstituted or substituted with a —O-alkyl-O-alkyl, In another embodiment, Formula (I) is represented by Formula (I)(A)

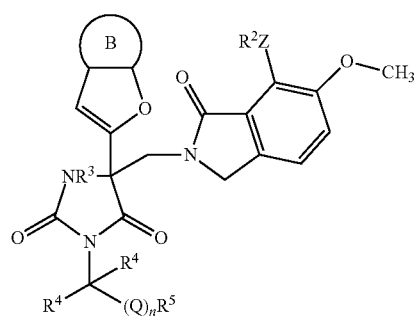

Formula (I)(A)

wherein:

ring B is a pyridine ring optionally substituted with an R$^{10}$;

Z is a covalent bond;

R$^2$ is H or halogen;

and Q, n, R$^3$, R$^4$, and R$^5$ are as defined for Formula (I) in claim 1.

In another embodiment in the compound of formula (I), T, U, and V together are

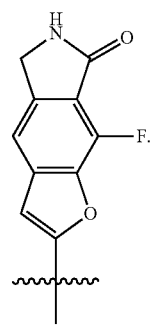 [SMILES: *c1cc2cc3c(c(F)c2o1)C(=O)NC3]

In one embodiment, the compound of formula is selected from the group consisting of consisting of:
| Compd # | STRUCTURE |
|---|---|
| 1 | 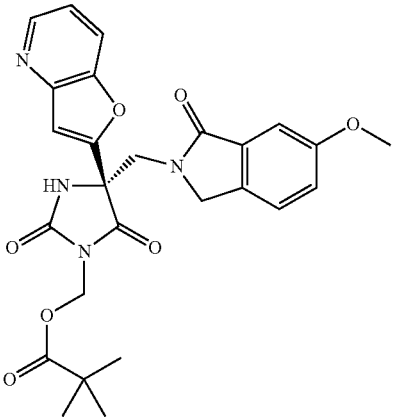 [SMILES: COc1ccc2c(c1)C(=O)N(C[C@@]1(c3cc4ncccc4o3)NC(=O)N(COC(=O)C(C)(C)C)C1=O)C2] |
| 2 | 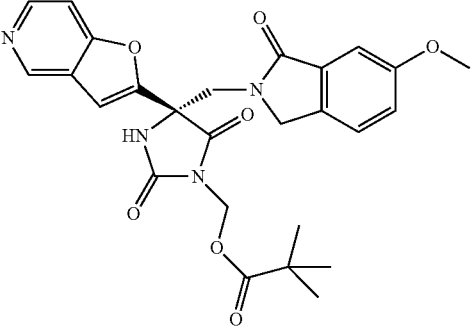 [SMILES: COc1ccc2c(c1)C(=O)N(C[C@@]1(c3cc4cnccc4o3)NC(=O)N(COC(=O)C(C)(C)C)C1=O)C2] |
| 3 | 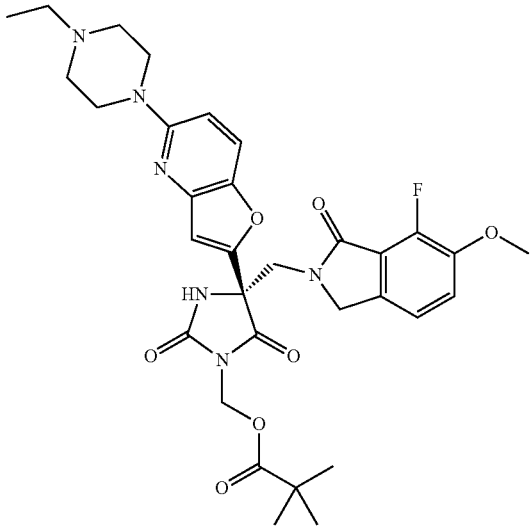 [SMILES: CCN1CCN(c2ccc3oc([C@]4(CN5Cc6ccc(OC)c(F)c6C5=O)NC(=O)N(COC(=O)C(C)(C)C)C4=O)cc3n2)CC1] |

-continued
| Compd # | STRUCTURE |
|---|---|
| 4 | 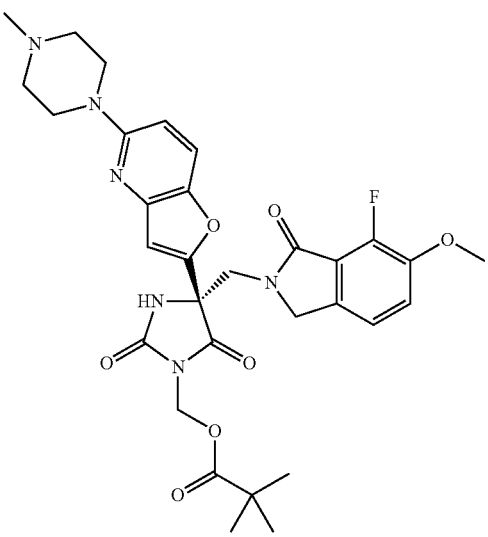 |
| 5 | 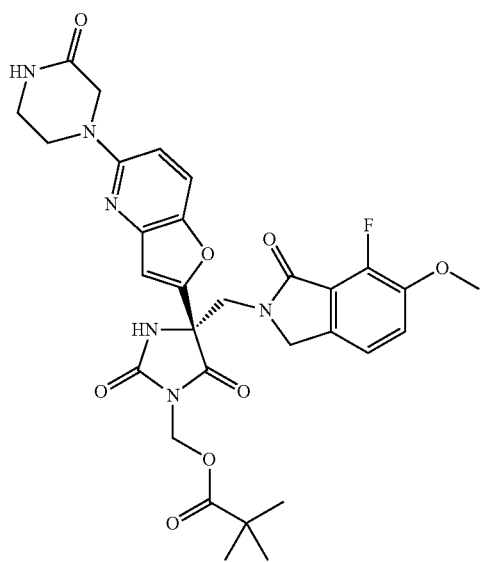 [SMILES: COc1ccc2c(c1F)C(=O)N(C[C@@]1(c3cc4nc(N5CCNC(=O)C5)ccc4o3)NC(=O)N(COC(=O)C(C)(C)C)C1=O)C2] |
| 6 | 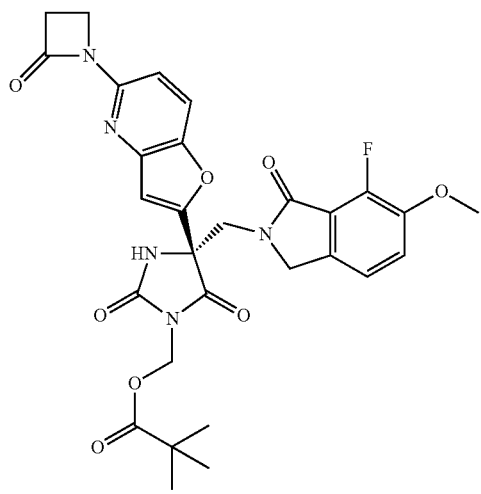 [SMILES: COc1ccc2c(c1F)C(=O)N(C[C@@]1(c3cc4nc(N5CCC5=O)ccc4o3)NC(=O)N(COC(=O)C(C)(C)C)C1=O)C2] |

| Compd # | STRUCTURE |
|---------|-----------|
| 7 | 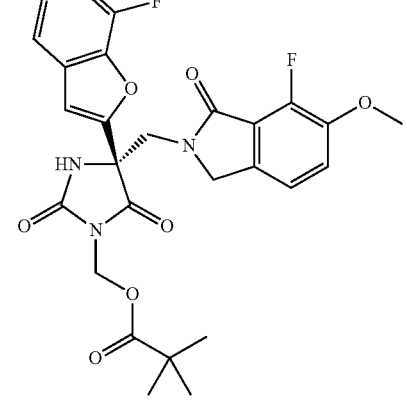 |
| 8 | 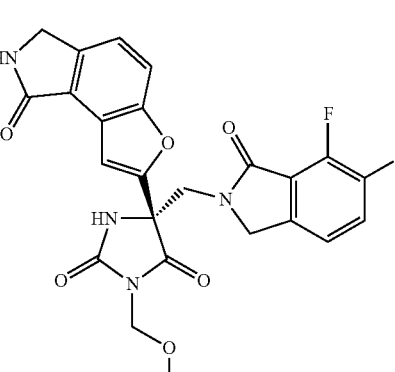 |
| 9 | 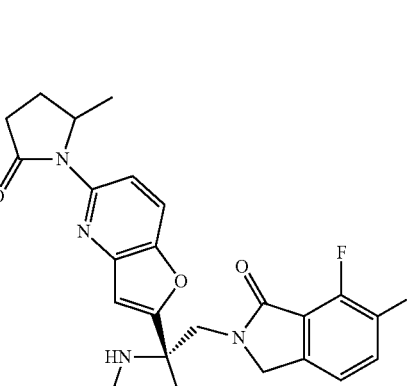 |

| Compd # | STRUCTURE |
|---|---|
| 10 | 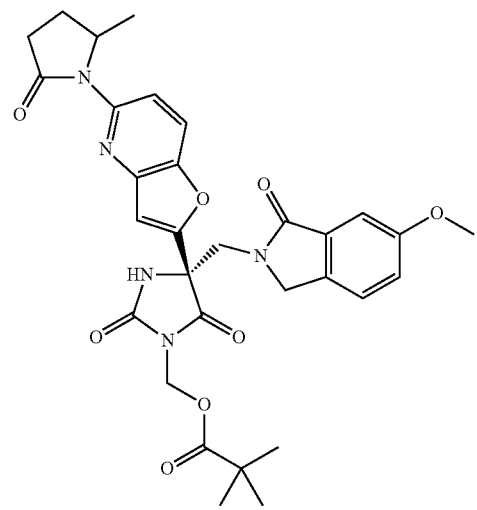 [SMILES: COc1ccc2c(c1)C(=O)N(C[C@@]1(c3cc4nc(N5C(=O)CCC5C)ccc4o3)NC(=O)N(COC(=O)C(C)(C)C)C1=O)C2] |
| 11 | 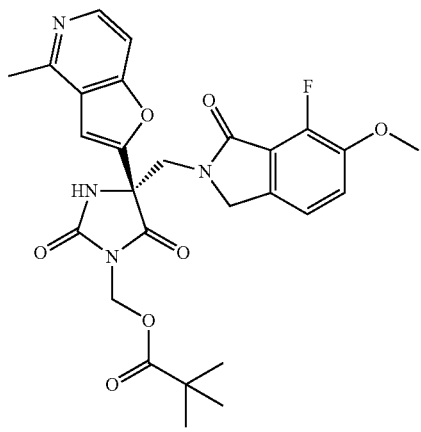 |
| 12 | 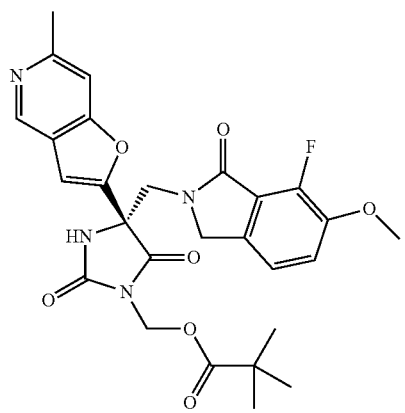 [SMILES: COc1ccc2c(c1F)C(=O)N(C[C@@]1(c3cc4cnc(C)cc4o3)NC(=O)N(COC(=O)C(C)(C)C)C1=O)C2] |

-continued

| Compd # | STRUCTURE |
|---|---|
| 13 | 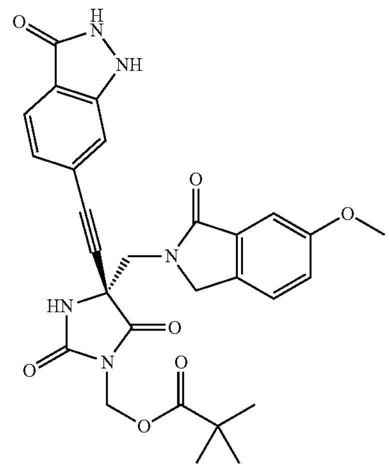 [SMILES: COc1ccc2c(c1)C(=O)N(C[C@@]1(C#Cc3ccc4c(=O)[nH][nH]c4c3)NC(=O)N(COC(=O)C(C)(C)C)C1=O)C2] |
| 14 | 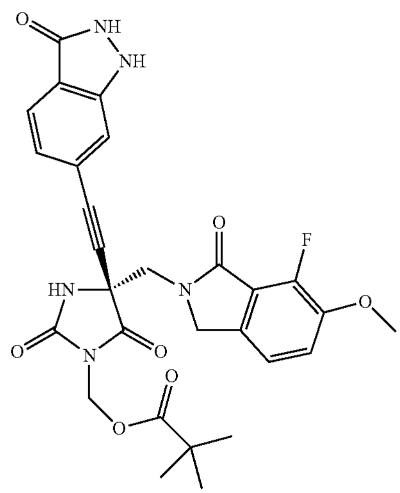 [SMILES: COc1ccc2c(c1F)C(=O)N(C[C@@]1(C#Cc3ccc4c(=O)[nH][nH]c4c3)NC(=O)N(COC(=O)C(C)(C)C)C1=O)C2] |
| 15 | 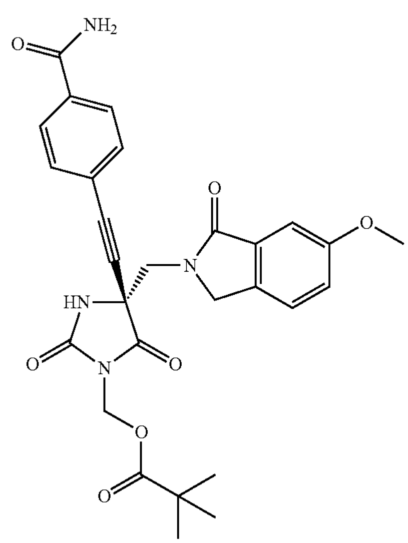 [SMILES: COc1ccc2c(c1)C(=O)N(C[C@@]1(C#Cc3ccc(C(N)=O)cc3)NC(=O)N(COC(=O)C(C)(C)C)C1=O)C2] |

| Compd # | STRUCTURE |
| --- | --- |
| 16 | 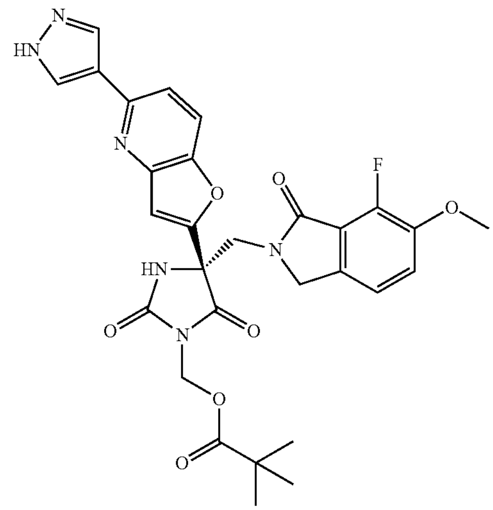 [SMILES: COc1ccc2c(c1F)C(=O)N(C[C@@]1(c3cc4nc(-c5cn[nH]c5)ccc4o3)NC(=O)N(COC(=O)C(C)(C)C)C1=O)C2] |
| 17 | 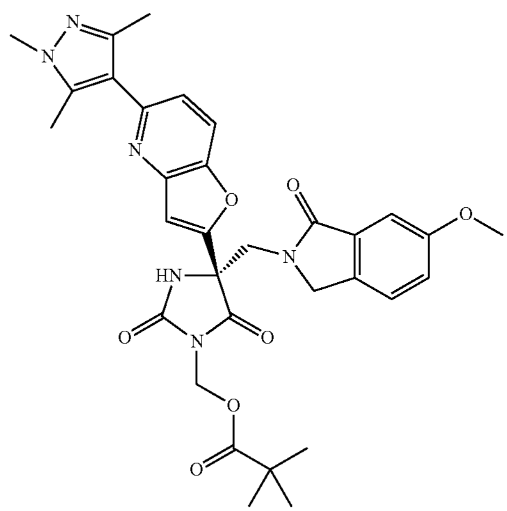 |
| 18 | 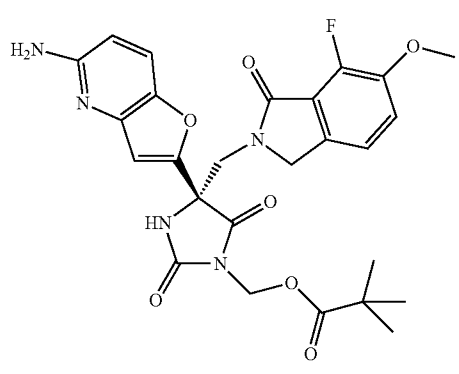 [SMILES: COc1ccc2c(c1F)C(=O)N(C[C@@]1(c3cc4nc(N)ccc4o3)NC(=O)N(COC(=O)C(C)(C)C)C1=O)C2] |

| Compd # | STRUCTURE |
|---|---|
| 19 | 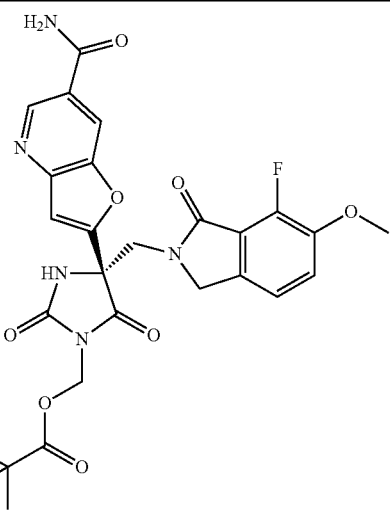 |
| 20 | 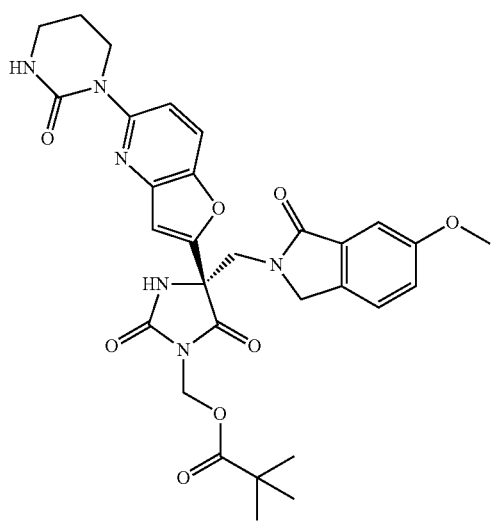 [SMILES: COc1ccc2c(c1)C(=O)N(C[C@@]1(c3cc4nc(N5CCCNC5=O)ccc4o3)NC(=O)N(COC(=O)C(C)(C)C)C1=O)C2] |
| 21 | 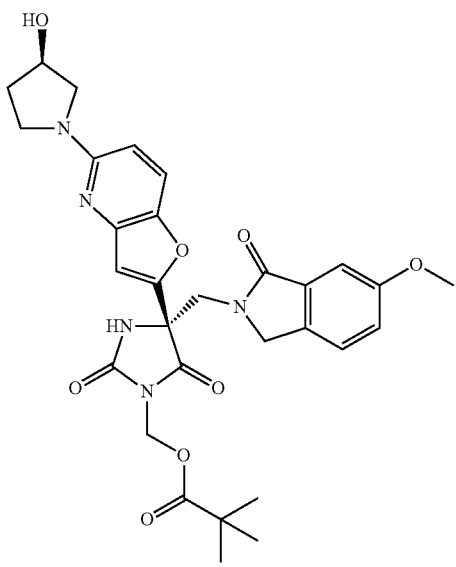 [SMILES: COc1ccc2c(c1)C(=O)N(C[C@@]1(c3cc4nc(N5CC[C@@H](O)C5)ccc4o3)NC(=O)N(COC(=O)C(C)(C)C)C1=O)C2] |

| Compd # | STRUCTURE |
|---|---|
| 22 | 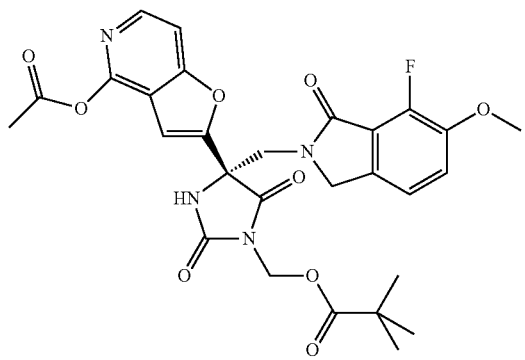 [SMILES: COc1ccc2c(c1F)C(=O)N(C[C@@]1(c3cc4c(OC(C)=O)nccc4o3)NC(=O)N(COC(=O)C(C)(C)C)C1=O)C2] |
| 23 | 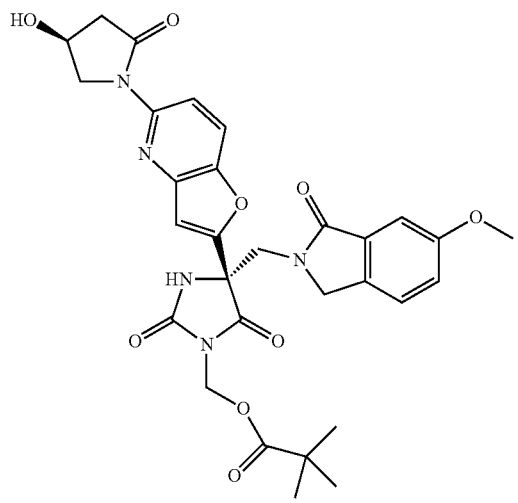 [SMILES: COc1ccc2c(c1)C(=O)N(C[C@@]1(c3cc4nc(N5C[C@@H](O)CC5=O)ccc4o3)NC(=O)N(COC(=O)C(C)(C)C)C1=O)C2] |
| 24 | 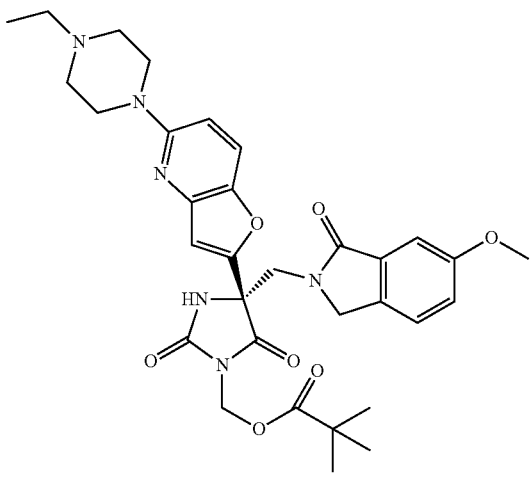 [SMILES: CCN1CCN(c2ccc3oc([C@]4(CN5Cc6ccc(OC)cc6C5=O)NC(=O)N(COC(=O)C(C)(C)C)C4=O)cc3n2)CC1] |

| Compd # | STRUCTURE |
|---|---|
| 25 | 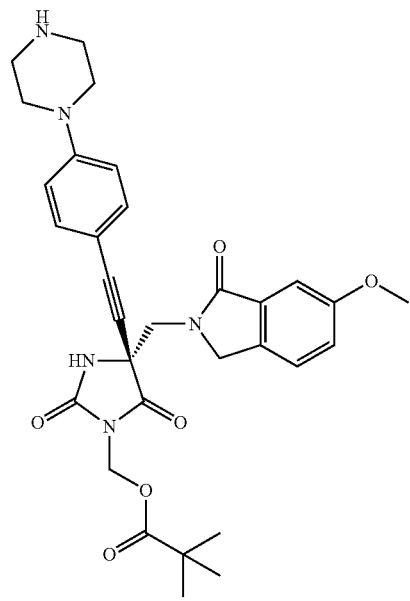 [SMILES: COc1ccc2c(c1)C(=O)N(C[C@@]1(C#Cc3ccc(N4CCNCC4)cc3)NC(=O)N(COC(=O)C(C)(C)C)C1=O)C2] |
| 26 | 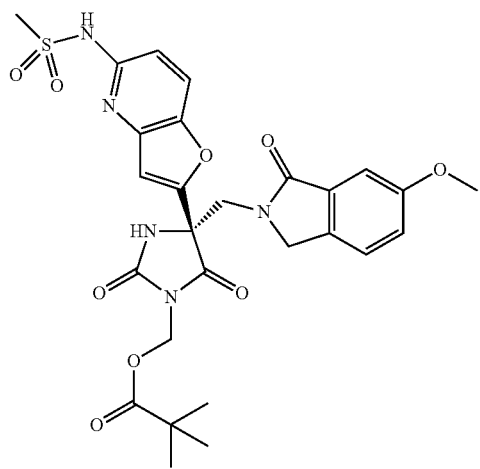 |
| 27 | 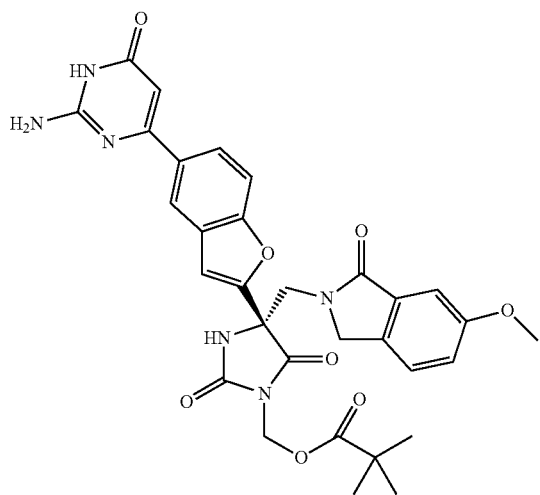 [SMILES: COc1ccc2c(c1)C(=O)N(C[C@@]1(c3cc4cc(-c5cc(=O)[nH]c(N)n5)ccc4o3)NC(=O)N(COC(=O)C(C)(C)C)C1=O)C2] |

-continued
| Compd # | STRUCTURE |
|---|---|
| 28 | 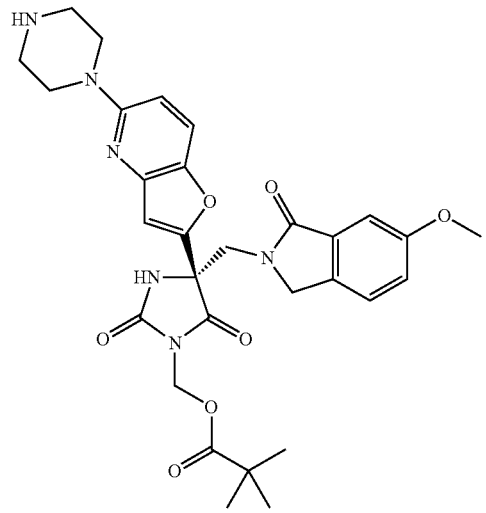 [SMILES: COc1ccc2c(c1)C(=O)N(C[C@@]1(c3cc4nc(N5CCNCC5)ccc4o3)NC(=O)N(COC(=O)C(C)(C)C)C1=O)C2] |
| 29 | 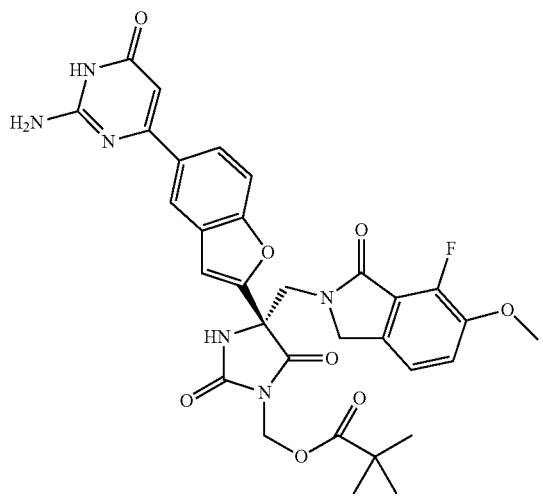 [SMILES: COc1ccc2c(c1F)C(=O)N(C[C@@]1(c3cc4cc(-c5cc(=O)[nH]c(N)n5)ccc4o3)NC(=O)N(COC(=O)C(C)(C)C)C1=O)C2] |
| 30 | 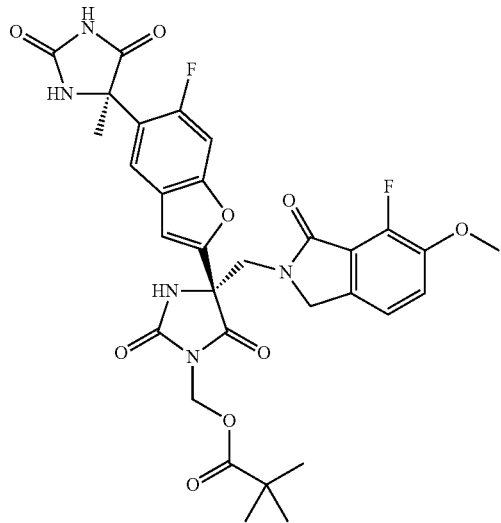 [SMILES: COc1ccc2c(c1F)C(=O)N(C[C@@]1(c3cc4cc([C@@]5(C)NC(=O)NC5=O)c(F)cc4o3)NC(=O)N(COC(=O)C(C)(C)C)C1=O)C2] |

| Compd # | STRUCTURE |
|---|---|
| 31 | 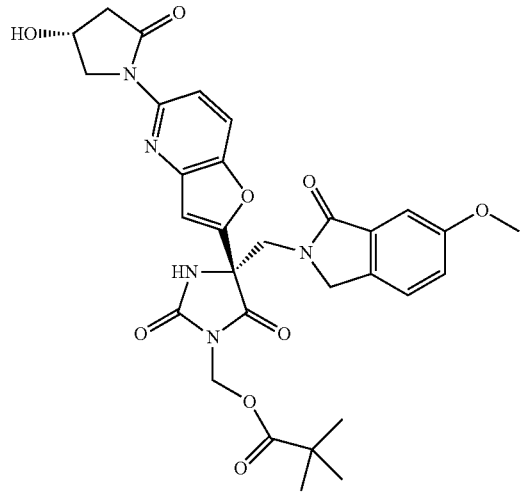 [SMILES: COc1ccc2c(c1)C(=O)N(C[C@@]1(c3cc4nc(N5C[C@H](O)CC5=O)ccc4o3)NC(=O)N(COC(=O)C(C)(C)C)C1=O)C2] |
| 32 | 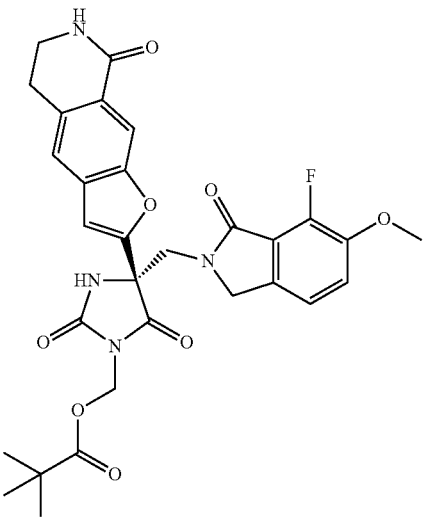 [SMILES: COc1ccc2c(c1F)C(=O)N(C[C@@]1(c3cc4cc5c(cc4o3)C(=O)NCC5)NC(=O)N(COC(=O)C(C)(C)C)C1=O)C2] |
| 33 | 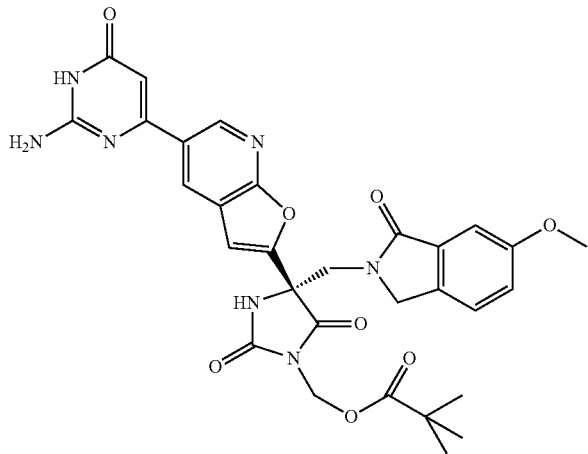 [SMILES: COc1ccc2c(c1)C(=O)N(C[C@@]1(c3cc4cc(-c5cc(=O)[nH]c(N)n5)cnc4o3)NC(=O)N(COC(=O)C(C)(C)C)C1=O)C2] |

| Compd # | STRUCTURE |
|---|---|
| 34 | 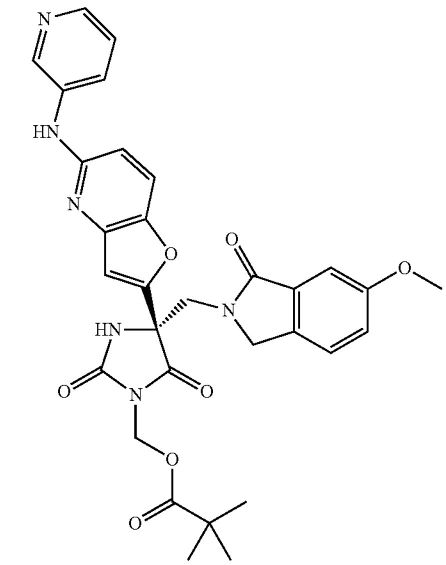 [SMILES: COc1ccc2c(c1)C(=O)N(C[C@@]1(c3cc4nc(Nc5cccnc5)ccc4o3)NC(=O)N(COC(=O)C(C)(C)C)C1=O)C2] |
| 35 | 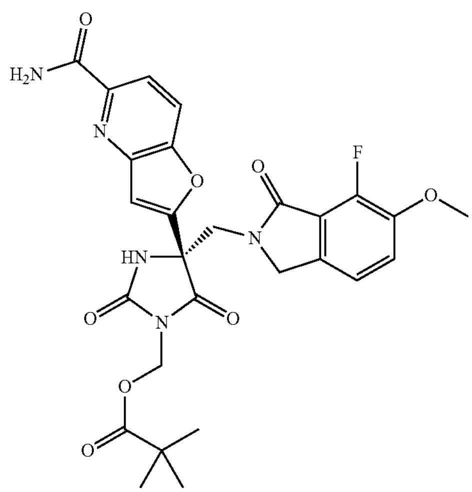 [SMILES: COc1ccc2c(c1F)C(=O)N(C[C@@]1(c3cc4nc(C(N)=O)ccc4o3)NC(=O)N(COC(=O)C(C)(C)C)C1=O)C2] |
| 35.1 | 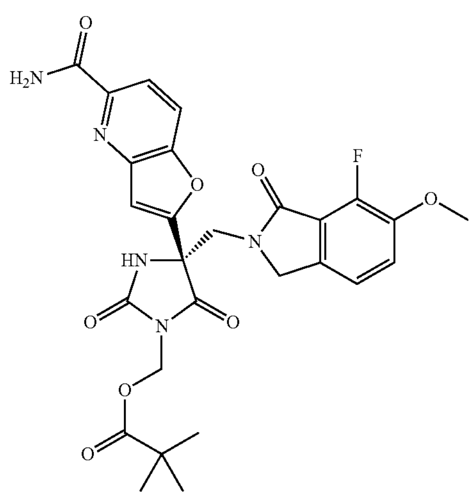 [SMILES: COc1ccc2c(c1F)C(=O)N(C[C@@]1(c3cc4nc(C(N)=O)ccc4o3)NC(=O)N(COC(=O)C(C)(C)C)C1=O)C2] |

| Compd # | STRUCTURE |
|---|---|
| 35.2 | 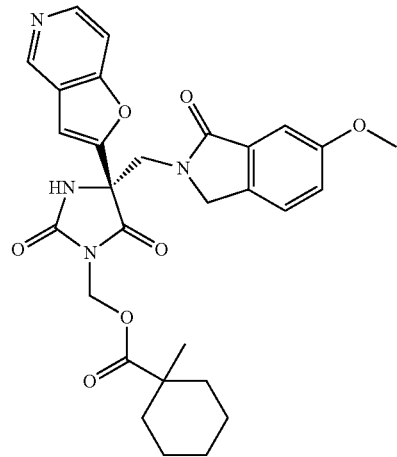 [SMILES: COc1ccc2c(c1)C(=O)N(C[C@@]1(c3cc4cnccc4o3)NC(=O)N(COC(=O)C3(C)CCCCC3)C1=O)C2] |
| 35.3 | 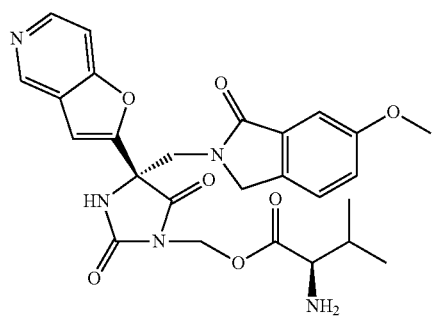 [SMILES: COc1ccc2c(c1)C(=O)N(C[C@@]1(c3cc4cnccc4o3)NC(=O)N(COC(=O)[C@H](N)C(C)C)C1=O)C2] |
| 35.4 | 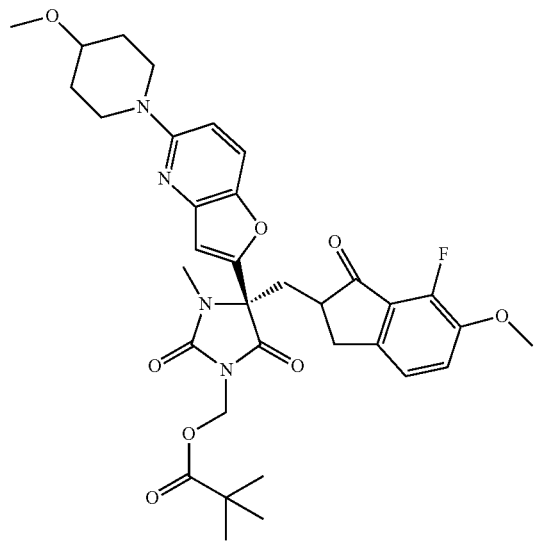 |

-continued

| Compd # | STRUCTURE |
|---------|-----------|
| 36 | 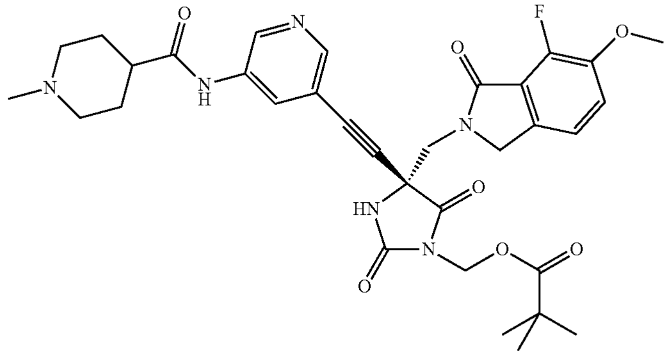 |
| 37 | 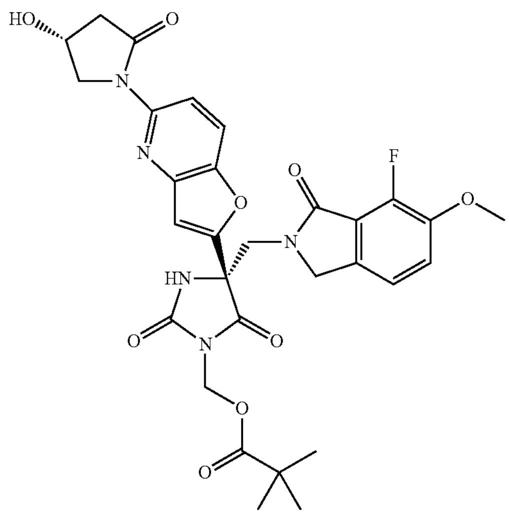 [SMILES: COc1ccc2c(c1F)C(=O)N(C[C@@]1(c3cc4nc(N5C[C@H](O)CC5=O)ccc4o3)NC(=O)N(COC(=O)C(C)(C)C)C1=O)C2] |
| 38 | 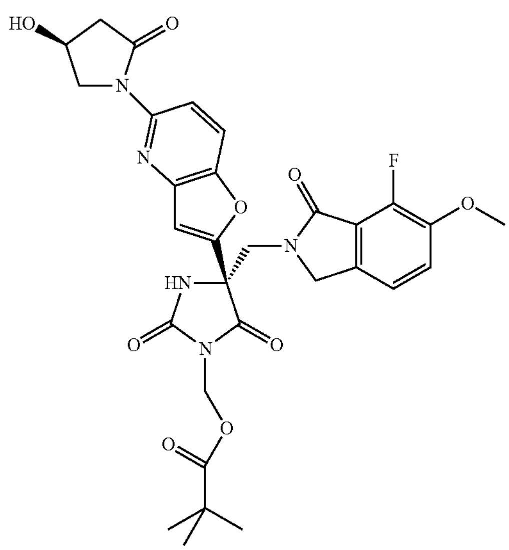 [SMILES: COc1ccc2c(c1F)C(=O)N(C[C@@]1(c3cc4nc(N5C[C@@H](O)CC5=O)ccc4o3)NC(=O)N(COC(=O)C(C)(C)C)C1=O)C2] |

| Compd # | STRUCTURE |
|---------|-----------|
| 39 | 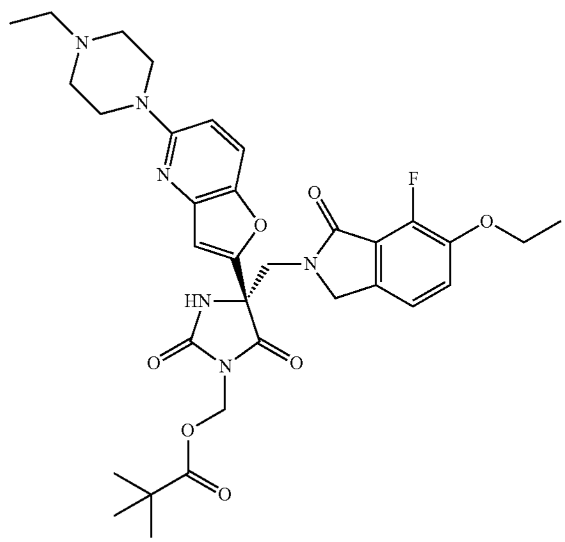 [SMILES: CCOc1ccc2c(c1F)C(=O)N(C[C@@]1(c3cc4nc(N5CCN(CC)CC5)ccc4o3)NC(=O)N(COC(=O)C(C)(C)C)C1=O)C2] |
| 40 | 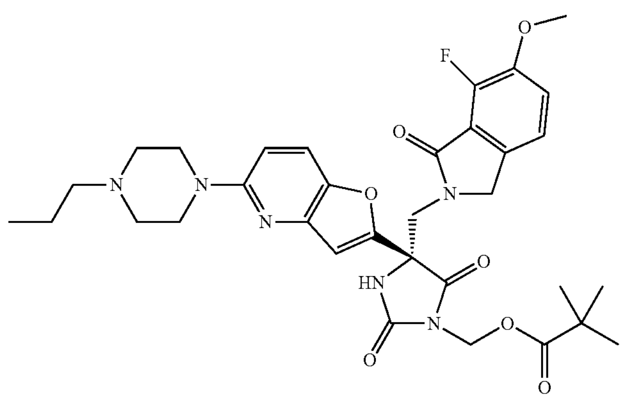 [SMILES: CCCN1CCN(c2ccc3oc([C@]4(CN5Cc6ccc(OC)c(F)c6C5=O)NC(=O)N(COC(=O)C(C)(C)C)C4=O)cc3n2)CC1] |
| 41 | 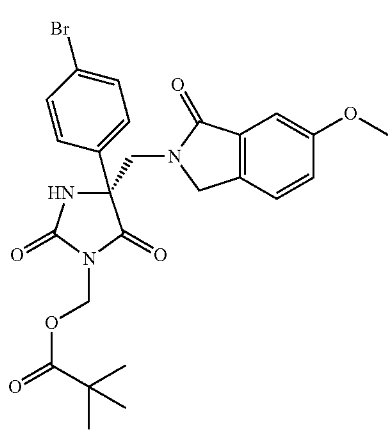 [SMILES: COc1ccc2c(c1)C(=O)N(C[C@@]1(c3ccc(Br)cc3)NC(=O)N(COC(=O)C(C)(C)C)C1=O)C2] |

| Compd # | STRUCTURE |
|---|---|
| 42 | 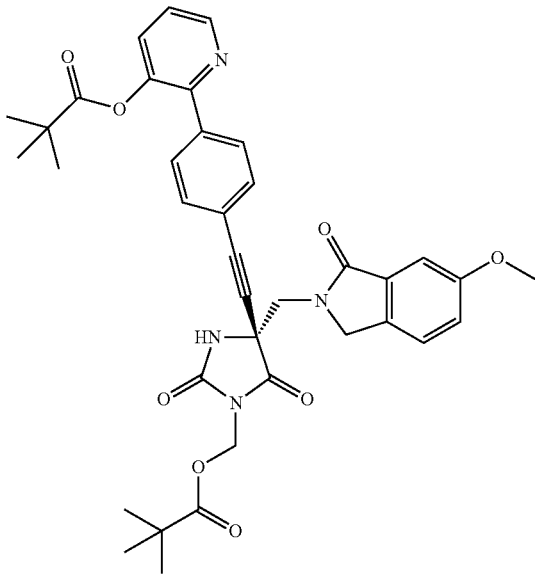 [SMILES: COc1ccc2c(c1)C(=O)N(C[C@@]1(C#Cc3ccc(-c4ncccc4OC(=O)C(C)(C)C)cc3)NC(=O)N(COC(=O)C(C)(C)C)C1=O)C2] |
| 43 | 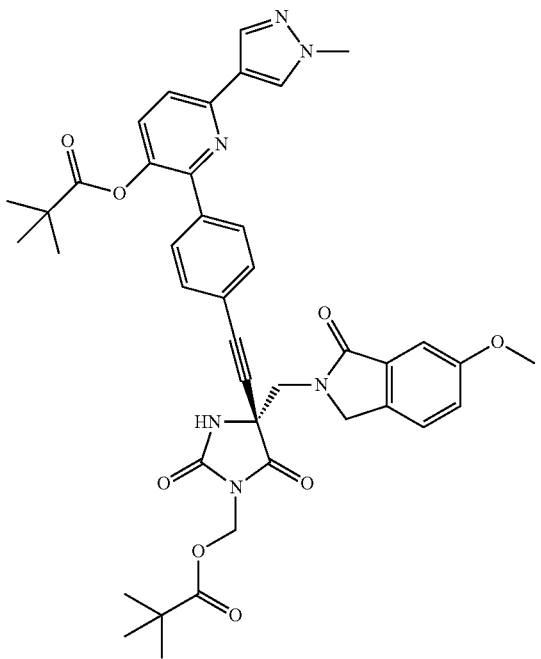 [SMILES: COc1ccc2c(c1)C(=O)N(C[C@@]1(C#Cc3ccc(-c4nc(-c5cnn(C)c5)ccc4OC(=O)C(C)(C)C)cc3)NC(=O)N(COC(=O)C(C)(C)C)C1=O)C2] |

-continued
| Compd # | STRUCTURE |
|---|---|
| 44 | 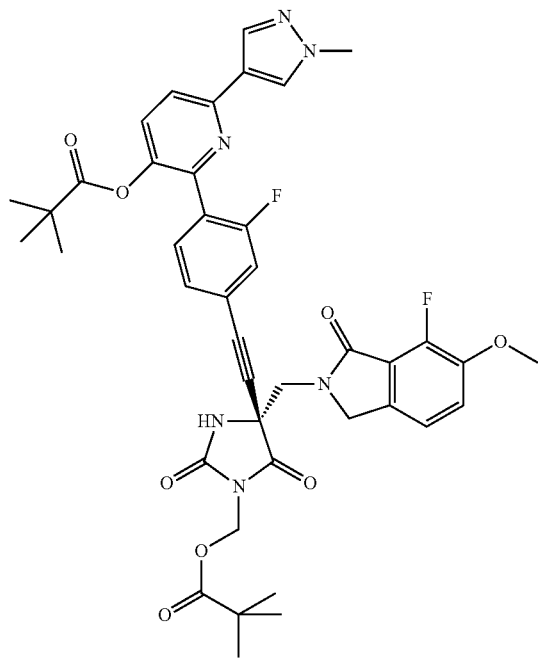 [SMILES: COc1ccc2c(c1F)C(=O)N(C[C@@]1(C#Cc3ccc(-c4nc(-c5cnn(C)c5)ccc4OC(=O)C(C)(C)C)c(F)c3)NC(=O)N(COC(=O)C(C)(C)C)C1=O)C2] |
| 45 | 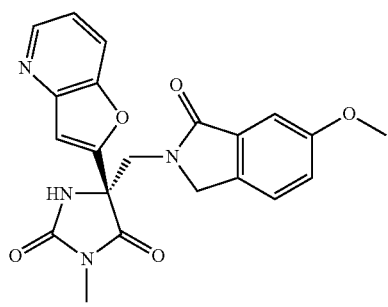 [SMILES: COc1ccc2c(c1)C(=O)N(C[C@@]1(c3cc4ncccc4o3)NC(=O)N(C)C1=O)C2] |
| 46 | 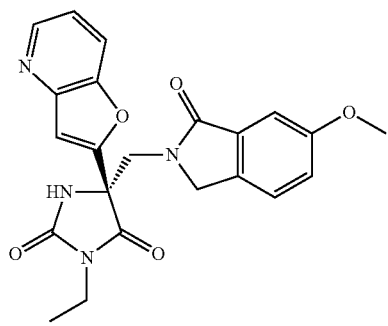 [SMILES: CCN1C(=O)N[C@@](CN2Cc3ccc(OC)cc3C2=O)(c2cc3ncccc3o2)C1=O] |

| Compd # | STRUCTURE |
|---|---|
| 47 | 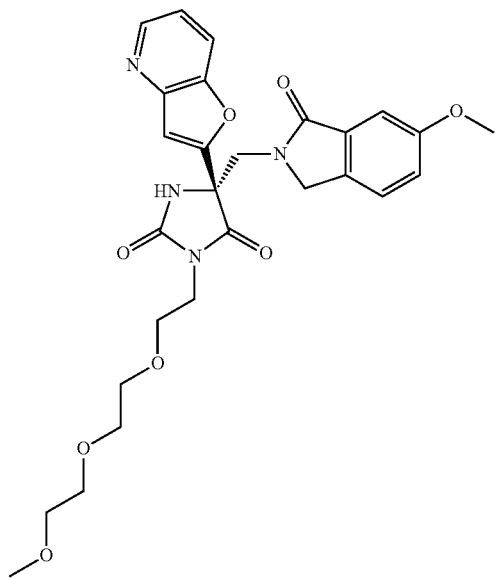 |
| 48 | 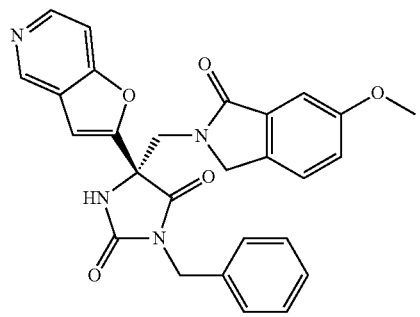 [SMILES: COc1ccc2c(c1)C(=O)N(C[C@@]1(c3cc4cnccc4o3)NC(=O)N(Cc3ccccc3)C1=O)C2] |
| 48.1 | 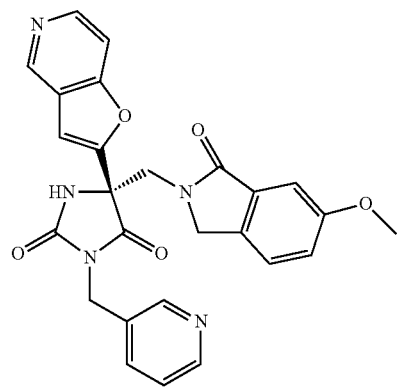 [SMILES: COc1ccc2c(c1)C(=O)N(C[C@@]1(c3cc4cnccc4o3)NC(=O)N(Cc3cccnc3)C1=O)C2] |

-continued
| Compd # | STRUCTURE |
|---|---|
| 49 | 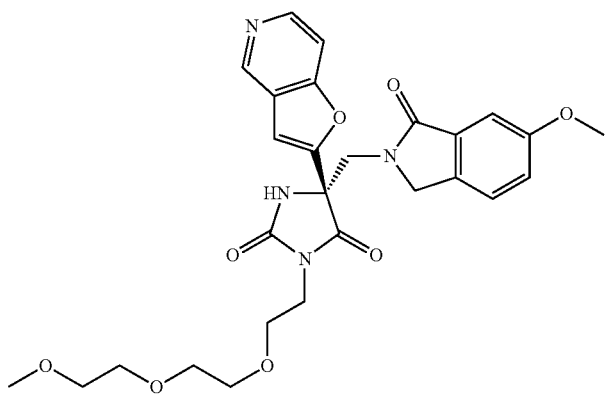 |
| 50 | 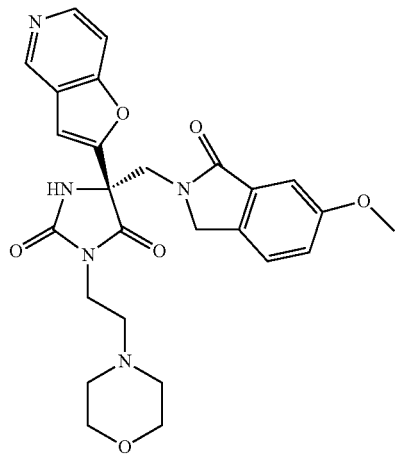 [SMILES: COc1ccc2c(c1)C(=O)N(C[C@@]1(c3cc4cnccc4o3)NC(=O)N(CCN3CCOCC3)C1=O)C2] |
| 51 | 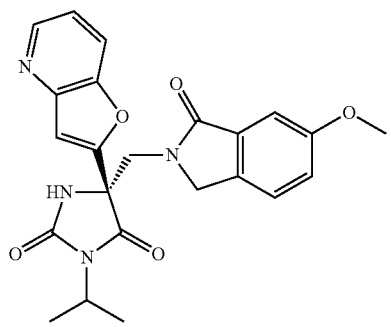 [SMILES: COc1ccc2c(c1)C(=O)N(C[C@@]1(c3cc4ncccc4o3)NC(=O)N(C(C)C)C1=O)C2] |
| 52 | 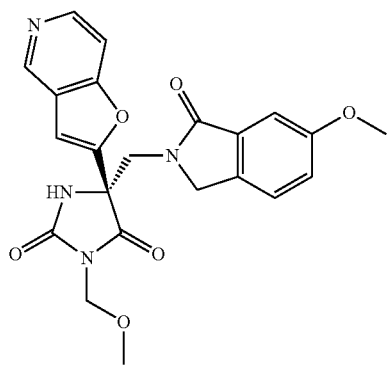 [SMILES: COCN1C(=O)N[C@@](CN2Cc3ccc(OC)cc3C2=O)(c2cc3cnccc3o2)C1=O] |

| Compd # | STRUCTURE |
|---|---|
| 53 | 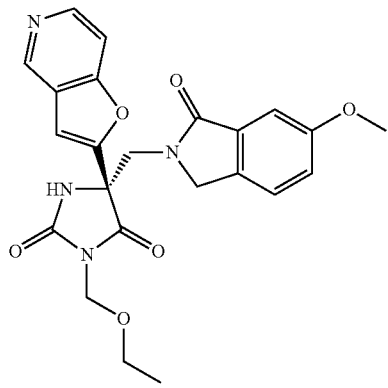 [SMILES: CCOCN1C(=O)N[C@@](CN2Cc3ccc(OC)cc3C2=O)(c2cc3cnccc3o2)C1=O] |
| 54 | 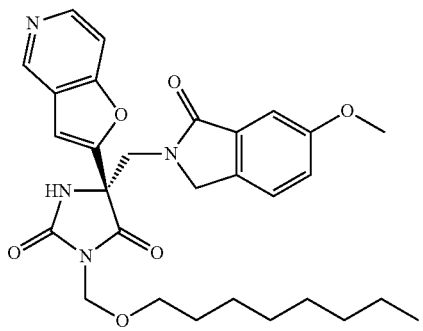 [SMILES: CCCCCCCCOCN1C(=O)N[C@@](CN2Cc3ccc(OC)cc3C2=O)(c2cc3cnccc3o2)C1=O] |
| 55 | 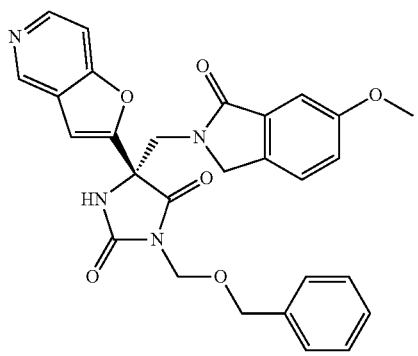 [SMILES: COc1ccc2c(c1)C(=O)N(C[C@@]1(c3cc4cnccc4o3)NC(=O)N(COCc3ccccc3)C1=O)C2] |
| 56 | 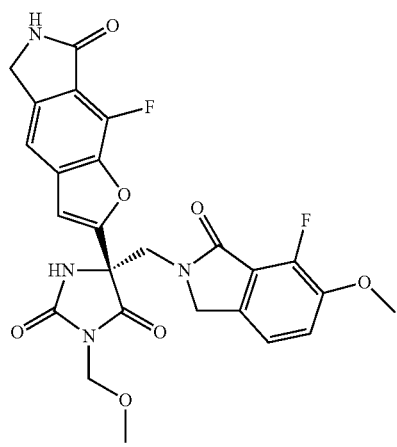 [SMILES: COCN1C(=O)N[C@@](CN2Cc3ccc(OC)c(F)c3C2=O)(c2cc3cc4c(c(F)c3o2)C(=O)NC4)C1=O] |

-continued
| Compd # | STRUCTURE |
|---|---|
| 57 | 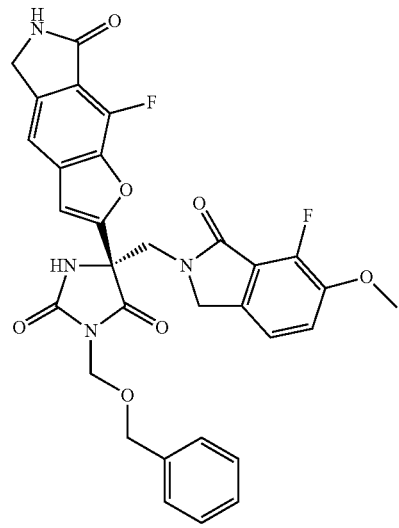 [SMILES: COc1ccc2c(c1F)C(=O)N(C[C@@]1(c3cc4cc5c(c(F)c4o3)C(=O)NC5)NC(=O)N(COCc3ccccc3)C1=O)C2] |
| 58 | 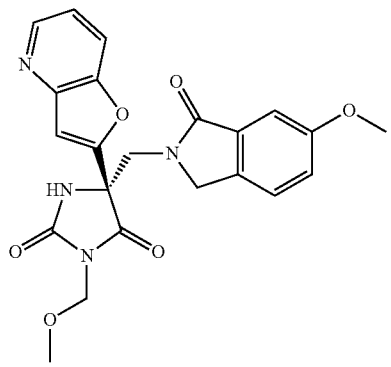 [SMILES: COCN1C(=O)N[C@@](CN2Cc3ccc(OC)cc3C2=O)(c2cc3ncccc3o2)C1=O] |
| 58.1 | 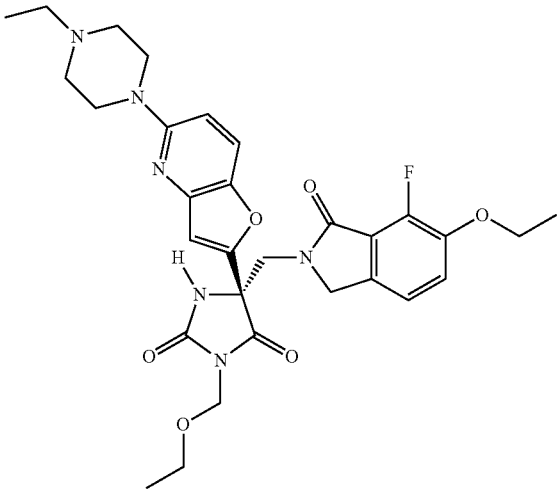 [SMILES: CCOCN1C(=O)N[C@@](CN2Cc3ccc(OCC)c(F)c3C2=O)(c2cc3nc(N4CCN(CC)CC4)ccc3o2)C1=O] |

-continued
| Compd # | STRUCTURE |
|---|---|
| 58.2 | 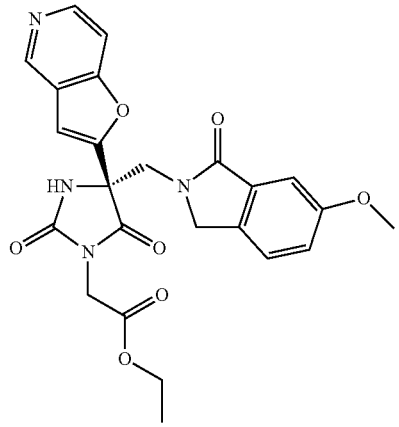 [SMILES: CCOC(=O)CN1C(=O)N[C@@](CN2Cc3ccc(OC)cc3C2=O)(c2cc3cnccc3o2)C1=O] |
| 58.3 | 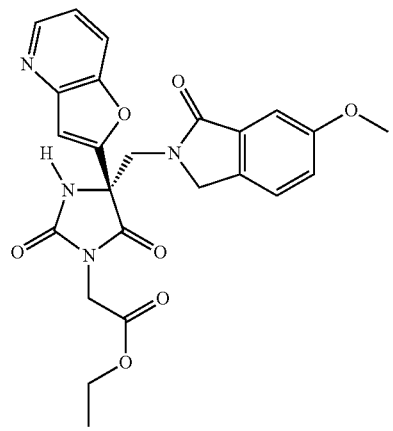 [SMILES: CCOC(=O)CN1C(=O)N[C@@](CN2Cc3ccc(OC)cc3C2=O)(c2cc3ncccc3o2)C1=O] |
| 59 | 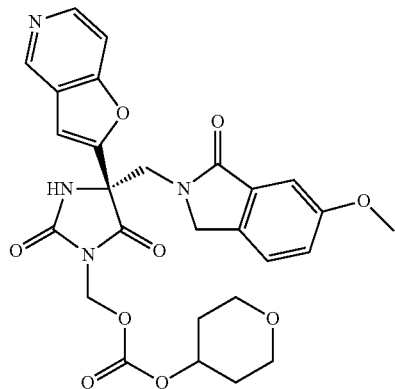 [SMILES: COc1ccc2c(c1)C(=O)N(C[C@@]1(c3cc4cnccc4o3)NC(=O)N(COC(=O)OC3CCOCC3)C1=O)C2] |

| Compd # | STRUCTURE |
|---|---|
| 60 | 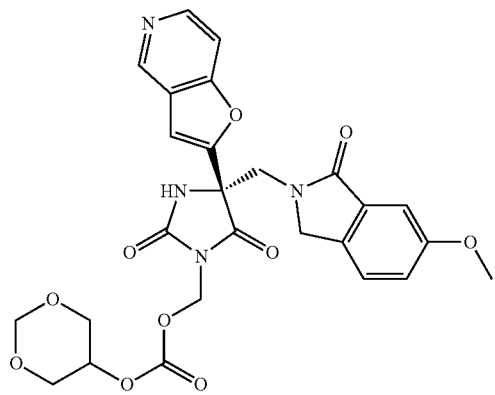 [SMILES: COc1ccc2c(c1)C(=O)N(C[C@@]1(c3cc4cnccc4o3)NC(=O)N(COC(=O)OC3COCOC3)C1=O)C2] |
| 61 | 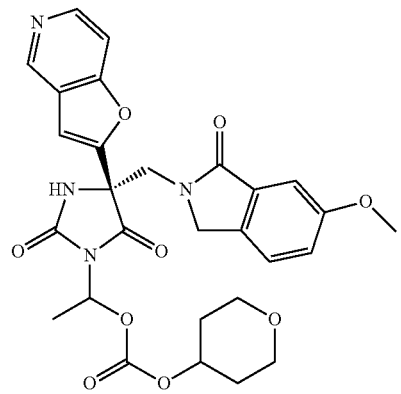 [SMILES: COc1ccc2c(c1)C(=O)N(C[C@@]1(c3cc4cnccc4o3)NC(=O)N(C(C)OC(=O)OC3CCOCC3)C1=O)C2] |
| 62 | 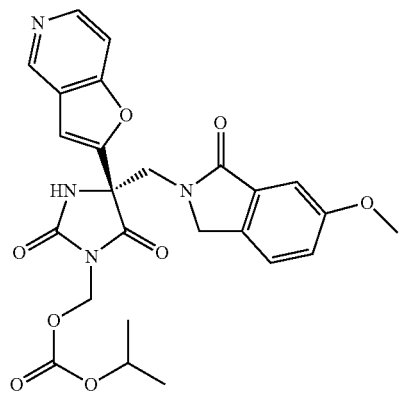 [SMILES: COc1ccc2c(c1)C(=O)N(C[C@@]1(c3cc4cnccc4o3)NC(=O)N(COC(=O)OC(C)C)C1=O)C2] |
| 63 | 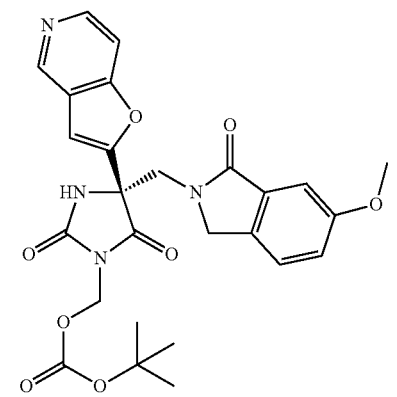 [SMILES: COc1ccc2c(c1)C(=O)N(C[C@@]1(c3cc4cnccc4o3)NC(=O)N(COC(=O)OC(C)(C)C)C1=O)C2] |

| Compd # | STRUCTURE |
|---|---|
| 63.1 | 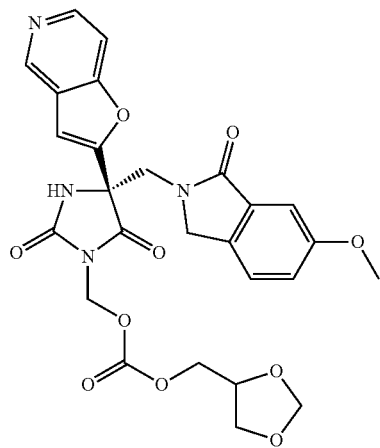 [SMILES: COc1ccc2c(c1)C(=O)N(C[C@@]1(c3cc4cnccc4o3)NC(=O)N(COC(=O)OCC3COCO3)C1=O)C2] |
| 63.2 | 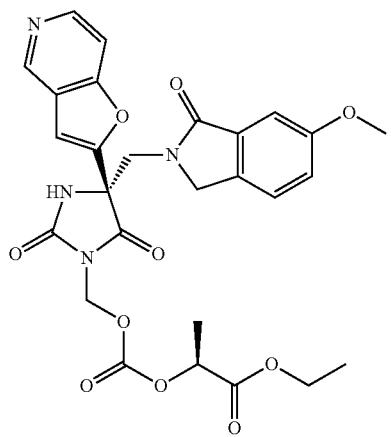 [SMILES: CCOC(=O)[C@H](C)OC(=O)OCN1C(=O)N[C@@](CN2Cc3ccc(OC)cc3C2=O)(c2cc3cnccc3o2)C1=O] |
| 63.3 | 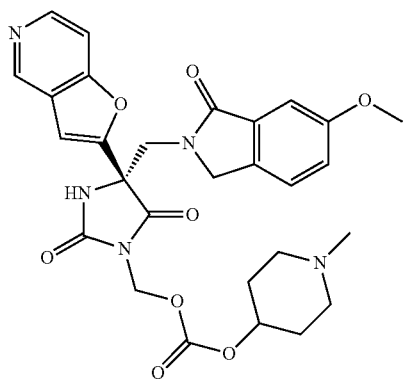 [SMILES: COc1ccc2c(c1)C(=O)N(C[C@@]1(c3cc4cnccc4o3)NC(=O)N(COC(=O)OC3CCN(C)CC3)C1=O)C2] |

| Compd # | STRUCTURE |
|---|---|
| 63.4 | 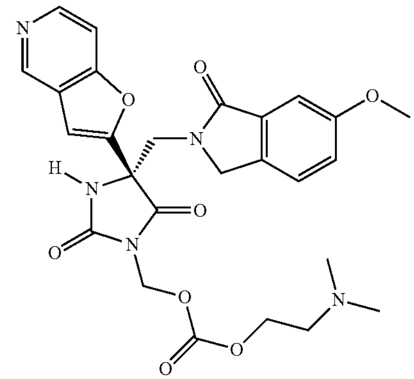 [SMILES: COc1ccc2c(c1)C(=O)N(C[C@@]1(c3cc4cnccc4o3)NC(=O)N(COC(=O)OCCN(C)C)C1=O)C2] |
| 63.5 | 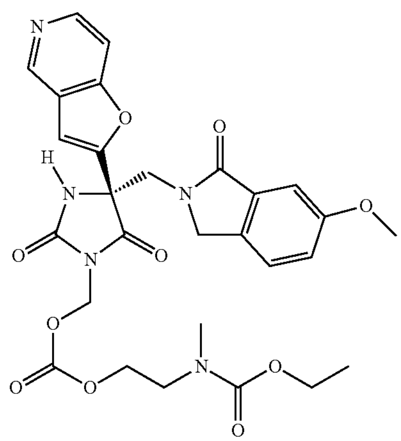 [SMILES: CCOC(=O)N(C)CCOC(=O)OCN1C(=O)N[C@@](CN2Cc3ccc(OC)cc3C2=O)(c2cc3cnccc3o2)C1=O] |
| 63.6 | 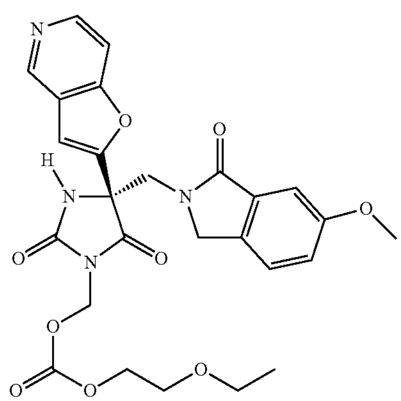 [SMILES: CCOCCOC(=O)OCN1C(=O)N[C@@](CN2Cc3ccc(OC)cc3C2=O)(c2cc3cnccc3o2)C1=O] |
| 63.7 | 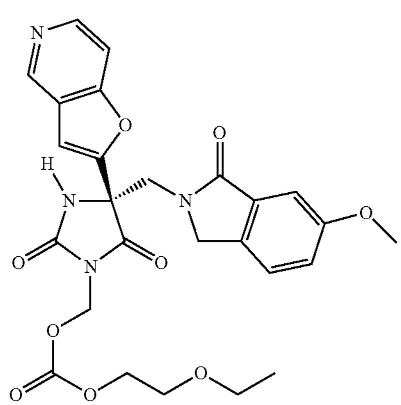 [SMILES: CCOCCOC(=O)OCN1C(=O)N[C@@](CN2Cc3ccc(OC)cc3C2=O)(c2cc3cnccc3o2)C1=O] |

| Compd # | STRUCTURE |
|---|---|
| 63.8 | 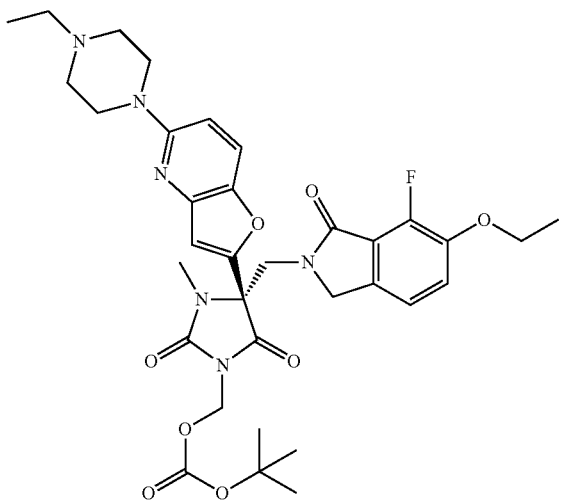 [SMILES: CCOc1ccc2c(c1F)C(=O)N(C[C@]1(c3cc4nc(N5CCN(CC)CC5)ccc4o3)C(=O)N(COC(=O)OC(C)(C)C)C(=O)N1C)C2] |
| 64 | 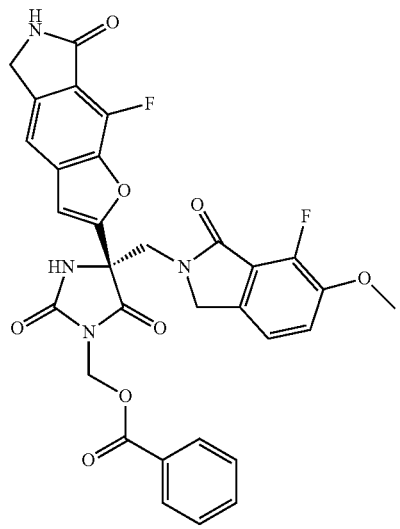 [SMILES: COc1ccc2c(c1F)C(=O)N(C[C@@]1(c3cc4cc5c(c(F)c4o3)C(=O)NC5)NC(=O)N(COC(=O)c3ccccc3)C1=O)C2] |
| 65 | 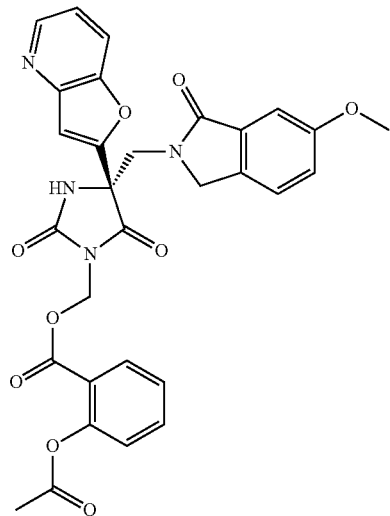 [SMILES: COc1ccc2c(c1)C(=O)N(C[C@@]1(c3cc4ncccc4o3)NC(=O)N(COC(=O)c3ccccc3OC(C)=O)C1=O)C2] |

| Compd # | STRUCTURE |
| --- | --- |
| 66 | 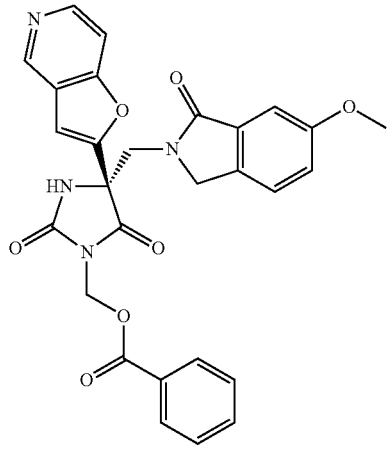 [SMILES: COc1ccc2c(c1)C(=O)N(C[C@@]1(c3cc4cnccc4o3)NC(=O)N(COC(=O)c3ccccc3)C1=O)C2] |
| 66.1 | 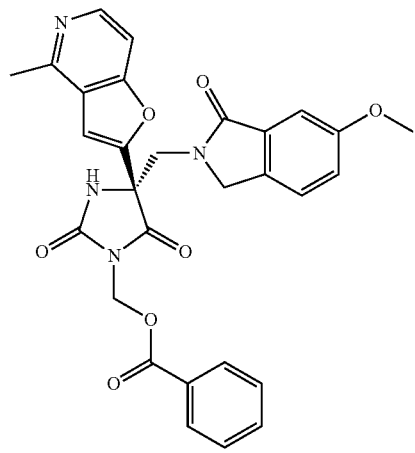 |
| 67 | 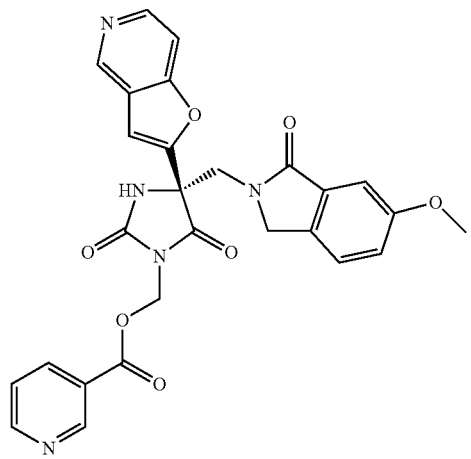 [SMILES: COc1ccc2c(c1)C(=O)N(C[C@@]1(c3cc4cnccc4o3)NC(=O)N(COC(=O)c3cccnc3)C1=O)C2] |

| Compd # | STRUCTURE |
|---|---|
| 67.1 | 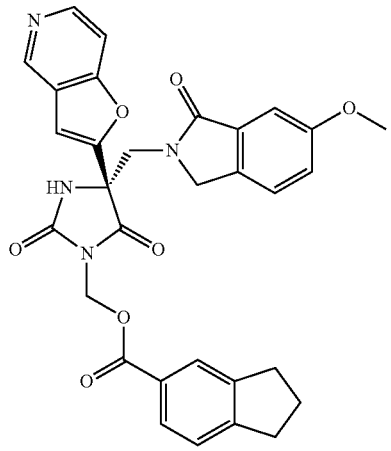 [SMILES: COc1ccc2c(c1)C(=O)N(C[C@@]1(c3cc4cnccc4o3)NC(=O)N(COC(=O)c3ccc4c(c3)CCC4)C1=O)C2] |
| 67.2 | 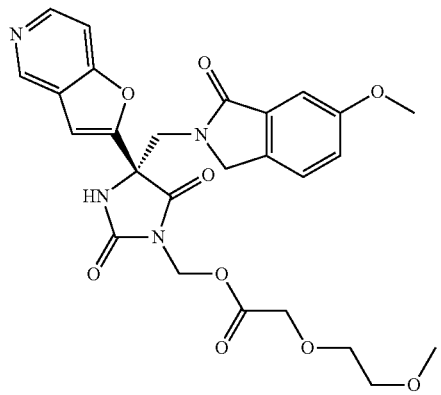 [SMILES: COCCOCC(=O)OCN1C(=O)N[C@@](CN2Cc3ccc(OC)cc3C2=O)(c2cc3cnccc3o2)C1=O] |
| 68 | 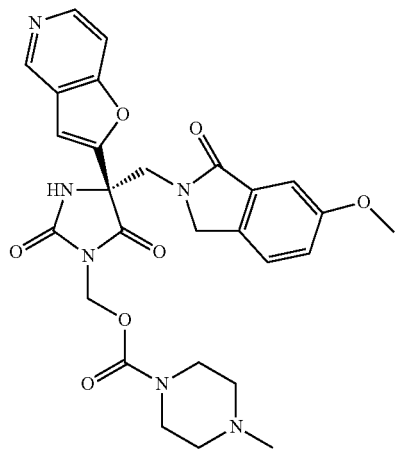 [SMILES: COc1ccc2c(c1)C(=O)N(C[C@@]1(c3cc4cnccc4o3)NC(=O)N(COC(=O)N3CCN(C)CC3)C1=O)C2] |

| Compd # | STRUCTURE |
|---|---|
| 69 | 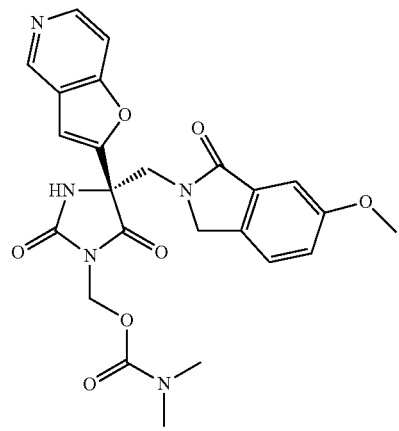 [SMILES: COc1ccc2c(c1)C(=O)N(C[C@@]1(c3cc4cnccc4o3)NC(=O)N(COC(=O)N(C)C)C1=O)C2] |
| 70 | 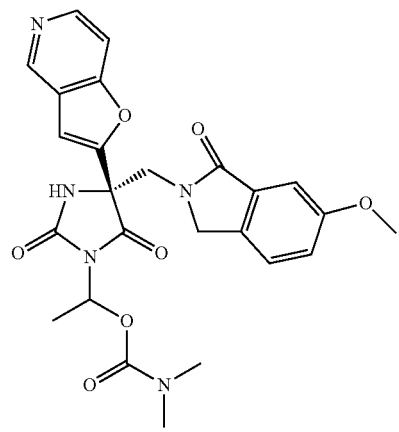 [SMILES: COc1ccc2c(c1)C(=O)N(C[C@@]1(c3cc4cnccc4o3)NC(=O)N(C(C)OC(=O)N(C)C)C1=O)C2] |
| 71 | 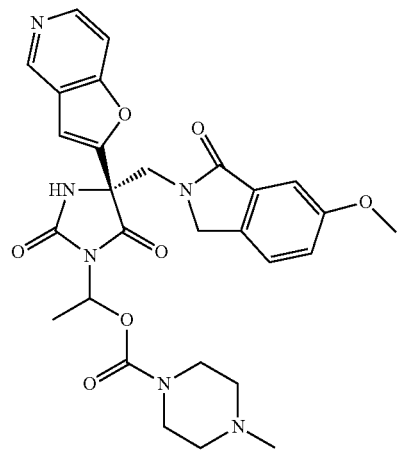 [SMILES: COc1ccc2c(c1)C(=O)N(C[C@@]1(c3cc4cnccc4o3)NC(=O)N(C(C)OC(=O)N3CCN(C)CC3)C1=O)C2] |

| Compd # | STRUCTURE |
|---|---|
| 72 | 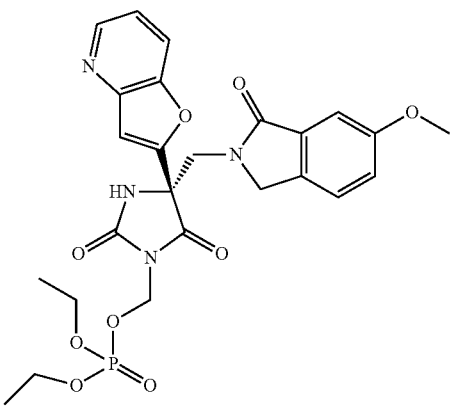 [SMILES: CCOP(=O)(OCC)OCN1C(=O)N[C@@](CN2Cc3ccc(OC)cc3C2=O)(c2cc3ncccc3o2)C1=O] |
| 73 | 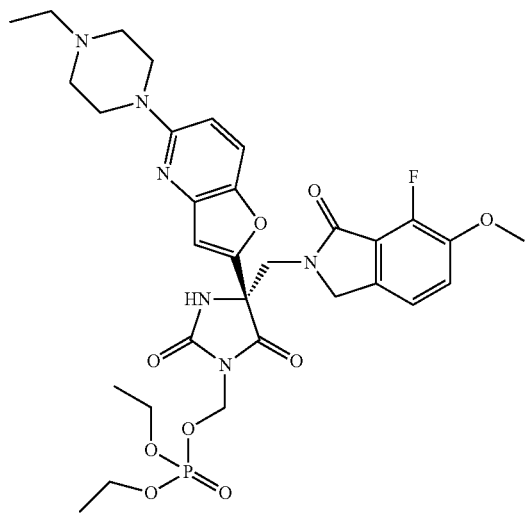 [SMILES: CCOP(=O)(OCC)OCN1C(=O)N[C@@](CN2Cc3ccc(OC)c(F)c3C2=O)(c2cc3nc(N4CCN(CC)CC4)ccc3o2)C1=O] |
| 74 | 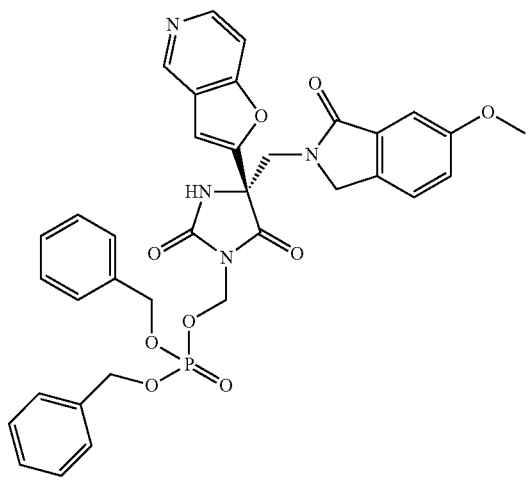 [SMILES: COc1ccc2c(c1)C(=O)N(C[C@@]1(c3cc4cnccc4o3)NC(=O)N(COP(=O)(OCc3ccccc3)OCc3ccccc3)C1=O)C2] |

| Compd # | STRUCTURE |
|---|---|
| 74.1 | 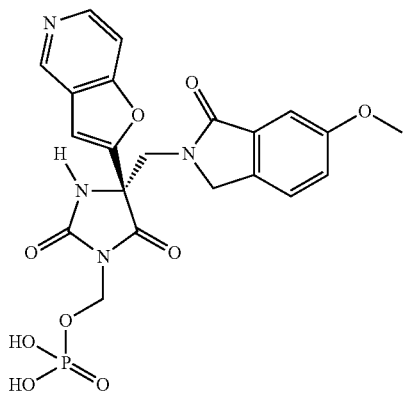 [SMILES: COc1ccc2c(c1)C(=O)N(C[C@@]1(c3cc4cnccc4o3)NC(=O)N(COP(=O)(O)O)C1=O)C2] |
| 75 | 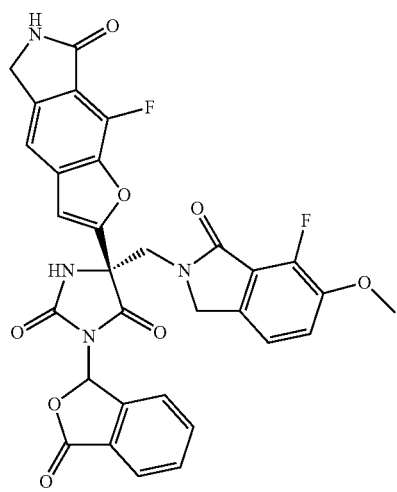 [SMILES: COc1ccc2c(c1F)C(=O)N(C[C@@]1(c3cc4cc5c(c(F)c4o3)C(=O)NC5)NC(=O)N(C3OC(=O)c4ccccc43)C1=O)C2] |
| 76 | 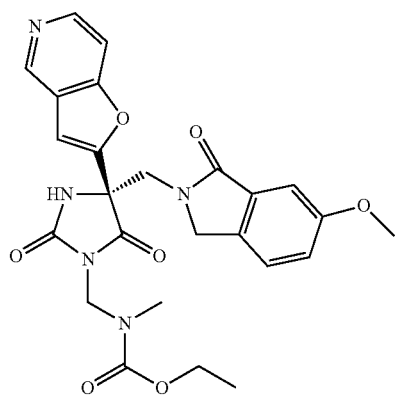 [SMILES: CCOC(=O)N(C)CN1C(=O)N[C@@](CN2Cc3ccc(OC)cc3C2=O)(c2cc3cnccc3o2)C1=O] |

| Compd # | STRUCTURE |
|---|---|
| 76.2 | 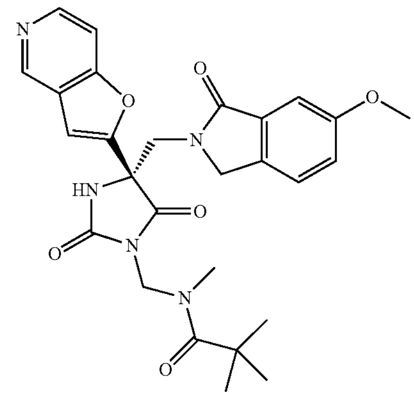 [SMILES: COc1ccc2c(c1)C(=O)N(C[C@@]1(c3cc4cnccc4o3)NC(=O)N(CN(C)C(=O)C(C)(C)C)C1=O)C2] |
| 76.1 | 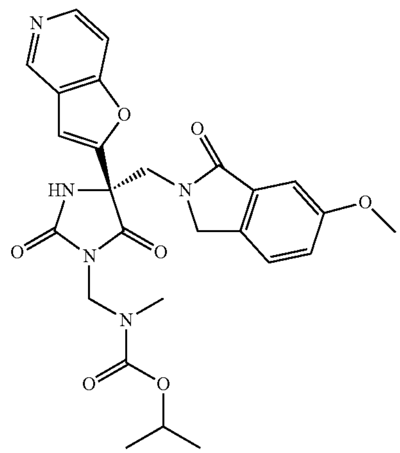 [SMILES: COc1ccc2c(c1)C(=O)N(C[C@@]1(c3cc4cnccc4o3)NC(=O)N(CN(C)C(=O)OC(C)C)C1=O)C2] |
| 77 | 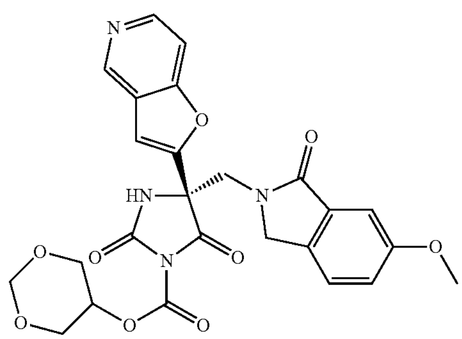 [SMILES: COc1ccc2c(c1)C(=O)N(C[C@@]1(c3cc4cnccc4o3)NC(=O)N(C(=O)OC3COCOC3)C1=O)C2] |
| 78 | 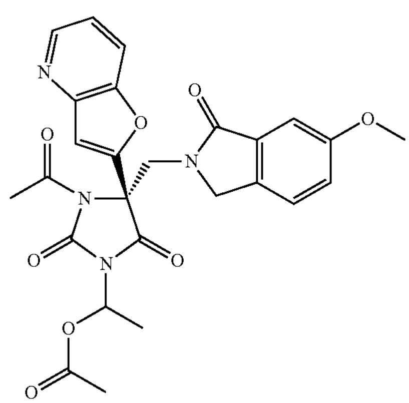 [SMILES: COc1ccc2c(c1)C(=O)N(C[C@]1(c3cc4ncccc4o3)C(=O)N(C(C)OC(C)=O)C(=O)N1C(C)=O)C2] |

| Compd # | STRUCTURE |
|---|---|
| 79 | 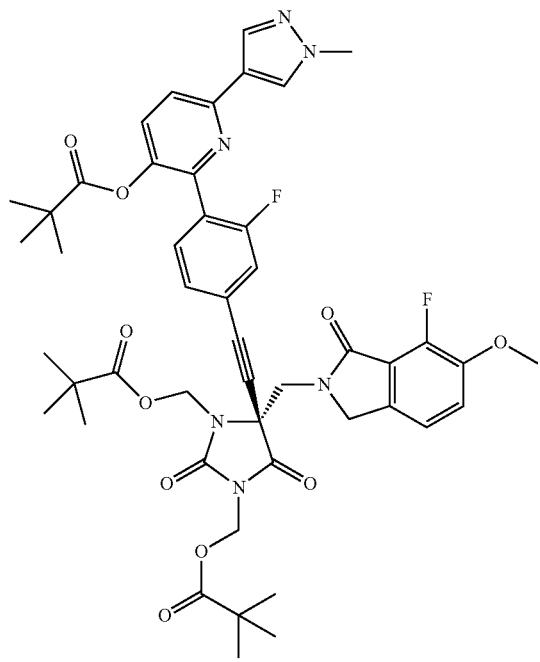 [SMILES: COc1ccc2c(c1F)C(=O)N(C[C@]1(C#Cc3ccc(-c4nc(-c5cnn(C)c5)ccc4OC(=O)C(C)(C)C)c(F)c3)C(=O)N(COC(=O)C(C)(C)C)C(=O)N1COC(=O)C(C)(C)C)C2] |
| 80 | 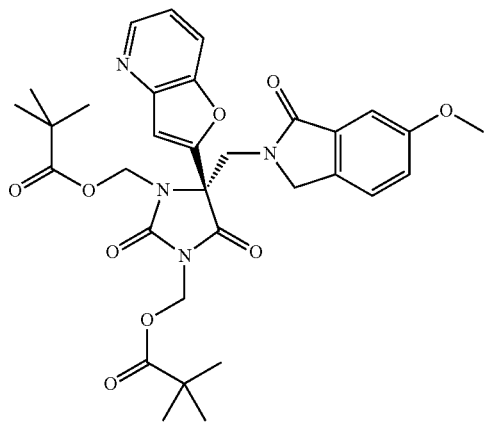 [SMILES: COc1ccc2c(c1)C(=O)N(C[C@]1(c3cc4ncccc4o3)C(=O)N(COC(=O)C(C)(C)C)C(=O)N1COC(=O)C(C)(C)C)C2] |
| 81 | 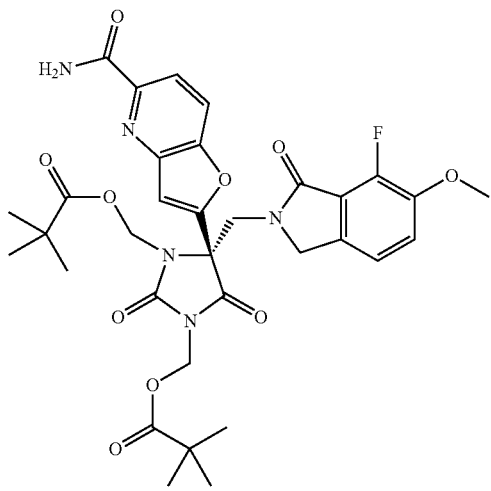 [SMILES: COc1ccc2c(c1F)C(=O)N(C[C@]1(c3cc4nc(C(N)=O)ccc4o3)C(=O)N(COC(=O)C(C)(C)C)C(=O)N1COC(=O)C(C)(C)C)C2] |

| Compd # | STRUCTURE |
|---|---|
| 82 | 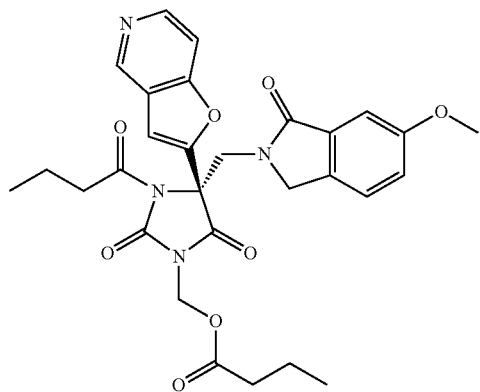 [SMILES: CCCC(=O)OCN1C(=O)N(C(=O)CCC)[C@@](CN2Cc3ccc(OC)cc3C2=O)(c2cc3cnccc3o2)C1=O] |
| 83 | 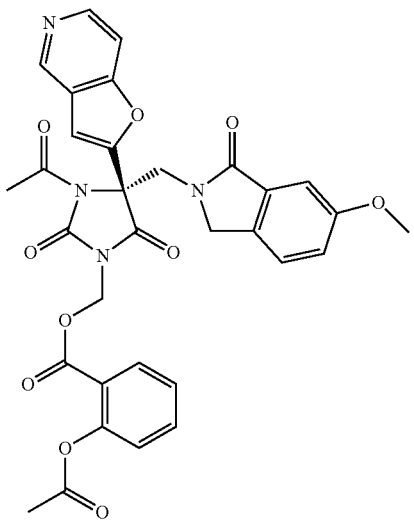 [SMILES: COc1ccc2c(c1)C(=O)N(C[C@]1(c3cc4cnccc4o3)C(=O)N(COC(=O)c3ccccc3OC(C)=O)C(=O)N1C(C)=O)C2] |
| 84 | 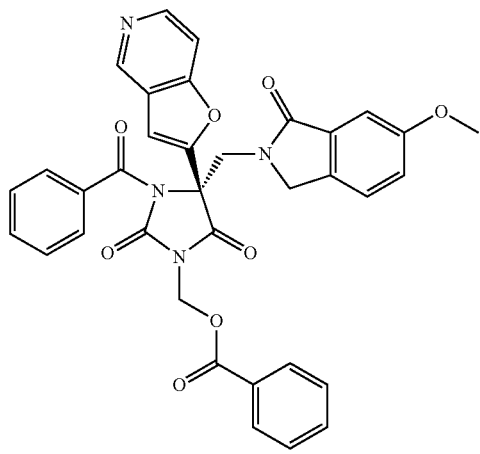 [SMILES: COc1ccc2c(c1)C(=O)N(C[C@]1(c3cc4cnccc4o3)C(=O)N(COC(=O)c3ccccc3)C(=O)N1C(=O)c1ccccc1)C2] |

| Compd # | STRUCTURE |
|---|---|
| 85 | 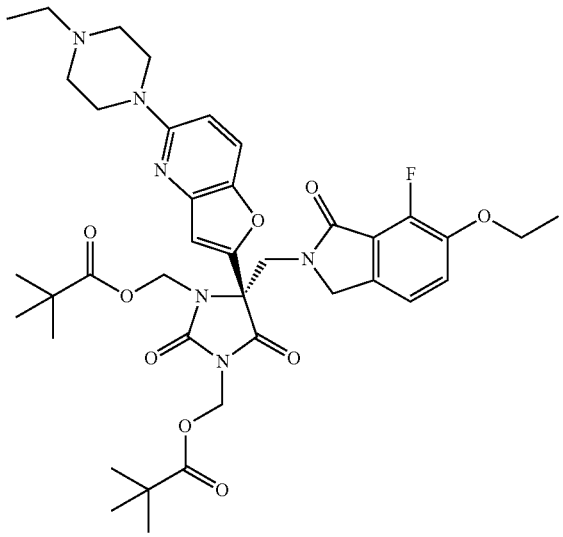 [SMILES: CCOc1ccc2c(c1F)C(=O)N(C[C@]1(c3cc4nc(N5CCN(CC)CC5)ccc4o3)C(=O)N(COC(=O)C(C)(C)C)C(=O)N1COC(=O)C(C)(C)C)C2] |
| 86 | 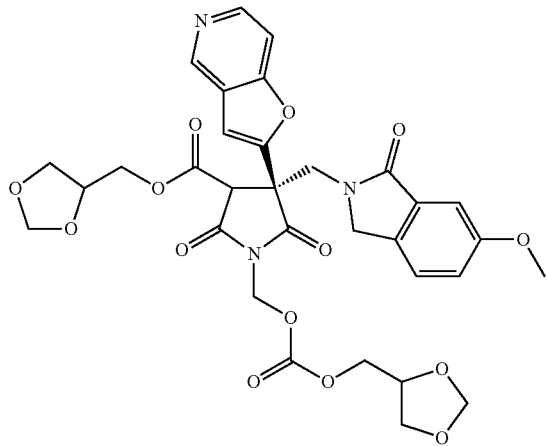 [SMILES: COc1ccc2c(c1)C(=O)N(C[C@]1(c3cc4cnccc4o3)C(=O)N(COC(=O)OCC3COCO3)C(=O)C1C(=O)OCC1COCO1)C2] |
| 87 | 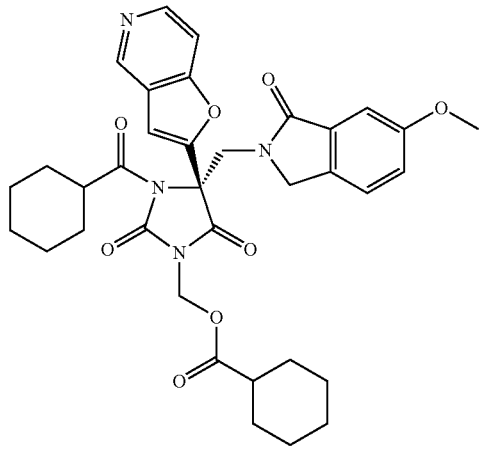 [SMILES: COc1ccc2c(c1)C(=O)N(C[C@]1(c3cc4cnccc4o3)C(=O)N(COC(=O)C3CCCCC3)C(=O)N1C(=O)C1CCCCC1)C2] |

| Compd # | STRUCTURE |
|---|---|
| 88 | 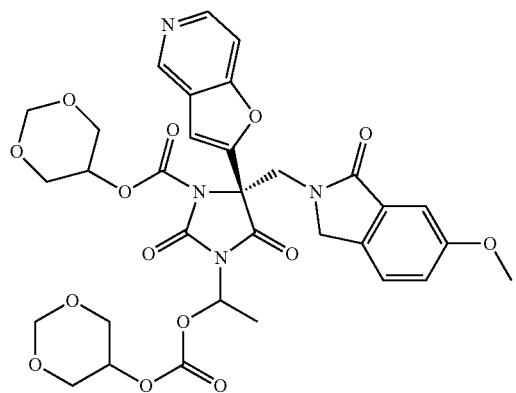 [SMILES: COc1ccc2c(c1)C(=O)N(C[C@]1(c3cc4cnccc4o3)C(=O)N(C(C)OC(=O)OC3COCOC3)C(=O)N1C(=O)OC1COCOC1)C2] |
| 89 | 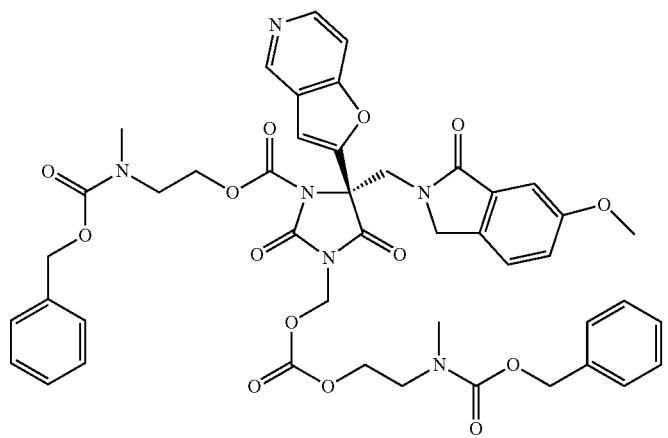 [SMILES: COc1ccc2c(c1)C(=O)N(C[C@]1(c3cc4cnccc4o3)C(=O)N(COC(=O)OCCN(C)C(=O)OCc3ccccc3)C(=O)N1C(=O)OCCN(C)C(=O)OCc1ccccc1)C2] |
| 89.1 | 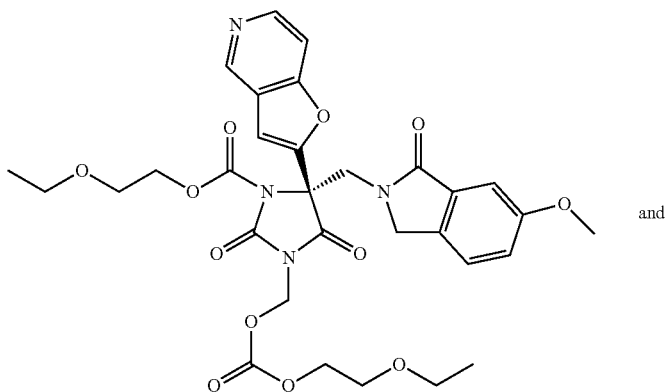 [SMILES: CCOCCOC(=O)OCN1C(=O)N(C(=O)OCCOCC)[C@@](CN2Cc3ccc(OC)cc3C2=O)(c2cc3cnccc3o2)C1=O] and |

| Compd # | STRUCTURE |
|---|---|
| 90 | *(structure)* | or a pharmaceutically acceptable salt, solvate, or ester thereof.

In another embodiment, the compound of formula (I) is selected from the group consisting of:

| Compd # | STRUCTURE |
|---|---|
| 1 | *(structure)* |
| 2 | *(structure)* |
| 3 | *(structure)* |
| 4 | *(structure)* |

| Compd # | STRUCTURE |
|---|---|
| 7 | 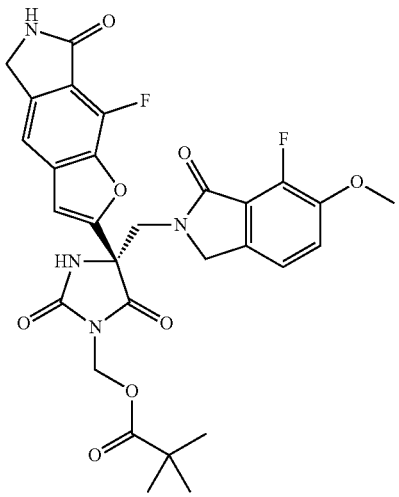 [SMILES: COc1ccc2c(c1F)C(=O)N(C[C@@]1(c3cc4cc5c(c(F)c4o3)C(=O)NC5)NC(=O)N(COC(=O)C(C)(C)C)C1=O)C2] |
| 8 | 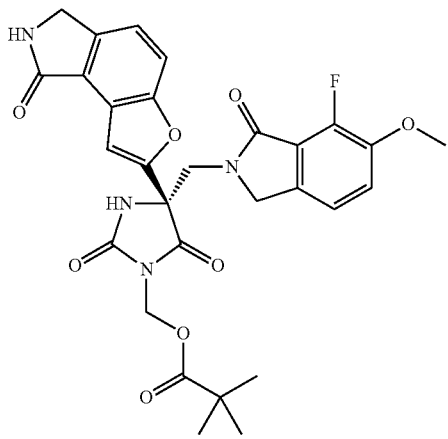 [SMILES: COc1ccc2c(c1F)C(=O)N(C[C@@]1(c3cc4c5c(ccc4o3)CNC5=O)NC(=O)N(COC(=O)C(C)(C)C)C1=O)C2] |
| 11 | 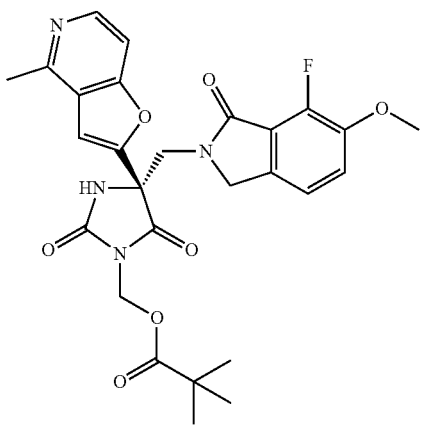 |
| Compd # | STRUCTURE |
|---|---|
| 12 | 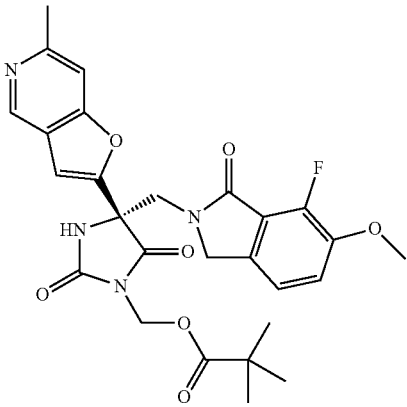 [SMILES: COc1ccc2c(c1F)C(=O)N(C[C@@]1(c3cc4cnc(C)cc4o3)NC(=O)N(COC(=O)C(C)(C)C)C1=O)C2] |
| 21 | 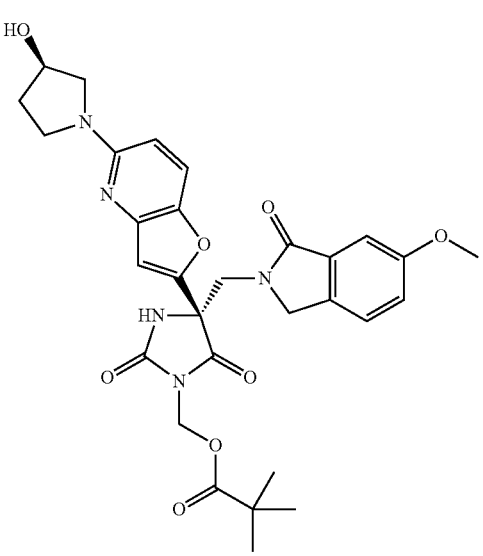 [SMILES: COc1ccc2c(c1)C(=O)N(C[C@@]1(c3cc4nc(N5CC[C@@H](O)C5)ccc4o3)NC(=O)N(COC(=O)C(C)(C)C)C1=O)C2] |
| 23 | 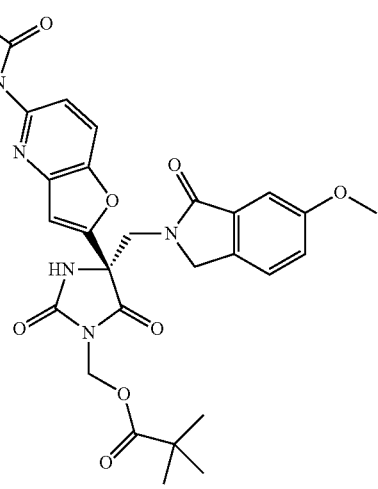 |

| Compd # | STRUCTURE |
|---|---|
| 35.4 | 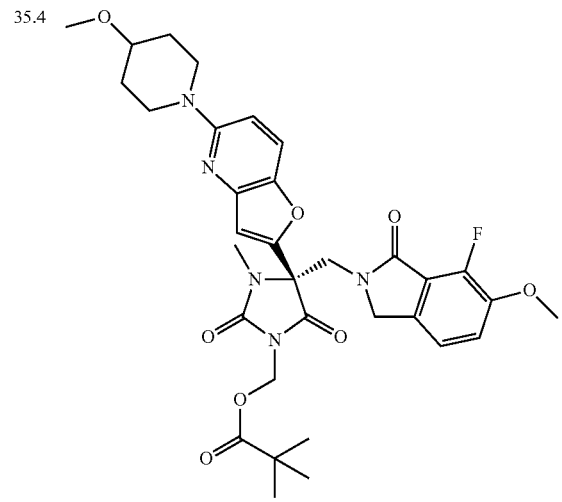 |
| 38 | 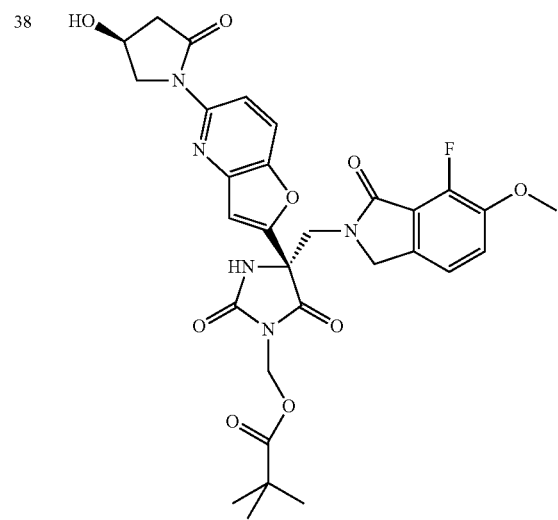 |
| 57 | 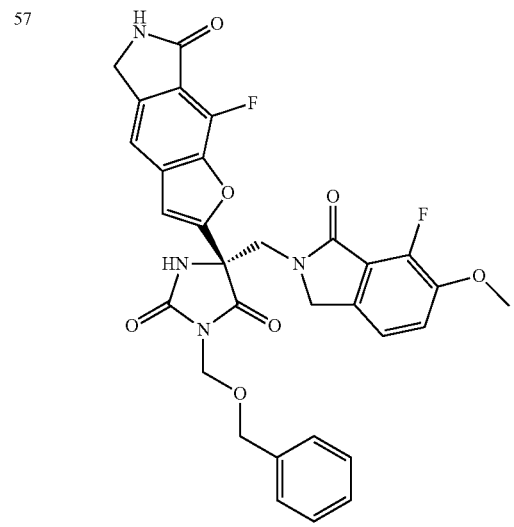 |
| Compd # | STRUCTURE |
|---|---|
| 64 | 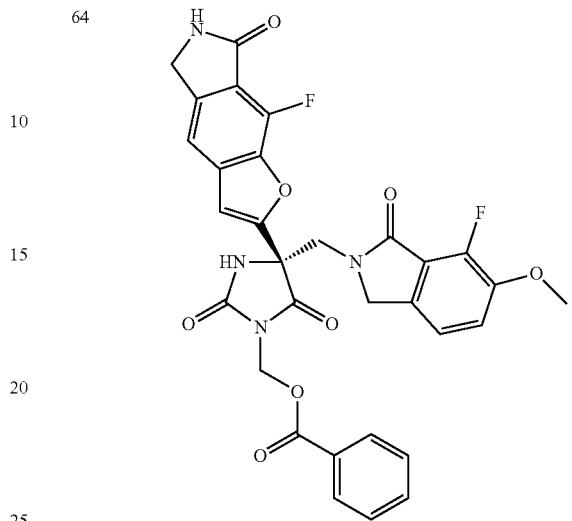 |
| 65 | 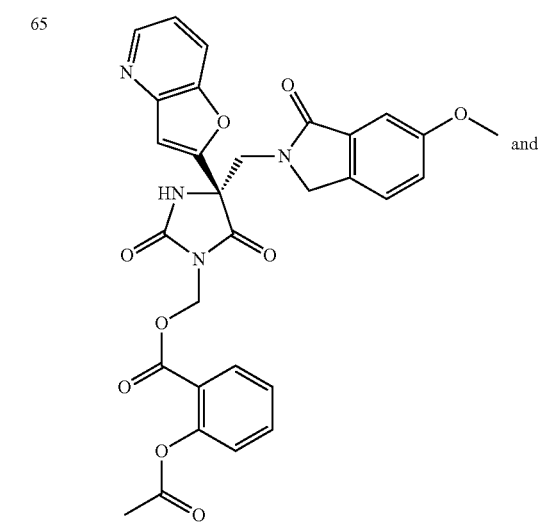 and |
| 66.1 | |
or a pharmaceutically acceptable salt, solvate, or ester thereof.

As used above, and throughout this disclosure, the following terms, unless otherwise indicated, shall be understood to have the following meanings:

"Patient" includes both human and animals.

"Mammal" means humans and other mammalian animals.

"Alkyl" means an aliphatic hydrocarbon group which may be straight or branched and comprising about 1 to about 20 carbon atoms in the chain. Preferred alkyl groups contain about 1 to about 12 carbon atoms in the chain. More preferred alkyl groups contain about 1 to about 6 carbon atoms in the chain. Branched means that one or more lower alkyl groups such as methyl, ethyl or propyl, are attached to a linear alkyl chain. "Lower alkyl" means a group having about 1 to about 6 carbon atoms in the chain which may be straight or branched. The alkyl group may be substituted by one or more substituents which may be the same or different, each substituent being independently selected from the group consisting of halo, alkyl, aryl, heteroaryl, cycloalkyl, cyano, hydroxy, alkoxy, alkylthio, amino, oxime (e.g., =N—OH), —NH(alkyl), —NH(cycloalkyl), —N(alkyl)$_2$, —O—C(O)-alkyl, —O—C(O)-aryl, —O—C(O)-cycloalkyl, carboxy and —C(O)O-alkyl. Non-limiting examples of suitable alkyl groups include methyl, ethyl, n-propyl, isopropyl and t-butyl.

"Alkenyl" means an aliphatic hydrocarbon group containing at least one carbon-carbon double bond and which may be straight or branched and comprising about 2 to about 15 carbon atoms in the chain. Preferred alkenyl groups have about 2 to about 12 carbon atoms in the chain; and more preferably about 2 to about 6 carbon atoms in the chain. Branched means that one or more lower alkyl groups such as methyl, ethyl or propyl, are attached to a linear alkenyl chain. "Lower alkenyl" means about 2 to about 6 carbon atoms in the chain which may be straight or branched. "Alkenyl" may be unsubstituted or optionally substituted by one or more substituents which may be the same or different, each substituent being independently selected from the group consisting of halo, alkyl aryl, heteroaryl, cycloalkyl, cyano, alkoxy and —S(alkyl). Non-limiting examples of suitable alkenyl groups include ethenyl, propenyl, n-butenyl, 3-methylbut-2-enyl, n-pentenyl, octenyl and decenyl.

"Alkylene" means a difunctional group obtained by removal of a hydrogen atom from an alkyl group that is defined above. Non-limiting examples of alkylene include methylene, ethylene and propylene.

"Alkynyl" means an aliphatic hydrocarbon group containing at least one carbon-carbon triple bond and which may be straight or branched and comprising about 2 to about 15 carbon atoms in the chain. Preferred alkynyl groups have about 2 to about 12 carbon atoms in the chain; and more preferably about 2 to about 4 carbon atoms in the chain. Branched means that one or more lower alkyl groups such as methyl, ethyl or propyl, are attached to a linear alkynyl chain. "Lower alkynyl" means about 2 to about 6 carbon atoms in the chain which may be straight or branched. Non-limiting examples of suitable alkynyl groups include ethynyl, propynyl, 2-butynyl and methylbutynyl, "Alkynyl" may be unsubstituted or optionally substituted by one or more substituents which may be the same or different, each substituent being independently selected from the group consisting of alkyl, aryl and cycloalkyl.

"Aryl" means an aromatic monocycle or multicyclic ring system comprising about 6 to about 14 carbon atoms, preferably about 6 to about 10 carbon atoms. The aryl group can be optionally substituted with one or more "ring system substituents" which may be the same or different, and are as defined herein. Non-limiting examples of suitable aryl groups include phenyl and naphthyl.

"Heteroaryl" means an aromatic monocyclic or multicyclic ring system comprising about 5 to about 14 ring atoms, preferably about 5 to about 10 ring atoms, in which one or more of the ring atoms is an element other than carbon, for example nitrogen, oxygen or sulfur, alone or in combination. Preferred heteroaryls contain about 5 to about 6 ring atoms. The "heteroaryl" can be optionally substituted by one or more "ring system substituents" which may be the same or different, and are as defined herein. The prefix aza, oxa or thia before the heteroaryl root name means that at least a nitrogen, oxygen or sulfur atom respectively, is present as a ring atom. A nitrogen atom of a heteroaryl can be optionally oxidized to the corresponding N-oxide. "Heteroaryl" may also include a heteroaryl as defined above fused to an aryl as defined above. Non-limiting examples of suitable heteroaryls include pyridyl, pyrazinyl, furanyl, thienyl, pyrimidinyl, pyridone (including N-substituted pyridones), isoxazolyl, isothiazolyl, oxazolyl, thiazolyl, pyrazolyl, furazanyl, pyrrolyl, pyrazolyl, triazolyl, 1,2,4-thiadiazolyl, pyrazinyl, pyridazinyl, quinoxalinyl, phthalazinyl, oxindolyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl and the like. The term "heteroaryl" also refers to partially saturated heteroaryl moieties such as, for example, tetrahydroisoquinolyl, tetrahydroquinolyl and the like.

"Aralkyl" or "arylalkyl" means an aryl-alkyl-group in which the aryl and alkyl are as previously described. Preferred aralkyls comprise a lower alkyl group. Non-limiting examples of suitable aralkyl groups include benzyl, 2-phenethyl and naphthalenylmethyl. The bond to the parent moiety is through the alkyl.

"Alkylaryl" means an alkyl-aryl-group in which the alkyl and aryl are as previously described. Preferred alkylaryls comprise a lower alkyl group. Non-limiting example of a suitable alkylaryl group is tolyl. The bond to the parent moiety is through the aryl.

"Cycloalkyl" means a non-aromatic mono- or multicyclic ring system comprising about 3 to about 10 carbon atoms, preferably about 5 to about 10 carbon atoms. Preferred cycloalkyl rings contain about 5 to about 7 ring atoms. The cycloalkyl can be optionally substituted with one or more "ring system substituents" which may be the same or different, and are as defined above. Non-limiting examples of suitable monocyclic cycloalkyls include cyclopropyl, cyclopentyl, cyclohexyl, cycloheptyl and the like. Non-limiting examples of suitable multicyclic cycloalkyls include 1-decalinyl, norbornyl, adamantyl and the like.

"Cycloalkylalkyl" means a cycloalkyl moiety as defined above linked via an alkyl moiety (defined above) to a parent core. Non-limiting examples of suitable cycloalkylalkyls include cyclohexylmethyl, adamantylmethyl and the like.

"Cycloalkenyl" means a non-aromatic mono or multicyclic ring system comprising about 3 to about 10 carbon atoms, preferably about 5 to about 10 carbon atoms which contains at least one carbon-carbon double bond. Preferred cycloalkenyl rings contain about 5 to about 7 ring atoms. The cycloalkenyl can be optionally substituted with one or more "ring system substituents" which may be the same or different, and are as defined above. Non-limiting examples of suitable monocyclic cycloalkenyls include cyclopentenyl, cyclohexenyl, cyclohepta-1,3-dienyl, and the like. Non-limiting example of a suitable multicyclic cycloalkenyl is norbornylenyl.

"Cycloalkenylalkyl" means a cycloalkenyl moiety as defined above finked via an alkyl moiety (defined above) to a parent core. Non-limiting examples of suitable cycloalkenylalkyls include cyclopentenylmethyl, cyclohexenylmethyl and the like.

"Halo" or "Halogen" means fluorine, chlorine, bromine, or iodine. Preferred are fluorine, chlorine and bromine.

"Ring system substituent" means a substituent attached to an aromatic or non-aromatic ring system which, for example, replaces an available hydrogen on the ring system. Ring system substituents may be the same or different, each being independently selected from the group consisting of alkyl, alkenyl, alkynyl, aryl, heteroaryl, aralkyl, alkylaryl, heteroaralkyl, heteroarylalkenyl, heteroarylalkynyl, alkylheteroaryl, hydroxy, hydroxyalkyl, alkoxy, aryloxy, aralkoxy, acyl, aroyl, halo, nitro, cyano, carboxy, alkoxycarbonyl, aryloxycarbonyl, aralkoxycarbonyl, alkylsulfonyl, arylsulfonyl, heteroarylsulfonyl, alkylthio, arylthio, heteroarylthio, aralkylthio, heteroaralkylthio, cycloalkyl, heterocyclyl, —O—C(O)-alkyl, —O—C(O)-aryl, —O—C(O)-cycloalkyl, —C(=N—CN)—NH$_2$, —C(=NH)—NH$_2$, —C(=NH)—NH(alkyl), oxime (e.g., =N—OH), —NY$_1$Y$_2$, -alkyl-NY$_1$Y$_2$, —C(O)NY$_1$Y$_2$, —SO$_2$NY$_1$Y$_2$ and —SO$_2$NY$_1$Y$_2$, wherein Y$_1$ and Y$_2$ can be the same or different and are independently selected from the group consisting of hydrogen, alkyl, aryl, cycloalkyl, and aralkyl. "Ring system substituent" may also mean a single moiety which simultaneously replaces two available hydrogens on two adjacent carbon atoms (one H on each carbon) on a ring system. Examples of such moiety are methylene dioxy, ethylenedioxy, —C(CH$_3$)$_2$— and the like which form moieties such as, for example:

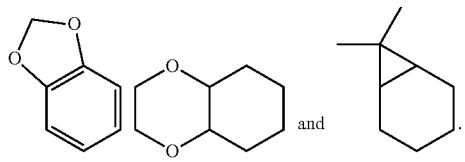

"Heteroarylalkyl" means a heteroaryl moiety as defined above finked via an alkyl moiety (defined above) to a parent core, Non-limiting examples of suitable heteroaryls include 2-pyridinylmethyl, quinolinylmethyl and the like.

"Heterocyclyl" means a non-aromatic saturated monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur, alone or in combination. There are no adjacent oxygen and/or sulfur atoms present in the ring system. Preferred heterocyclyls contain about 5 to about 6 ring atoms. The prefix aza, axe or thio before the heterocyclyl root name means that at least a nitrogen, oxygen or sulfur atom respectively is present as a ring atom. Any —NH in a heterocyclyl ring may exist protected such as, for example, as an —N(Boc), —N(CBz), —N(Tos) group and the like; such protections are also considered part of this invention. The heterocyclyl can be optionally substituted by one or more "ring system substituents" which may be the same or different, and are as defined herein. The nitrogen or sulfur atom of the heterocyclyl can be optionally oxidized to the corresponding N-oxide, S-oxide or S,S-dioxide. Non-limiting examples of suitable monocyclic heterocyclyl rings include piperidyl, pyrrolidinyl, piperazinyl, morpholinyl, thiomorpholinyl, thiazolidinyl, 1,4-dioxanyl, tetrahydrofuranyl, tetrahydrothiophenyl, lactam, lactone, and the like. "Heterocyclyl" also includes heterocyclyl rings as described above wherein =O replaces two available hydrogens on the same ring carbon atom. An example of such moiety is pyrrolidone:

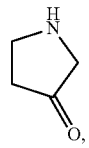

"Heterocyclylalkyl" means a heterocyclyl moiety as defined above linked via an alkyl moiety (defined above) to a parent core. Non-limiting examples of suitable heterocyclylalkyls include piperidinylmethyl, piperazinylmethyl and the like.

"Heterocyclenyl" means a non-aromatic monocyclic or multicyclic ring system; comprising about 3 to about 10 ring atoms, preferably about 5 to about 10 ring atoms, in which one or more of the atoms in the ring system is an element other than carbon, for example nitrogen, oxygen or sulfur atom, alone or in combination, and which contains at least one carbon-carbon double bond or carbon-nitrogen double bond. There are no adjacent oxygen and/or sulfur atoms present in the ring system. Preferred heterocyclenyl rings contain about 5 to about 6 ring atoms. The prefix aza, oxa or thia before the heterocyclenyl root name means that at least a nitrogen, oxygen or sulfur atom respectively is present as a ring atom. The heterocyclenyl can be optionally substituted by one or more ring system substituents, wherein "ring system substituent" is as defined above. The nitrogen or sulfur atom of the heterocyclenyl can be optionally oxidized to the corresponding N-oxide, S-oxide or S,S-dioxide. Non-limiting examples of suitable heterocyclenyl groups include 1,2,3,4-tetrahydropyridinyl, 1,2-dihydropyridinyl, 1,4-dihydropyridinyl, 1,2,3,6-tetrahydropyridinyl, 1,4,5,6-tetrahydropyrimidinyl, 2-pyrrolinyl, 3-pyrrolinyl, 2-imidazolinyl, 2-pyrazolinyl, dihydroimidazolyl, dihydrooxazolyl, dihydrooxadiazolyl, dihydrothiazolyl, 3,4-dihydro-2H-pyranyl, dihydrofuranyl, fluorodihydrofuranyl, 7-oxabicyclo[2.2.1]heptenyl, dihydrothiophenyl, dihydrothiopyranyl, and the like. "Heterocyclenyl" also includes heterocyclenyl rings as described above wherein =O replaces two available hydrogens on the same ring carbon atom. An example of such moiety is pyrrolidinone:

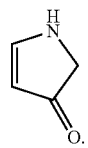

"Heterocyclenylalkyl" means a heterocyclenyl moiety as defined above linked via an alkyl moiety (defined above) to a parent core.

It should be noted that in hetero-atom containing ring systems of this invention, there are no hydroxyl groups on carbon atoms adjacent to a N, O or S, as well as there are no N or S groups on carbon adjacent to another heteroatom. Thus, for example, in the ring:

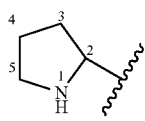

there is no —OH attached directly to carbons marked 2 and 5.

It should also be noted that tautomeric forms such as, for example, the moieties:

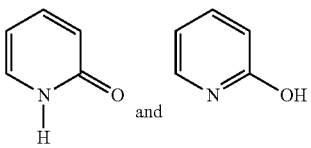 [SMILES: O=c1cccc[nH]1 ; Oc1ccccn1]

are considered equivalent in certain embodiments of this invention.

"Alkynylalkyl" means an alkynyl-alkyl-group in which the alkynyl and alkyl are as previously described. Preferred alkynylalkyls contain a lower alkynyl and a lower alkyl group. The bond to the parent moiety is through the alkyl. Non-limiting examples of suitable alkynylalkyl groups include propargylmethyl.

"Heteroaralkyl" means a heteroaryl-alkyl-group in which the heteroaryl and alkyl are as previously described. Preferred heteroaralkyls contain a lower alkyl group. Non-limiting examples of suitable aralkyl groups include pyridylmethyl, and quinolin-3-ylmethyl. The bond to the parent moiety is through the alkyl.

"Hydroxyalkyl" means a HO-alkyl-group in which alkyl is as previously defined. Preferred hydroxyalkyls contain lower alkyl. Non-limiting examples of suitable hydroxyalkyl groups include hydroxymethyl and 2-hydroxyethyl.

"Acyl" means an H—C(O)—, alkyl-C(O)— or cycloalkyl-C(O)—, group in which the various groups are as previously described. The bond to the parent moiety is through the carbonyl. Preferred acyls contain a lower alkyl. Non-limiting examples of suitable acyl groups include formyl, acetyl and propanoyl, "Aroyl" means an aryl-C(O)— group in which the aryl group is as previously described. The bond to the parent moiety is through the carbonyl. Non-limiting examples of suitable groups include benzoyl and 1-naphthoyl.

"Alkoxy" means an alkyl-O— group in which the alkyl group is as previously described. Non-limiting examples of suitable alkoxy groups include methoxy, ethoxy, n-propoxy, isopropoxy and n-butoxy. The bond to the parent moiety is through the ether oxygen.

"Aryloxy" means an aryl-O— group in which the aryl group is as previously described. Non-limiting examples of suitable aryloxy groups include phenoxy and naphthoxy. The bond to the parent moiety is through the ether oxygen.

"Aralkyloxy" means an aralkyl-O— group in which the aralkyl group is as previously described. Non-limiting examples of suitable aralkyloxy groups include benzyloxy and 1- or 2-naphthalenemethoxy. The bond to the parent moiety is through the ether oxygen.

"Alkylthio" means an alkyl-S— group in which the alkyl group is as previously described. Non-limiting examples of suitable alkylthio groups include methyl thio and ethylthio. The bond to the parent moiety is through the sulfur.

"Arylthio" means an aryl-S— group in which the aryl group is as previously described. Non-limiting examples of suitable arylthio groups include phenylthio and naphthylthio. The bond to the parent moiety is through the sulfur.

"Aralkylthio" means an aralkyl-S— group in which the aralkyl group is as previously described. Non-limiting example of a suitable aralkylthio group is benzylthio. The bond to the parent moiety is through the sulfur.

"Alkoxycarbonyl" means an alkyl-O—CO— group. Non-limiting examples of suitable alkoxycarbonyl groups include methoxycarbonyl and ethoxycarbonyl. The bond to the parent moiety is through the carbonyl.

"Aryloxycarbonyl" means an aryl-O—C(O)— group. Non-limiting examples of suitable aryloxycarbonyl groups include phenoxycarbonyl and naphthoxycarbonyl. The bond to the parent moiety is through the carbonyl.

"Aralkoxycarbonyl" means an aralkyl-O—C(O)— group. A non-limiting example of a suitable aralkoxycarbonyl group is benzyloxycarbonyl. The bond to the parent moiety is through the carbonyl.

"Alkylsulfonyl" means an alkyl-S(O$_2$)— group. Preferred groups are those in which the alkyl group is lower alkyl. The bond to the parent moiety is through the sulfonyl.

"Arylsulfonyl" means an aryl-S(O$_2$)— group. The bond to the parent moiety is through the sulfonyl.

The term "substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds. By "stable compound" or "stable structure" is meant a compound that is sufficiently robust to survive isolation to a useful degree of purity from a reaction mixture, and formulation into an efficacious therapeutic agent.

The term "optionally substituted" means optional substitution with the specified groups, radicals or moieties.

The term "purified", "in purified form" or "in isolated and purified form" for a compound refers to the physical state of said compound after being isolated from a synthetic process (e.g. from a reaction mixture), or natural source or combination thereof. Thus, the term "purified", "in purified form" or "in isolated and purified form" for a compound refers to the physical state of said compound after being obtained from a purification process or processes described herein or well known to the skilled artisan (e.g., chromatography, recrystallization and the like), in sufficient purity to be characterizable by standard analytical techniques described herein or well known to the skilled artisan.

It should also be noted that any carbon as well as heteroatom with unsatisfied valences in the text, schemes, examples and Tables herein is assumed to have the sufficient number of hydrogen atom(s) to satisfy the valences.

When a functional group in a compound is termed "protected", this means that the group is in modified form to preclude undesired side reactions at the protected site when the compound is subjected to a reaction. Suitable protecting groups will be recognized by those with ordinary skill in the art as well as by reference to standard textbooks such as, for example, T. W. Greene et al, *Protective Groups in organic Synthesis* (1991), Wiley, New York.

When any variable (e.g., aryl, heterocycle. $R^2$, etc.) occurs more than one time in any constituent or in Formula I, its definition on each occurrence is independent of its definition at every other occurrence.

As used herein, the term "composition" is intended to encompass a product comprising the specified ingredients in the specified amounts, as well as any product which results, directly or indirectly, from combination of the specified ingredients in the specified amounts.

Prodrugs and solvates of the compounds of the invention are also contemplated herein. The term "prodrug", as employed herein, denotes a compound that is a drug precursor which, upon administration to a subject, undergoes chemical conversion by metabolic or chemical processes to yield a compound of Formula I or a salt and/or solvate thereof. A discussion of prodrugs is provided in T. Higuchi and V. Stella, *Pro-drugs as Novel Delivery Systems* (1987) 14 of the A.C.S. Symposium Series, and in *Bioreversible Carriers in Drug Design*, (1987) Edward B. Roche, ed., American Pharmaceutical Association and Pergamon Press, both of which are incorporated herein by reference thereto. The term "prodrug" means a compound (e.g, a drug precursor) that is transformed in vivo to yield a compound of Formula (I) or a pharmaceutically acceptable salt, hydrate or solvate of the compound. The transformation may occur by various mechanisms (e.g., by metabolic or chemical processes), such as, for example, through hydrolysis in blood. A discussion of the use of pro-drugs is provided by T. Higuchi and W. Stella, "Pro-drugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987.

For example, if a compound of Formula (I) or a pharmaceutically acceptable salt, hydrate or solvate of the compound contains a carboxylic acid functional group, a prodrug can comprise an ester formed by the replacement of the hydrogen atom of the acid group with a group such as, for example, $(C_1-C_8)$alkyl, $(C_2-C_{12})$alkanoyloxymethyl, 1-(alkanoyloxy) ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N—$(C_1-C_2)$alkylamino$(C_2-C_3)$alkyl (such as β-dimethylaminoethyl), carbamoyl-$(C_1-C_2)$alkyl, N,N-di $(C_1-C_2)$alkylcarbamoyl-$(C_1-C_2)$alkyl and piperidino-, pyrrolidino- or morpholino$(C_2-C_3)$ alkyl, and the like.

Similarly, if a compound of Formula (I) contains an alcohol functional group, a prodrug can be formed by the replacement of the hydrogen atom of the alcohol group with a group such as, for example, $(C_1-C_8)$alkanoyloxymethyl, 1-(($C_1-C_6$)alkanoyloxy)ethyl, 1-methyl-1(($C_1-C_6$)alkanoyloxy)ethyl, $(C_1-C_6)$alkoxycarbonyloxymethyl, N—$(C_1-C_8)$alkoxycarbonylaminomethyl, succinoyl, $(C_1-C_8)$alkanoyl, α-amino$(C_1-C_4)$alkanyl, arylacyl and α-aminoacyl, or aminoacyl-α-aminoacyl, where each α-aminoacyl group is independently selected from the naturally occurring t-amino acids, P(O)(OH)$_2$, —P(O)(O($C_1-C_6$)alkyl)$_2$ or glycosyl (the radical resulting from the removal of a hydroxyl group of the hemiacetal form of a carbohydrate), and the like.

If a compound of Formula (I) incorporates an amine functional group, a prodrug can be formed by the replacement of a hydrogen atom in the amine group with a group such as, for example, R-carbonyl, RO-carbonyl, NRR'-carbonyl where R and R' are each independently $(C_1-C_{10})$alkyl, $(C_3-C_7)$ cycloalkyl, benzyl, or R-carbonyl is a natural α-aminoacyl or natural α-aminoacyl, —C(OH)C(O)OY$^1$ wherein Y$^1$ is $(C_1-C_6)$alkyl or benzyl, —C(OY$^2$)Y$^3$ wherein Y$^2$ is $(C_1-C_4)$ alkyl and Y$^3$ is $(C_1-C_6)$alkyl, carboxy $(C_1-C_6)$alkyl, amino$(C_1-C_4)$ alkyl or mono-N— or di-N,N—$(C_1-C_6)$alkylaminoalkyl, —C(Y$^4$)Y$^5$ wherein Y$^4$ is H or methyl and Y$^5$ is mono-N— or di-N,N—$(C_1-C_6)$alkylamino morpholino, piperidin-1-yl or pyrrolidin-1-yl, and the like.

"Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates, Non-limiting examples of suitable solvates include ethanolates, methanolates, and the like, "Hydrate" is a solvate wherein the solvent molecule is H$_2$O.

"Effective amount" or "therapeutically effective amount" is meant to describe an amount of compound or a composition of the present invention effective in inhibiting TACE, the production of TNF-α, MMPs, ADAMS or any combination thereof and thus producing the desired therapeutic, ameliorative, inhibitory or preventative effect.

The compounds of Formula I can form salts which are also within the scope of this invention. Reference to a compound of Formula I herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a compound of Formula I contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful. Salts of the compounds of the Formula may be formed, for example, by reacting a compound of Formula I with an amount of add or base, such as an equivalent amount, in a medium such as one in which the salt precipitates or in an aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates,) and the like. Additionally, acids which are generally considered suitable for the formation of pharmaceutically useful salts from basic pharmaceutical compounds are discussed, for example, by P. Stahl et al, Camille G. (eds.) *Handbook of Pharmaceutical Salts. Properties, Selection and Use*. (2002) Zurich: Wiley-VCH; S. Berge et al, *Journal of Pharmaceutical Sciences* (1977) 66(1)1-19: P. Gould, *International J. of Pharmaceutics* (1986) 33 201-217; Anderson et al, *The Practice of Medicinal Chemistry* (1996), Academic Press, New York; and in *The Orange Book* (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamines, t-butyl amines, and salts with amino acids such as arginine, lysine and the like. Basic nitrogen-containing groups may be quarternized with agents such as lower alkyl halides (e.g. methyl, ethyl, and butyl chlorides, bromides and iodides), dialkyl sulfates (e.g. dimethyl, diethyl, and dibutyl sulfates), long chain halides (e.g. decyl, lauryl and stearyl chlorides, bromides and iodides), aralkyl halides (e.g. benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

Compounds of Formula I, and salts, solvates and prodrugs thereof, may exist in their tautomeric form (for example, as an amide or imino ether). All such tautomeric forms are contemplated herein as part of the present invention.

All stereoisomers (for example, geometric isomers, optical isomers and the like) of the present compounds (including those of the salts, solvates and prodrugs of the compounds as well as the salts and solvates of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention, as are positional isomers (such as, for example, 4-pyridyl and 3-pyridyl). Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the IUPAC 1974 Recommendations. The use of the terms "salt", "solvate" "prodrug" and the like, is intended to equally apply to the salt, solvate and prodrug of enantiomers, stereoisomers, rotamers, tautomers, positional isomers, racemates or prodrugs of the inventive compounds.

The present invention also embraces isotopically-labelled compounds of the present invention which are identical to those recited herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorus, fluorine and chlorine and iodine, such as $^{2}H$, $^{3}H$, $^{11}C$, $^{13}C$, $^{14}C$, $^{15}N$, $^{18}O$, $^{17}O$, $^{31}P$, $^{32}P$, $^{35}S$, $^{18}F$, $^{36}Cl$ and $^{123}I$, respectively.

Certain isotopically-labelled compounds of Formula (I) (e.g., those labeled with $^{3}H$ and $^{14}C$) are useful in compound and/or substrate tissue distribution assays. Tritiated (i.e., $^{3}H$) and carbon-14 (i.e., $^{14}C$) isotopes are particularly preferred for their ease of preparation and detectability. Certain isotopically-labelled compounds of Formula (I) can be useful for medical imaging purposes. E.g., those labeled with positron-emitting isotopes like $^{11}C$ or $^{18}F$ can be useful for application in Positron Emission Tomography (PET) and those labeled with gamma ray emitting isotopes like $^{123}I$ can be useful for application in Single photon emission computed tomography (SPECT). Further, substitution with heavier isotopes such as deuterium (i.e., $^{2}H$) may afford certain therapeutic advantages resulting from greater metabolic stability (e.g., increased in vivo half-life or reduced dosage requirements) and hence may be preferred in some circumstances. Additionally, isotopic substitution at a site where epimerization occurs may slow or reduce the epimerization process and thereby retain the more active or efficacious form of the compound for a longer period of time. Isotopically labeled compounds of Formula (I) can generally be prepared by following procedures analogous to those disclosed in the Schemes and/or in the Examples herein below, by substituting an appropriate isotopically labeled reagent for a non-isotopically labeled reagent.

Polymorphic forms of the compounds of Formula I, and of the salts, solvates and prodrugs of the compounds of Formula I, are intended to be included in the present invention.

The compounds according to the invention have pharmacological properties; in particular, the compounds of Formula I can be inhibitors of TACE, aggrecanase, TNF-α and/or MMP activity.

In one aspect, the invention provides a pharmaceutical composition comprising as an active ingredient at least one compound of formula (I).

In another aspect, the invention provides a pharmaceutical composition comprising a compound of formula (I) additionally comprising at least one pharmaceutically acceptable carrier.

In another aspect, the invention provides a method of treating disorders associated with TACE, aggrecanase, TNF-α, MMPs, ADAMs or any combination thereof, said method comprising administering to a patient in need of such treatment an effective amount of at least one compound of formula (I).

In another aspect, the invention provides a use of a compound of formula (I) for the manufacture of a medicament to treat disorders associated with TACE, aggrecanase, TNF-α, MMPs, ADAMs or any combination thereof.

The compounds of Formula (I) can have anti-inflammatory activity and/or immunomodulatory activity and can be useful in the treatment of diseases including but not limited to septic shock, haemodynamic shock, sepsis syndrome, post ischaemic reperfusion injury, malaria, mycobacterial infection, meningitis, psoriasis, congestive heart failure, fibrotic diseases, cachexia, graft rejection, cancers such as cutaneous T-cell lymphoma, diseases involving angiogenesis, autoimmune diseases, skin inflammatory diseases, inflammatory bowel diseases such as Crohn's disease and colitis, OA and RA, ankylosing spondylitis, psoriatic arthritis, adult Still's disease, ureitis, Wegener's granulomatosis, Behcehe disease, Sjogren's syndrome, sarcoidosis, polymyositis, dermatomyositis, multiple sclerosis, sciatica, complex regional pain syndrome, radiation damage, hyperoxic alveolar injury, periodontal disease, HIV, non-insulin dependent diabetes mellitus, systemic lupus erythematosus, glaucoma, sarcoidosis, idiopathic pulmonary fibrosis, bronchopulmonary dysplasia, retinal disease, scleroderma, osteoporosis, renal ischemia, myocardial infarction, cerebral stroke, cerebral ischemia, nephritis, hepatitis, glomerulonephritis, cryptogenic fibrosing aveolitis, psoriasis, transplant rejection, atopic dermatitis, vasculitis, allergy, seasonal allergic rhinitis, reversible airway obstruction, adult respiratory distress syndrome, asthma, chronic obstructive pulmonary disease (COPD) and/or bronchitis. It is contemplated that a compound of this invention may be useful in treating one or more of the diseases listed.

In another aspect, the invention provides a method of preparing a pharmaceutical composition for treating the disorders associated with TACE, aggrecanase, TNF-α, MMPs, ADAMs or any combination thereof, said method comprising bringing into intimate contact at least one compound of formula (I) and at least one pharmaceutically acceptable carrier.

In another aspect, the invention provides a compound of formula (I) exhibiting TACE, TNF-α, MMPs, ADAMS or any combination thereof inhibitory activity, including enantiomers, stereoisomers and tautomers of said compound, and pharmaceutically acceptable salts, solvates, or esters of said compound, said compound being selected from the compounds of structures listed in Table 1 set forth below.

In another aspect, the invention provides a method for treating disorders associated with TACE, aggrecanase, TNF-α, MMP, ADAM or any combination thereof in a patient comprising, administering to the patient in need of such treatment a therapeutically effective amount of at least one compound of formula (I) or a pharmaceutically acceptable salt, solvate, ester, or isomer thereof.

In another aspect, the invention provides a compound of formula (I) in purified form.

In another aspect, the invention provides a method of treating a condition or disease mediated by TACE, MMPs, TNF-α, aggrecanase, or any combination thereof in a patient comprising: administering to the patient in need of such treatment a therapeutically effective amount of at least one compound of formula (I) or a pharmaceutically acceptable salt, solvate, ester or isomer thereof.

In another aspect, the invention provides a method of treating a condition or disease selected from the group consisting of rheumatoid arthritis, osteoarthritis, periodontitis, gingivitis, corneal ulceration, solid tumor growth and tumor invasion by secondary metastases, neovascular glaucoma, inflammatory bowel disease, multiple sclerosis and psoriasis in a patient, comprising: administering to the patient in need of such treatment a therapeutically effective amount of at least one compound of formula (I) or a pharmaceutically acceptable salt, solvate, ester or isomer thereof.

In another aspect, the invention provides a method of treating rheumatoid arthritis, psoriasis, or inflammatory bowel disease (e.g., Crohn's disease or colitis) comprising: administering to a patient in need of such treatment a therapeutically effective amount of at least one compound of formula (I) or a pharmaceutically acceptable salt, solvate, ester or isomer thereof.

In another aspect, the invention provides a method of treating a condition or disease selected from the group consisting of fever, cardiovascular conditions, hemorrhage, coagulation, cachexia, anorexia, alcoholism, acute phase response, acute infection, shock, graft versus host reaction, autoimmune disease and HIV infection in a patient comprising administering to the patient in need of such treatment a therapeutically effective amount of at least one compound of formula (I) or a pharmaceutically acceptable salt, solvate, ester, or isomer thereof.

In another aspect, the invention provides a method of treating a condition or disease selected from the group consisting of septic shock, haemodynamic shock, sepsis syndrome, post ischaemic reperfusion injury, malaria, mycobacterial infection, meningitis, psoriasis, congestive heart failure, fibrotic diseases, cachexia, graft rejection, cancers such as cutaneous T-cell lymphoma, diseases involving angiogenesis, autoimmune diseases, skin inflammatory diseases, inflammatory bowel diseases such as Crohn's disease and colitis, osteo and rheumatoid arthritis, ankylosing spondylitis, psoriatic arthritis, adult Still's disease, ureitis, Wegener's granulomatosis, Behcehe disease, Sjogren's syndrome, sarcoidosis, polymyositis, dermatomyositis, multiple sclerosis, sciatica, complex regional pain syndrome, radiation damage, hyperoxic alveolar injury, periodontal disease, HIV, non-insulin dependent diabetes mellitus, systemic lupus erythematosus, glaucoma, sarcoidosis, idiopathic pulmonary fibrosis, bronchopulmonary dysplasia, retinal disease, scleroderma, osteoporosis, renal ischemia, myocardial infarction, cerebral stroke, cerebral ischemia, nephritis, hepatitis, glomerulonephritis, cryptogenic fibrosing aveolitis, psoriasis, transplant rejection, atopic dermatitis, vasculitis, allergy, seasonal allergic rhinitis, reversible airway obstruction, adult respiratory distress syndrome, asthma, chronic obstructive pulmonary disease (COPD) and bronchitis in a patient comprising administering to the patient in need of such treatment a therapeutically effective amount of at least one compound of formula (I) or a pharmaceutically acceptable salt, solvate, ester or isomer thereof.

In another aspect, the invention provides a method of treating a condition or disease associated with COPD, comprising: administering to the patient in need of such treatment a therapeutically effective amount of at least one compound of Formula (I) or a pharmaceutically acceptable salt, solvate, ester or isomer thereof.

In another aspect, the invention provides a method of treating a condition or disease associated with rheumatoid arthritis, comprising: administering to the patient in need of such treatment a therapeutically effective amount of at least one compound of formula (I) or a pharmaceutically acceptable salt, solvate, ester, or isomer thereof.

In another aspect, the invention provides a method of treating a condition or disease associated with Crohn's disease, comprising: administering to the patient in need of such treatment a therapeutically effective amount of at least one compound of formula (I) or a pharmaceutically acceptable salt, solvate ester or isomer thereof.

In another aspect, the invention provides a method of treating a condition or disease associated with psoriasis, comprising: administering to the patient in need of such treatment a therapeutically effective amount of at least one compound of formula (I) or a pharmaceutically acceptable salt, solvate, ester, or isomer thereof. In specific embodiments, the therapeutically effective amount of at least one compound of formula (I) or a pharmaceutically acceptable salt, solvate, ester, or isomer thereof is topically administered to the patient in need of treatment for psoriasis.

In another aspect, the invention provides a method of treating a condition or disease associated with ankylosing spondylitis, comprising: administering to the patient in need of such treatment a therapeutically effective amount of at least one compound of formula (I) or a pharmaceutically acceptable salt, solvate, ester or isomer thereof.

In another aspect, the invention provides a method of treating a condition or disease associated with sciatica, comprising: administering to the patient in need of such treatment a therapeutically effective amount of at least one compound of formula (I) or a pharmaceutically acceptable salt, solvate, ester or isomer thereof.

In another aspect, the invention provides a method of treating a condition or disease associated with complex regional pain syndrome, comprising: administering to the patient in need of such treatment a therapeutically effective amount of at least one compound of formula (I) or a pharmaceutically acceptable salt, solvate, ester, or isomer thereof.

In another aspect, the invention provides a method of treating a condition or disease associated with psoriatic arthritis, comprising: administering to the patient in need of such treatment a therapeutically effective amount of at least one compound of formula (I), or a pharmaceutically acceptable salt, solvate, ester, or isomer thereof.

In another aspect, the invention provides a method of treating a condition or disease associated with multiple sclerosis, comprising: administering to the patient in need of such treatment a therapeutically effective amount of at least one compound of formula (I) or a pharmaceutically acceptable salt, solvate, ester or isomer thereof, in combination with a compound selected from the group consisting of Avonex®, Betaseron, Copaxone or other compounds indicated for the treatment of multiple sclerosis.

Additionally, a compound of the present invention may be co-administered or used in combination with disease-modifying antirheumatic drugs (DMARDS) such as methotrexate, azathioprine, leflunomide, pencillinamine, gold salts, mycophenolate mofetil, cyclophosphamide and other similar drugs. They may also be co-administered with or used in combination with non-steroidal anti-inflammatory drugs (NSAIDs) such as piroxicam, naproxen, indomethacin, ibuprofen and the like: cyclooxygenase-2 selective (COX-2) inhibitors such as Vioxx® and Ceiebrex® immunosuppressives such as steroids, cyclosporin, Tacrolimus, rapamycin and the like; biological response modifiers (BRMs) such as Enbrel®, Remicade®, IL-1 antagonists, anti-CD40, anti-CD28, IL-10, anti-adhesion molecules and the like; and other anti-inflammatory agents such as p38 kinase inhibitors, PDE4 inhibitors, other chemically different TACE inhibitors, chemokine receptor antagonists, Thalidomide and other small molecule inhibitors of pro-inflammatory cytokine production.

Also, a compound of the present invention may be co-administered or used in combination with an H1 antagonist for the treatment of seasonal allergic rhinitis and/or asthma. Suitable H1 antagonists may be, for example, Claritin®, Allegra®, or Zyrtec®.

In another aspect, the invention provides a method of treating a condition or disease mediated by TACE, MMPs, TNF-α, aggrecanase, or any combination thereof in a patient comprising: administering to the patient in need of such treatment a therapeutically effective amount of at least one compound of formula (I) or a pharmaceutically acceptable salt, solvate or isomer thereof in combination with a therapeutically effective amount of at least one medicament selected from the group consisting of disease modifying anti-rheumatic drugs (DMARDS), NSAIDs, COX-2 inhibitors, COX-1 inhibitors, immunosuppressives, biological response modifiers (BRMs), anti-inflammatory agents and H1 antagonists.

In another aspect, the invention provides a method of treating a condition or disease selected from the group consisting of rheumatoid arthritis, osteoarthritis, periodontitis, gingivitis, corneal ulceration, solid tumor growth and tumor invasion by secondary metastases, neovascular glaucoma, inflammatory bowel disease, multiple sclerosis and psoriasis in a patient, comprising: administering to the patient in need of such treatment a therapeutically effective amount of at least one compound of Formula (I) or a pharmaceutically acceptable salt, solvate, ester, or isomer thereof in combination with a therapeutically effective amount of at least one medicament selected from the group consisting of DMARDS, NSAIDs, COX-2 inhibitors, COX-1 inhibitors, immunosuppressives, BRMs, anti-inflammatory agents and H1 antagonists.

In another aspect, the invention provides a method of treating a condition or disease selected from the group consisting of septic shock, haemodynamic shock, sepsis syndrome, post ischaemic reperfusion injury, malaria, mycobacterial infection, meningitis, psoriasis, congestive heart failure, fibrotic diseases, cachexia, graft rejection, cancers such as cutaneous T-cell lymphoma, diseases involving angiogenesis, autoimmune diseases, skin inflammatory diseases, inflammatory bowel diseases such as Crohn's disease and colitis, osteo and rheumatoid arthritis, ankylosing spondylitis, psoriatic arthritis, adult Still's disease, ureitis, Wegener's granulomatosis, Behcehe disease, Sjogren's syndrome, sarcoidosis, polymyositis, dermatomyositis, multiple sclerosis, sciatica, complex regional pain syndrome, radiation damage, hyperoxic alveolar injury, periodontal disease, HIV, non-insulin dependent diabetes mellitus, systemic lupus erythematosus, glaucoma, sarcoidosis, idiopathic pulmonary fibrosis, bronchopulmonary dysplasia, retinal disease, scleroderma, osteoporosis, renal ischemia, myocardial infarction, cerebral stroke, cerebral ischemia, nephritis, hepatitis, glomerulonephritis, cryptogenic fibrosing aveolitis, psoriasis, transplant rejection, atopic dermatitis, vasculitis, allergy, seasonal allergic rhinitis, reversible airway obstruction, adult respiratory distress syndrome, asthma, chronic obstructive pulmonary disease (COPD) and bronchitis in a patient comprising administering to the patient in need of such treatment a therapeutically effective amount of at least one compound of Formula (I), or a pharmaceutically acceptable salt, solvate, ester or isomer thereof in combination with a therapeutically effective amount of at least one medicament selected from the group consisting of DMARDS, NSAIDs, COX-2 inhibitors, COX-1 inhibitors, immunosuppressives, BRMs, anti-inflammatory agents and H1 antagonists, In another aspect, the invention provides a method for treating RA comprising administering a compound of the formula I in combination with compound selected from the class consisting of a COX-2 inhibitor e.g. Celebrex®, or Vioxx®; a COX-1 inhibitor, e.g., Feldene®; an immunosuppressive, e.g., methotrexate or cyclosporin; a steroid, e.g., β-methasone; and anti-TNF-α compound, e.g., Enbrel® or Remicade®; a PDE IV inhibitor, or other classes of compounds indicated for the treatment of RA.

In another aspect, the invention provides a method for treating multiple sclerosis comprising administering a compound of the formula (I) in combination with a compound selected from the group consisting of Avonex®, Betaseron, Copaxone or other compounds indicated for the treatment of multiple sclerosis.

TACE activity is determined by a kinetic assay measuring the rate of increase in fluorescent intensity generated by TACE catalyzed cleavage of an internally quenched peptide substrate (SPDL-3). The purified catalytic domain of recombinant human TACE (rhTACEc, Residue 215 to 477 with two mutations (S266A and N452Q) and a 6×His tail) is used in the assay. It is purified from the baculovirus/Hi5 cells expression system using affinity chromatography. The substrate SPDL-3 is an internally quenched peptide (MCA-Pro-Leu-Ala-Gin-Ala-Val-Arg-Ser-Ser-Ser-Dpa-Arg-NH2), with its sequence derived from the pro-TNFα cleavage site. MCA is (7-Methoxycoumarin-4-yl)acetyl. Dpa is N-3-(2,4-Dinitrophenyl)-L-2,3-diaminopropionyl.

A 50 µl assay mixture contains 20 mM HEPES, pH 7.3, 5 mM $CaCl_2$, 100 µM $ZnCl_2$, 2% DMSO, 0.04% Methylcellulose, 30 µM SPDL-3, 70 µM rhTACEc and a test compound. RhTACEc is pre-incubated with the test compound for 90 min. at 25° C. Reaction is started by addition of the substrate. The fluorescent intensity (excitation at 320 nm, emission at 405 nm) was measured every 45 seconds for 30 min. using a fluorospectrometer (GEMINI XS, Molecular Devices). Rate of enzymatic reaction is shown as Units per second. Effect of a test compound is shown as % of TACE activity in the absence of the compound.

The compounds' ability to inhibit TACE activity can also be determined in human whole blood using the assay conditions described n Example 15 below.

The pharmaceutical compositions containing the active ingredient may be in a form suitable for oral use, for example, as tablets, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients that are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the technique described in U.S. Pat. Nos. 4,256,108; 4,166,452; and 4,265,874 to form osmotic therapeutic tablets for controlled release.

The term pharmaceutical composition is also intended to encompass both the bulk composition and individual dosage units comprised of more than one (e.g., two) pharmaceutically active agents such as, for example, a compound of the present invention and an additional agent selected from the of the additional agents described herein, along with any pharmaceutically inactive excipients. The bulk composition and each individual dosage unit can contain fixed amounts of the afore-said "more than one pharmaceutically active agents". The bulk composition is material that has not yet been formed into individual dosage units. An illustrative dosage unit is an oral dosage unit such as tablets, pills and the like. Similarly, the herein-described method of treating a patient by administering a pharmaceutical composition of the present invention is also intended to encompass the administration of the afore-said bulk composition and individual dosage units.

Formulations for oral use may also be presented as hard gelatin capsules wherein the active ingredients is mixed with an inert solid diluent, for example, calcium carbonate, calcium phosphate or kaolin, or a soft gelatin capsules where in the active ingredient is mixed with water or an oil medium, for example peanut oil, liquid paraffin or olive oil.

Aqueous suspensions contain the active material in admixture with excipients suitable for the manufacture of aqueous suspensions. Such excipients are suspending agents, for example, sodium carboxymethylcellulose, methylcellulose, hydroxypropylmethyl-cellulose, sodium alginate, polyvinylpyrrolidone, gum tragacanth and gum acacia; dispersing or wetting agents may be a naturally-occurring phosphatide, for example, lecithin, or condensation products of an alkylene oxide with fatty acids, for example polyoxyethylene stearate, or condensation products of ethylene oxide with long chain aliphatic alcohols, for example, heptadecaethylene-oxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example, polyethylene sorbitan monooleate. The aqueous suspensions may also contain one or more preservatives, for example, ethyl or n-propyl, p-hydroxybenzoate, one or more coloring agents, one or more flavoring agents, and one or more sweetening agents, such as sucrose, saccharin or aspartame.

Oily suspensions may be formulated by suspending the active ingredient in a vegetable oil, for example, arachis oil, olive oil, sesame oil or coconut oil, or in mineral oil such as liquid paraffin. The oily suspensions may contain a thickening agent, for example, beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, e.g., sweetening, flavoring and coloring agents, may also be present.

The pharmaceutical compositions of the invention may also be in the form of an oil-in-water emulsion. The oily phase may be a vegetable oil, e.g., olive oil or arachis oil, or a mineral oil, e.g., liquid paraffin or mixtures of these. Suitable emulsifying agents may be naturally-occurring phosphatides, e.g., soy beans, lecithin, and esters or partial esters derived from fatty acids and hexitol anhydrides, for example, sorbitan monooleate, and condensation products of the said partial esters with ethylene oxide, e.g., polyoxyethylene sorbitan monooleate. The emulsions may also contain sweetening and flavoring agents.

Syrups and elixirs may be formulated with sweetening agents, for example, glycerol, propylene glycol, sorbitol or sucrose. Such formulations may also contain a demulcent, a preservative, and flavoring and coloring agents.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, e.g., as a solution in 1,3-butane diol. Among the acceptable vehicles and solvents that may be employed are water, Ringer's solution and isotonic sodium chloride solution, In addition, sterile fixed oils are conventionally employed as a solvent or suspending medium. For this purpose any bland fixed oil may be employed including synthetic mono- or diglycerides. In addition, fatty acids such as oleic acid find use in the preparation of injectables.

Compounds of the invention may also be administered in the form of suppositories for rectal administration of the drug. The compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc., containing the compounds of the invention are employed. (For purposes of this application, topical application shall include mouthwashes and gargles.)

The compounds for the present invention can be administered in the intranasal form via topical use of suitable intranasal vehicles, or via transdermal routes, using those forms of transdermal skin patches well known to those of ordinary skill in the art. To be administered in the form of a transdermal delivery system, the dosage administration will, of course, be continuous rather than intermittent throughout the dosage regimen. Compounds of the present invention may also be delivered as a suppository employing bases such as cocoa butter, glycerinated gelatin, hydrogenated vegetable oils, mixtures of polyethylene glycols of various molecular weights and fatty acid esters of polyethylene glycol.

The dosage regimen utilizing the compounds of the present invention is selected in accordance with a variety of factors including type, species, weight, sex and medical condition of the patient; the severity of the condition to be treated; the route of administration; the renal and hepatic function of the patient; and the particular compound thereof employed. A physician or veterinarian of ordinary skill can readily determine and prescribe the effective amount of the drug required to prevent, counter, arrest or reverse the progress of the condition. Optimal precision in achieving concentration of drug within the range that yields efficacy without toxicity requires a regimen based on the kinetics of the drug's availability to target sites. This involves a consideration of the distribution, equilibrium, and elimination of a drug. Preferably, doses of the compound of Formula I useful in the method of the present invention range from 0.01 to 1000 mg per day. More preferably, dosages range from 0.1 to 1000 mg/day. Most preferably, dosages range from 0.1 to 500 mg/day. For oral administration, the compositions are preferably provided in the form of tablets containing 0.01 to 1000 milligrams of the active ingredient, particularly 0.01, 0.05, 0.1, 0.5, 1.0, 2.5, 5.0, 10.0, 15.0, 25.0, 50.0, 100 and 500 milligrams of the active ingredient for the symptomatic adjustment of the dosage to the patient to be treated. An effective amount of the drug is ordinarily supplied at a dosage level of from about 0.0002 mg/kg to about 50 mg/kg of body weight per day. The range is more particularly from about 0.001 mg/kg to 1 mg/kg of body weight per day.

Advantageously, the active agent of the present invention may be administered in a single daily dose, or the total daily dosage may be administered in dividend doses of two, three or four time daily.

The amount of active ingredient that may be combined with the carrier materials to produce single dosage form will vary depending upon the host treated and the particular mode of administration.

It will be understood, however, that the specific dose level for any particular patient will depend upon a variety of factors including the age, body weight, general health, sex, diet, time of administration, route or administration, rate of excretion, drug combination and the severity of the particular disease undergoing therapy, The compounds of the invention may be produced by processes known to those skilled in the art and as shown in the following reaction schemes and in the preparations and examples described below.

EXAMPLES

The following abbreviations may be used in the procedures and schemes:
Abbreviations
aq aqueous
DIPEA diisopropylethylamine
DMF N,N-dimethylformamide
EtOAc Ethyl Acetate
$Et_2O$ diethyl ether
h hours
min minutes
mL milliliters
rb round bottomed
rt room temperature
sgc silica gel chromatography General Synthesis I

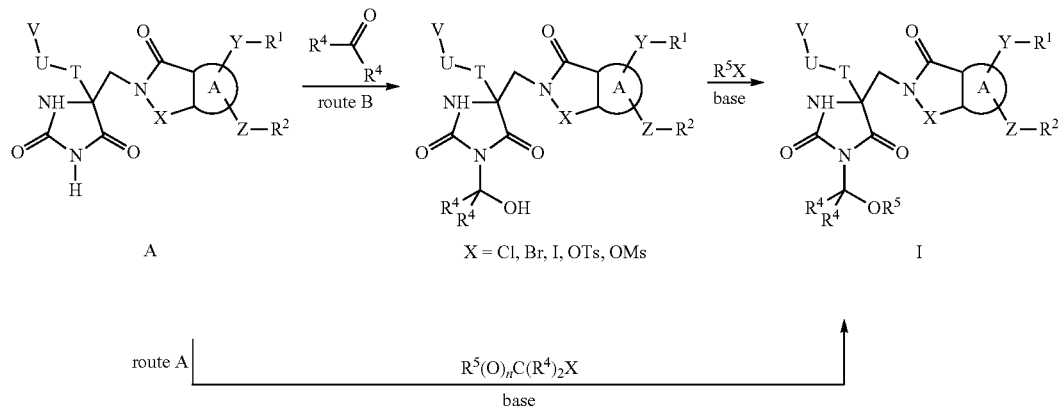

Route A:
Compound A (prepared following patent procedures described in PCT publications WO2006/019768, WO2007/084415, WO2007/084451, and WO2007/084455 is dissolved in polar solvents like DMF, DMSO and treated with 2.2 equivalents of a base like LiH, NaH, $Na_2CO_3$, or NaOH. The resulting solution is then treated with 1.1 equivalents of $R^5(O)$ $nC(R^4)2\times$ (either commercially available or readily prepared using literature procedures) and the mixture was stirred for 12-24 h. The reaction is quenched with dilute 1N HCl. The product was extracted into ethyl acetate and the organics were dried over $MgSO_4$ or $Na_2SO_4$. The solvent was removed under reduced pressure and the product I was isolated by HPLC using appropriate eluting solvents.
Route B:
Compound A is dissolved in basic solvent like pyridine, and treated with 2.2 equivalents carbonyl containing $R^4COR^4$. The resulting solution is stirred for 5-10 h and then treated with 1.1 equivalents of $R^5\times$ and the mixture was stirred for 12-24 h. The reaction is quenched with dilute 1N HCl. The product was extracted into ethyl acetate and the organics were dried over $MgSO_4$ or $Na_2SO_4$. The solvent was removed under reduced pressure and the product was isolated by HPLC using appropriate eluting solvents.

General Synthesis II

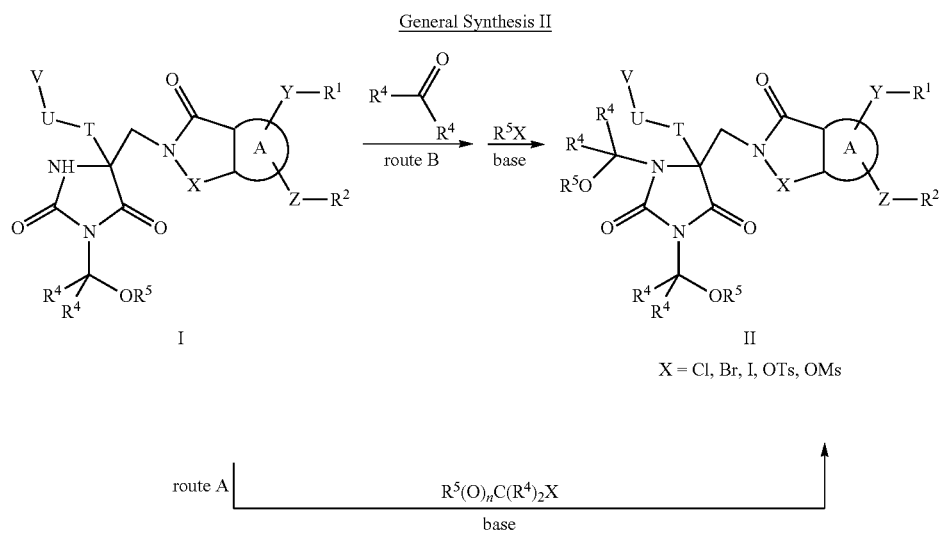

X = Cl, Br, I, OTs, OMs

Compound I is resubjected to conditions described above to provide II. Alternatively, treatment of I with excess reagents provides compound II directly.

Example 1

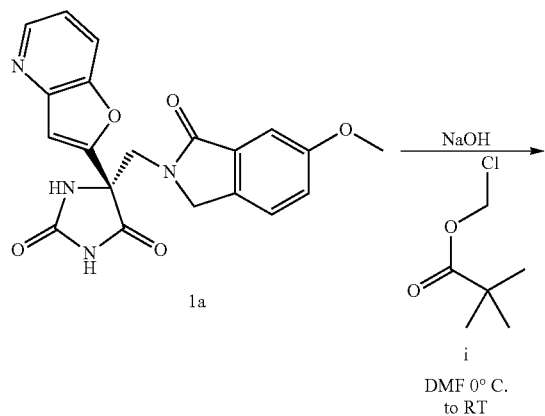

A suspension of compound 1a 6.54 g (16.64 mmol) (disclosed in PCT publications WO2006/019768, WO2007/084415, WO2007/084451, and WO2007/084455) in MeOH (65 ml) was treated with 17.47 ml (17.47 mmol) of 1N NaOH standard solution at 25° C. After completion of the addition, the mixture was stirred for 0.5 h under $N_2$. The solution was concentrated and dried in vacuo and the residue was dissolved in DMF (30 ml). To this was added dropwise chloromethyl pivalate (2.61 ml, 17.47 mmol) at 25° C. After stirring for 24 h, more chloromethyl pivalate (0.26 ml, 1.74 mmol) was added to the suspension followed by vigorous stirring for another 24 h. Upon completion of the reaction, the mixture was diluted with EtOAc (800 ml). The organic solution was washed with water (3×200 ml) and brine, dried ($Na_2SO_4$), and concentrated in vacuo. The residue was purified by Supelco (100 g) $SiO_2$ column (eluted with 1% MeOH in $CH_2Cl_2$/1% MeOH in EtOAc) to afford a crude product which was further purified by crystallization in ether and 10% MeOH—$CH_2Cl_2$ to give pure 1 (4.5 g, 54%).

Example 2

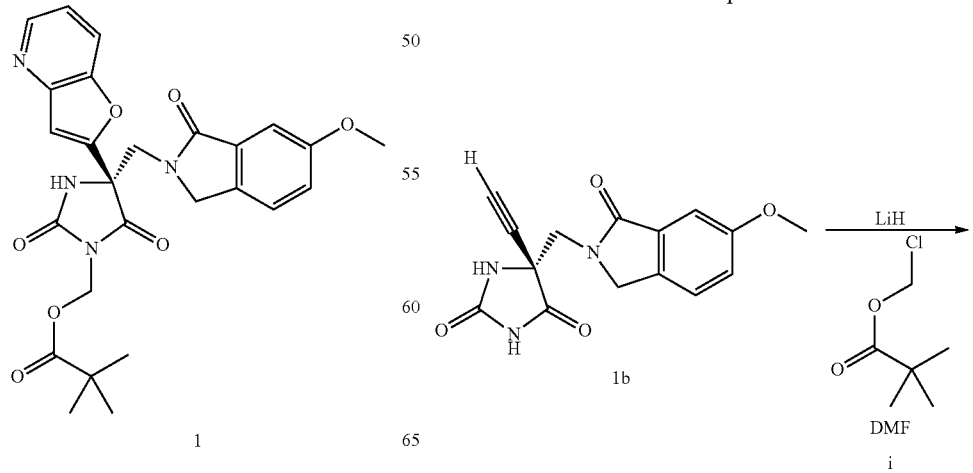

113

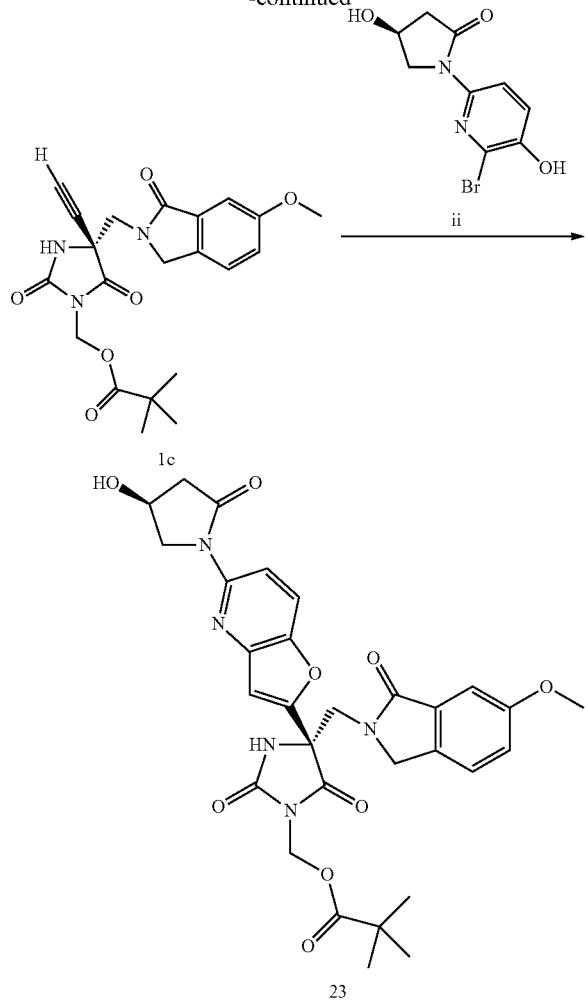

Step I
A mixture of 1b (0.3 g, 1.0 mmol) (disclosed in PCT publications WO2006/019768, WO2007/084415, WO2007/084451, and WO2007/084455) and K₂CO₃ (0.166 g, 1.204 mmol) in DMF (4 ml) was stirred at ambient temperature for 0.5 h. The reaction was cooled to 0° C. (ice bath), then a solution of chloromethyl pivalate i (0.15 g, 1.02 mmoles) in DMF (1 ml) was added dropwise. After complete addition, the reaction was stirred at room temperature for 10-15 h. The reaction was diluted with EtOAc, washed with water (3×20 ml) and saline (1×15 ml), dried (Na₂SO₄), and filtered. The solvent was removed under vacuum to a give crude solid which was purified by flash column chromatography (ISCO CombiFlash Rf, SiO₂, 12 g cartridge, CH₂Cl₂ to 10% MeOH in CH₂Cl₂ to provide 1 C (0.17 g, 41% yield).

Step II
A mixture of 1c (0.05 g, 0.12 mmoles), 2-bromo-3-hydroxypyridine derivative ii (0.033 g, 012 mmol), CuI (2.3 mg, 0.012 mmoles), PdCl₂(PPh₃)₂ (3.4 mg, 0.0048 mmol), and DMF (2 ml) was placed in microwave tube and sealed. Derivative ii was prepared using literature procedures described in Koch, V.; Schnatterer, S. Synthesis, 1990, 6, 497 (b) Koch, V.; Schnatterer, Se Synthesis, 1990, 6, 499 (c) Chapman, G. M; Stanforth, S. P.; Tarbit, B.; Watson, M. D. Journal of the Chemical Society, Perkin Transactions 1 2002, 5, 581. (d) Zhang, Cai, Q.; Ma, D. Journal of Organic Chem-

114 istry, 2005, 70, 5164. (e) Klapars, A.; Huang, X; Buchwald, S. L. Journal of the American Chemical Society, 2002, 124, 7421. The reaction was purged with N₂ three times. Et₃N (0.0337 ml, 0.24 mmol) was added via syringe through the seal then heated in the microwave at 70° C. for 10 minutes. The reaction was diluted with EtOAc, washed with water (3×20 ml), and saline (1×15 ml), dried (Na₂SO₄), and filtered. The solvent was removed under vacuum to give a crude prodcut. It was purified by flash column chromatography (ISCO CombiFlash Rf, SiO₂, 4 g cartridge, CH₂Cl₂ to 5% MeOH to provide 23: 16 mg (22%).

Alternate Procedure for 1 to 23:
A mixture of 1c (0.05 g, 0.12 mmol), 2-bromo-3-hydroxypyridine derivative ii (0.033 g, 0.12 mmol), CuI (3.3 mg, 0.0173 mmol), Pd(PPh₃)₂Cl₂ (3.4 mg, 0.0048 mmol) and DMF (1 ml) was placed in a tube and sealed. The reaction was purged with N₂ three times. Diisopropylamine (0.034 ml, 0.24 mmoles) was added through the seal and the reaction was heated at 70° C. for 18 h. After similar workup (see above), it was purified by purified by flash column chromatography (ISCO CombiFlash Rf, SiO₂, 4 g cartridge, CH₂Cl₂ to 5% MeOH in CH₂Cl₂ to provide 23 as light brown solid 0.058 g (79%). Compounds 1-44 in Table 1 below were prepared employing procedures described above.

Example 3

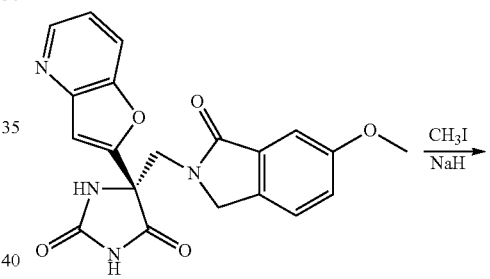

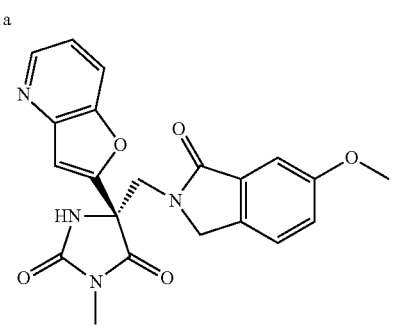

A suspension of 1a 7.52 g (19.19 mmol) in MeOH (100 ml) was treated with 17.27 ml (17.27 mmol, 0.9 eq) of 1N NaOH standard solution at 25° C. After completion of the addition, the mixture was stirred for 0.5 h under N₂. The solution was concentrated in vacuo and the residue was dissolved in water (50 ml) followed by lyophilization to afford 7.59 g of 1a-Na salt.

A suspension of 1a-Na salt 40 mg (0.096 mmol) in DMF (0.5 mL) was treated with methyl iodide 0.009 mL (0.14 mmol) at 25° C. The mixture was stirred for 1 h and purified by ISCO reverse phase C-18 column (eluted with 0.1%

HCO₂H in water and 0.1% HCO₂H in CH₃CN) to afford compound 45, 27 mg (69% yield).

Example 4

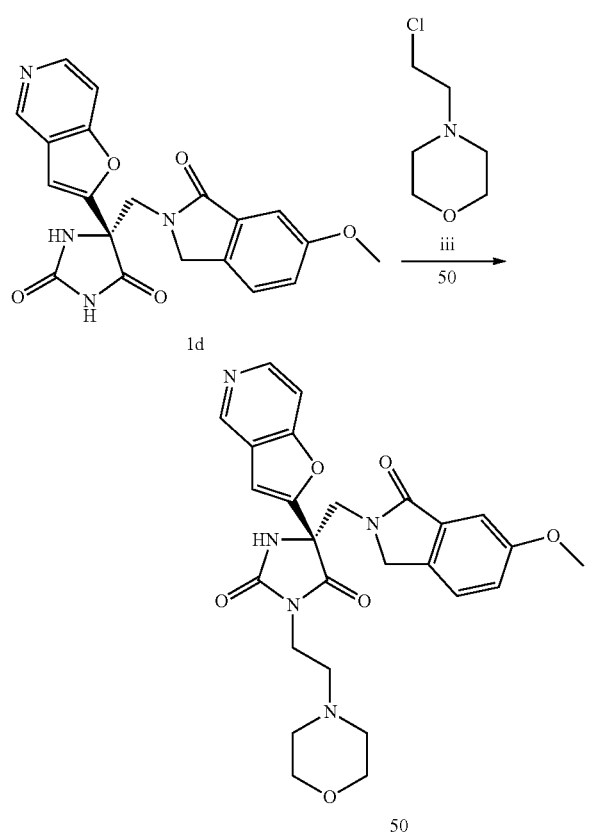

1d

50

Compound 1d 0.395 g, 1.01 mmol, 1.0 eq), potassium carbonate (0.279 g, 2.02 mmol, 2.0 eq), and N-2-chloroethylmorpholine hydrochloride (189 mg, 1.02 mmol, 1.01 eq) were added to a rb flask equipped with a stir bar. DMF was added and the reaction mixture was stirred at room temp. for 26 h, The reaction mixture was diluted with EtOAc (90 mL), aq Na₂CO₃ (5 mL of 1.0 M aq), and water (10 mL). The layers were separated. The organic layer was filtered, dried with MgSO₄, filtered again, and concentrated to a clear oil. Toluene was added (100 mL) and the solution was concentrated to dryness.

Additional toluene was added and the solution was concentrated to give a clear oil. The crude product was purified via silica gel chromatography. The column was eluted with 1:1 EtOAc:hexanes with 2% added Et₃N, followed by EtOAc with 2% added Et₃N, followed by 93:5:2 EtOAc;absolute ethanol: Et₃N. The first major peak off the column was collected as product giving a white solid. The product was converted to its HCl salt by dissolving it in 15 mL of CH₂Cl₂ and adding 5 mL of 2 M HCl in diethyl ether. A white solid precipitated from solution upon the addition of the HCl. Additional diethyl ether (30 mL) was added to the flask with stirring. The solid was allowed to settle and the solvent was decanted off, Additional Et₂O was added (40 mL), with stirring, then decanted a second time. The remaining material was concentrated to dryness giving 0.13 g of white solid 50.

Compounds 45-58 in Table 1 below were prepared using procedures similar to described above.

Example 5

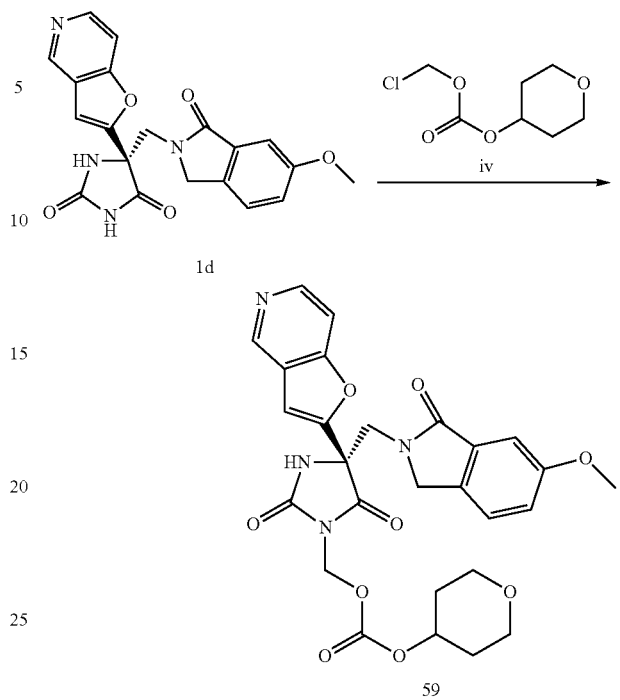

1d

59

To a stirred solution of the chloromethylcarbonate iv (107 mg, 0.55 mmol, in 1 mL DMF was added 1d (196 mg, 0.5 mmol), followed by 1 mL DMF and K₂CO₃ (72.6 mg, 0.525 mmol). I chloromethylcarbonate iv was prepared by the methods adapted from Ichikawa, T.; Kitazaki, T,; Matsushita, Y.; Yamada, M.;

Hayashi, H.; Yamaguchi, M.: Kiyota, Y,: Okonogi, K.; Itoh, K. Chem. Pharm. Bull, 2001, 49(9), 1102-1109 and Pothukanuri, S.; Winssinger, N. Org. Lett. 2007, 9, 2223-2225. After stirring for 16 h, the reaction was concentrated to dryness and purified by flash column chromatography (ISCO CombiFlash Rf, SiO₂, 4 g cartridge. CH₂Cl₂ to 10% MeOH in CH₂Cl₂) to give a white solid. This material was then dissolved in a mixture of 2 mL MeCN, 0.2 mL 1.0 N HCl, and 2 mL H₂O, and lyophilized to give a crystalline white solid that corresponds to the HO salt of 59 (54.7 mg, 19%).

Compounds 59 to 63.6 in Table 1 below were prepared by the procedure described above.

Example 6

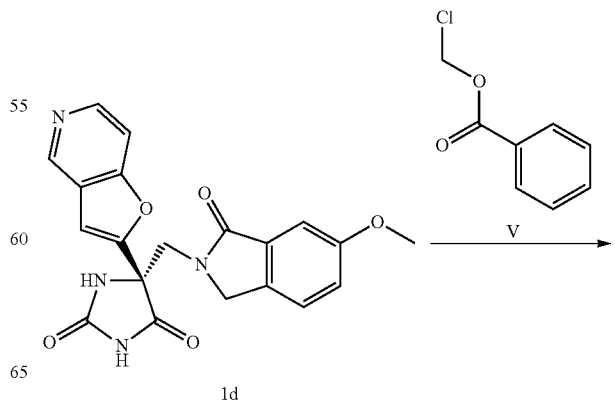

1d

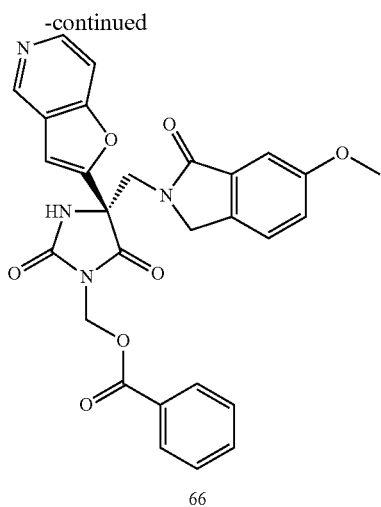

66

To a solution of compound Id (120.0 mg, 0.306 mmol) in DMF (3 mL) was added LiH (4.8 mg, 0.61 mmol) at 0° C. Then chloromethyl benzoate v (57.4 mg, 0.337 mmol, dissolved in 0.5 mL DMF) was added. The solution was stirred at 0° C. for 3 hours, and then was gradually warmed up to 25° C. and stirred at 25° C. for overnight. AcOH (0.042 mL, 0.733 mmol) was added and the product was purified by C18 chromatography (CH$_3$CN/H$_2$O: 5% to 90%, with 0.1% HCO$_2$H) to give compound 66 (110.5 mg, 68.6%).

Compounds 64 to 67.2 in Table 1 below were prepared by the procedures described above.

Example 7

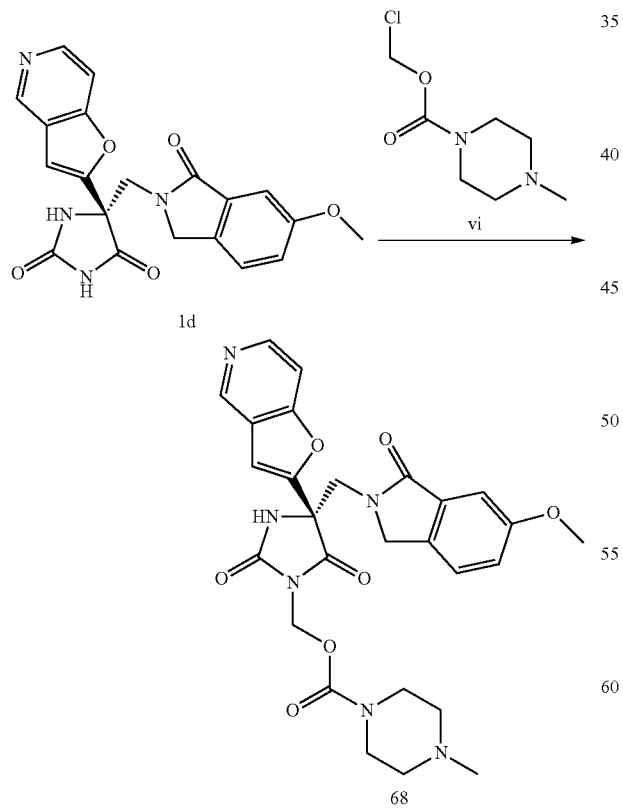

68

To a stirred solution of the chloromethylcarbonate vi (106 mg, 0.55 mmol, prepared using a procedure adapted from Majumdar et. al.) in 1 mL DMF was added 1 g (196 mg, 0.5 mmol), followed by 1 mL DMF then K$_2$CO$_3$ (72.6 mg, 0.525 mmol). Chloromethylcarbonate vi was prepared using a procedure adapted from Majumdar. S.; Sloan, K. B. *Synthetic Communications,* 2006, 36, 3537-3548. After stirring for 16 h, the reaction was concentrated to dryness and purified by flash column chromatography (ISCO CombiFlash Rf, SiO$_2$, 4 g cartridge, CH$_2$Cl$_2$ to 10% MeOH in CH$_2$Cl$_2$) to give a white solid. This material was then dissolved in a mixture of 2 mL MeCN, 0.2 mL. 1.0 N HCl, and 2 mL H$_2$O, and lyophilized to give a crystalline white solid that corresponds to the HCl salt of 68 (44.8 mg, 15%).

Compounds 68 to 71 in Table 1 below were prepared by the procedure described above.

Example 8

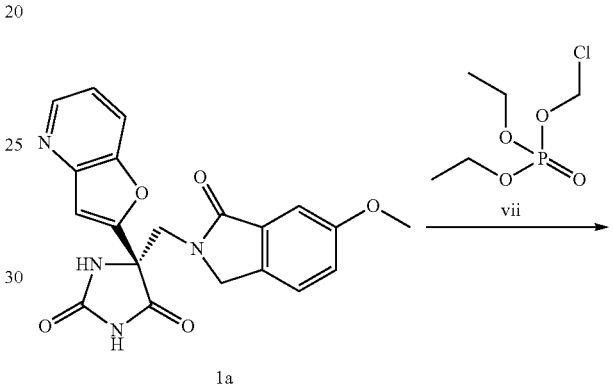

72

A suspension of 1a-Na salt 80 mg (0.19 mmol) in DMF (1 mL) was treated with diethyl chloromethylphosphate vii 0.051 mL (0.25 mmol) at 25° C. The mixture was stirred for 18 h and then added to cold water (10 mL). The aqueous layer was extracted with EtOAc and the combined organics were washed with brine, dried (Na$_2$SO$_4$) and concentrated in vacuo. The residue was purified by flash column chromatography (ISCO CombiFlash Rf, SiO$_2$, 4 g cartridge, CH$_2$Cl$_2$ to 5% MeOH in CH$_2$Cl$_2$) to give to afford compound 72 (52 mg; 49% yield). Compounds 72 to 74 in Table 1 below were prepared by the procedures described above.

Example 8.1

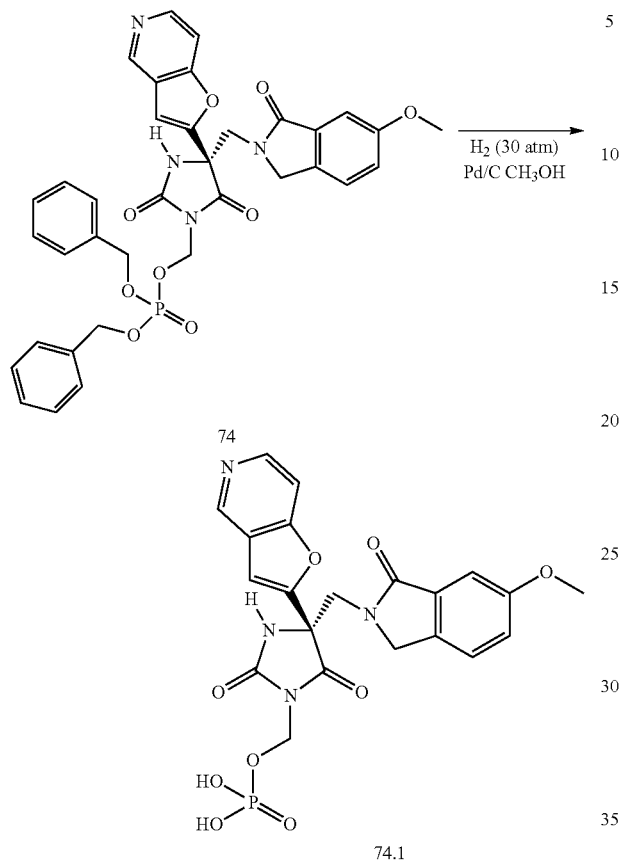

Compound 74 (0.032 g, 0.047 mmol) in CH₃OH (5 mL) and 0.01 g of Pd/C (10%) was charged into hydrogenation vessel and purged with N₂ followed by H₂ and then filled with H₂ to 30 atm. pressure. The mixture was stirred for 4 h. The vessel was evacuated and purged with Nitrogen. The reaction was filtered over celite to remove the Pd catalyst. The filtrate was concentrated and the product was isolated by C18 chromatography (CH₃CN/H₂O: 15% to 90%, with 0.1% HCO₂H) to give compound 74.1 (0.0022 g).

Example 9

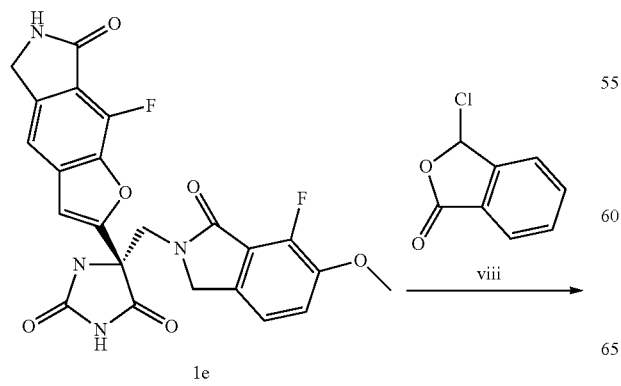

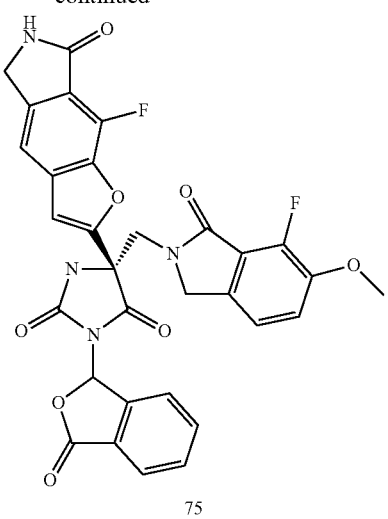

Compound 1e (50.6 mg, 0.11 mmol), compound viii (25 mg, 0.12 mmol), and DIPEA (0.053 mL, 0.315 mmol) were mixed in DMF (1 mL). The solution was stirred at 25° C. for 20 h. Acetic acid (0.1 mL) was added and the solution was purified by C18 chromatography (CH3CN/H2O, 5% to 90%, with 0.1% HCO2H) to obtain compound 75. (41.5 mg, 64.3%)

Example 10

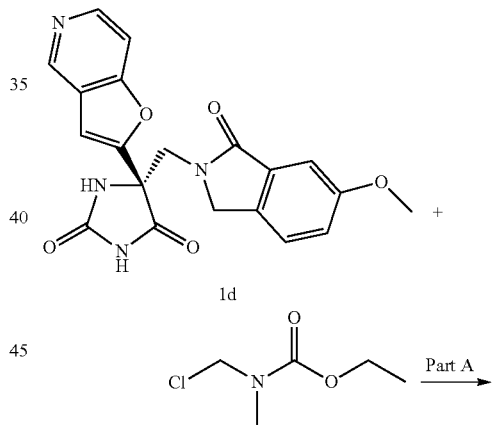

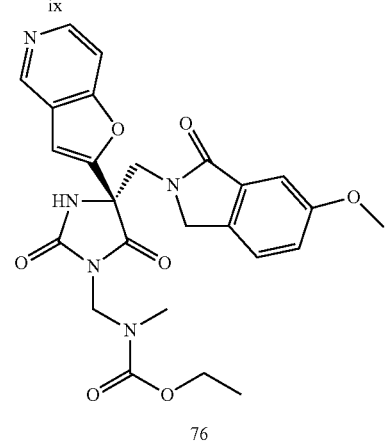

Part A:

A mixture of 1d (200 mg, 0.51 mmol), compound ix (84.7 mg, 0.56 mmol); and potassium carbonate (77.5 mg, 0.56 mmol) in DMF (2 mL) was stirred at rt overnight. Compound ix was synthesized according to the procedure described in Majumdar, S.; Sloan, K. B. *Synthetic Communications,* 2006, 36, 3537-3548. After removal of the solvent, the crude residue was purified by column chromatography (0 to 10% MeOH in $CH_2Cl_2$) to give 76 (30 mg. 12%). HPLC-MS $t_R$=1.17 min (ELSD);

Compounds 76 to 76.2 in Table 1 below were prepared by the procedure described above.

Example 11

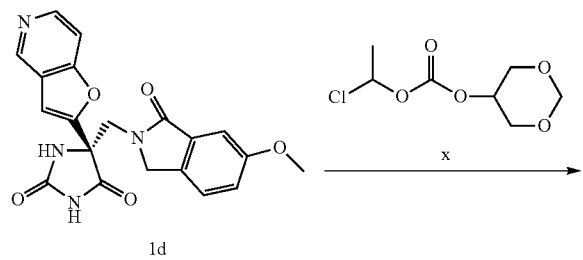

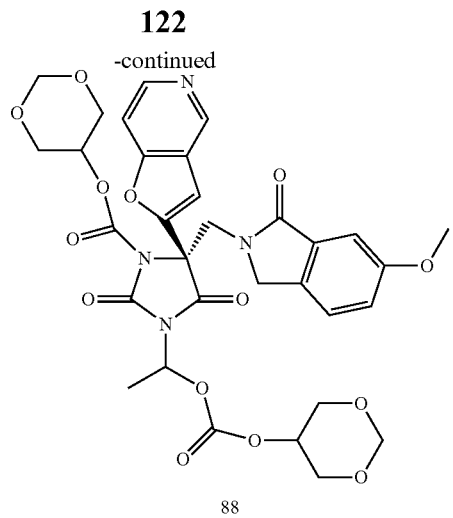

To a stirred solution of monosodium salt of compound Id (920 mg, 2.22 mm l) in 10 mL of DMF, added x (390 mg, 1.85 mmol). The resulting mixture was then stirred at 38° C. for 3 days. Water and ethyl acetate were added and layers were separated. The aqueous layer was extracted with ethyl acetate. The combined organic layers were dried over $Na_2SO_4$ and then concentrated to dryness. The crude material was purified with preparative TLC plates eluted with 46:4 DCM: MeOH. Compound 77 in Table 1 below was isolated as white solid (30 mg. 3%), compound 60.1 was isolated as a white solid (22 mg, 2%) and compound 88 in Table 1 below was isolated as a white solid (50 mg, 4%).

Example 12

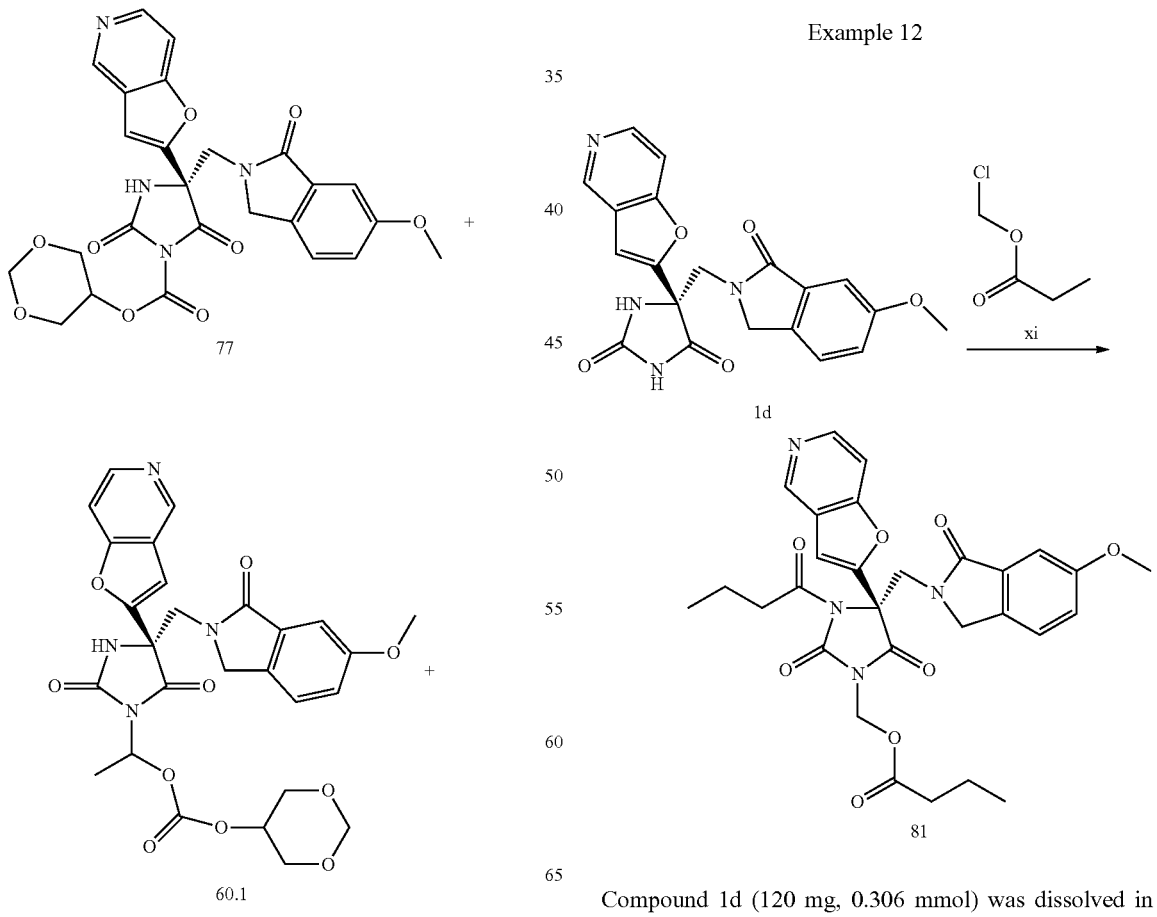

Compound 1d (120 mg, 0.306 mmol) was dissolved in DMF (3 mL) and cooled to 0° C. LiH (4.8 mg, 0.62 mmol)

was added. After the solution was stirred at 0° C. for 5 minutes, Chloromethyl butyrate xi (46 mg, 0.34 mmol) was added. The solution was stirred at 0° C. for three hours, then was allowed to warm up to room temperature and stirred overnight. AcOH (37 mg, 0.62 mmol) was added. The solution was purified by C18 chromatography ($CH_3CN/H_2O$, 5% to 90%, containing 0.1% $HCO_2H$) to give compound 81 (45.2 mg, 26.3%).

Example 13

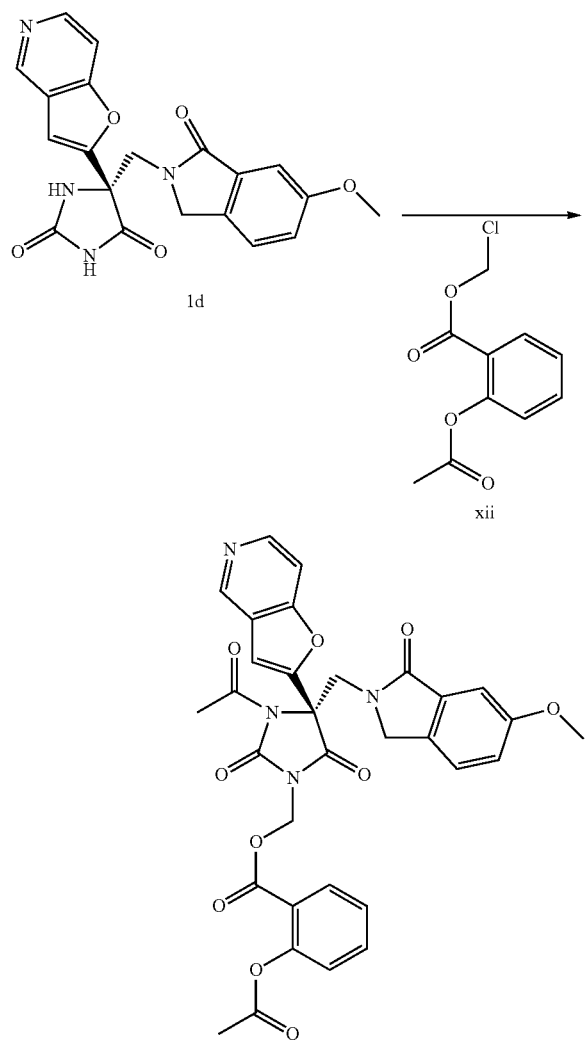

A suspension of 1d (200 mg, 0.51 mmol) in DMF (2 ml) was treated with $K_2CO_3$ (73 mg, 0.53 mmol) at 25° C. for 0.5 h. To this suspension was added O-acetyl chloromethylsalicylate xii (121 mg, 0.53 mmol) and the mixture was stirred at 25° C. for 20 h. The crude product was isolated through reverse phase column chromatography ($H_2O$—$CH_3CN$) and further purification by Prep TLC (5% MeOH in $CH_2Cl_2$) gave the compound 82 (34 mg, 11% yield).

Compounds 78 to 89 in Table 1 below were prepared by the procedures described above.

Example 14

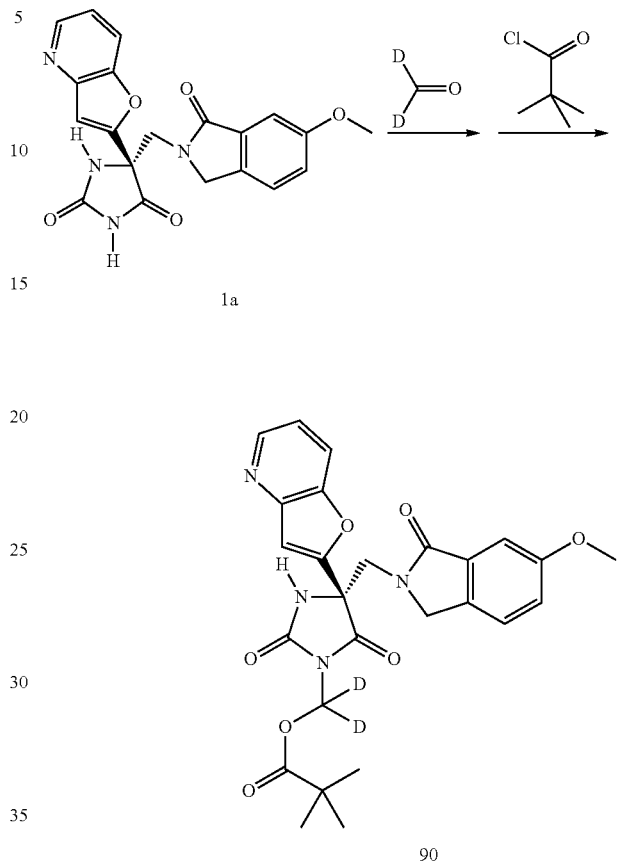

In this example, a deuterated compound of the invention is prepared. Compound 1a is dissolved in a basic solvent such as pyridine, and treated with 2.2 equivalents of deuterated formaldehyde. The resulting solution is stirred for 5-10 h and then treated with 1.1 equivalents of pivaloyi chloride. The mixture is stirred for 12-24 h. The reaction is quenched with dilute 1N HCl. The product is extracted into ethyl acetate and the organics are dried over $MgSO_4$ or $Na_2SO_4$. The solvent is removed under reduced pressure and the product 90 can be isolated by HPLC using appropriate eluting solvents.

Example 15

Assay for Inhibition of TNF-α Production from Human Whole Blood (hWBA)

Human whole blood was diluted 1:1 with serum free medium (RPMI, L-glutamine, Pen-Strep, HEPES) and incubated with a test compound in a final volume of 360 μl for 1 h at 37° C. Forty microliters of LPS (10 μg/mL) was then added. Supernatant was collected after 3.5 h incubation and the concentration of TNF-α was determined by ELISA (R&D Systems). The concentration of the test compound which inhibits 50% of the amount of TNF-α from the untreated control was determined. The $IC_{50}$ values for representative compounds of formula (I) are shown below in Table 1.

Example 16

Area Under the Curve Determinations of Plasma Levels in Rats (rrAUC)

To gain insight into the pharmacokinetic properties of the compounds of formula (I), plasma levels of the compounds in rats were determined according to the protocol described in Korfmacher, W. A.; Cox, K. A.; Ng, K. J.; Veals, J.; Hsieh, Y.; Wainhaus, S.; Broske, L; Prelusky, D.; Nomeir, A.; White, R. E. *Rapid Commun. Mass Spectrorn*, 2001, 15, 335. Briefly, rats, after an overnight fast, were dosed orally with the test compound at a dose of 10 mg/kg in a 5 mL/kg dose volume. Blood was collected at 0.5, 1, 2, 3, 4, and 6 h post-dosing. Mass spectrometry using high performance liquid chromatography was used to identify and measure the concentrations of the test compounds in the plasma at the various time points. The parent ion of each test compound was used to identify and quantitate the compounds in plasma. The area under the curve (AUC) data for representative compounds of the formula (I) are shown below in Table 1.

TABLE 1

| Compd # | STRUCTURE | hWBA IC$_{50}$ nM | PK (rrAUC[1]) parent | MS (M + 1)$^+$ | LC retention time[2] |
|---|---|---|---|---|---|
| 1 | 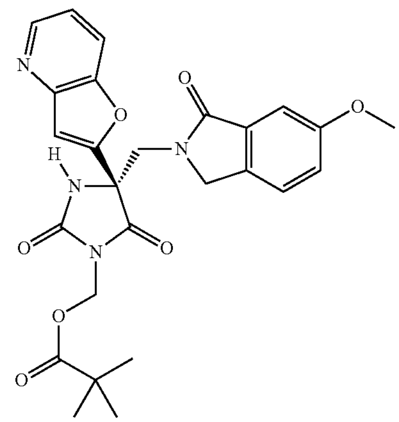 [SMILES: COc1ccc2c(c1)C(=O)N(C[C@@]1(c3cc4ncccc4o3)NC(=O)N(COC(=O)C(C)(C)C)C1=O)C2] | 281 | 13101 | 507.3 | 2.93 |
| 2 | 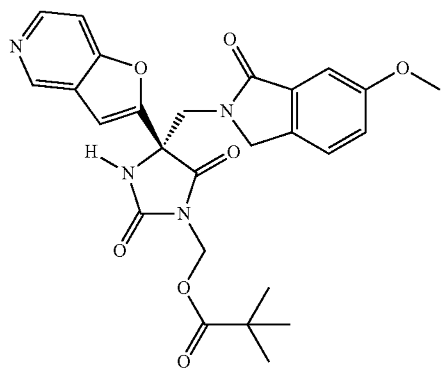 [SMILES: COc1ccc2c(c1)C(=O)N(C[C@@]1(c3cc4cnccc4o3)NC(=O)N(COC(=O)C(C)(C)C)C1=O)C2] | 273 | 13539 | 507 | 1.26 |
| 3 | 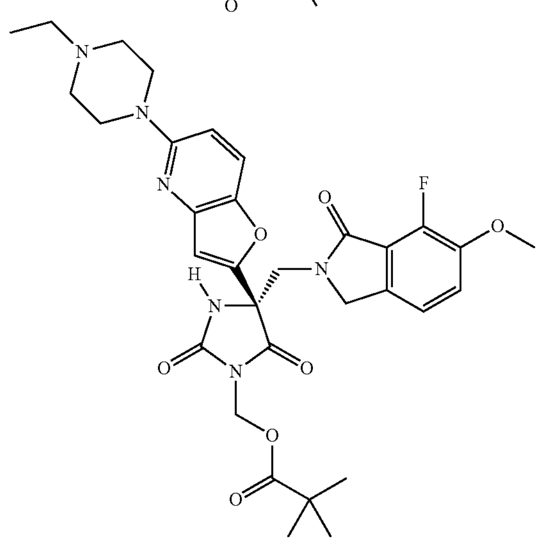 | 61 | 19953 | 637.4 | 2.93 |

TABLE 1-continued
| Compd # | STRUCTURE | hWBA IC$_{50}$ nM | PK (rrAUC$^1$) parent | MS (M + 1)$^+$ | LC retention time$^2$ |
|---|---|---|---|---|---|
| 4 | 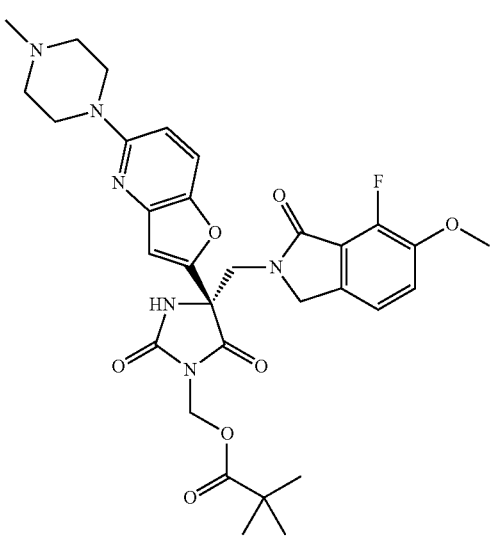 | 92 | 8621 | 623.3 | 2.89 |
| 5 | 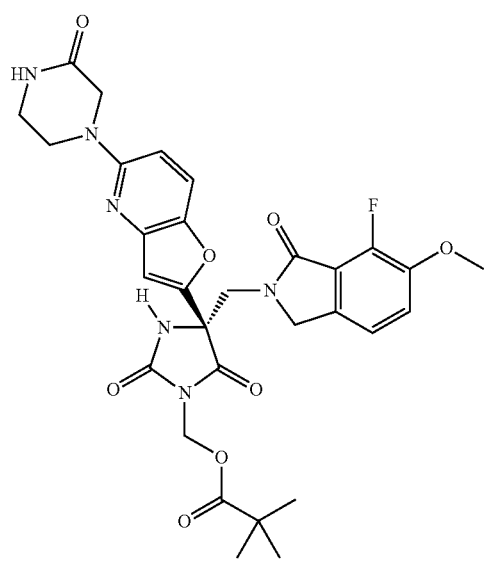 [SMILES: COc1ccc2c(c1F)C(=O)N(C[C@@]1(c3cc4nc(N5CCNC(=O)C5)ccc4o3)NC(=O)N(COC(=O)C(C)(C)C)C1=O)C2] | 104 | 121 | 623.3 | 3.13 |
| 6 | 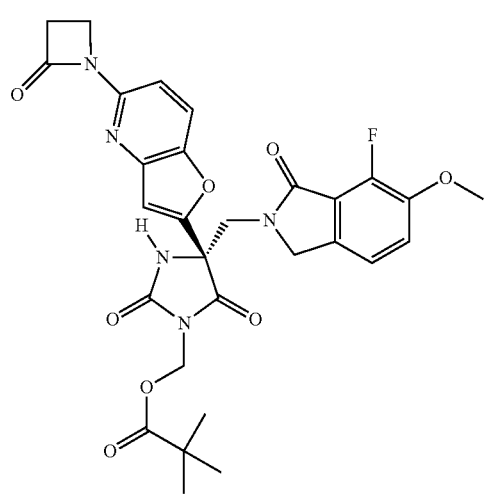 [SMILES: COc1ccc2c(c1F)C(=O)N(C[C@@]1(c3cc4nc(N5CCC5=O)ccc4o3)NC(=O)N(COC(=O)C(C)(C)C)C1=O)C2] | 447 | 2283 | 594.3 | 3.91 |

TABLE 1-continued

| Compd # | STRUCTURE | hWBA IC$_{50}$ nM | PK (rrAUC[1]) parent | MS (M + 1)$^+$ | LC retention time[2] |
|---|---|---|---|---|---|
| 7 | 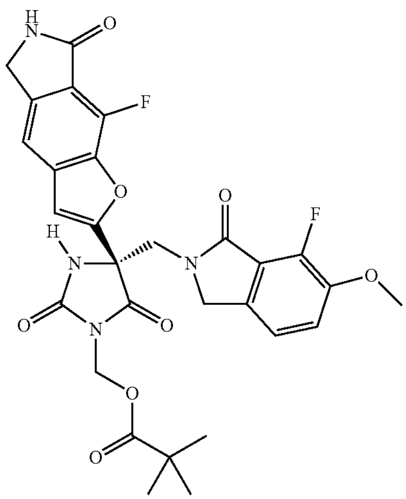 [SMILES: COc1ccc2c(c1F)C(=O)N(C[C@@]1(c3cc4cc5c(c(F)c4o3)C(=O)NC5)NC(=O)N(COC(=O)C(C)(C)C)C1=O)C2] | N/D[3] | 1898 | 597.3 | 3.49 |
| 8 | 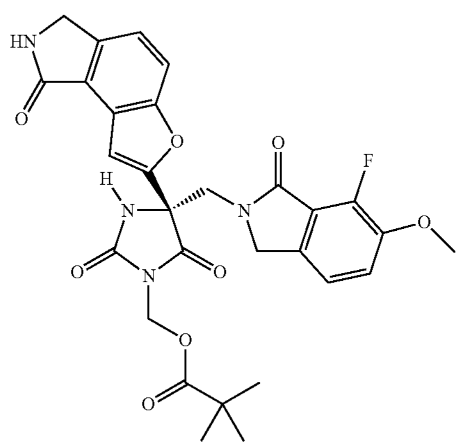 [SMILES: COc1ccc2c(c1F)C(=O)N(C[C@@]1(c3cc4c5c(ccc4o3)CNC5=O)NC(=O)N(COC(=O)C(C)(C)C)C1=O)C2] | N/D | 2193 | 579.3 | 3.53 |
| 9 | 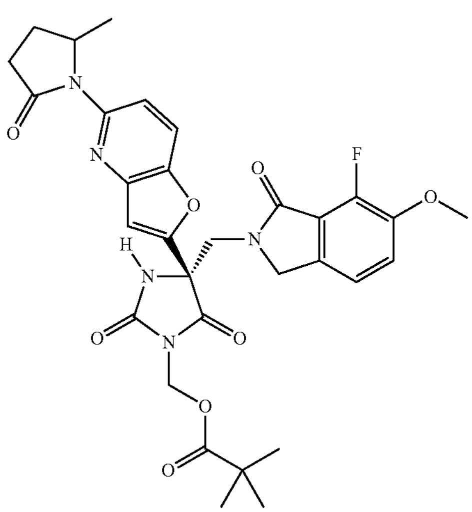 [SMILES: COc1ccc2c(c1F)C(=O)N(C[C@@]1(c3cc4nc(N5C(=O)CCC5C)ccc4o3)NC(=O)N(COC(=O)C(C)(C)C)C1=O)C2] | 192 | 4557 | 622.3 | 4.14 |

TABLE 1-continued

| Compd # | STRUCTURE | hWBA IC$_{50}$ nM | PK (rrAUC[1]) parent | MS (M + 1)$^+$ | LC retention time[2] |
|---|---|---|---|---|---|
| 10 | 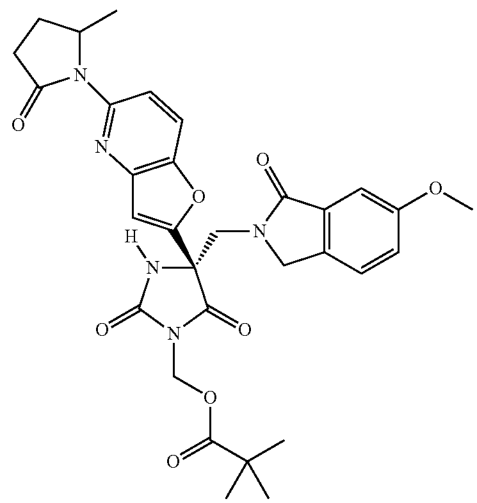 [SMILES: COc1ccc2c(c1)C(=O)N(C[C@@]1(c3cc4nc(N5C(=O)CCC5C)ccc4o3)NC(=O)N(COC(=O)C(C)(C)C)C1=O)C2] | 266 | 1202 | 604.3 | 4.18 |
| 11 | 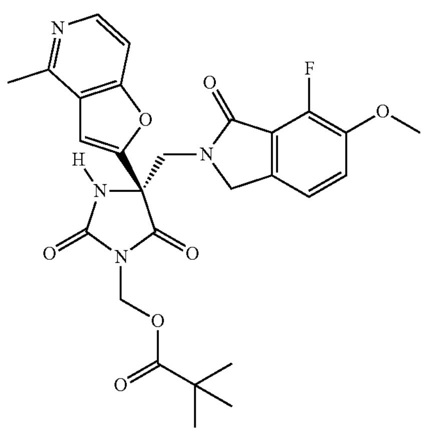 | 235 | 1827 | 539.3 | 2.96 |
| 12 | 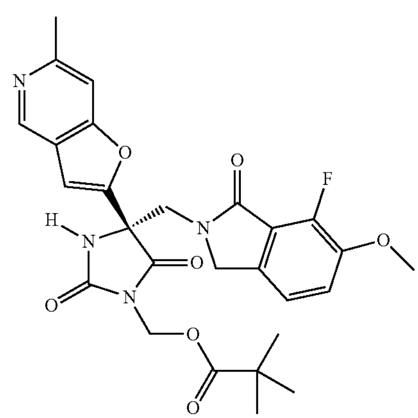 [SMILES: COc1ccc2c(c1F)C(=O)N(C[C@@]1(c3cc4cnc(C)cc4o3)NC(=O)N(COC(=O)C(C)(C)C)C1=O)C2] | 187 | 45,213 | 539.2 | 1.17 |

TABLE 1-continued

| Compd # | STRUCTURE | hWBA IC$_{50}$ nM | PK (rrAUC[1]) parent | MS (M + 1)$^+$ | LC retention time[2] |
|---|---|---|---|---|---|
| 13 | 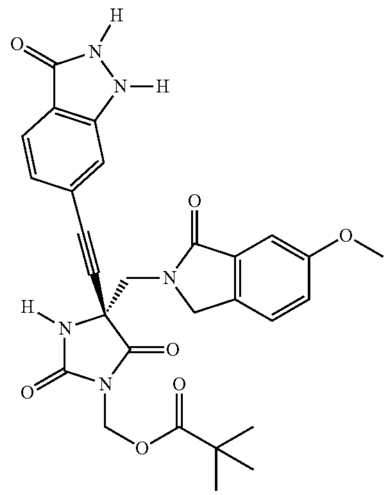 [SMILES: COc1ccc2c(c1)C(=O)N(C[C@@]1(C#Cc3ccc4c(=O)[nH][nH]c4c3)NC(=O)N(COC(=O)C(C)(C)C)C1=O)C2] | 213 | 0 | 546.1 | 1.525 |
| 14 | 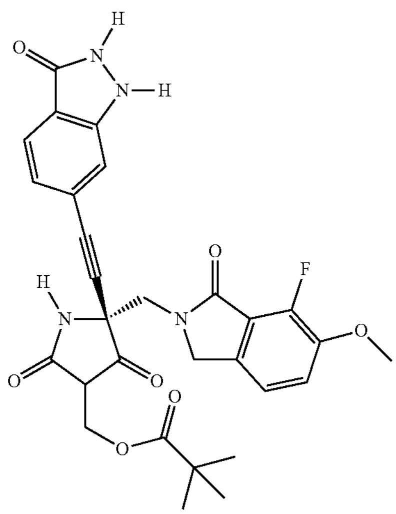 [SMILES: COc1ccc2c(c1F)C(=O)N(C[C@@]1(C#Cc3ccc4c(=O)[nH][nH]c4c3)NC(=O)C(COC(=O)C(C)(C)C)C1=O)C2] | 275 | 0 | 564.3 | 1.671 |
| 15 | 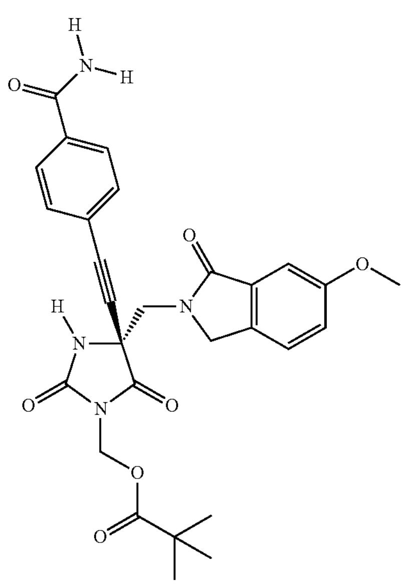 [SMILES: COc1ccc2c(c1)C(=O)N(C[C@@]1(C#Cc3ccc(C(N)=O)cc3)NC(=O)N(COC(=O)C(C)(C)C)C1=O)C2] | 188 | 0 | 419.2 | 2.54 |

TABLE 1-continued

| Compd # | STRUCTURE | hWBA IC$_{50}$ nM | PK (rrAUC[1]) parent | MS (M + 1)$^+$ | LC retention time[2] |
|---|---|---|---|---|---|
| 16 | 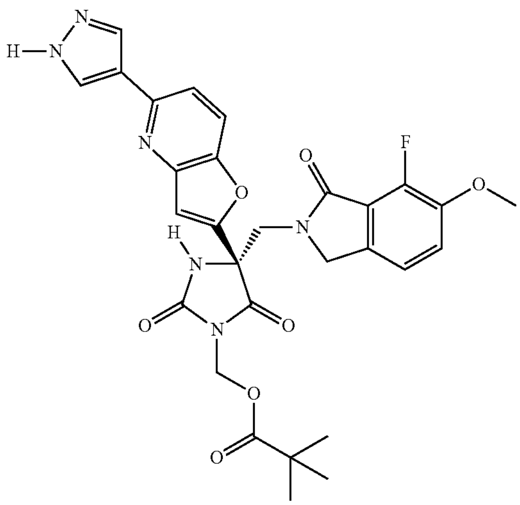 [SMILES: COc1ccc2c(c1F)C(=O)N(C[C@@]1(c3cc4nc(-c5cn[nH]c5)ccc4o3)NC(=O)N(COC(=O)C(C)(C)C)C1=O)C2] | 141 | 249 | 591.3 | 4.07 |
| 17 | 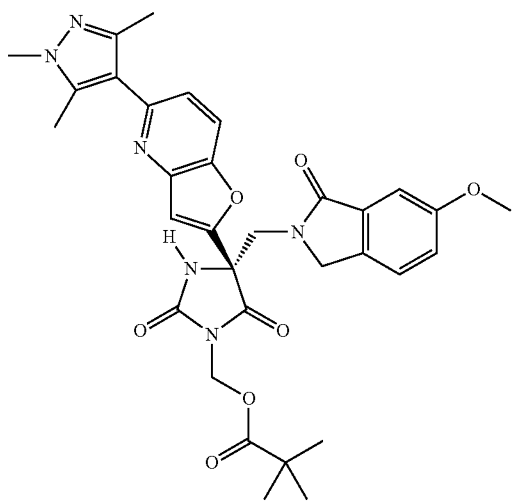 | 626 | 2005 | 615.3 | 3.98 |
| 18 | 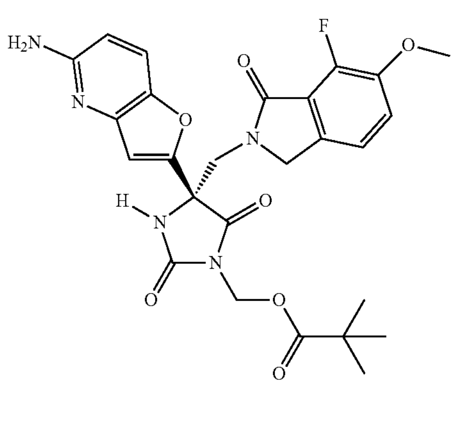 [SMILES: COc1ccc2c(c1F)C(=O)N(C[C@@]1(c3cc4nc(N)ccc4o3)NC(=O)N(COC(=O)C(C)(C)C)C1=O)C2] | 178 | 351 | 540 | 2.71 |

TABLE 1-continued

| Compd # | STRUCTURE | hWBA IC$_{50}$ nM | PK (rrAUC[1]) parent | MS (M + 1)$^+$ | LC retention time[2] |
|---|---|---|---|---|---|
| 19 | 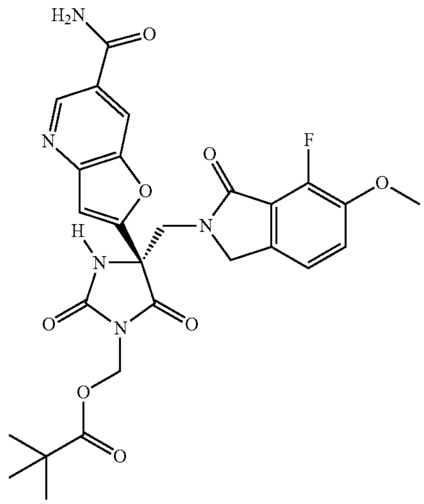 [SMILES: COc1ccc2c(c1F)C(=O)N(C[C@@]1(c3cc4ncc(C(N)=O)cc4o3)NC(=O)N(COC(=O)C(C)(C)C)C1=O)C2] | 101 | 94 | 568 | 3.1 |
| 20 | 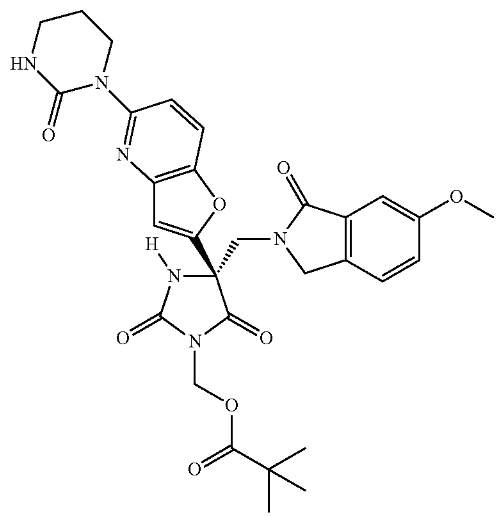 [SMILES: COc1ccc2c(c1)C(=O)N(C[C@@]1(c3cc4nc(N5CCCNC5=O)ccc4o3)NC(=O)N(COC(=O)C(C)(C)C)C1=O)C2] | 282 | 148 | 605.3 | 3.59 |
| 21 | 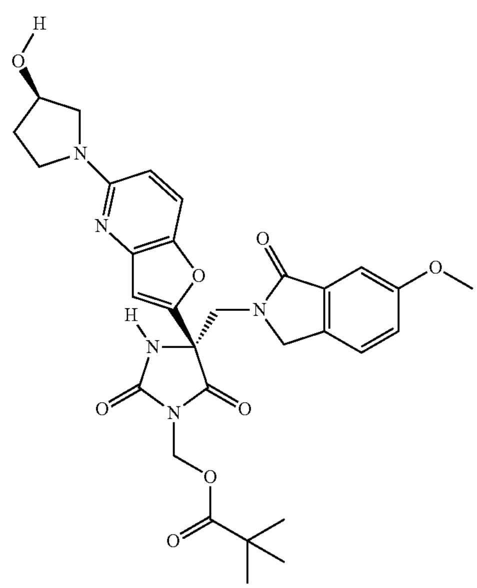 [SMILES: COc1ccc2c(c1)C(=O)N(C[C@@]1(c3cc4nc(N5CC[C@@H](O)C5)ccc4o3)NC(=O)N(COC(=O)C(C)(C)C)C1=O)C2] | 339 | 2684 | 592.3 | 2.71 |

TABLE 1-continued
| Compd # | STRUCTURE | hWBA IC$_{50}$ nM | PK (rrAUC[1]) parent | MS (M + 1)$^+$ | LC retention time[2] |
|---|---|---|---|---|---|
| 22 | 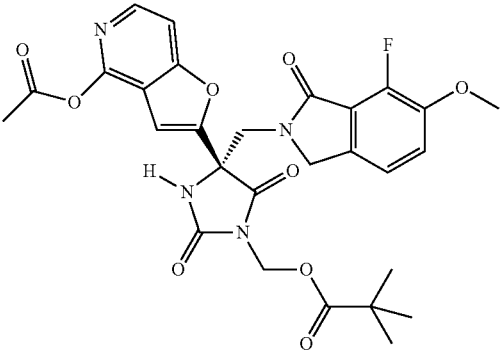 [SMILES: COc1ccc2c(c1F)C(=O)N(C[C@@]1(c3cc4c(OC(C)=O)nccc4o3)NC(=O)N(COC(=O)C(C)(C)C)C1=O)C2] | 2820 | 823 | 583 | 3.53 |
| 23 | 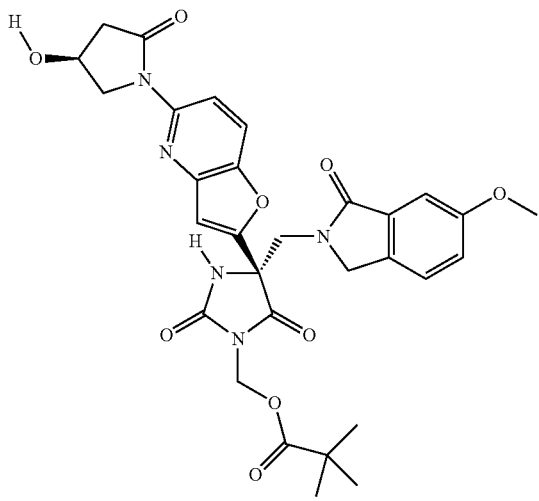 [SMILES: COc1ccc2c(c1)C(=O)N(C[C@@]1(c3cc4nc(N5C[C@@H](O)CC5=O)ccc4o3)NC(=O)N(COC(=O)C(C)(C)C)C1=O)C2] | N/D | 60895 | 606.3 | 3.41 |
| 24 | 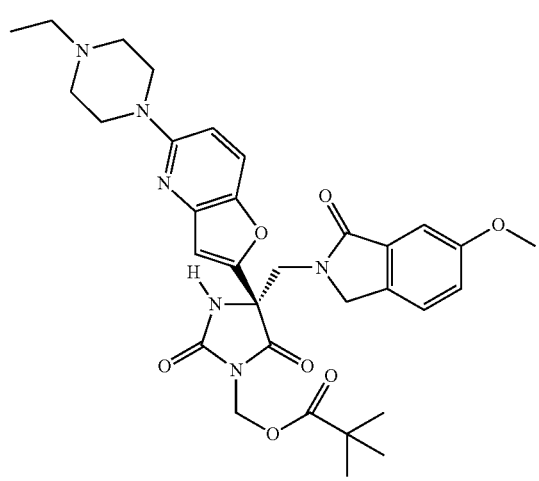 [SMILES: CCN1CCN(c2ccc3oc([C@]4(CN5Cc6ccc(OC)cc6C5=O)NC(=O)N(COC(=O)C(C)(C)C)C4=O)cc3n2)CC1] | 176 | 655 | 619.3 | 2.97 |

TABLE 1-continued

| Compd # | STRUCTURE | hWBA IC$_{50}$ nM | PK (rrAUC[1]) parent | MS (M + 1)$^+$ | LC retention time[2] |
|---|---|---|---|---|---|
| 25 | 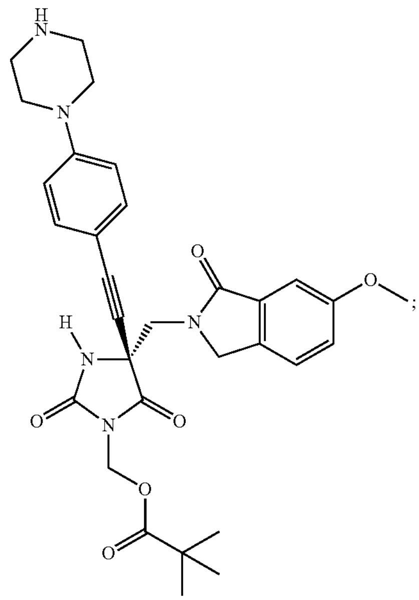 [SMILES: COc1ccc2c(c1)C(=O)N(C[C@@]1(C#Cc3ccc(N4CCNCC4)cc3)NC(=O)N(COC(=O)C(C)(C)C)C1=O)C2] | 212 | 0 | 574.3 | 3.35 |
| 26 | 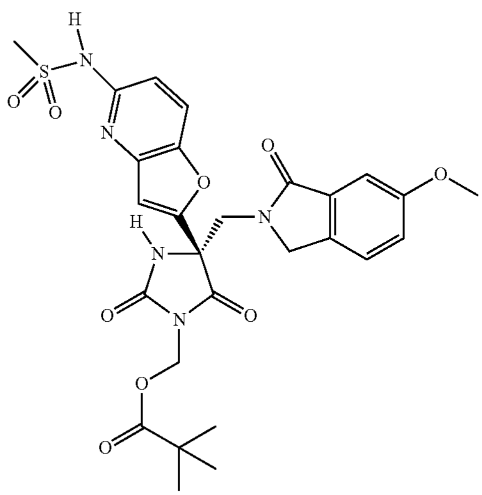 | 645 | 0 | 600 | 3.66 |
| 27 | 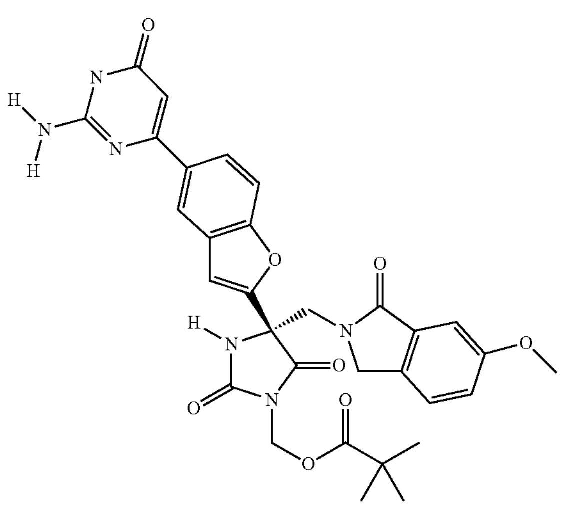 [SMILES: COc1ccc2c(c1)C(=O)N(C[C@@]1(c3cc4cc(-c5cc(=O)[nH]c(N)n5)ccc4o3)NC(=O)N(COC(=O)C(C)(C)C)C1=O)C2] | 940 | 0 | 615.2 | 1.616 |

TABLE 1-continued
| Compd # | STRUCTURE | hWBA IC$_{50}$ nM | PK (rrAUC[1]) parent | MS (M + 1)$^+$ | LC retention time[2] |
|---|---|---|---|---|---|
| 28 | 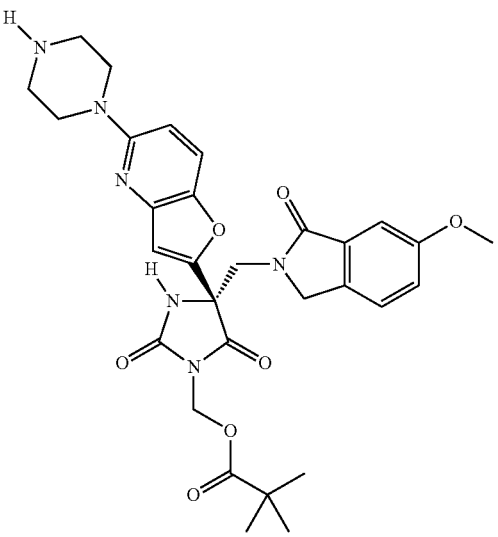 [SMILES: COc1ccc2c(c1)C(=O)N(C[C@@]1(c3cc4nc(N5CCNCC5)ccc4o3)NC(=O)N(COC(=O)C(C)(C)C)C1=O)C2] | 156 | 0 | 591.3 | 2.84 |
| 29 | 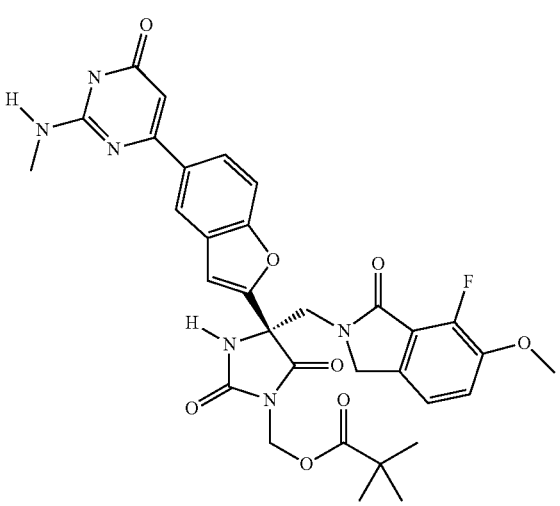 [SMILES: CNc1nc(-c2ccc3oc([C@]4(CN5Cc6ccc(OC)c(F)c6C5=O)NC(=O)N(COC(=O)C(C)(C)C)C4=O)cc3c2)cc(=O)[nH]1] | 199 | 0 | 633.2 | 1.564 |

TABLE 1-continued

| Compd # | STRUCTURE | hWBA IC$_{50}$ nM | PK (rrAUC[1]) parent | MS (M + 1)$^+$ | LC retention time[2] |
|---|---|---|---|---|---|
| 30 | 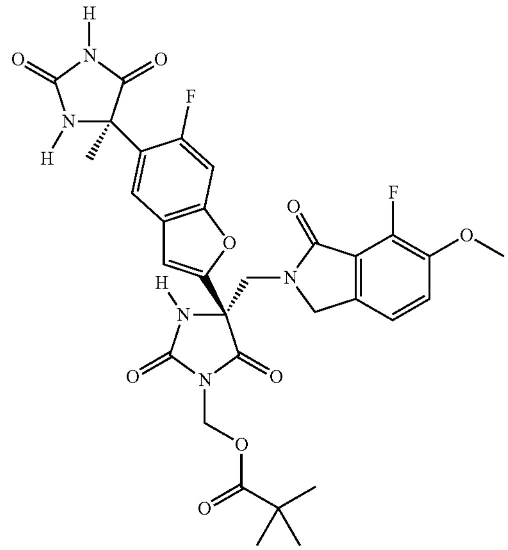 [SMILES: COc1ccc2c(c1F)C(=O)N(C[C@@]1(c3cc4cc([C@@]5(C)NC(=O)NC5=O)c(F)cc4o3)NC(=O)N(COC(=O)C(C)(C)C)C1=O)C2] | N/D | 335 | 654.4 | 3.65 |
| 31 | 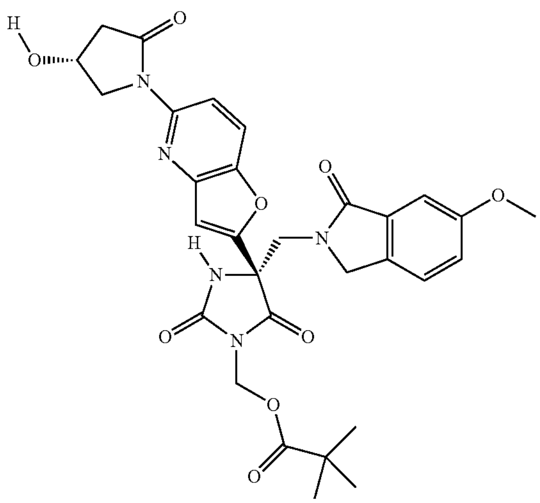 [SMILES: COc1ccc2c(c1)C(=O)N(C[C@@]1(c3cc4nc(N5C[C@H](O)CC5=O)ccc4o3)NC(=O)N(COC(=O)C(C)(C)C)C1=O)C2] | 224 | 334 | 606.3 | 3.57 |
| 32 | 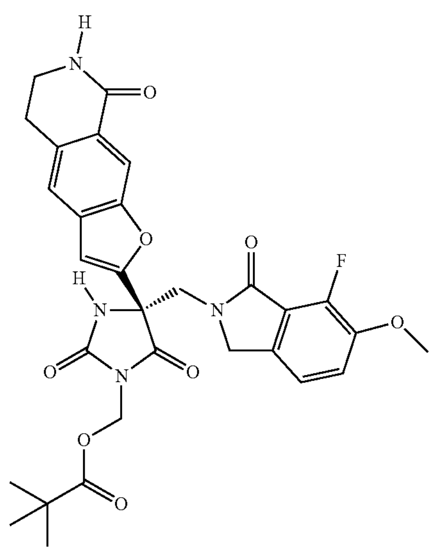 [SMILES: COc1ccc2c(c1F)C(=O)N(C[C@@]1(c3cc4cc5c(cc4o3)C(=O)NCC5)NC(=O)N(COC(=O)C(C)(C)C)C1=O)C2] | 135 | | 593.3 | 3.71 |

TABLE 1-continued

| Compd # | STRUCTURE | hWBA IC$_{50}$ nM | PK (rrAUC[1]) parent | MS (M + 1)$^+$ | LC retention time[2] |
|---|---|---|---|---|---|
| 33 | 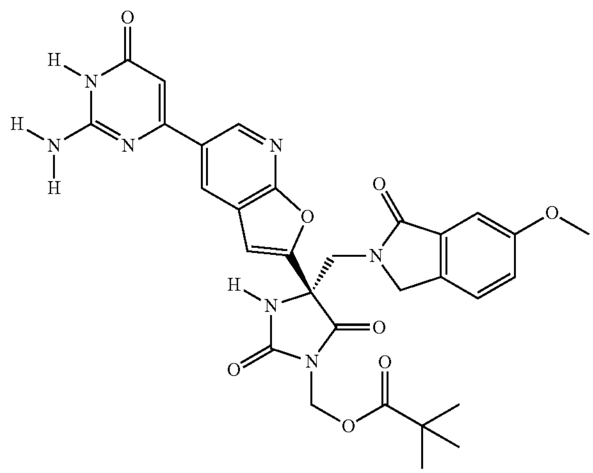 [SMILES: COc1ccc2c(c1)C(=O)N(C[C@@]1(c3cc4cc(-c5cc(=O)[nH]c(N)n5)cnc4o3)NC(=O)N(COC(=O)C(C)(C)C)C1=O)C2] | 375 | 0 | 616.2 | 1.613 |
| 34 | 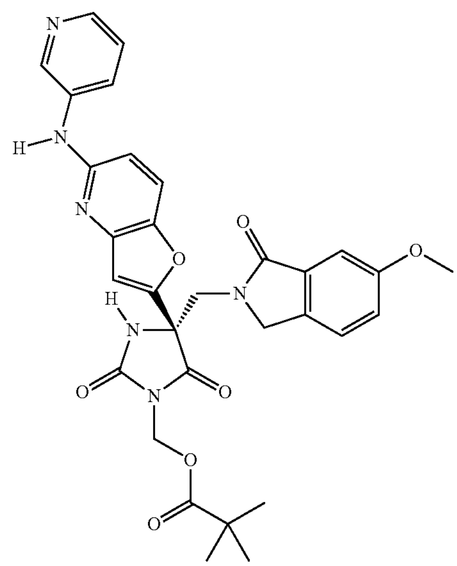 [SMILES: COc1ccc2c(c1)C(=O)N(C[C@@]1(c3cc4nc(Nc5cccnc5)ccc4o3)NC(=O)N(COC(=O)C(C)(C)C)C1=O)C2] | 1327 | 94 | 599.3 | 3.09 |
| 35 | 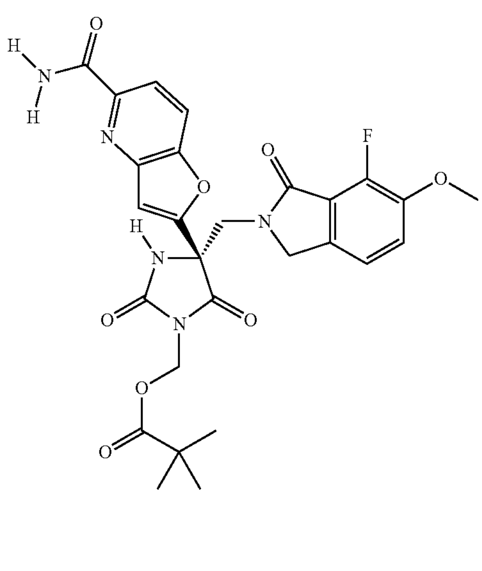 [SMILES: COc1ccc2c(c1F)C(=O)N(C[C@@]1(c3cc4nc(C(N)=O)ccc4o3)NC(=O)N(COC(=O)C(C)(C)C)C1=O)C2] | 79 | | 568 | 3.47 |

TABLE 1-continued

| Compd # | STRUCTURE | hWBA IC$_{50}$ nM | PK (rrAUC[1]) parent | MS (M + 1)$^+$ | LC retention time[2] |
|---|---|---|---|---|---|
| 35.1 | 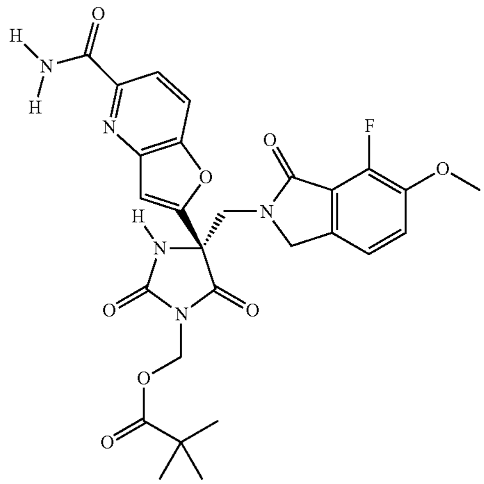 [SMILES: COc1ccc2c(c1F)C(=O)N(C[C@@]1(c3cc4nc(C(N)=O)ccc4o3)NC(=O)N(COC(=O)C(C)(C)C)C1=O)C2] | 355 | | 607.3 | 3.69 |
| 35.2 | 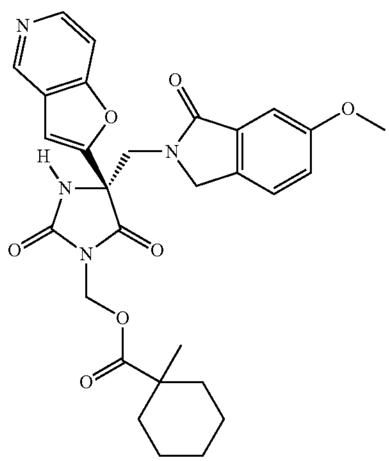 [SMILES: COc1ccc2c(c1)C(=O)N(C[C@@]1(c3cc4cnccc4o3)NC(=O)N(COC(=O)C3(C)CCCCC3)C1=O)C2] | 35.2 | | 547.3 | 3.14 |
| 35.3 | 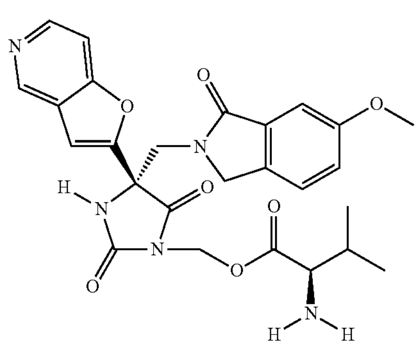 [SMILES: COc1ccc2c(c1)C(=O)N(C[C@@]1(c3cc4cnccc4o3)NC(=O)N(COC(=O)[C@H](N)C(C)C)C1=O)C2] | 244 | 4316 | 522 | 1.47 |

TABLE 1-continued

| Compd # | STRUCTURE | hWBA IC$_{50}$ nM | PK (rrAUC[1]) parent | MS (M + 1)$^+$ | LC retention time[2] |
|---|---|---|---|---|---|
| 35.4 | 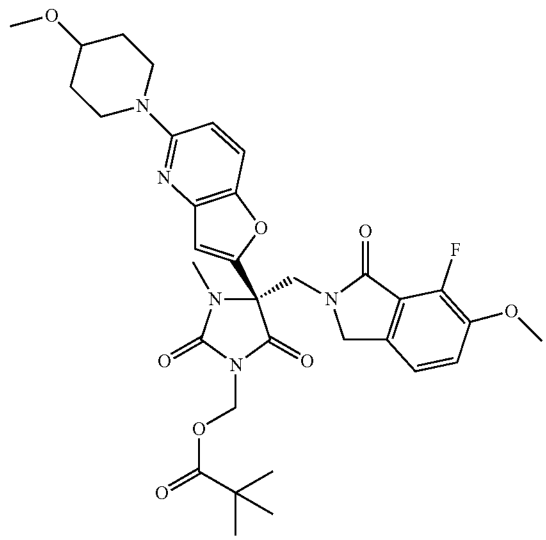 | 367 | 11275 | 638.4 | 3.23 |
| 36 | 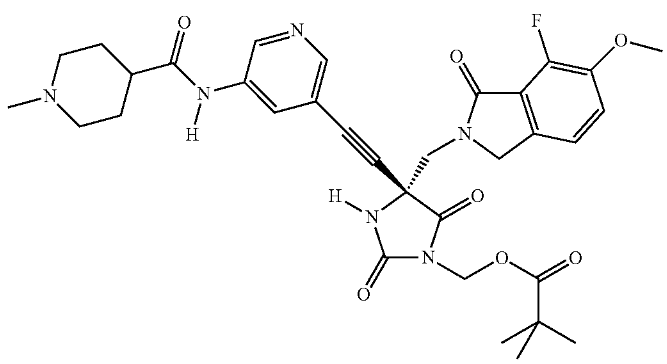 | 171 | 0 | 648 | 3.04 |
| 37 | 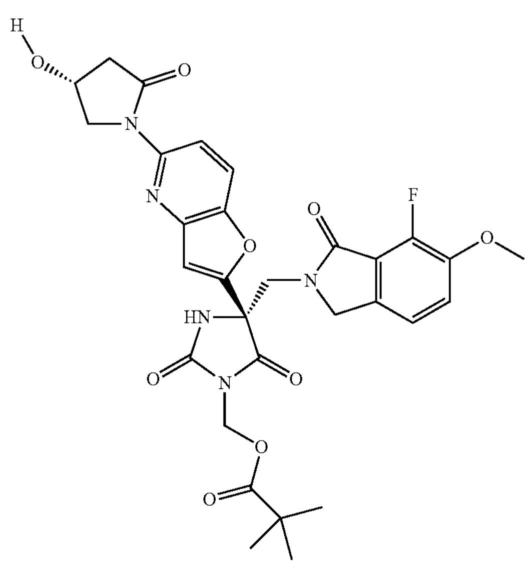 [SMILES: COc1ccc2c(c1F)C(=O)N(C[C@@]1(c3cc4nc(N5C[C@H](O)CC5=O)ccc4o3)NC(=O)N(COC(=O)C(C)(C)C)C1=O)C2] | 148 | 0 | 624.3 | 3.5 |

TABLE 1-continued

| Compd # | STRUCTURE | hWBA IC$_{50}$ nM | PK (rrAUC[1]) parent | MS (M + 1)$^+$ | LC retention time[2] |
|---|---|---|---|---|---|
| 38 | 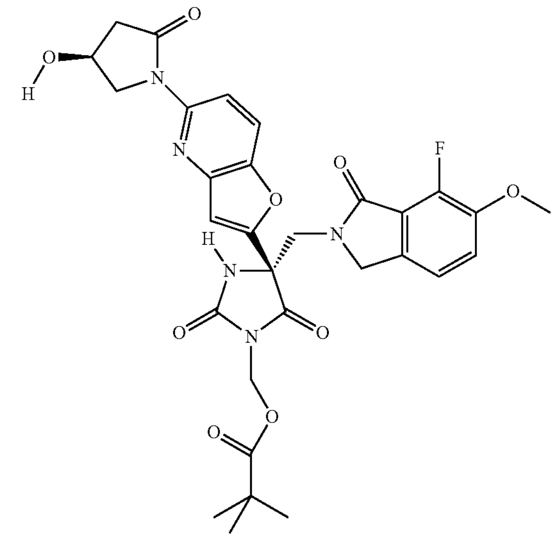 [SMILES: COc1ccc2c(c1F)C(=O)N(C[C@@]1(c3cc4nc(N5C[C@@H](O)CC5=O)ccc4o3)NC(=O)N(COC(=O)C(C)(C)C)C1=O)C2] | 94 | 1736 | 624.3 | 3.42 |
| 39 | 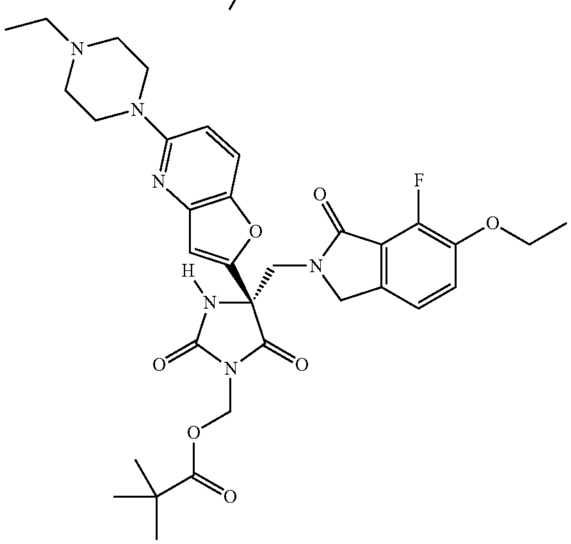 | 241 | 927 | 651.4 | 3.11 |
| 40 | 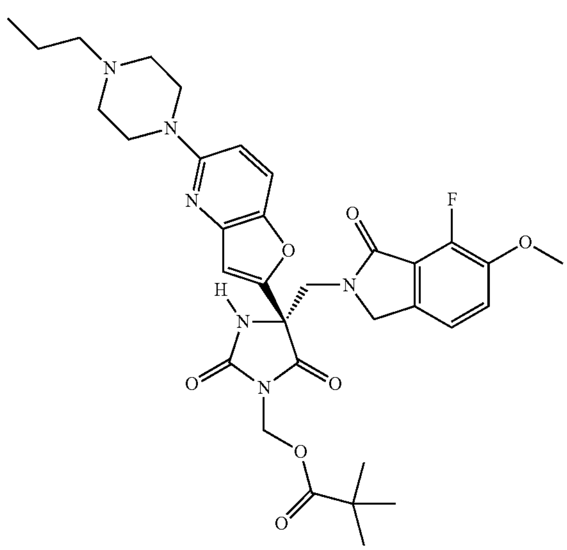 [SMILES: CCCN1CCN(c2ccc3oc([C@]4(CN5Cc6ccc(OC)c(F)c6C5=O)NC(=O)N(COC(=O)C(C)(C)C)C4=O)cc3n2)CC1] | 258 | | 651.4 | 2.96 |

TABLE 1-continued

| Compd # | STRUCTURE | hWBA IC$_{50}$ nM | PK (rrAUC[1]) parent | MS (M + 1)$^+$ | LC retention time[2] |
|---|---|---|---|---|---|
| 41 | 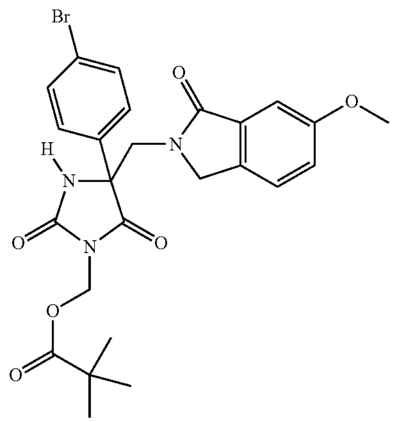 [SMILES: COc1ccc2c(c1)C(=O)N(CC1(c3ccc(Br)cc3)NC(=O)N(COC(=O)C(C)(C)C)C1=O)C2] | 7531 | | 545.3 | 4.55 |
| 42 | 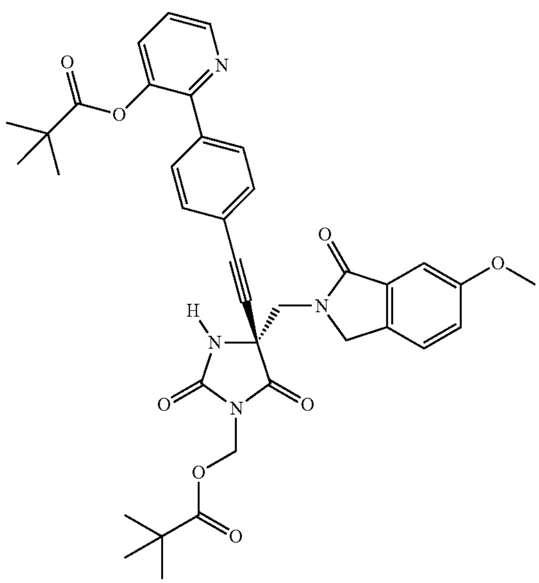 [SMILES: COc1ccc2c(c1)C(=O)N(C[C@@]1(C#Cc3ccc(-c4ncccc4OC(=O)C(C)(C)C)cc3)NC(=O)N(COC(=O)C(C)(C)C)C1=O)C2] | 794 | | 667.4 | 4.76 |

TABLE 1-continued

| Compd # | STRUCTURE | hWBA IC$_{50}$ nM | PK (rrAUC[1]) parent | MS (M + 1)$^+$ | LC retention time[2] |
|---|---|---|---|---|---|
| 43 | 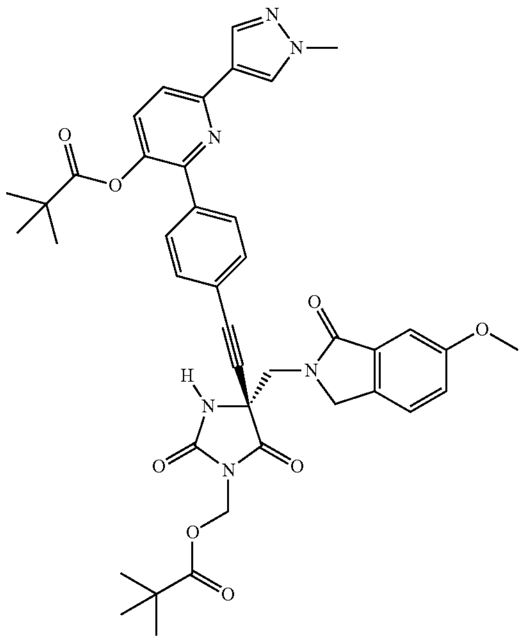 [SMILES: COc1ccc2c(c1)C(=O)N(C[C@@]1(C#Cc3ccc(-c4nc(-c5cnn(C)c5)ccc4OC(=O)C(C)(C)C)cc3)NC(=O)N(COC(=O)C(C)(C)C)C1=O)C2] | 336 | 0 | 747.4 | 4.92 |
| 44 | 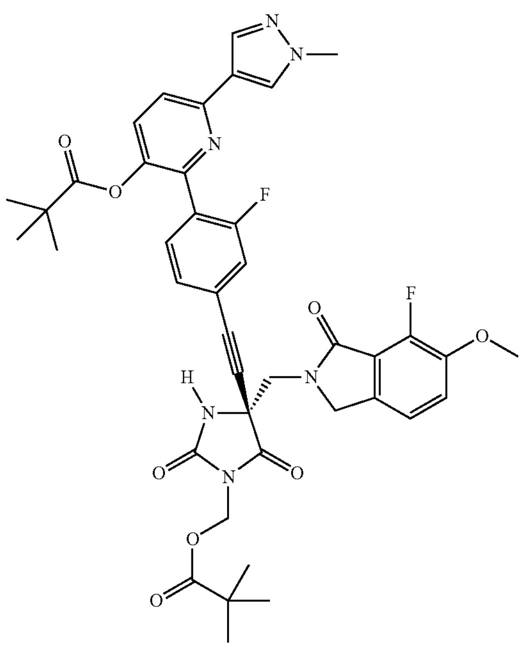 [SMILES: COc1ccc2c(c1F)C(=O)N(C[C@@]1(C#Cc3ccc(-c4nc(-c5cnn(C)c5)ccc4OC(=O)C(C)(C)C)c(F)c3)NC(=O)N(COC(=O)C(C)(C)C)C1=O)C2] | 281 | 0 | 783.4 | 4.74 |
| 45 | 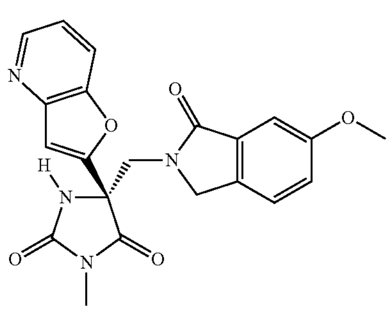 [SMILES: COc1ccc2c(c1)C(=O)N(C[C@@]1(c3cc4ncccc4o3)NC(=O)N(C)C1=O)C2] | N/D | 947 | 407.2 | 2.6 |

TABLE 1-continued

| Compd # | STRUCTURE | hWBA IC$_{50}$ nM | PK (rrAUC[1]) parent | MS (M + 1)$^+$ | LC retention time[2] |
|---|---|---|---|---|---|
| 46 | 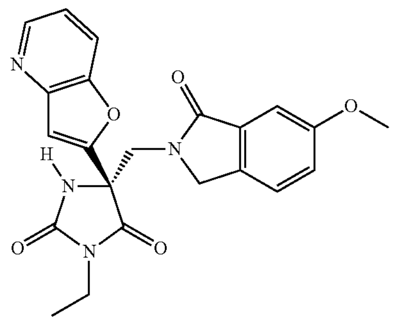 [SMILES: CCN1C(=O)N[C@@](CN2Cc3ccc(OC)cc3C2=O)(c2cc3ncccc3o2)C1=O] | N/A[4] | 868 | 421.2 | 2.51 |
| 47 | 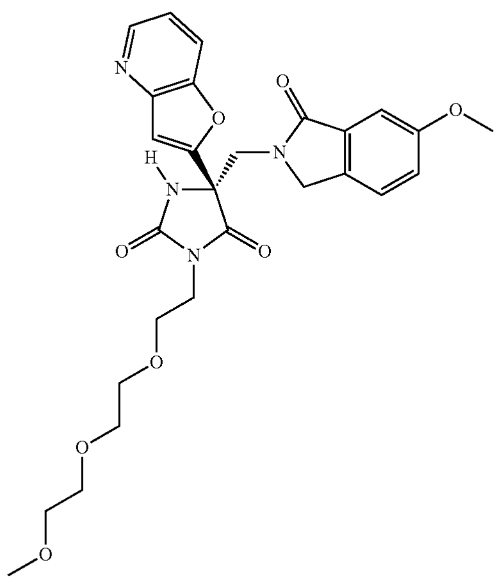 | N/A | 19 | 539.3 | 2.64 |
| 48 | 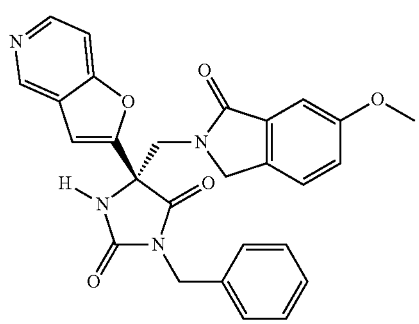 [SMILES: COc1ccc2c(c1)C(=O)N(C[C@@]1(c3cc4cnccc4o3)NC(=O)N(Cc3ccccc3)C1=O)C2] | N/A | | 483 | 3.24 |

TABLE 1-continued

| Compd # | STRUCTURE | hWBA IC$_{50}$ nM | PK (rrAUC[1]) parent | MS (M + 1)$^+$ | LC retention time[2] |
|---|---|---|---|---|---|
| 48.1 | 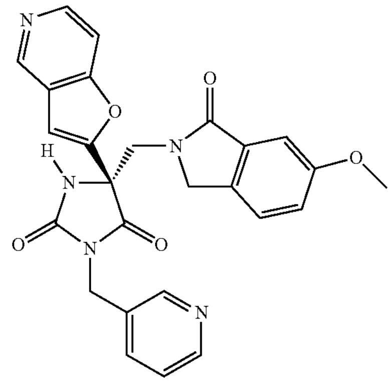 [SMILES: COc1ccc2c(c1)C(=O)N(C[C@@]1(c3cc4cnccc4o3)NC(=O)N(Cc3cccnc3)C1=O)C2] | N/A | 0 | 484.3 | 1.67 |
| 49 | 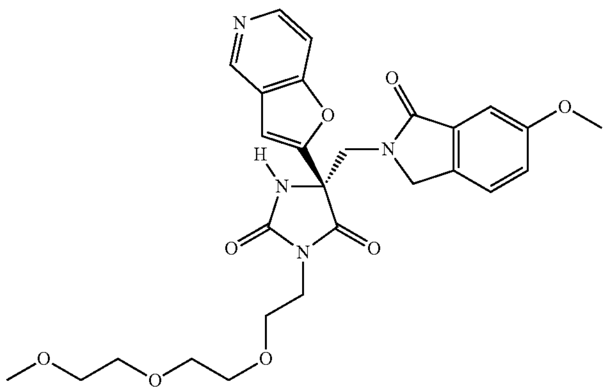 | N/A | 88 | 539.3 | 2.24 |
| 50 | 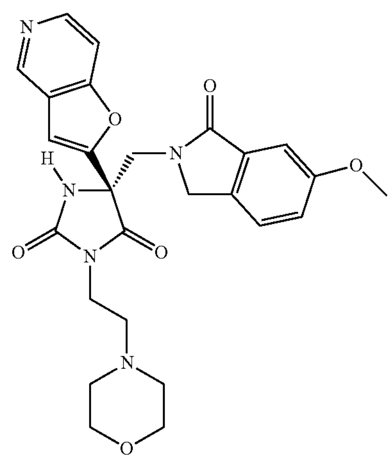 [SMILES: COc1ccc2c(c1)C(=O)N(C[C@@]1(c3cc4cnccc4o3)NC(=O)N(CCN3CCOCC3)C1=O)C2] | N/A | 0 | 506.3 | 1.72 |
| 51 | 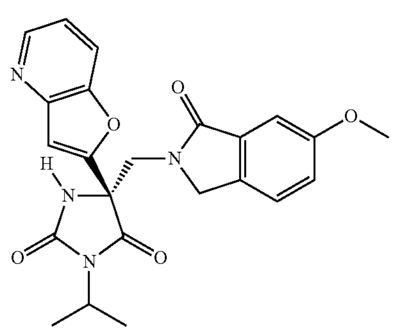 | 7151 | 370 | 435.2 | 2.74 |

TABLE 1-continued

| Compd # | STRUCTURE | hWBA IC$_{50}$ nM | PK (rrAUC[1]) parent | MS (M + 1)$^+$ | LC retention time[2] |
|---|---|---|---|---|---|
| 52 | 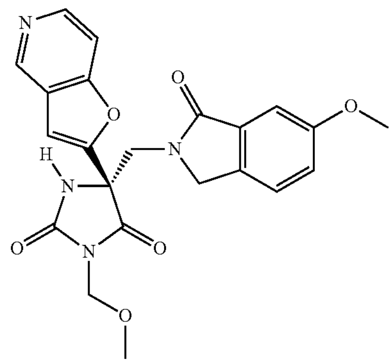 [SMILES: COCN1C(=O)N[C@@](CN2Cc3ccc(OC)cc3C2=O)(c2cc3cnccc3o2)C1=O] | N/D | 1072 | 437.4 | 2.31 |
| 53 | 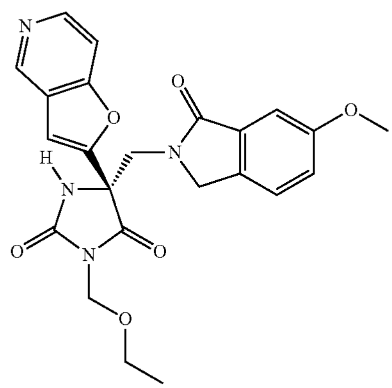 [SMILES: CCOCN1C(=O)N[C@@](CN2Cc3ccc(OC)cc3C2=O)(c2cc3cnccc3o2)C1=O] | N/D | 5183 | 451.2 | 2.39 |
| 54 | 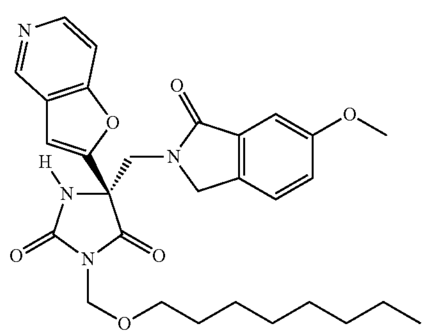 [SMILES: CCCCCCCCOCN1C(=O)N[C@@](CN2Cc3ccc(OC)cc3C2=O)(c2cc3cnccc3o2)C1=O] | N/D | 571 | 535.3 | 3.45 |
| 55 | 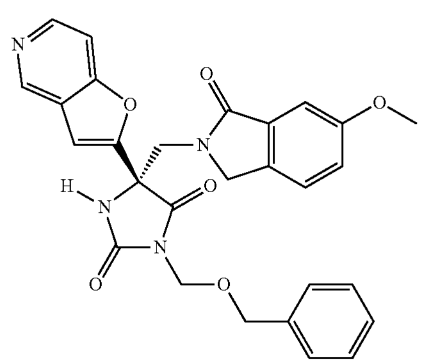 [SMILES: COc1ccc2c(c1)C(=O)N(C[C@@]1(c3cc4cnccc4o3)NC(=O)N(COCc3ccccc3)C1=O)C2] | N/A | | 513 | 3.23 |

TABLE 1-continued
| Compd # | STRUCTURE | hWBA IC$_{50}$ nM | PK (rrAUC[1]) parent | MS (M + 1)$^+$ | LC retention time[2] |
|---|---|---|---|---|---|
| 56 | 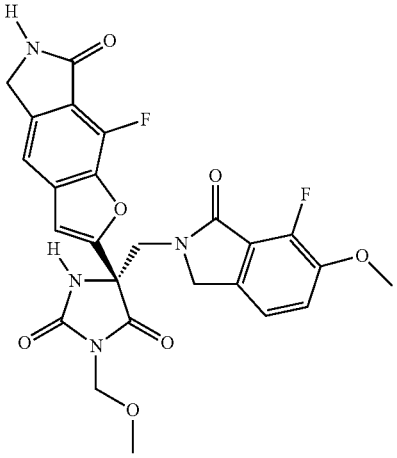 [SMILES: COCN1C(=O)N[C@@](CN2Cc3ccc(OC)c(F)c3C2=O)(c2cc3cc4c(c(F)c3o2)C(=O)NC4)C1=O] | N/A | 0 | 527.3 | 3 |
| 57 | 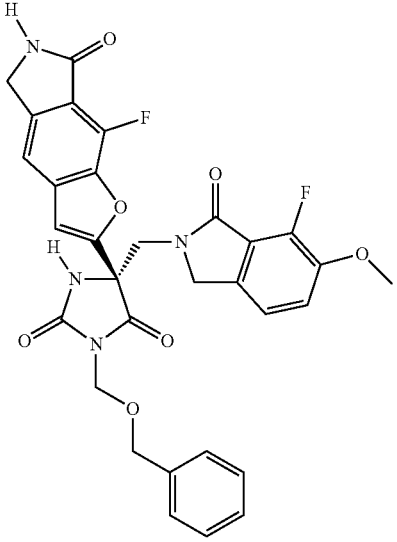 [SMILES: COc1ccc2c(c1F)C(=O)N(C[C@@]1(c3cc4cc5c(c(F)c4o3)C(=O)NC5)NC(=O)N(COCc3ccccc3)C1=O)C2] | N/A | 2244 | 603.3 | 3.67 |
| 58 | 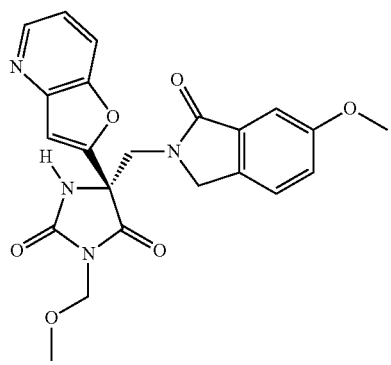 [SMILES: COCN1C(=O)N[C@@](CN2Cc3ccc(OC)cc3C2=O)(c2cc3ncccc3o2)C1=O] | N/A | 2125 | 437.2 | 2.7 |

TABLE 1-continued

| Compd # | STRUCTURE | hWBA IC$_{50}$ nM | PK (rrAUC[1]) parent | MS (M + 1)$^+$ | LC retention time[2] |
|---|---|---|---|---|---|
| 58.1 | 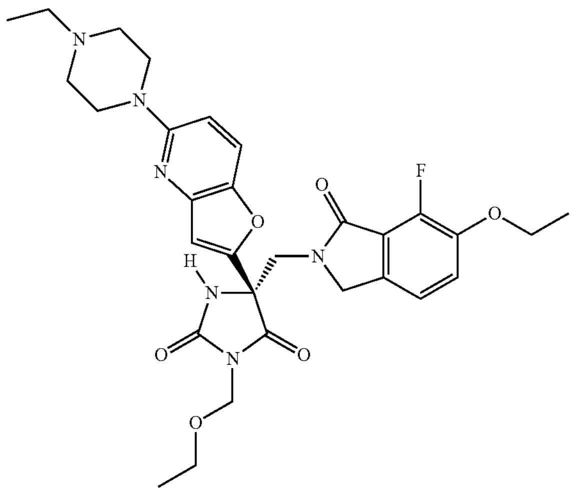 [SMILES: CCOCN1C(=O)N[C@@](CN2Cc3ccc(OCC)c(F)c3C2=O)(c2cc3nc(N4CCN(CC)CC4)ccc3o2)C1=O] | N/A | | 595.3 | 2.51 |
| 58.2 | 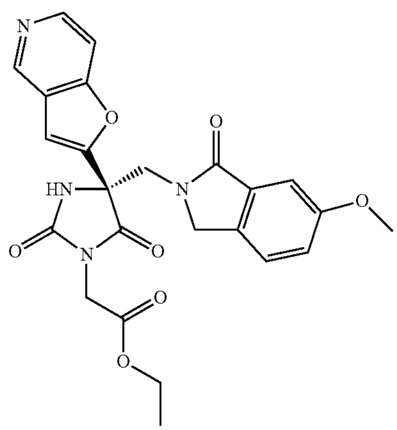 [SMILES: CCOC(=O)CN1C(=O)N[C@@](CN2Cc3ccc(OC)cc3C2=O)(c2cc3cnccc3o2)C1=O] | N/A | 0 | 479.3 | 2.40 |
| 58.3 | 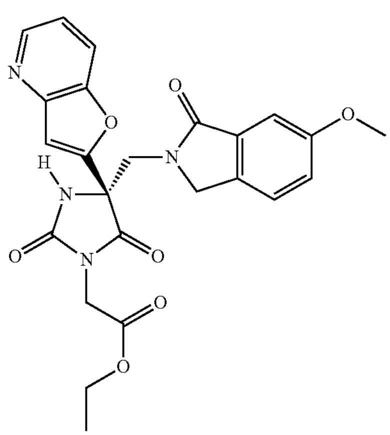 [SMILES: CCOC(=O)CN1C(=O)N[C@@](CN2Cc3ccc(OC)cc3C2=O)(c2cc3ncccc3o2)C1=O] | N/A | | 479.3 | 3.04 |

TABLE 1-continued

| Compd # | STRUCTURE | hWBA IC$_{50}$ nM | PK (rrAUC[1]) parent | MS (M + 1)$^+$ | LC retention time[2] |
|---|---|---|---|---|---|
| 59 | 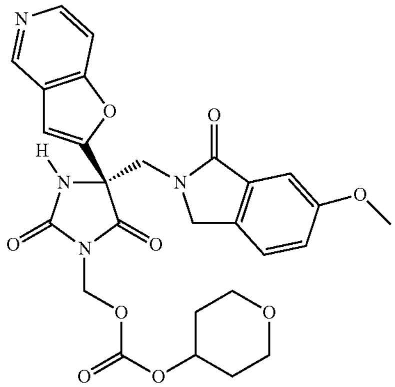 [SMILES: COc1ccc2c(c1)C(=O)N(C[C@@]1(c3cc4cnccc4o3)NC(=O)N(COC(=O)OC3CCOCC3)C1=O)C2] | 184 | 13539 | 551.2 | 1.169 |
| 60 | 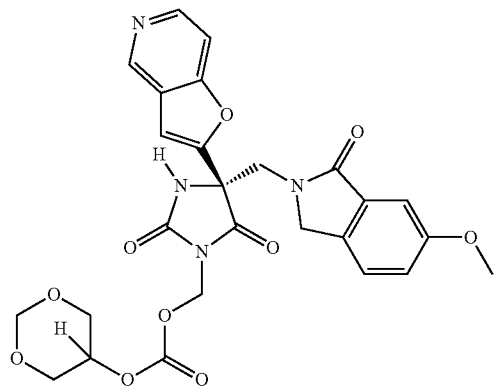 | 214 | 3181 | 523.3 | 2.28 |
| 60.1 | 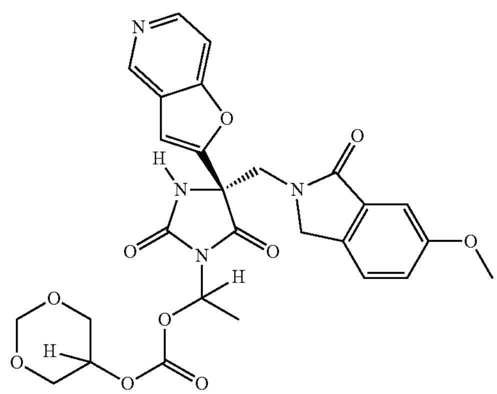 | N/D | 0 | 567.3 | 2.39 |
| 61 | 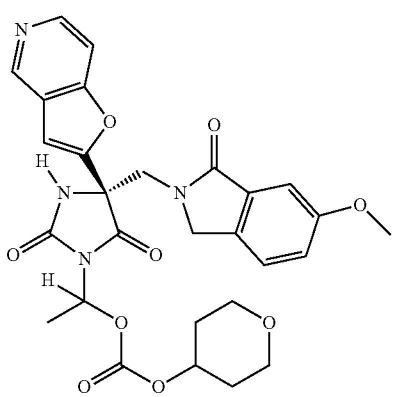 [SMILES: COc1ccc2c(c1)C(=O)N(C[C@@]1(c3cc4cnccc4o3)NC(=O)N(C(C)OC(=O)OC3CCOCC3)C1=O)C2] | 685 | 0 | 565.2 | 1.23 |

TABLE 1-continued
| Compd # | STRUCTURE | hWBA IC$_{50}$ nM | PK (rrAUC[1]) parent | MS (M + 1)$^+$ | LC retention time[2] |
|---|---|---|---|---|---|
| 62 | 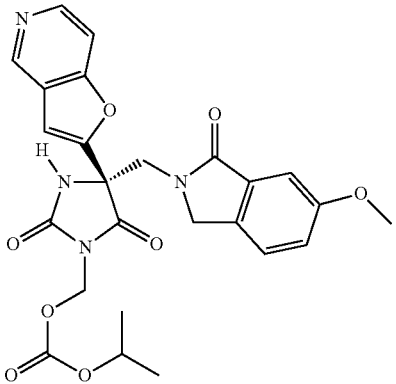 [SMILES: COc1ccc2c(c1)C(=O)N(C[C@@]1(c3cc4cnccc4o3)NC(=O)N(COC(=O)OC(C)C)C1=O)C2] | 250 | 0 | 509.3 | 2.71 |
| 63 | 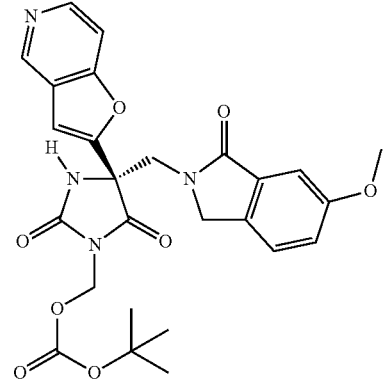 [SMILES: COc1ccc2c(c1)C(=O)N(C[C@@]1(c3cc4cnccc4o3)NC(=O)N(COC(=O)OC(C)(C)C)C1=O)C2] | N/A | 0 | 523.3 | 2.86 |
| 63.1 | 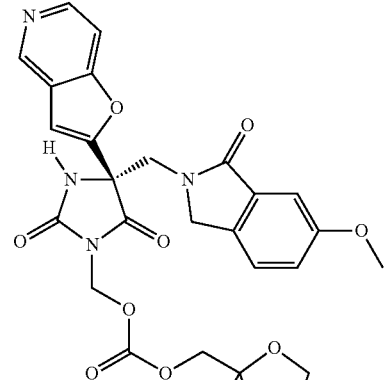 | 449 | 0 | 553.3 | 2.44 |

TABLE 1-continued

| Compd # | STRUCTURE | hWBA IC$_{50}$ nM | PK (rrAUC[1]) parent | MS (M + 1)$^+$ | LC retention time[2] |
|---|---|---|---|---|---|
| 63.2 | 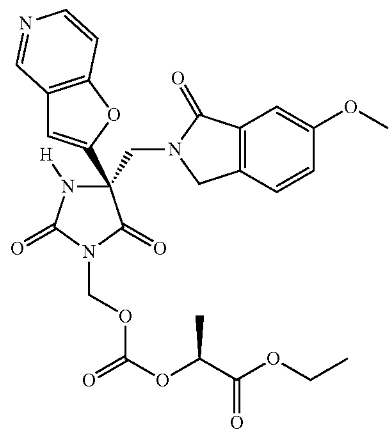 [SMILES: CCOC(=O)[C@H](C)OC(=O)OCN1C(=O)N[C@@](CN2Cc3ccc(OC)cc3C2=O)(c2cc3cnccc3o2)C1=O] | 738 | 0 | 567.3 | 2.75 |
| 63.3 | 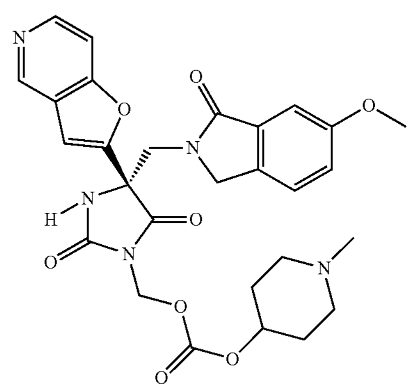 [SMILES: COc1ccc2c(c1)C(=O)N(C[C@@]1(c3cc4cnccc4o3)NC(=O)N(COC(=O)OC3CCN(C)CC3)C1=O)C2] | 1397 | 13539 | 564.1 | 0.818 |
| 63.4 | 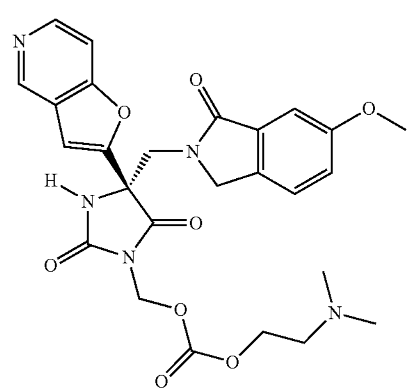 [SMILES: COc1ccc2c(c1)C(=O)N(C[C@@]1(c3cc4cnccc4o3)NC(=O)N(COC(=O)OCCN(C)C)C1=O)C2] | 427 | 1604 | 538.2 | 0.811 |

TABLE 1-continued

| Compd # | STRUCTURE | hWBA IC$_{50}$ nM | PK (rrAUC[1]) parent | MS (M + 1)$^+$ | LC retention time[2] |
|---|---|---|---|---|---|
| 63.5 | 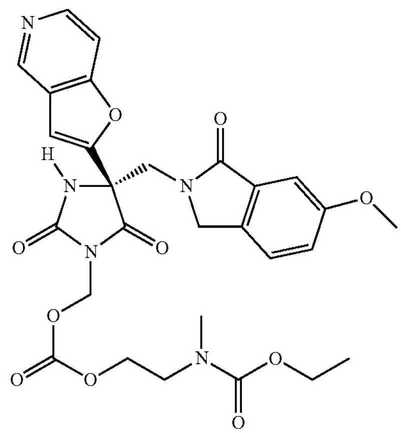 [SMILES: CCOC(=O)N(C)CCOC(=O)OCN1C(=O)N[C@@](CN2Cc3ccc(OC)cc3C2=O)(c2cc3cnccc3o2)C1=O] | N/A | 0 | 596.3 | |
| 63.6 | 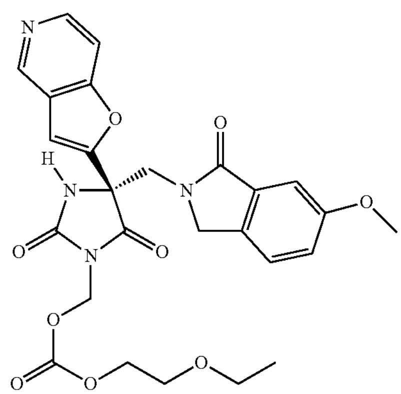 [SMILES: CCOCCOC(=O)OCN1C(=O)N[C@@](CN2Cc3ccc(OC)cc3C2=O)(c2cc3cnccc3o2)C1=O] | 208 | | 539.3 | 2.44 |
| 63.7 | 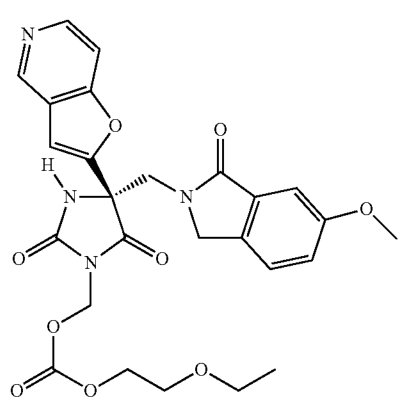 [SMILES: CCOCCOC(=O)OCN1C(=O)N[C@@](CN2Cc3ccc(OC)cc3C2=O)(c2cc3cnccc3o2)C1=O] | 328 | | 525.3 | 2.31 |

TABLE 1-continued

| Compd # | STRUCTURE | hWBA IC$_{50}$ nM | PK (rrAUC[1]) parent | MS (M + 1)$^+$ | LC retention time[2] |
|---|---|---|---|---|---|
| 63.8 | 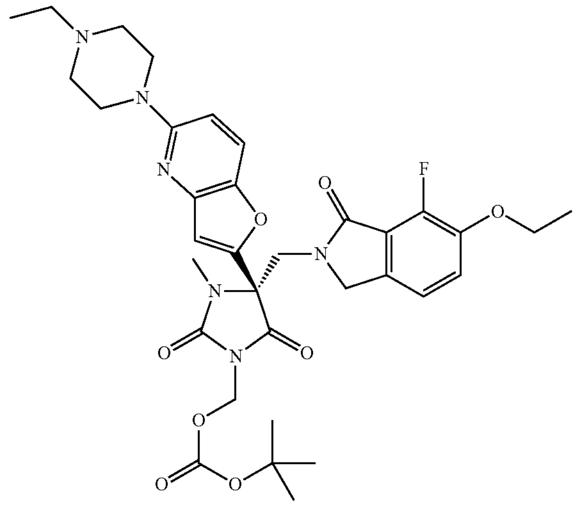 [SMILES: CCOc1ccc2c(c1F)C(=O)N(C[C@]1(c3cc4nc(N5CCN(CC)CC5)ccc4o3)C(=O)N(COC(=O)OC(C)(C)C)C(=O)N1C)C2] | N/D | | 667.4 | 3.26 |
| 64 | 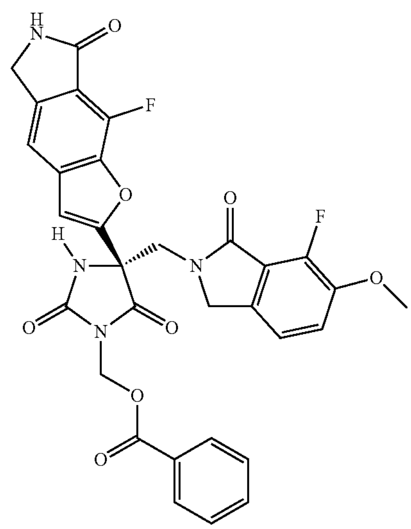 [SMILES: COc1ccc2c(c1F)C(=O)N(C[C@@]1(c3cc4cc5c(c(F)c4o3)C(=O)NC5)NC(=O)N(COC(=O)c3ccccc3)C1=O)C2] | 169 | 5393 | 617.3 | 3.58 |
| 65 | 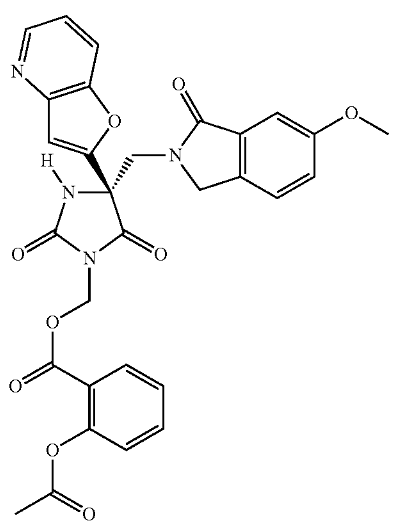 [SMILES: COc1ccc2c(c1)C(=O)N(C[C@@]1(c3cc4ncccc4o3)NC(=O)N(COC(=O)c3ccccc3OC(C)=O)C1=O)C2] | 560 | 4426 | 585.3 | 3.2 |

TABLE 1-continued

| Compd # | STRUCTURE | hWBA IC$_{50}$ nM | PK (rrAUC[1]) parent | MS (M + 1)$^+$ | LC retention time[2] |
|---|---|---|---|---|---|
| 66 | 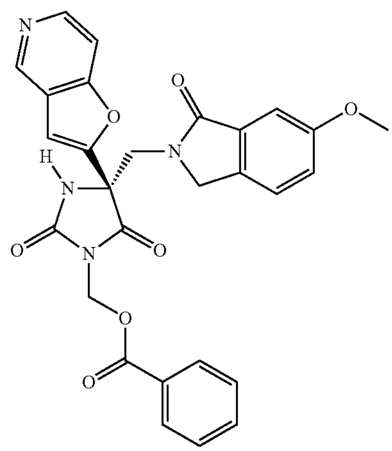 [SMILES: COc1ccc2c(c1)C(=O)N(C[C@@]1(c3cc4cnccc4o3)NC(=O)N(COC(=O)c3ccccc3)C1=O)C2] | N/D | 1861 | 527.3 | 2.8 |
| 66.1 | 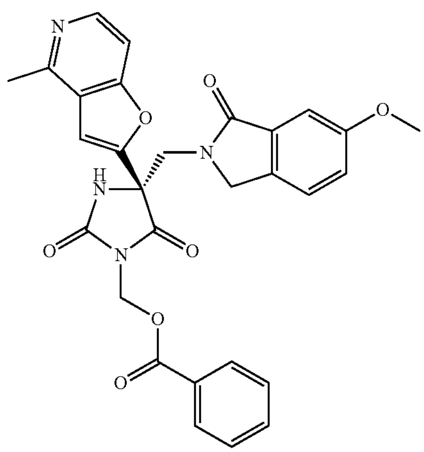 | N/D | 12047 | 559.3 | 2.67 |
| 67 | 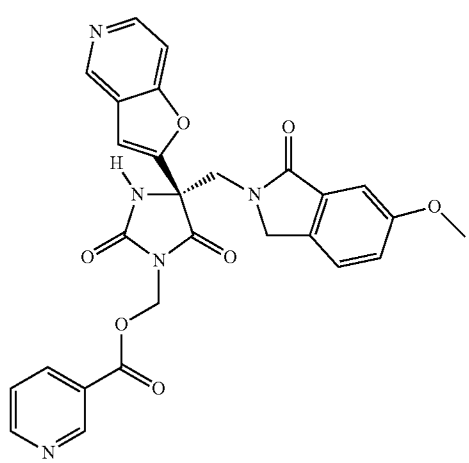 [SMILES: COc1ccc2c(c1)C(=O)N(C[C@@]1(c3cc4cnccc4o3)NC(=O)N(COC(=O)c3cccnc3)C1=O)C2] | 504 | 3448 | 528.3 | 1.95 |

| Compd # | STRUCTURE | hWBA IC$_{50}$ nM | PK (rrAUC[1]) parent | MS (M + 1)$^+$ | LC retention time[2] |
|---|---|---|---|---|---|
| 67.1 | 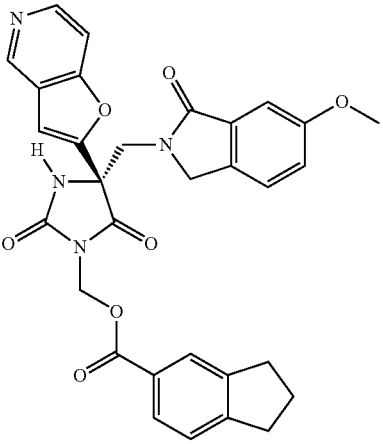 [SMILES: COc1ccc2c(c1)C(=O)N(C[C@@]1(c3cc4cnccc4o3)NC(=O)N(COC(=O)c3ccc4c(c3)CCC4)C1=O)C2] | N/D | | 567.3 | 3.16 |
| 67.2 | 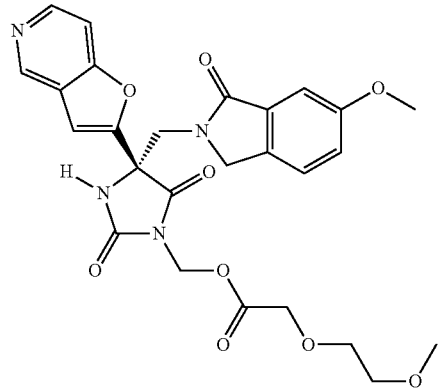 [SMILES: COCCOCC(=O)OCN1C(=O)N[C@@](CN2Cc3ccc(OC)cc3C2=O)(c2cc3cnccc3o2)C1=O] | 313 | | 539 | 2.54 |
| 68 | 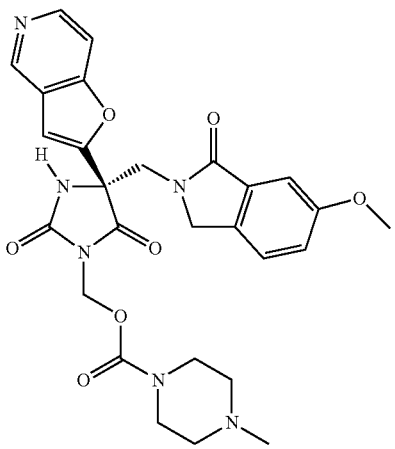 [SMILES: COc1ccc2c(c1)C(=O)N(C[C@@]1(c3cc4cnccc4o3)NC(=O)N(COC(=O)N3CCN(C)CC3)C1=O)C2] | 1310 | 13539 | 549.2 | 0.724 |

TABLE 1-continued

| Compd # | STRUCTURE | hWBA IC$_{50}$ nM | PK (rrAUC[1]) parent | MS (M + 1)$^+$ | LC retention time[2] |
|---|---|---|---|---|---|
| 69 | 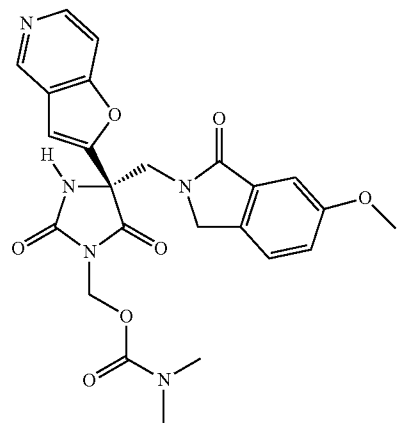 [SMILES: COc1ccc2c(c1)C(=O)N(C[C@@]1(c3cc4cnccc4o3)NC(=O)N(COC(=O)N(C)C)C1=O)C2] | N/A | 13539 | 494.1 | 1.061 |
| 70 | 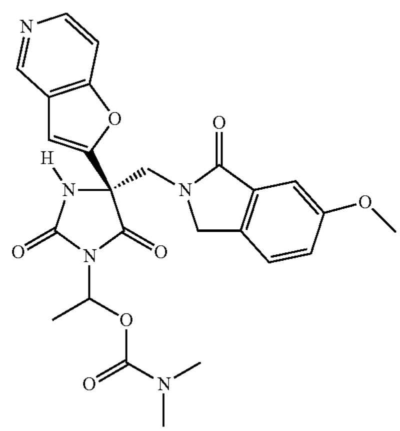 [SMILES: COc1ccc2c(c1)C(=O)N(C[C@@]1(c3cc4cnccc4o3)NC(=O)N(C(C)OC(=O)N(C)C)C1=O)C2] | 774 | | 508.1 | 1.15 |
| 71 | 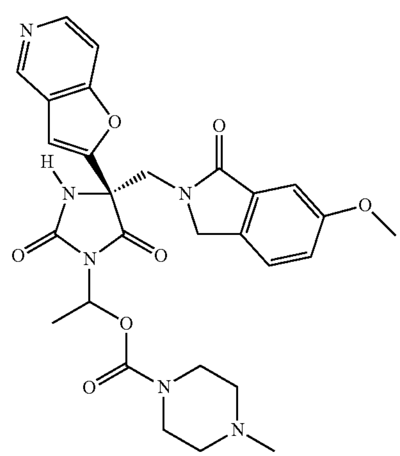 [SMILES: COc1ccc2c(c1)C(=O)N(C[C@@]1(c3cc4cnccc4o3)NC(=O)N(C(C)OC(=O)N3CCN(C)CC3)C1=O)C2] | 9918 | | 563.2 | 0.64 |

TABLE 1-continued

| Compd # | STRUCTURE | hWBA IC$_{50}$ nM | PK (rrAUC[1]) parent | MS (M + 1)$^+$ | LC retention time[2] |
|---|---|---|---|---|---|
| 72 | 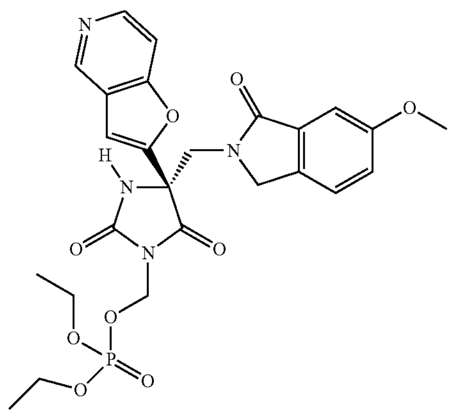 [SMILES: CCOP(=O)(OCC)OCN1C(=O)N[C@@](CN2Cc3ccc(OC)cc3C2=O)(c2cc3cnccc3o2)C1=O] | N/A | 48 | 559.3 | 2.86 |
| 73 | 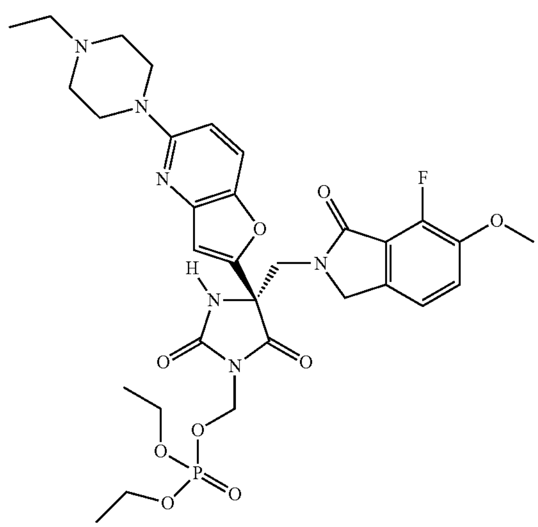 [SMILES: CCOP(=O)(OCC)OCN1C(=O)N[C@@](CN2Cc3ccc(OC)c(F)c3C2=O)(c2cc3nc(N4CCN(CC)CC4)ccc3o2)C1=O] | 255 | | 689.4 | 2.33 |
| 74 | 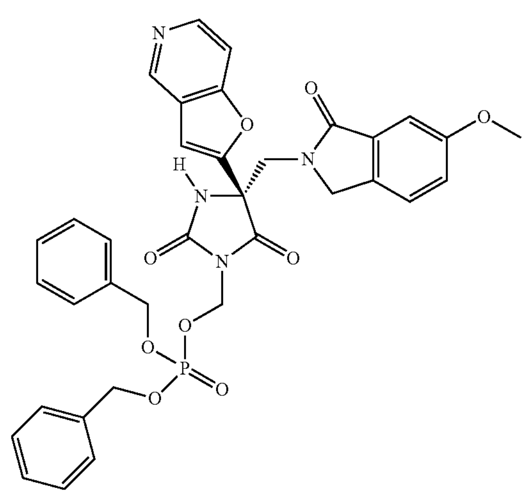 [SMILES: COc1ccc2c(c1)C(=O)N(C[C@@]1(c3cc4cnccc4o3)NC(=O)N(COP(=O)(OCc3ccccc3)OCc3ccccc3)C1=O)C2] | 3154 | | 683.4 | 3.39 |

TABLE 1-continued

| Compd # | STRUCTURE | hWBA IC$_{50}$ nM | PK (rrAUC[1]) parent | MS (M + 1)$^+$ | LC retention time[2] |
|---|---|---|---|---|---|
| 74.1 | 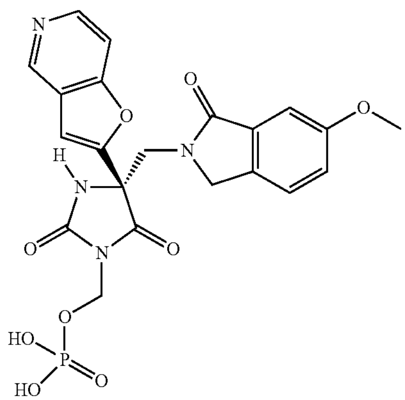 [SMILES: COc1ccc2c(c1)C(=O)N(C[C@@]1(c3cc4cnccc4o3)NC(=O)N(COP(=O)(O)O)C1=O)C2] | 720 | | 503.3 | 1.87 |
| 75 | 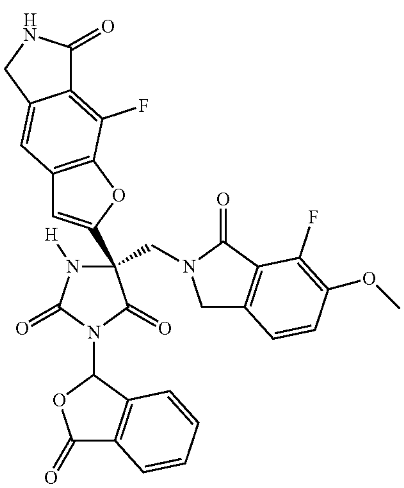 [SMILES: COc1ccc2c(c1F)C(=O)N(C[C@@]1(c3cc4cc5c(c(F)c4o3)C(=O)NC5)NC(=O)N(C3OC(=O)c4ccccc43)C1=O)C2] | N/D | 189 | 615.3 | 3.46 |
| 76 | 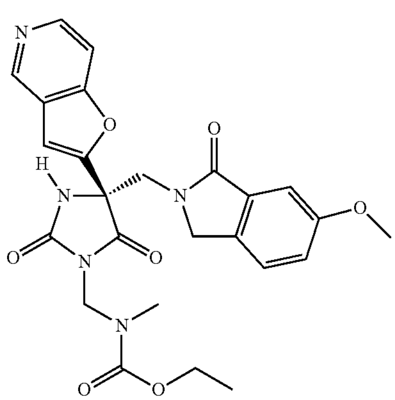 [SMILES: CCOC(=O)N(C)CN1C(=O)N[C@@](CN2Cc3ccc(OC)cc3C2=O)(c2cc3cnccc3o2)C1=O] | N/A | | 508.1 | 1.17 |

TABLE 1-continued

| Compd # | STRUCTURE | hWBA IC$_{50}$ nM | PK (rrAUC[1]) parent | MS (M + 1)$^+$ | LC retention time[2] |
|---|---|---|---|---|---|
| 76.1 | 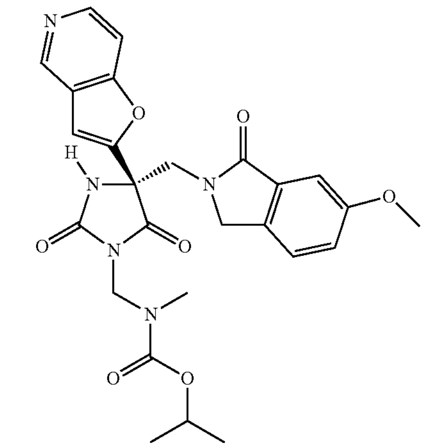 [SMILES: COc1ccc2c(c1)C(=O)N(C[C@@]1(c3cc4cnccc4o3)NC(=O)N(CN(C)C(=O)OC(C)C)C1=O)C2] | N/A | 528 | 507 | 2.71 |
| 76.2 | 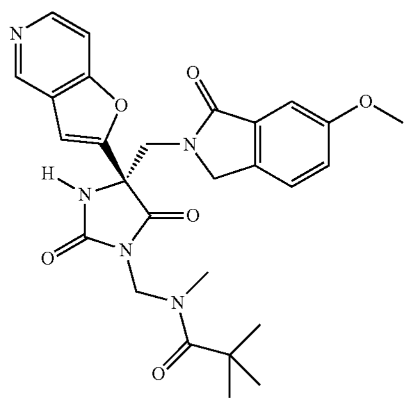 [SMILES: COc1ccc2c(c1)C(=O)N(C[C@@]1(c3cc4cnccc4o3)NC(=O)N(CN(C)C(=O)C(C)(C)C)C1=O)C2] | 754 | 310 | 520.2 | 1.259 |
| 77 | 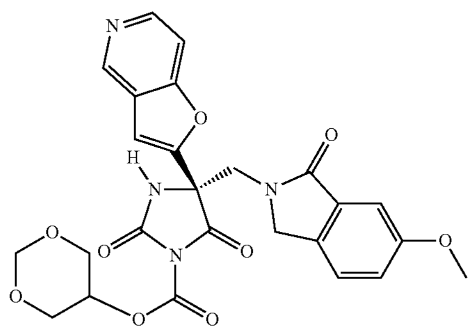 [SMILES: COc1ccc2c(c1)C(=O)N(C[C@@]1(c3cc4cnccc4o3)NC(=O)N(C(=O)OC3COCOC3)C1=O)C2] | N/A | 0 | 523.3 | 2.19 |
| 78 | 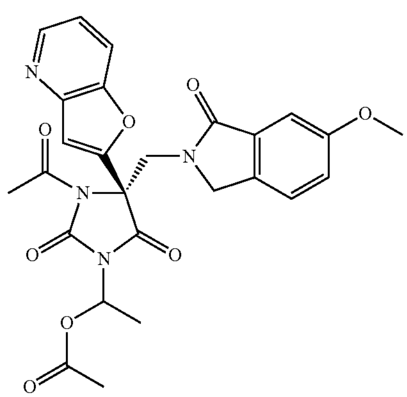 [SMILES: COc1ccc2c(c1)C(=O)N(C[C@]1(c3cc4ncccc4o3)C(=O)N(C(C)OC(C)=O)C(=O)N1C(C)=O)C2] | 2122 | | 521.3 | 2.87 |

TABLE 1-continued

| Compd # | STRUCTURE | hWBA IC$_{50}$ nM | PK (rrAUC$^1$) parent | MS (M + 1)$^+$ | LC retention time$^2$ |
|---|---|---|---|---|---|
| 79 | 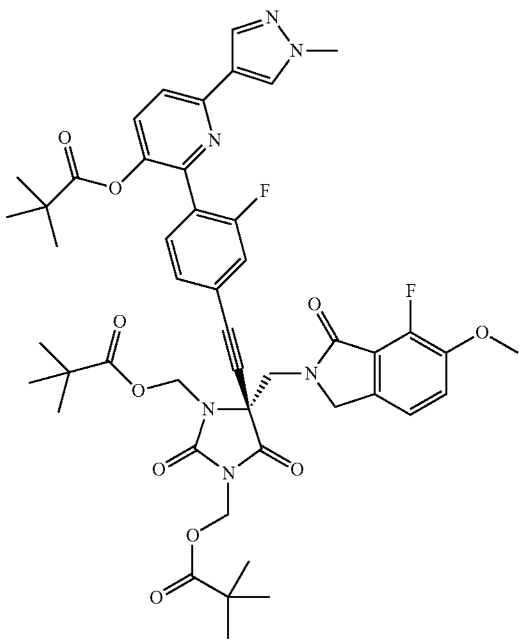 [SMILES: COc1ccc2c(c1F)C(=O)N(C[C@]1(C#Cc3ccc(-c4nc(-c5cnn(C)c5)ccc4OC(=O)C(C)(C)C)c(F)c3)C(=O)N(COC(=O)C(C)(C)C)C(=O)N1COC(=O)C(C)(C)C)C2] | N/A | | 897.5 | 5.41 |
| 80 | 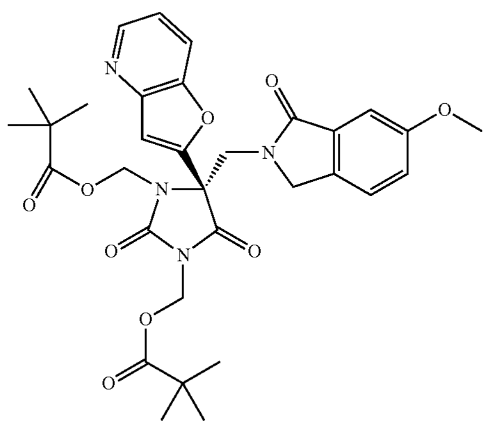 [SMILES: COc1ccc2c(c1)C(=O)N(C[C@]1(c3cc4ncccc4o3)C(=O)N(COC(=O)C(C)(C)C)C(=O)N1COC(=O)C(C)(C)C)C2] | N/A | 3092 | 621.3 | 4.36 |
| 81 | 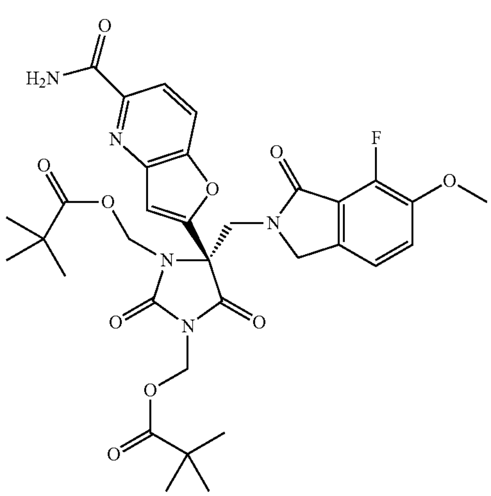 [SMILES: COc1ccc2c(c1F)C(=O)N(C[C@]1(c3cc4nc(C(N)=O)ccc4o3)C(=O)N(COC(=O)C(C)(C)C)C(=O)N1COC(=O)C(C)(C)C)C2] | 159 | | 682 | 4.32 |

TABLE 1-continued

| Compd # | STRUCTURE | hWBA IC$_{50}$ nM | PK (rrAUC[1]) parent | MS (M + 1)$^+$ | LC retention time[2] |
|---|---|---|---|---|---|
| 82 | 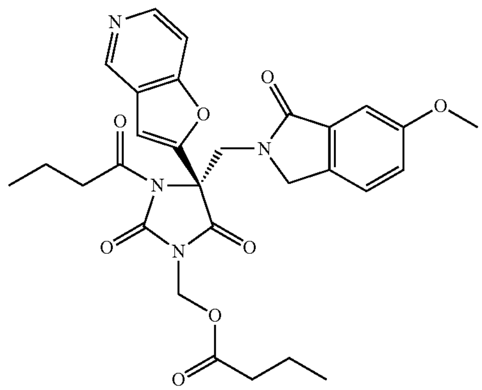 [SMILES: CCCC(=O)OCN1C(=O)N(C(=O)CCC)[C@@](CN2Cc3ccc(OC)cc3C2=O)(c2cc3cnccc3o2)C1=O] | N/D | 783 | 563.3 | 3.13 |
| 83 | 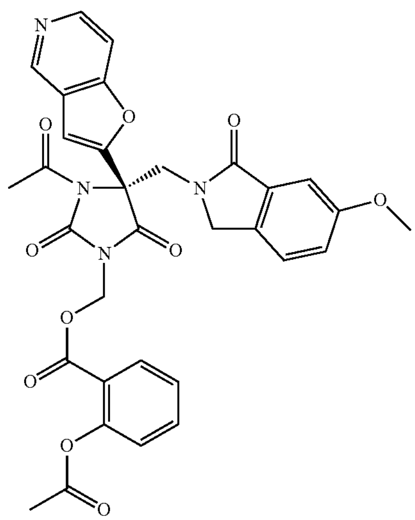 [SMILES: COc1ccc2c(c1)C(=O)N(C[C@]1(c3cc4cnccc4o3)C(=O)N(COC(=O)c3ccccc3OC(C)=O)C(=O)N1C(C)=O)C2] | 931 | 0 | 627.3 | 2.87 |
| 84 | 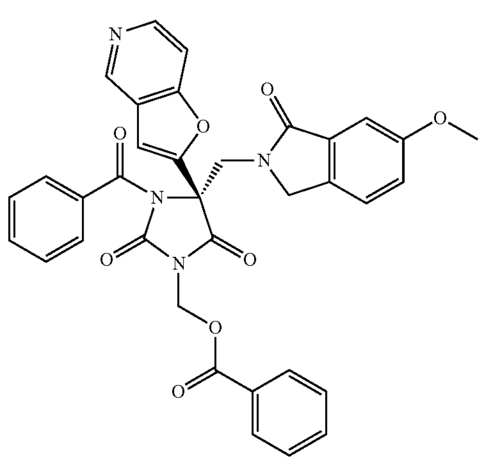 [SMILES: COc1ccc2c(c1)C(=O)N(C[C@]1(c3cc4cnccc4o3)C(=O)N(COC(=O)c3ccccc3)C(=O)N1C(=O)c1ccccc1)C2] | N/D | 126 | 631.3 | 3.21 |

TABLE 1-continued

| Compd # | STRUCTURE | hWBA IC$_{50}$ nM | PK (rrAUC[1]) parent | MS (M + 1)$^+$ | LC retention time[2] |
|---|---|---|---|---|---|
| 85 | 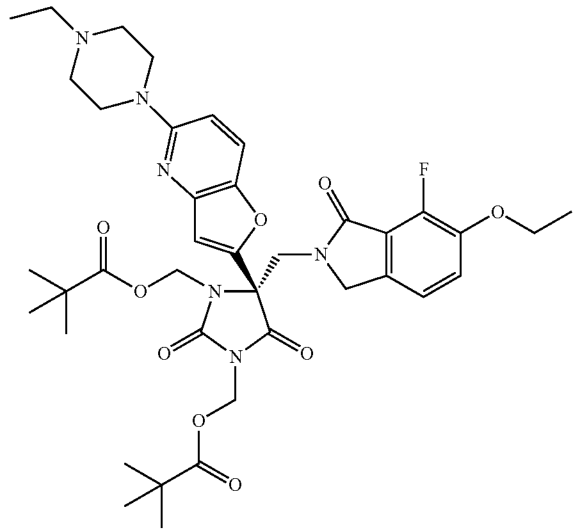 [SMILES: CCOc1ccc2c(c1F)C(=O)N(C[C@]1(c3cc4nc(N5CCN(CC)CC5)ccc4o3)C(=O)N(COC(=O)C(C)(C)C)C(=O)N1COC(=O)C(C)(C)C)C2] | 381 | | 765.4 | 3.5 |
| 86 | 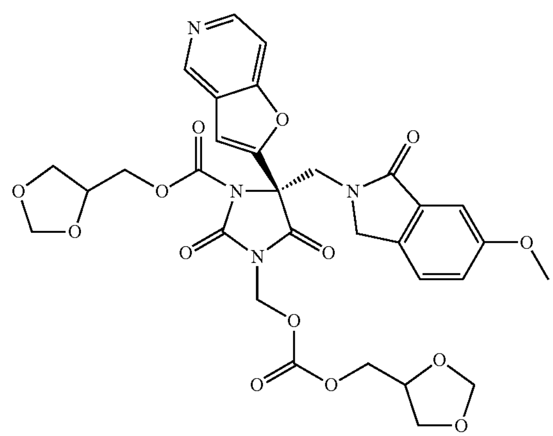 [SMILES: COc1ccc2c(c1)C(=O)N(C[C@]1(c3cc4cnccc4o3)C(=O)N(COC(=O)OCC3COCO3)C(=O)N1C(=O)OCC1COCO1)C2] | 5408 | 56 | 683.4 | 2.64 |
| 87 | 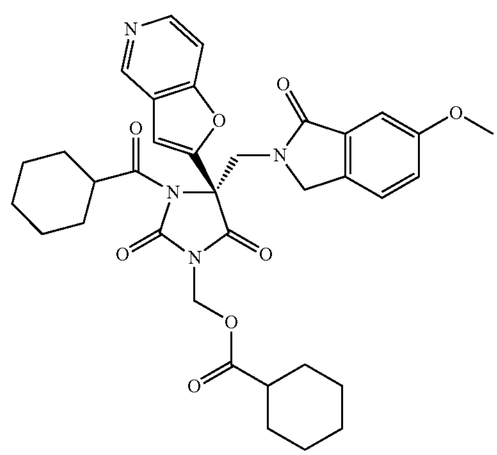 [SMILES: COc1ccc2c(c1)C(=O)N(C[C@]1(c3cc4cnccc4o3)C(=O)N(COC(=O)C3CCCCC3)C(=O)N1C(=O)C1CCCCC1)C2] | N/D | 0 | 643.4 | 3.85 |

TABLE 1-continued

| Compd # | STRUCTURE | hWBA IC$_{50}$ nM | PK (rrAUC[1]) parent | MS (M + 1)$^+$ | LC retention time[2] |
|---|---|---|---|---|---|
| 88 | 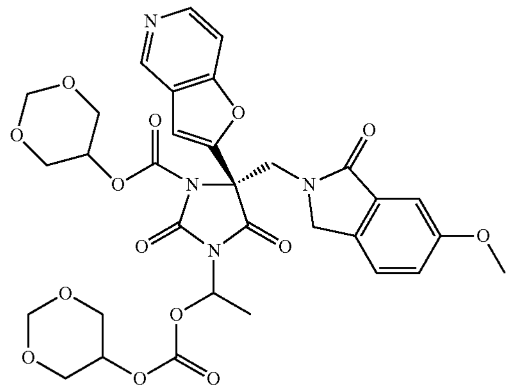 [SMILES: COc1ccc2c(c1)C(=O)N(C[C@]1(c3cc4cnccc4o3)C(=O)N(C(C)OC(=O)OC3COCOC3)C(=O)N1C(=O)OC1COCOC1)C2] | N/A | 0 | 697.4 | 2.57 |
| 89 | 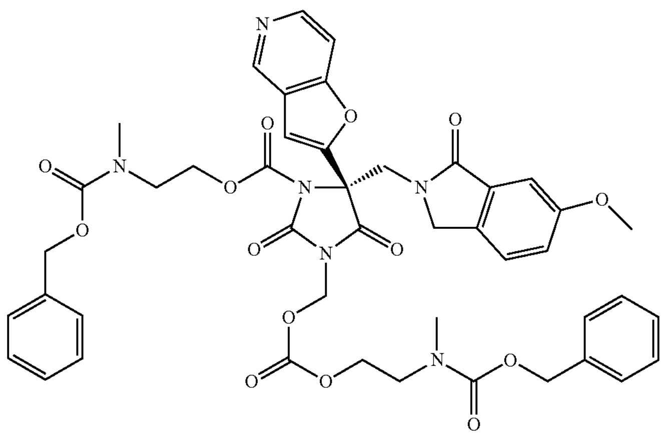 [SMILES: COc1ccc2c(c1)C(=O)N(C[C@]1(c3cc4cnccc4o3)C(=O)N(COC(=O)OCCN(C)C(=O)OCc3ccccc3)C(=O)N1C(=O)OCCN(C)C(=O)OCc1ccccc1)C2] | 4890 | | 893.5 | 3.55 |
| 89.1 | 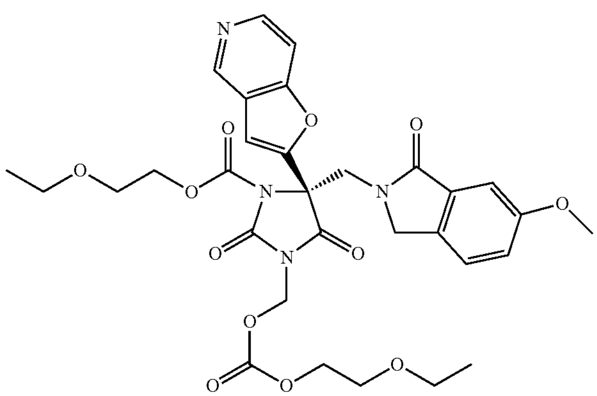 [SMILES: CCOCCOC(=O)OCN1C(=O)N(C(=O)OCCOCC)[C@@](CN2Cc3ccc(OC)cc3C2=O)(c2cc3cnccc3o2)C1=O] | 3146 | | 655.4 | 2.76 |

[1] rapid rat AUC (rrAUC) nM · h of the drug.

[2] Instrument (MS) name: PE Sciex API 150-EX single stage quadrupole

Solvent pumps: Shimadzu LC-10AD

Column: Phenomenex (Gemini, 5 micron, C18, 4.6 i.d.)

Solvent A: Water w/0.05% TFA (v/v)

Solvent B: Acetonitrile w/0/05% TFA (v/v)

Flow rate: 1 ml/min

Starting B conc: 10%

Gradient B 10%-95% in 5 mins, hold 2 mins, 95%-10% in 1 min

[3] N/D = Not Determined

[4] N/A = Not Active

It will be appreciated by those skilled in the art that changes could be made to the embodiments described above without departing from the broad inventive concept thereof. It is understood, therefore, that this invention is not limited to the particular embodiments disclosed, but it is intended to cover modifications that are within the spirit and scope of the invention, as defined by the appended claims.

Each document referred to herein is incorporated by reference in its entirety for ail purposes.

Therefore, we claim:

1. A compound represented by Formula (I):

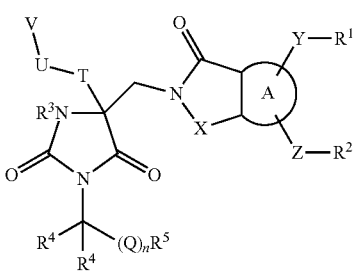

or a pharmaceutically acceptable salt thereof, wherein:

ring A is selected from the group consisting of aryl and heteroaryl, each of which is substituted with —Y—$R^1$ and —Z—$R^2$ as shown;

Q is —O—;

X is selected from the group consisting of —S—, —O—, —S(O)$_2$—, —S(O)—, —(CR$_2$)$_p$— and —N(R')—;

T is absent or present, and if present, T is selected from the group consisting of alkyl, alkenyl, alkynyl, cycloalkyl, cycloalkenyl, heterocyclyl, heterocyclenyl, aryl, and heteroaryl, wherein when each of said T cycloalkyl, cycloalkenyl, heterocyclyl, heterocyclenyl, aryl and heteroaryl contains two radicals on adjacent carbon atoms, said radicals may optionally be taken together with the carbon atoms to which they are attached to form a second five- or six-membered cycloalkyl, cycloalkenyl, heterocyclyl, heterocyclenyl, aryl or heteroaryl ring, wherein when each of said optional second five- or six-membered cycloalkyl, cycloalkenyl, heterocyclyl, heterocyclenyl, aryl or heteroaryl further contains two radicals on adjacent carbon atoms, said radicals may optionally be taken together with the carbon atoms to which they are attached to form a further third five- or six-membered cycloalkyl, cycloalkenyl, heterocyclyl, heterocyclenyl, aryl or heteroaryl ring wherein each of the aforementioned T aryl, and heteroaryl, optionally with said first and/or second five- to six-membered cycloalkyl, cycloalkenyl, heterocyclyl, heterocyclenyl, aryl or heteroaryl is independently unsubstituted or substituted with one to four $R^{10}$ moieties which can be the same or different;

U is absent or present or absent, and if present, U is selected from the group consisting of —N($R^6$)—, —N($R^6$)C($R^6$)$_2$—, —N($R^6$)C(O)—, —N($R^6$)S(O)—, —N($R^6$)S(O)$_2$—, —N($R^6$)C(O)N($R^6$)—, —N($R^6$)C(S)N($R^6$)—, —O—, —O—C(O)NH—, —OC(O)N(alkyl)-, —C(O)—, —C(O)O—, —C(O)NH—, —C(O)N(alkyl)-, —C(=N—OH)-alkyl-, and —C(=N—O-alkyl)-alkyl-;

V is absent or present and if present V is selected from the group consisting of alkyl, alkenyl, alkynyl, cycloalkyl, cycloalkenyl, heterocyclyl, heterocyclenyl, aryl, and heteroaryl, wherein when each of said V cycloalkyl, cycloalkenyl, heterocyclyl, heterocyclenyl, aryl, and heteroaryl contains two radicals on adjacent carbon atoms, said radicals may optionally be taken together with the carbon atoms to which they are attached to form a five- or six-membered cycloalkyl, aryl, heterocyclyl or heteroaryl ring; wherein each of said V alkyl, alkynyl, cycloalkyl, heterocyclyl, aryl, and heteroaryl heterocyclyl, optionally with said five- or six-membered cycloalkyl, aryl, heterocyclyl, or heteroaryl is independently unsubstituted or substituted with one to four $R^{10}$ moieties which can be the same or different;

Y is selected from the group consisting of a covalent bond, —(C($R^6$)$_2$)$_q$—, —N($R^6$)—, —C(O)N($R^6$)—, —N($R^6$)C(O)—, —N($R^6$)C(O)N($R^6$)—, —S(O)$_2$N($R^6$)—, —N($R^6$)—S(O)$_2$—, —O—, —S—, —C(O)—, —S(O)—, and —S(O)$_2$—;

Z is selected from the group consisting of a covalent bond, —(C($R^6$)$_2$)$_q$—, —N($R^6$)—, —C(O)N($R^6$)—, —N($R^6$)C(O)—, —N($R^6$)C(O)N($R^6$)—, —S(O)$_2$N($R^6$)—, —N($R^6$)—S(O)$_2$—, —O—, —S—, —C(O)—, —S(O)—, and —S(O)$_2$—;

n is 1 p is 1 to 3;

q is 1 to 3;

each R independently is selected from the group consisting of H, alkyl, and aryl;

R' is selected from the group consisting of H, alkyl, and aryl;

$R^1$ is selected from the group consisting of H, cyano, —C(O)OH, —C(O)O-alkyl, —C(O)NH$_2$, —C(O)NH(alkyl), —C(O)N(alkyl)$_2$, alkynyl, halogen, alkyl, cycloalkyl, haloalkyl, aryl, heteroaryl, and heterocyclyl, wherein when each of said cycloalkyl, heterocyclyl, aryl and heteroaryl contains two radicals on adjacent carbon atoms, said radicals may optionally be taken together with the carbon atoms to which they are attached to form a five- or six-membered cycloalkyl, aryl, heterocyclyl or heteroaryl ring; wherein each of the $R^1$ alkyl, alkynyl, aryl, heteroaryl, and heterocyclyl, optionally with the five or six-membered cycloalkyl, aryl, heterocyclyl or heteroaryl ring is unsubstituted or optionally independently substituted with one to four $R^{20}$ moieties which can be the same or different; with the proviso that when Y is —N($R^{15}$)—, —S— or —O—, then $R^1$ is not halogen or cyano;

$R^2$ is selected from the group consisting of H, cyano, —C(O)OH, —C(O)O-alkyl, —C(O)NH$_2$, —C(O)NH(alkyl), —C(O)N(alkyl)$_2$, alkynyl, halogen, alkyl, cycloalkyl, cycloalkenyl, haloalkyl, aryl, heteroaryl, heterocyclenyl, and heterocyclyl, wherein when each of said cycloalkyl, cycloalkenyl, heterocyclyl, heterocyclenyl, aryl and heteroaryl contains two radicals on adjacent carbon atoms, said radicals may optionally be taken together with the carbon atoms to which they are attached to form a five- or six-membered cycloalkyl, cyclalkenyl, aryl, heterocyclyl, heterocyclenyl, or heteroaryl ring; wherein each of the $R^2$ alkyl, cycloalkyl, cycloalkenyl, aryl, heteroaryl, heterocyclenyl, and heterocyclyl, optionally with the five or six-membered cycloalkyl, cycloalkenyl, aryl, heterocyclyl, heterocyclenyl, or heteroaryl ring is unsubstituted or optionally independently substituted with one to four $R^{20}$ moieties which can be the same or different; with the proviso that when Y is —N($R^{15}$)—, —S— or —O—, then $R^2$ is not halogen or cyano;

$R^3$ is selected from the group consisting of H, alkyl, alkyl substituted with —O—C(=O)alkyl, cycloalkyl, cycloalkenyl, heterocyclyl, heterocyclenyl, aryl, heteroaryl, —C(=O)alkyl, —C(=O)cycloalkyl, —C(=O)heterocyclyl, —C(=O)aryl, —C(=O)heteroaryl, —C(=O)O-alkyl, —C(=O)O-alkyl substituted on the alkyl with alkoxy, —C(=O)O-alkyl substituted on the alkyl with —N(alkyl)-C(=O)—O-alkyl-aryl, —C(=O)O-cycloalkyl, —C(=O)O-heterocyclyl, —C(=O)O-aryl, and —C(=O)O-heteroaryl;

each $R^4$ is H;

$R^5$ is selected from the group consisting of H, alkyl, alkyl substituted with —O-alkyl-O-alkyl-O-alkyl, alkyl substituted with heterocyclyl, alkyl substituted with aryl, heterocyclyl, aryl, heteroaryl, —C(=O)N($R^7$)$_2$, —C(=O)-alkyl, —C(=O)-alkyl substituted on the alkyl with —O-alkyl-O-alkyl, —C(=O)-cycloalkyl, —C(=O)-heterocyclyl, —C(=O)-aryl, —C(=O)-heteroaryl, —C(=O)—O-alkyl, —C(=O)—O-alkyl substituted on the alkyl with —N($R^7$)$_2$, —C(=O)—O-alkyl substituted on the alkyl with —C(=O)—O-alkyl, —C(=O)—O-alkyl substituted on the alkyl with —N($R^7$)—C(=O)-alkyl-aryl, —C(=O)—O-alkyl substituted on the alkyl with heterocyclyl, —C(=O)-β-cycloalkyl, —C(=O)—O-heterocyclyl, —C(=O)—O-aryl, —C(=O)—O-heteroaryl, —P(=O)(—OH)$_2$, —P(=O)(—O-alkyl)$_2$, wherein when each of said "cycloalkyl", "heterocyclyl", "aryl", or "heteroaryl" in any of the aforementioned $R^5$ groups contains two radicals on adjacent carbon atoms, said radicals may optionally be taken together with the carbon atoms to which they are attached to form a five- or six-membered cycloalkyl, aryl, heterocyclyl or heteroaryl ring;

each $R^6$ is the same or different and is independently selected from the group consisting of H, alkyl, cycloalkyl, cycloalkenyl, haloalkyl, hydroxy, -alkylcycloalkyl, -alkyl-N(alkyl)$_2$, heterocyclyl, heterocyclenyl, aryl, and heteroaryl, wherein when each of said cycloalkyl, cycloalkenyl, heterocyclyl, heterocyclenyl, aryl, and heteroaryl contains two radicals on adjacent carbon atoms, said radicals may optionally be taken together with the carbon atoms to which they are attached to form a five- or six-membered cycloalkyl, cycloalkenyl, aryl, heterocyclyl, heterocyclenyl or heteroaryl ring;

each $R^7$ is the same or different and is independently H or alkyl;

$R^{10}$ is selected from the group consisting of hydrogen, cyano, nitro, —OC(O)$R^{15}$, —C($R^{15}$)=N—O$R^{15}$, —O$R^{15}$, —S$R^{15}$, —N($R^{15}$)$_2$, —S(O)$R^{15}$, —S(O)$_2R^{15}$, —N($R^{15}$)S(O)$_2R^{15}$, —N($R^{15}$)—C(O)—$R^{15}$, —N($R^{15}$)—C(O)—N($R^{15}$)$_2$, —N($R^{15}$)—C(O)—O$R^{15}$, —OC(O)N($R^{15}$)$_2$, —C(O)N($R^{15}$)—S(O)$_2R^{15}$, —S(O)$_2$N($R^{15}$)—C(O)—$R^{15}$, —C(O)N($R^{15}$)C(O)$R^{15}$, —C(O)N($R^{15}$)C(O)N$R^{15}$, —S(O)$_2$N($R^{15}$)$_2$, —N($R^{15}$)—C(=N$R^{15}$)—N($R^{15}$)$_2$, —N($R^{15}$)—C(=N—CN)—N($R^{15}$)$_2$, -haloalkoxy, —C(O)O$R^{15}$, —C(O)$R^{15}$, —C(O)N($R^{15}$)$_2$, halogen, alkyl, haloalkyl, aryl, heteroaryl, heterocyclyl, heterocyclenyl, cycloalkenyl, and cycloalkyl, wherein each of the $R^{10}$ alkyl, aryl, heteroaryl, heterocyclyl, heterocyclenyl, cycloalkenyl, and cycloalkyl is unsubstituted or optionally independently substituted with one to four $R^{30}$ moieties which can be the same or different;

or wherein two $R^{10}$ moieties, when attached to the same or adjacent carbon atoms may optionally be taken together with the carbon atom(s) to which they are attached to form a cycloalkyl, cycloalkenyl, heterocyclyl, heterocyclenyl, aryl, or heteroaryl ring;

each $R^{15}$ is the same or different and is independently selected from the group consisting of H, alkyl, cycloalkyl, haloalkyl, hydroxy, heterocyclyl, aryl, and heteroaryl, wherein when each of said cycloalkyl, heterocyclyl, aryl, and heteroaryl contains two radicals on adjacent carbon atoms, said radicals may optionally be taken together with the carbon atoms to which they are attached to form a five- or six-membered cycloalkyl, aryl, heterocyclyl or heteroaryl ring;

$R^{20}$ is selected from the group consisting of hydrogen, cyano, nitro, —OC(O)$R^{15}$, —C($R^{15}$)=N—O$R^{15}$, —O$R^{15}$, —S$R^{15}$, —N($R^{15}$)$_2$, —S(O)$R^{15}$, —S(O)$_2R^{15}$, —N($R^{15}$)S(O)$_2R^{15}$, —N($R^{15}$)—C(O)—$R^{15}$, —N($R^{15}$)—C(O)—N($R^{15}$)$_2$—N($R^{15}$)—C(O)O$R^{15}$, —OC(O)N($R^{15}$)$_2$, —C(O)N($R^{15}$)—S(O)$_2R^{15}$, —S(O)$_2$N($R^{15}$)—C(O)—$R^{15}$, —C(O)N($R^{15}$)C(O)$R^{15}$, —C(O)N($R^{15}$)C(O)N$R^{15}$, —S(O)$_2$N($R^{15}$)$_2$, —N($R^{15}$)—C(=N$R^{15}$)—N($R^{15}$)$_2$, —N($R^{15}$)—C(=N—CN)—N($R^{15}$)$_2$, -haloalkoxy, —C(O)O$R^{15}$, —C(O)$R^{15}$, —C(O)N($R^{15}$)$_2$, halogen, alkyl, haloalkyl, aryl, heteroaryl, heterocyclyl, heterocyclenyl, cycloalkenyl, and cycloalkyl, wherein when each of said $R^{20}$ aryl, heteroaryl, heterocyclyl, heterocyclenyl, cycloalkenyl, and cycloalkyl contains two radicals on adjacent carbon atoms, said radicals may optionally be taken together with the carbon atoms to which they are attached to form a five- or six-membered cycloalkyl, cycloalkenyl, aryl, heterocyclyl, heterocyclenyl, or heteroaryl ring; wherein each of said $R^{20}$ alkyl, aryl, heteroaryl, heterocyclyl, heterocyclenyl, cycloalkenyl, and cycloalkyl, optionally with said five- or six-membered cycloalkyl, cycloalkenyl, aryl, heterocyclyl, heterocyclenyl, or heteroaryl ring is unsubstituted or substituted with one to four moieties selected independently from the group consisting of alkyl, halo, haloalkyl, hydroxy, alkoxy, haloalkoxy, hydroxyalkyl, cyano, nitro, —NH$_2$, —NH(alkyl), and —N(alkyl)$_2$;

or when two $R^{20}$ moieties when attached to the same or adjacent carbon atoms may optionally be taken together with the carbon atom(s) to which they are attached to form a cycloalkyl, cycloalkenyl, heterocyclyl, aryl, or heteroaryl ring;

$R^{30}$ is selected from the group consisting of hydrogen, cyano, nitro, —OC(O)$R^{15}$, —C($R^{15}$)=N—O$R^{15}$, —O$R^{15}$, —S$R^{15}$, —N($R^{15}$)$_2$, —S(O)$R^{15}$, —S(O)$_2R^{15}$, —N($R^{15}$)S(O)$_2R^{15}$, —N($R^{15}$)—C(O)—$R^{15}$, —N($R^{15}$)—C(O)—N($R^{15}$)$_2$, —N($R^{15}$)—C(O)—O$R^{15}$, —OC(O)N($R^{15}$)$_2$, —C(O)N($R^{15}$)—S(O)$_2R^{15}$, —S(O)$_2$N($R^{15}$)—C(O)—$R^{15}$, —C(O)N($R^{15}$)C(O)$R^{15}$, —C(O)N($R^{15}$)C(O)N$R^{15}$, —S(O)$_2$N($R^{15}$)$_2$, —N($R^{15}$)—C(=N$R^{15}$)—N($R^{15}$)$_2$, —N($R^{15}$)—C(=N—CN)—N($R^{15}$)$_2$, -haloalkoxy, —C(O)O$R^{15}$, —C(O)$R^{15}$, —C(O)N($R^{15}$)$_2$, halogen, alkyl, haloalkyl, aryl, heteroaryl, heterocyclyl, heterocyclenyl, cycloalkenyl, and cycloalkyl, wherein when each of said $R^{30}$ aryl, heteroaryl, heterocyclyl, heterocyclenyl, cycloalkenyl, and cycloalkyl contains two radicals on adjacent carbon atoms, said radicals may optionally be taken together with the carbon atoms to which they are attached to form a five- or six-membered cycloalkyl, cycloalkenyl, aryl, heterocyclyl, heterocyclenyl, or heteroaryl ring; wherein each of said $R^{30}$ alkyl, aryl, heteroaryl, heterocyclyl, heterocyclenyl, cycloalkenyl and cycloalkyl, optionally with said five- or six-membered cycloalkyl, cycloalkenyl aryl, heterocyclyl, heterocyclenyl, or heteroaryl ring is unsubstituted or substituted with one to four moieties selected independently from the group consisting of alkyl, halo, haloalkyl, hydroxy, alkoxy, haloalkoxy, cyano, nitro, —NH₂, —NH(alkyl), and —N(alkyl)₂;

or when two $R^{30}$ moieties when attached to the same or adjacent carbon atoms may optionally be taken together with the carbon atom(s) to which they are attached to form a cycloalkyl, cycloalkenyl, heterocyclyl, aryl, or heteroaryl ring;

with the proviso that at least one of T, U, and V must be present.

2. The compound of claim 1, wherein X is —(C(R)₂)$_p$—, wherein p is 1 or 2.

3. The compound of claim 1, wherein T is selected from the group consisting of aryl, heteroaryl and alkynyl, wherein when any of said T heteroaryl or aryl contains two radicals on adjacent carbon atoms, said radicals may optionally be taken together with the carbon atoms to which they are attached to form a second five- or six-membered heterocyclyl, aryl or heteroaryl ring, wherein when each of said optional second five- or six-membered heterocyclyl, aryl or heteroaryl further contains two radicals on adjacent carbon atoms, said radicals may optionally be taken together with the carbon atoms to which they are attached to form a further third five- or six-membered heterocyclyl, aryl or heteroaryl ring, wherein the aforementioned T heteroaryl or aryl, optionally with said second and/or third five- to six-membered heterocyclyl, aryl or heteroaryl is independently unsubstituted or substituted with one to four $R^{10}$ moieties which can be the same or different.

4. The compound of claim 3, wherein T is heteroaryl, wherein said heteroaryl optionally with said second and/or third five- to six-membered heterocyclyl, aryl or heteroaryl is selected from the group consisting of:

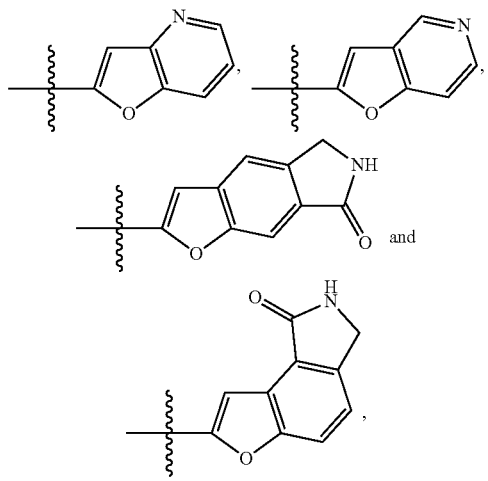

each of which is optionally substituted.

5. The compound of claim 1, wherein U is selected from the group consisting of —N(H)C(O)—, —N(H)—S(=O)₂—, and —N(H)—.

6. The compound of claim 1, wherein V is selected from the group consisting of heterocyclyl, aryl, heteroaryl, wherein when each of said V heterocyclyl, aryl, and heteroaryl contains two radicals on adjacent carbon atoms, said radicals may optionally be taken together with the carbon atoms to which they are attached to form a five- or six-membered aryl, het-erocyclyl or heteroaryl ring; wherein each of said V heterocyclyl, aryl, and heteroaryl optionally with said five- or six-membered aryl, heterocyclyl, or heteroaryl is independently unsubstituted or substituted with one to four $R^{10}$ moieties which can be the same or different.

7. The compound of claim 6, wherein V is selected from the group consisting of heterocyclyl and heteroaryl, wherein said heterocyclyl and heteroaryl are selected from the group consisting of pyridinyl, piperazinyl, azetidin-2-one-1-yl, 2-pyrrolidinone-1-yl, pyrazolyl, benzopyrazolyl, pyrrolyl,

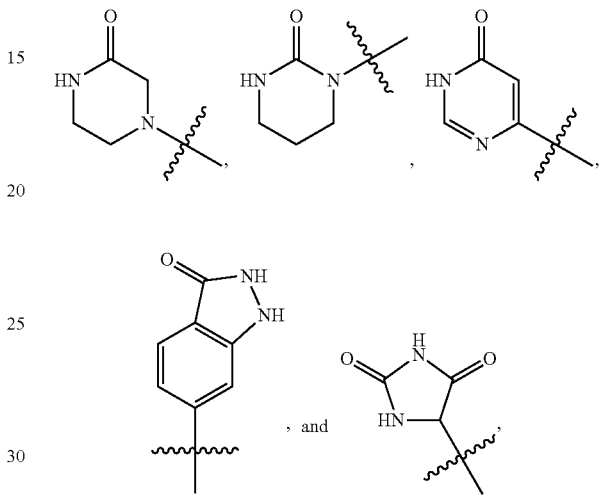

each of which is optionally substituted.

8. The compound of claim 1, wherein ring A is selected from the group consisting of phenyl, thiophenyl, pyridyl, pyrimidyl, and

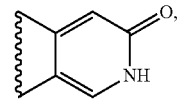

each of which is substituted with —Y—$R^1$ and —Z—$R^2$ as shown.

9. The compound of claim 8, wherein ring A is phenyl.

10. The compound of claim 1, wherein each of Y and Z is independently selected from the group consisting of a covalent bond and —O—.

11. The compound of claim 1, wherein $R^3$ is selected from the group consisting of H, alkyl, —C(=O)alkyl, —C(=O) cycloalkyl, —C(=O)aryl, —C(=O)O-alkyl, -and —C(=O)O-heterocyclyl.

12. The compound of claim 1, wherein $R^5$ is selected from the group consisting of H, alkyl, aryl, heteroaryl, —C(=O)-alkyl, —C(=O)-aryl, —C(=O)-heteroaryl, —C(=O)—O-alkyl, —C(=O)-cycloalkyl, and —C(=O)—O-heterocyclyl, wherein when each of said "cycloalkyl", "heterocyclyl", "aryl", or "heteroaryl" in any of the aforementioned $R^5$ groups contains two radicals on adjacent carbon atoms, said radicals may optionally be taken together with the carbon atoms to which they are attached to form a five- or six-membered cycloalkyl, aryl, heterocyclyl or heteroaryl ring.

13. The compound of claim 1, wherein Formula (I) is represented by Formula (I)(A)
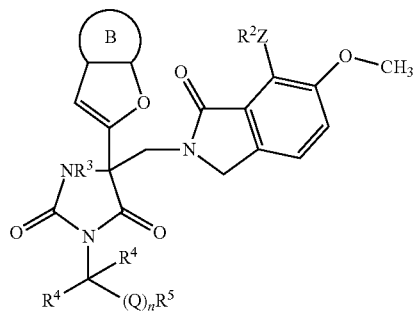
Formula (I)(A)
wherein:
  ring B is a pyridine ring optionally substituted with an $R^{10}$;
  Z is a covalent bond;
  $R^2$ is H or halogen;
  and Q, n, $R^3$, $R^4$, and $R^5$ are as defined for Formula (I) in claim 1.
14. The compound of claim 1, selected from the group consisting of:
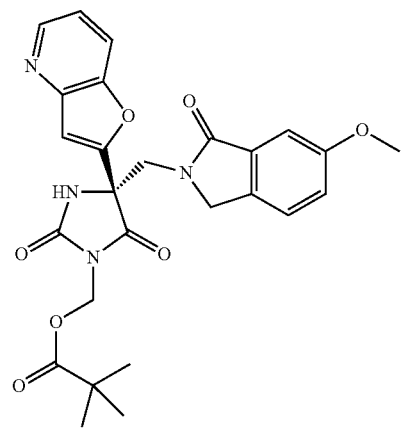
1
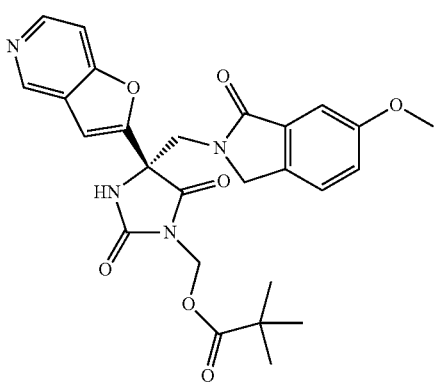
2
-continued
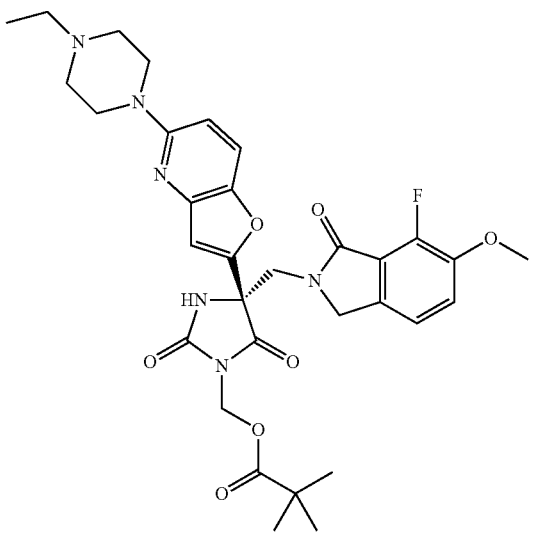
3
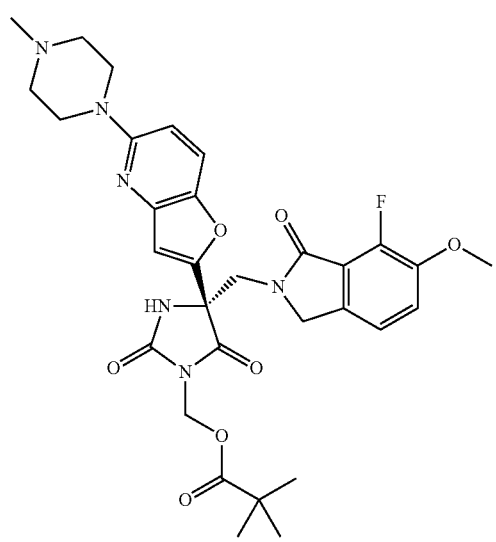
4
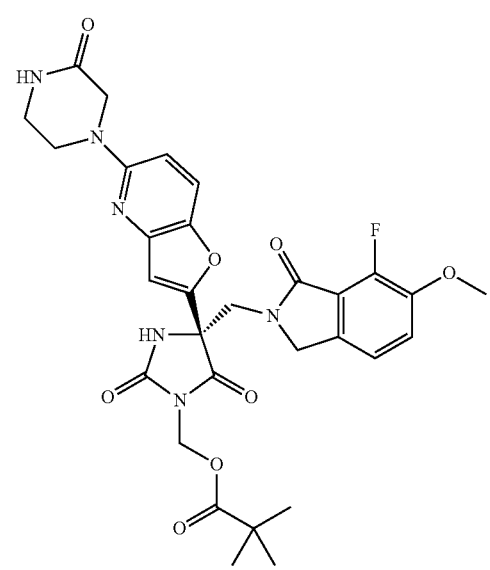
5

-continued
6
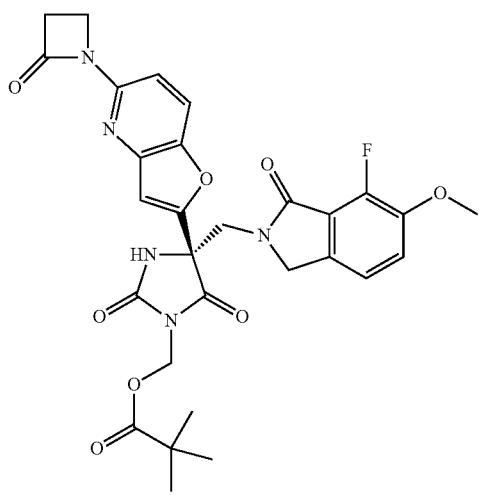
7
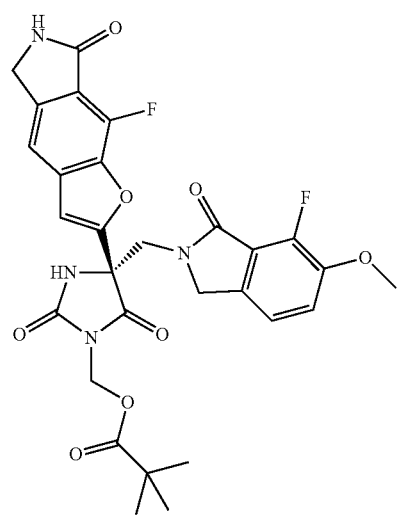
8
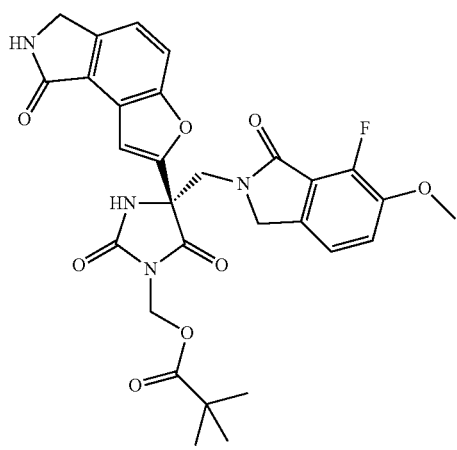
-continued
9
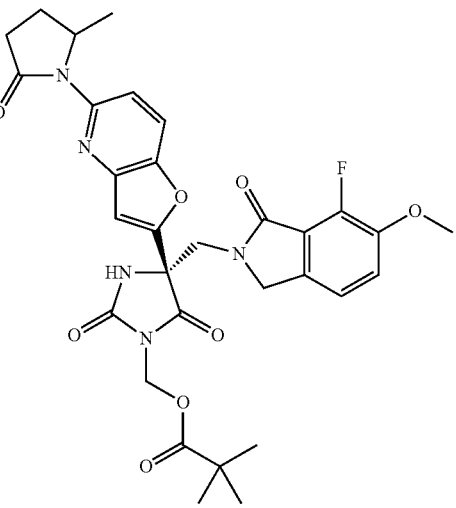
10
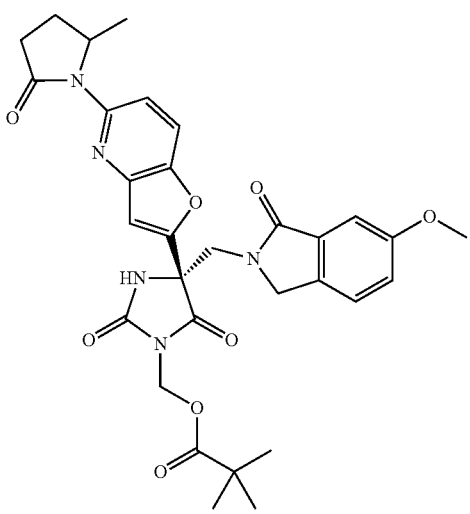
11
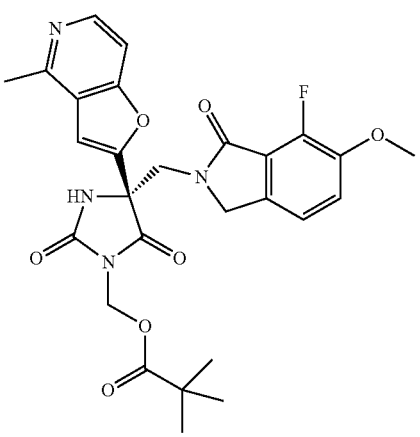

12
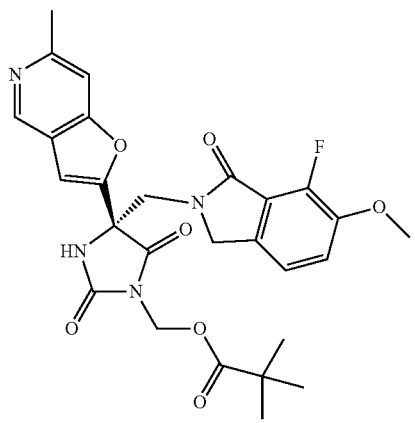
13
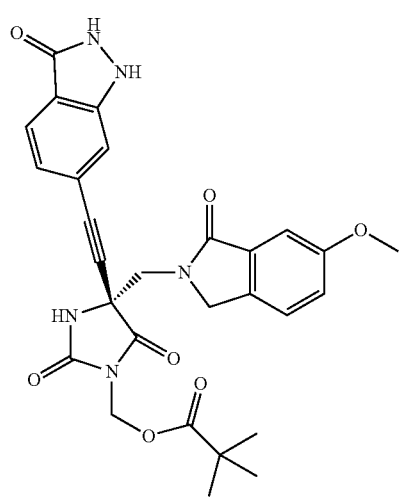
14
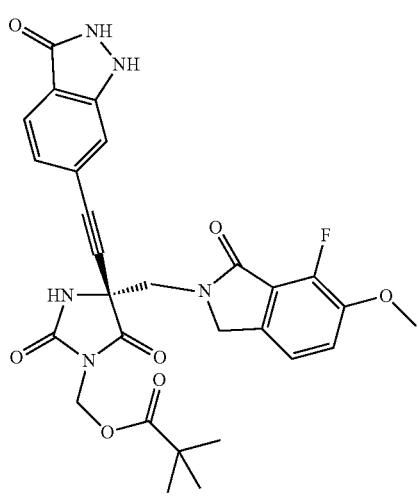
15
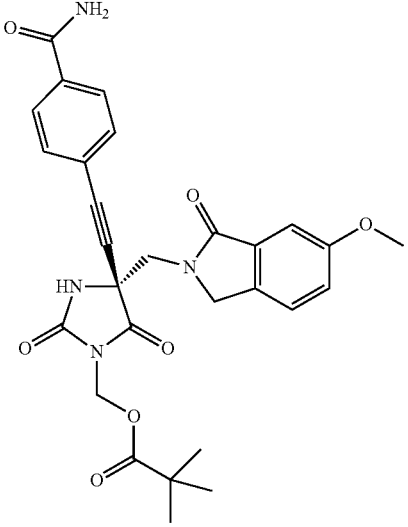
16
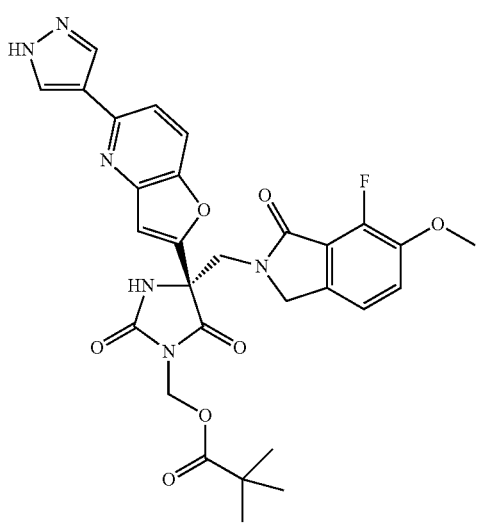
17
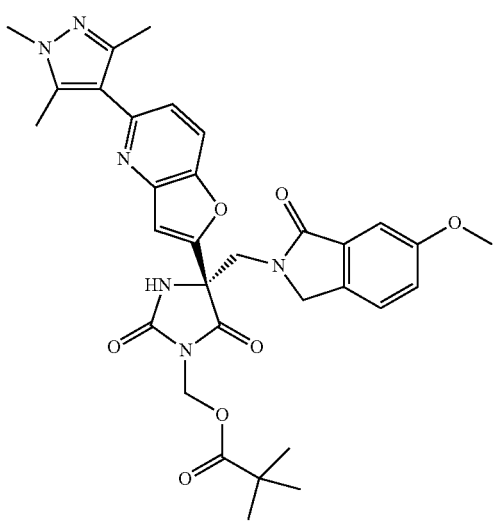

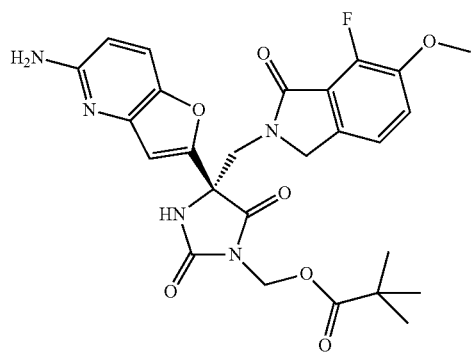
18
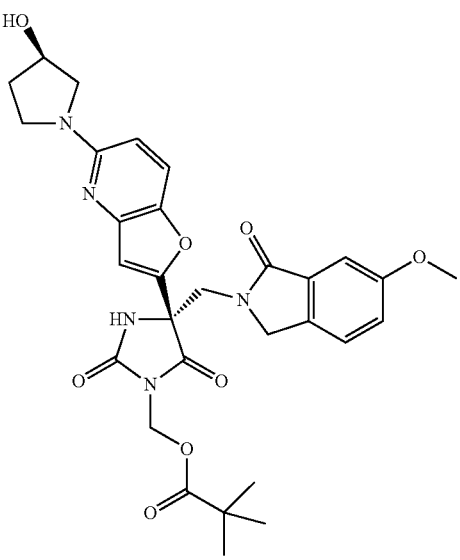
21
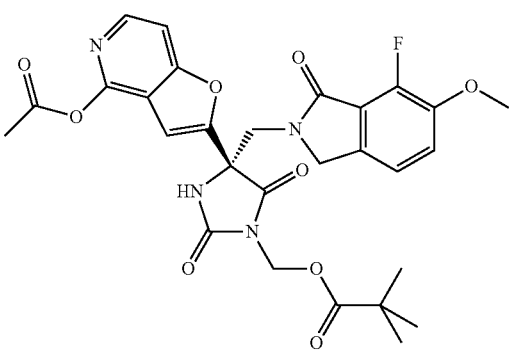
22
19
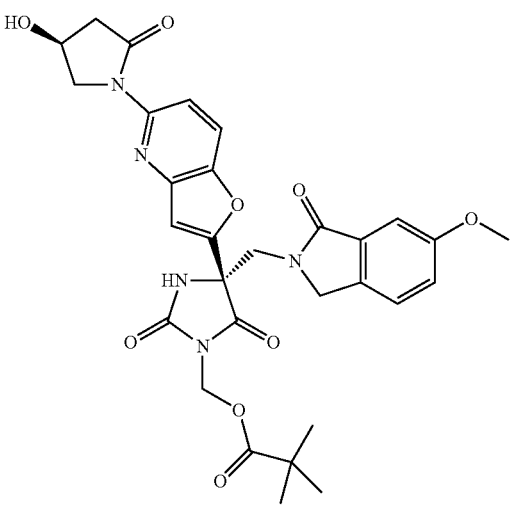
20
23

213
-continued
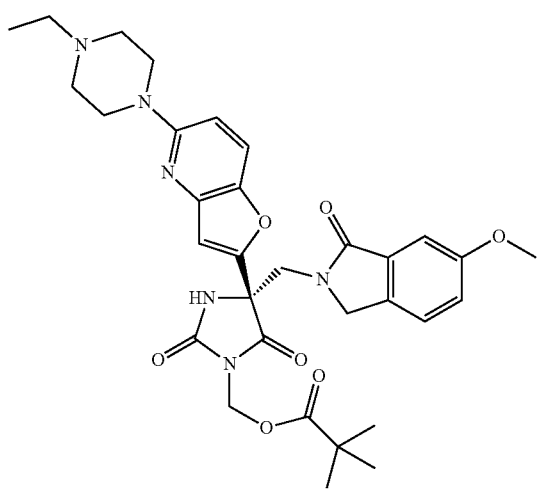
24
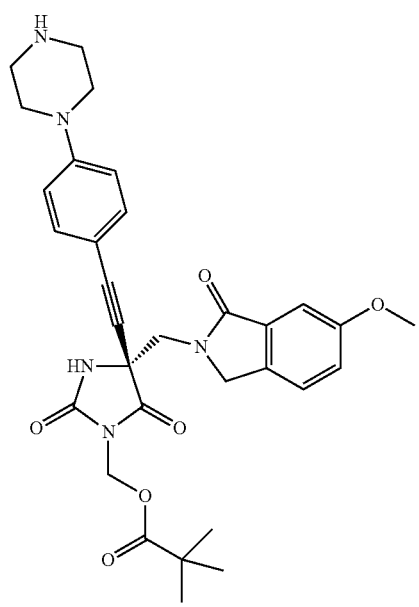
25
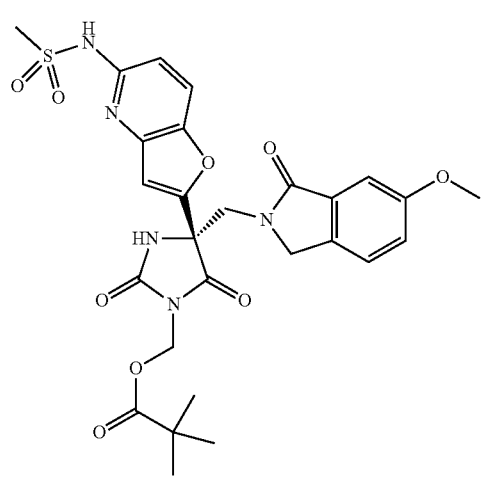
26
214
-continued
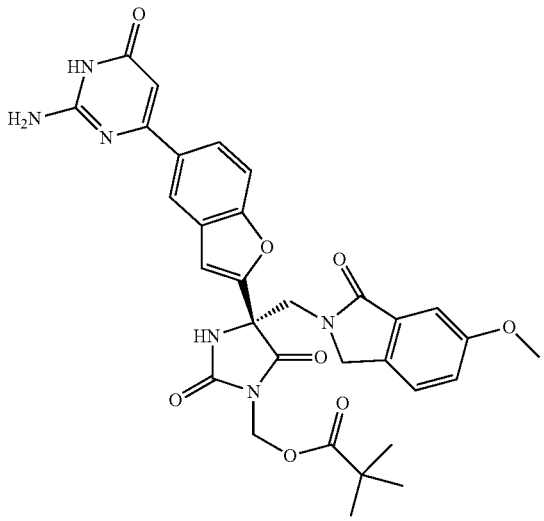
27
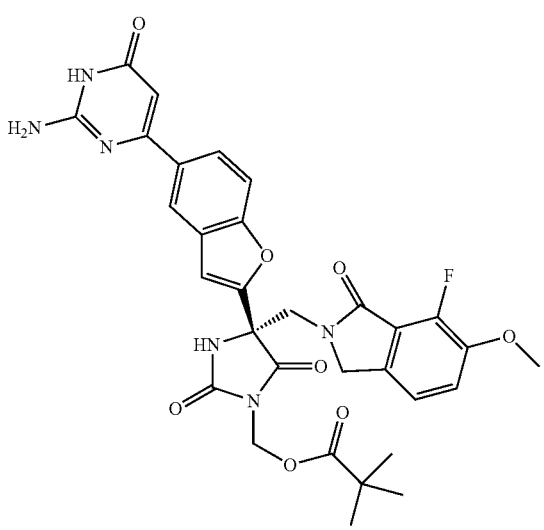
28
29

30
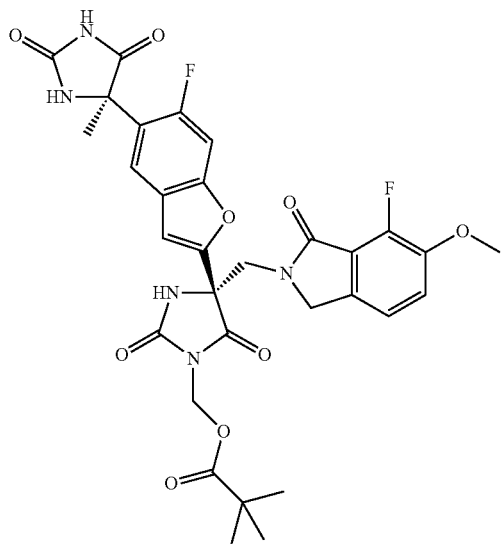
31
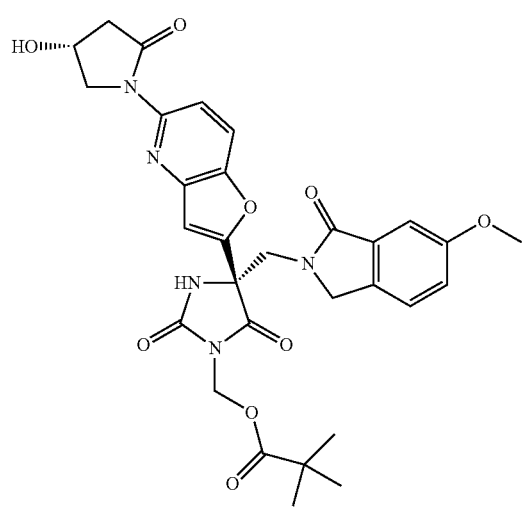
32
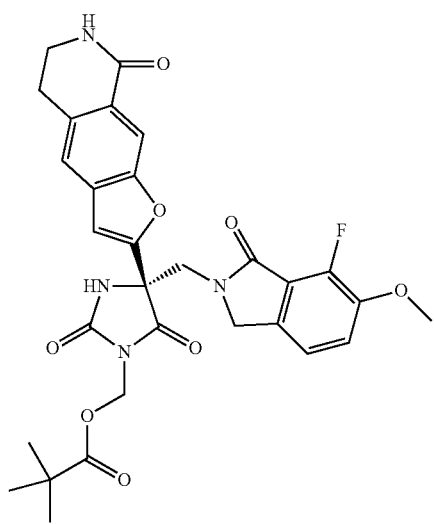
33
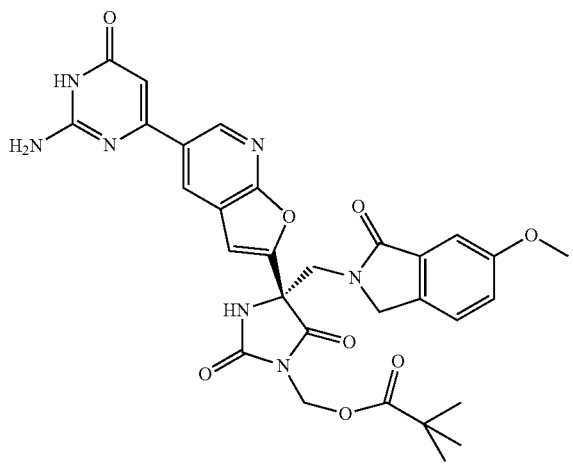
34
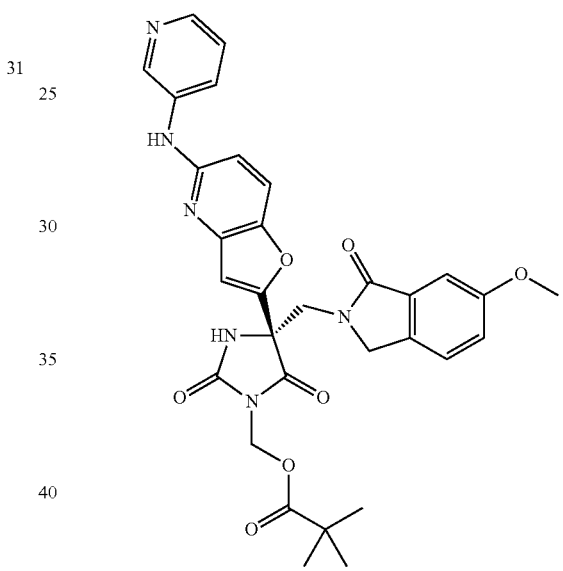
35
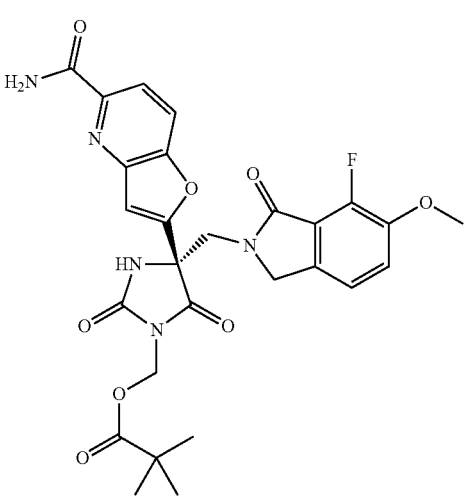

35.1 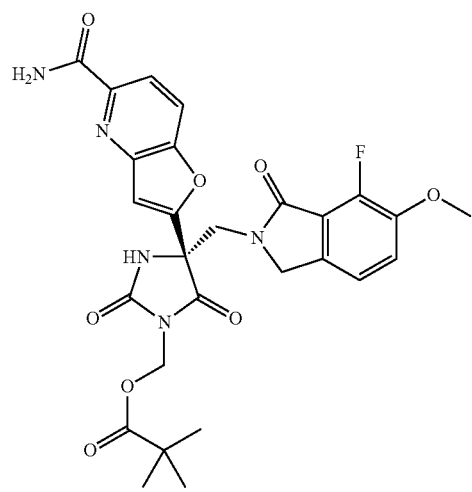
35.4 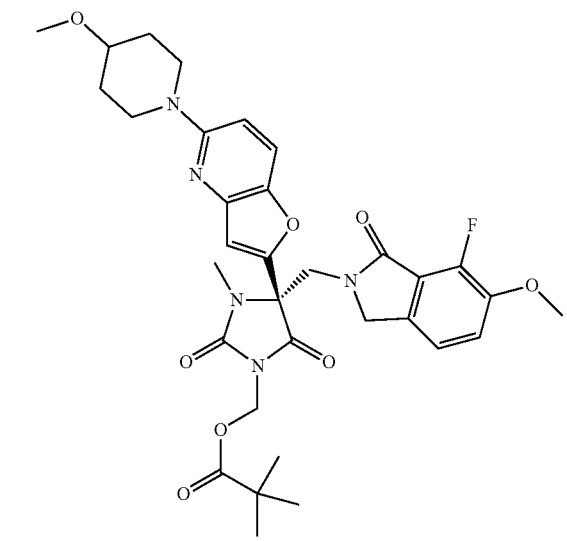
35.2 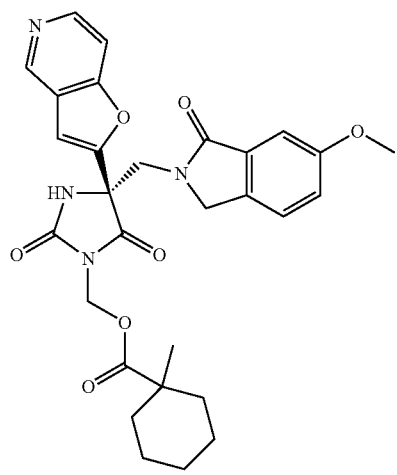
36 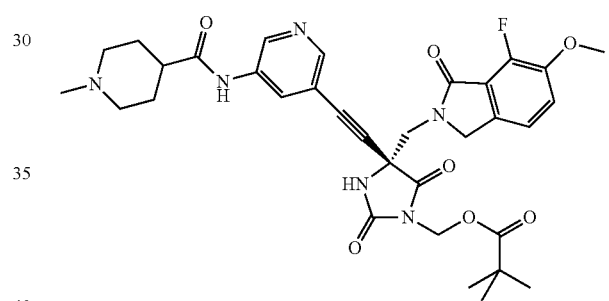
35.3 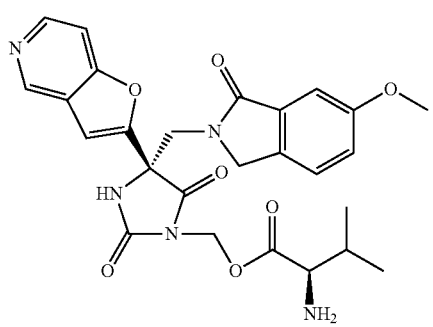
37 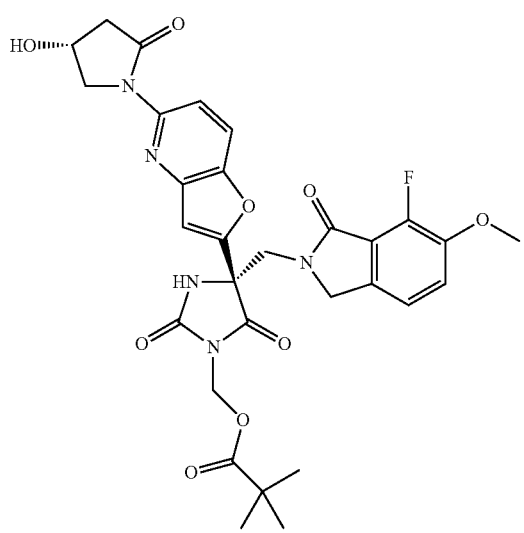

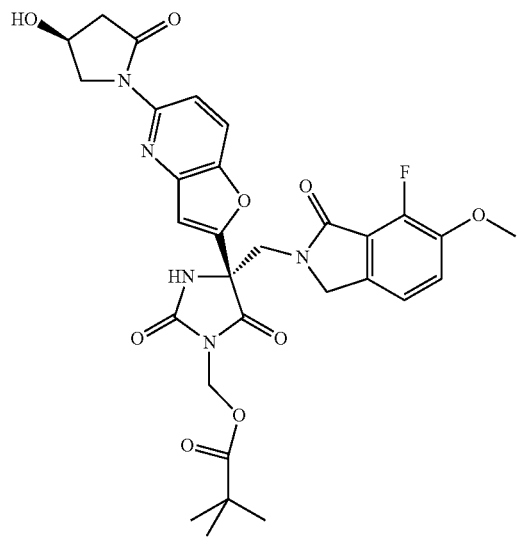
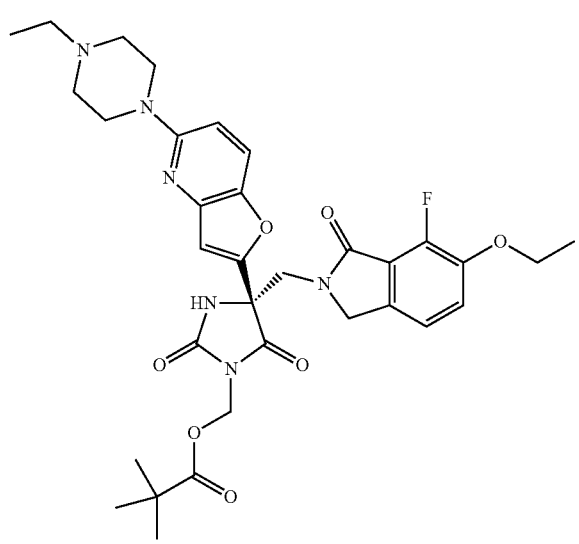
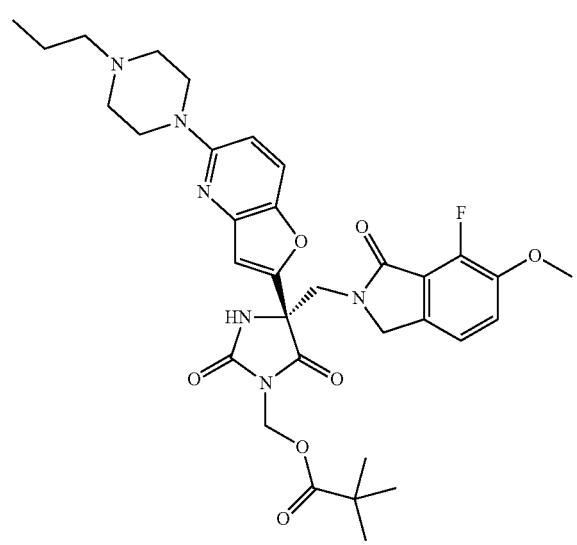
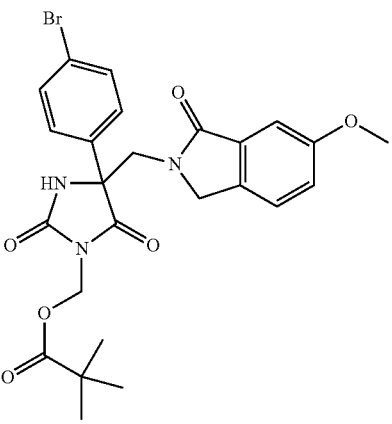
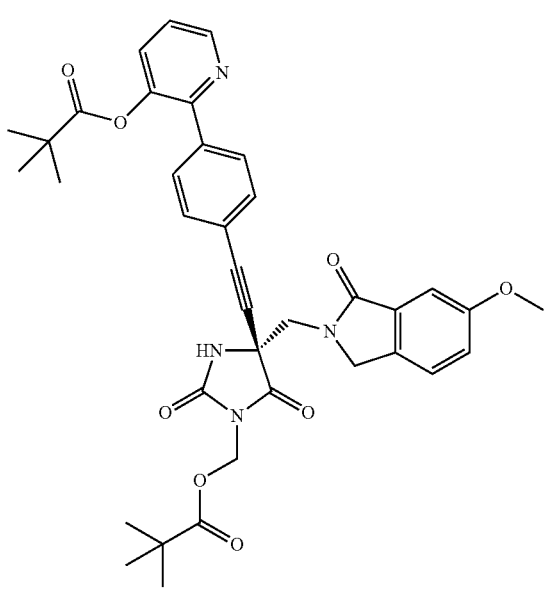
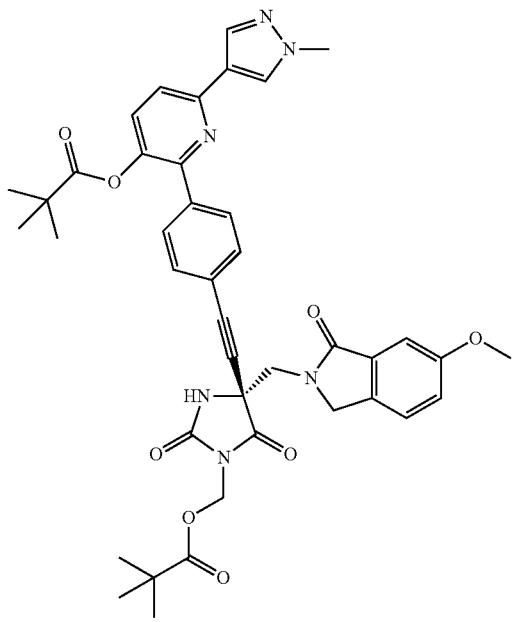

44
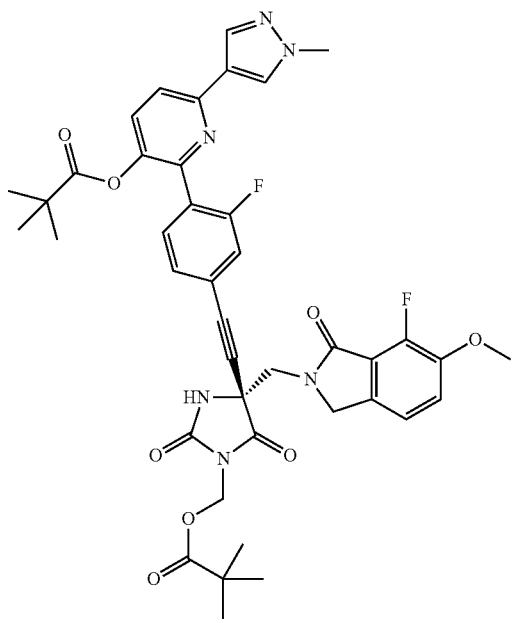
52
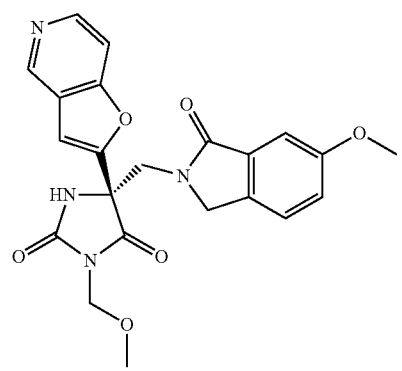
53
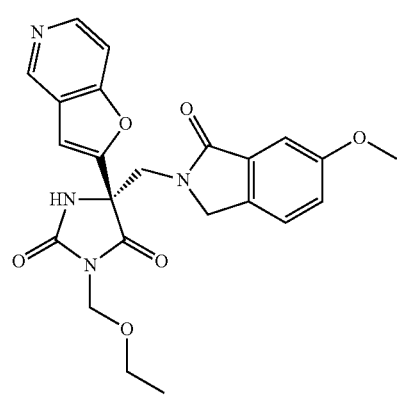
54
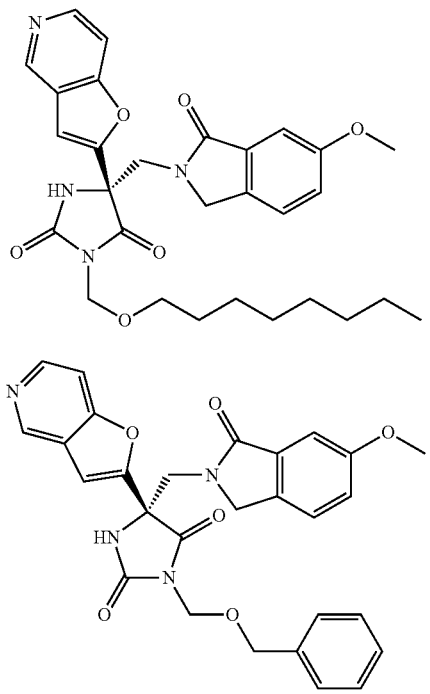
55
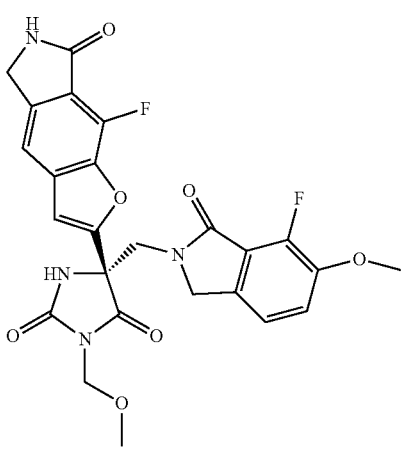
56
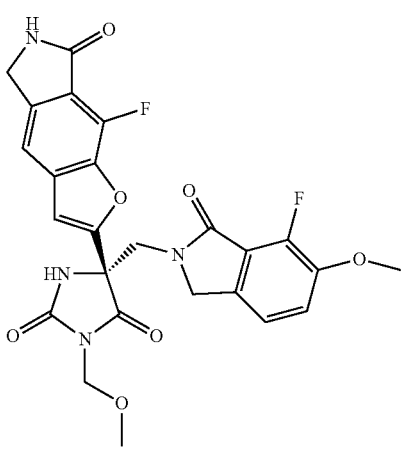
57
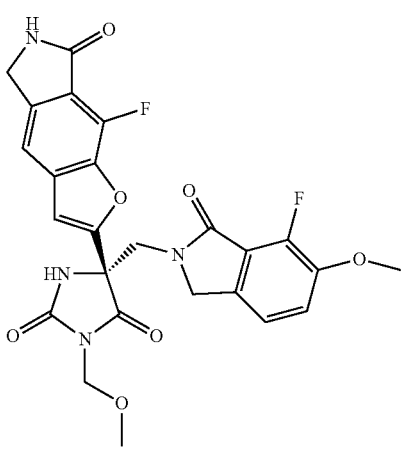

223
-continued
58
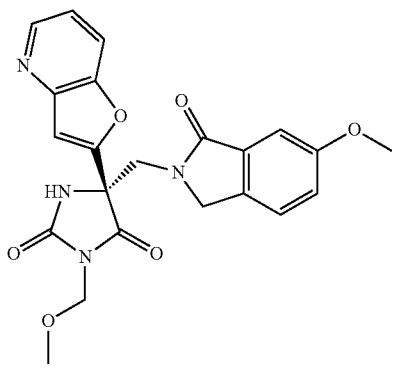
58.1
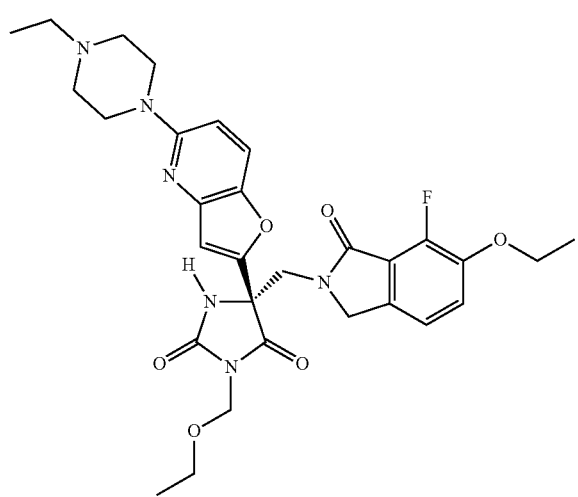
59
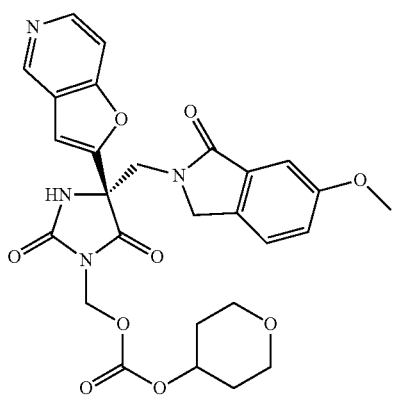
224
-continued
60
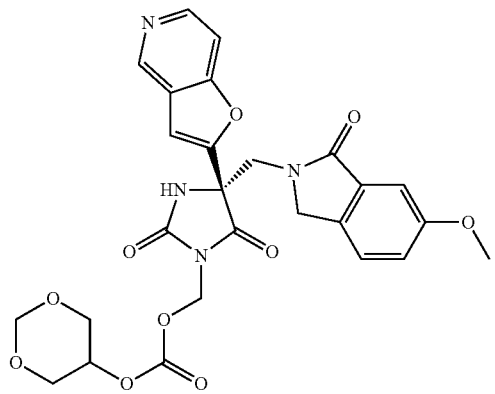
62
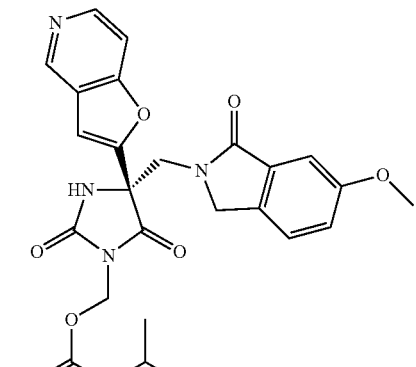
63
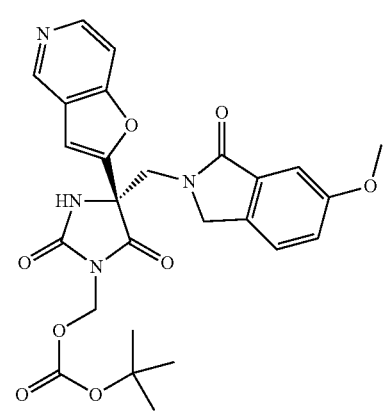
63.1
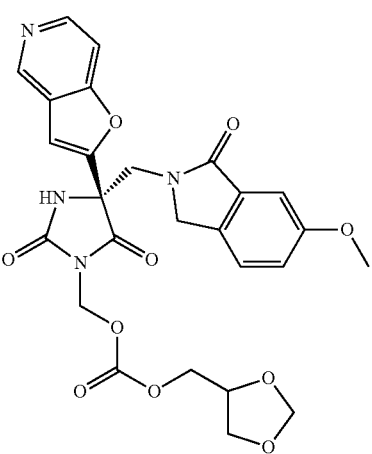

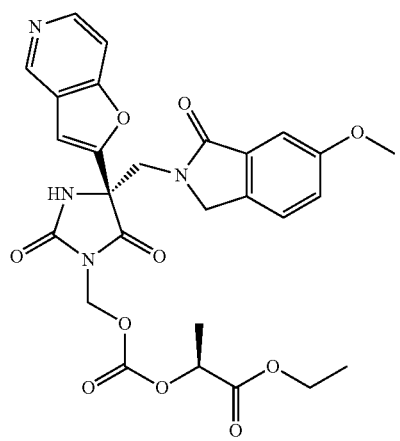
63.2
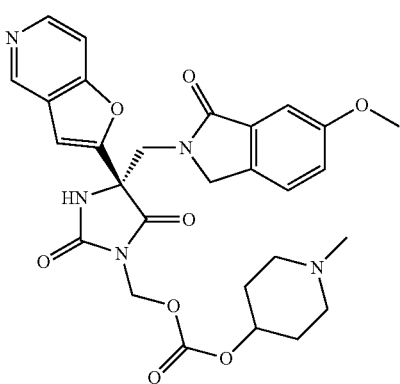
63.3
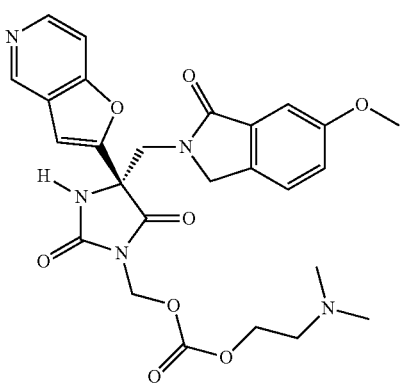
63.4
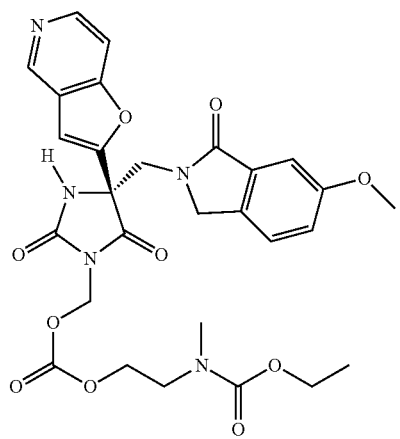
63.5
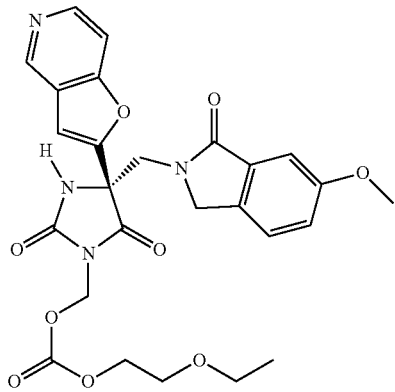
63.6
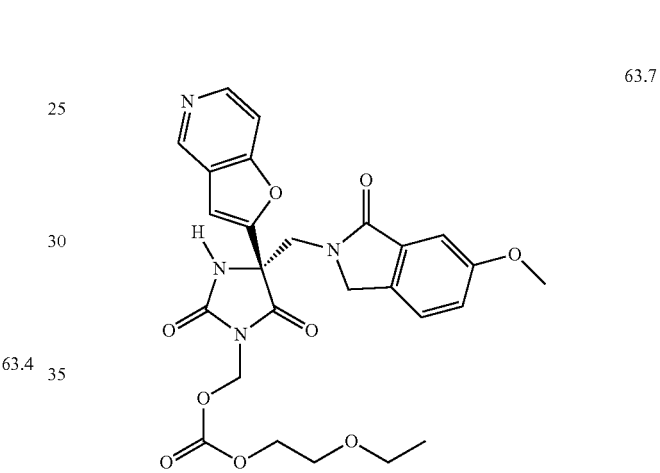
63.7
63.8
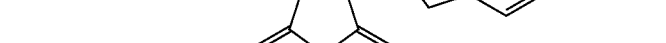
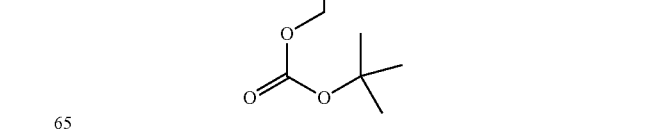

227
-continued
64
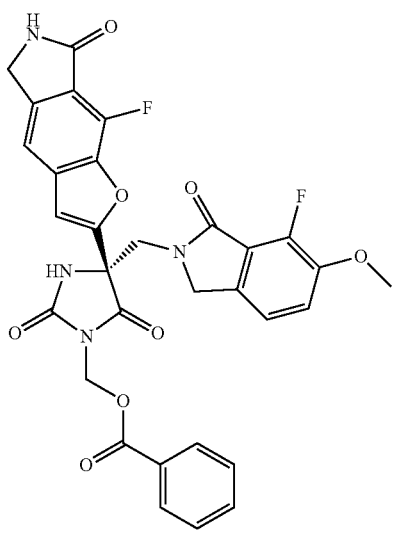
65
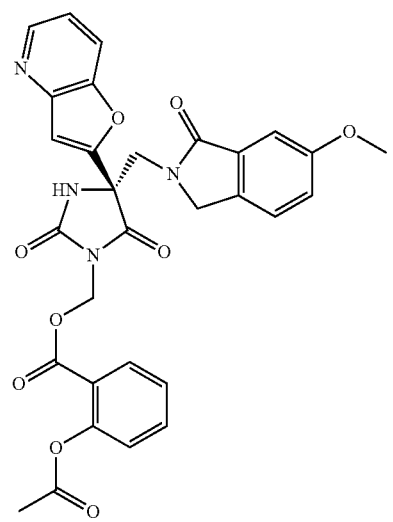
66
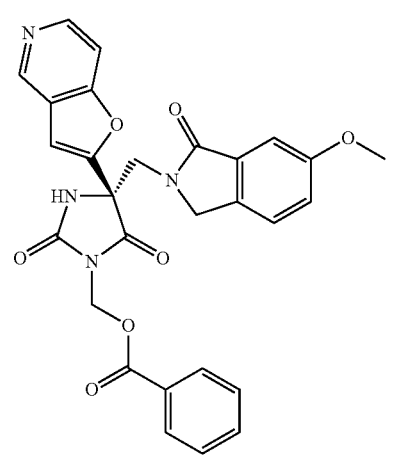
228
-continued
66.1
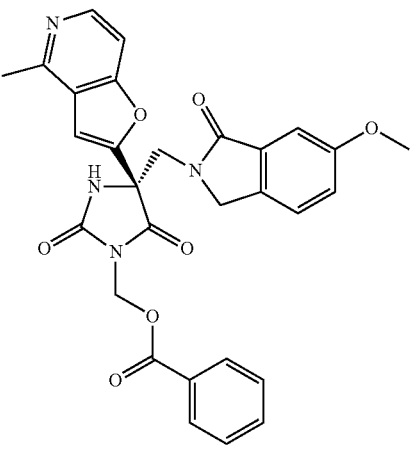
67
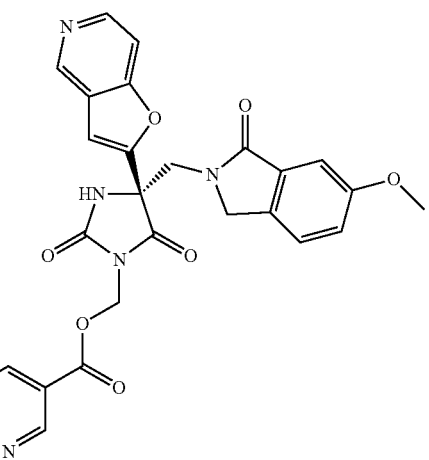
67.1
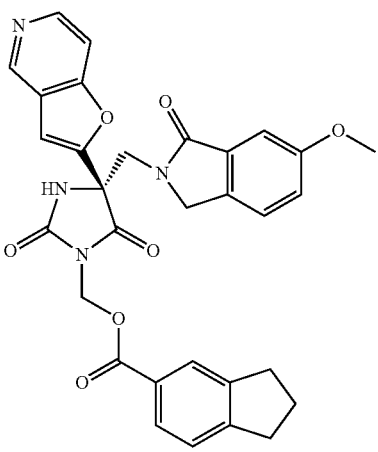

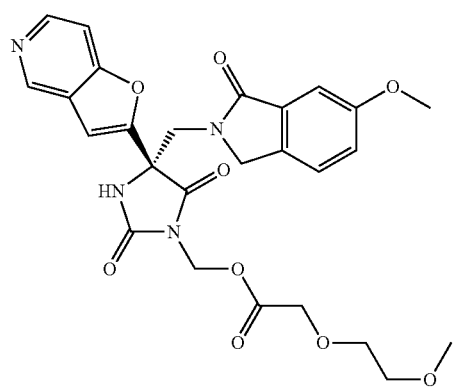 67.2
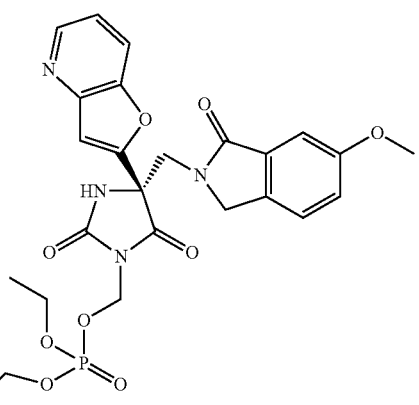 72
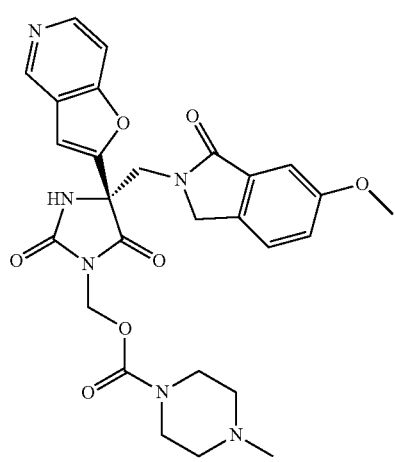 68
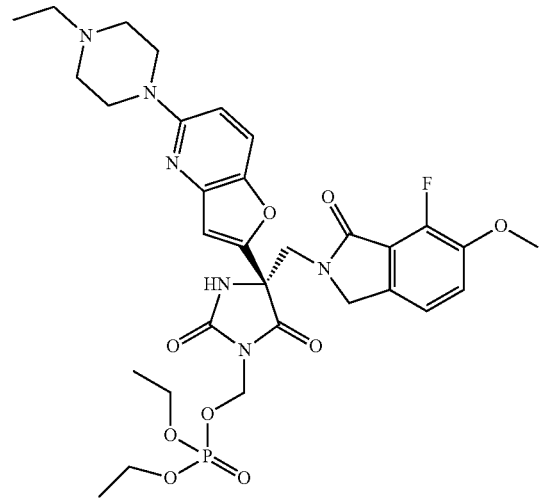 73
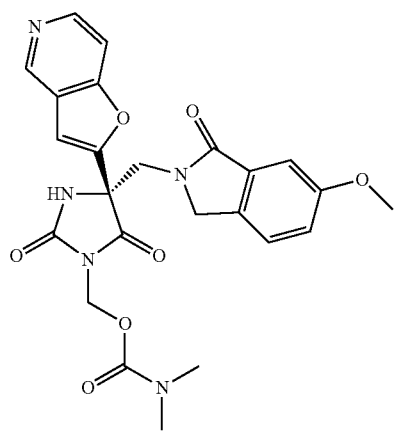 69
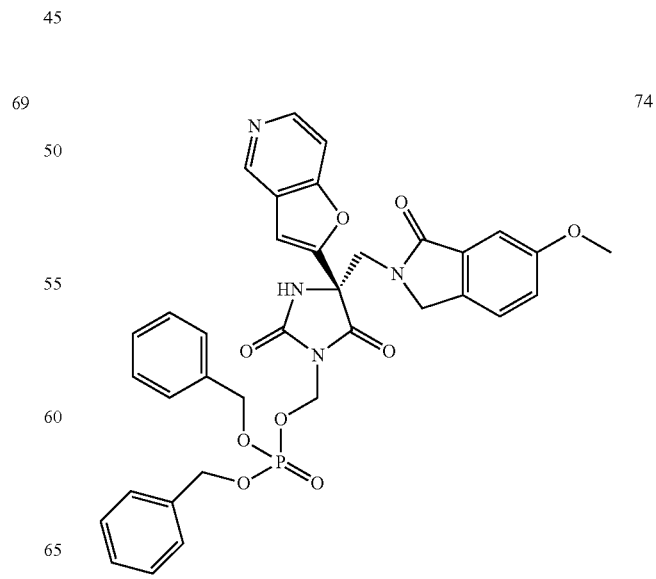 74

231
-continued
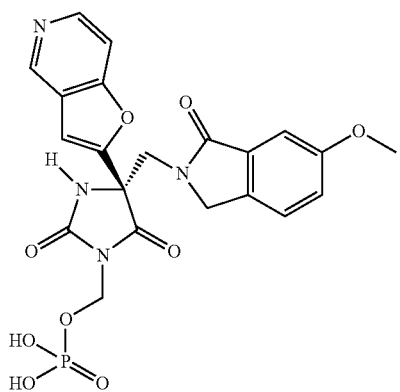
74.1
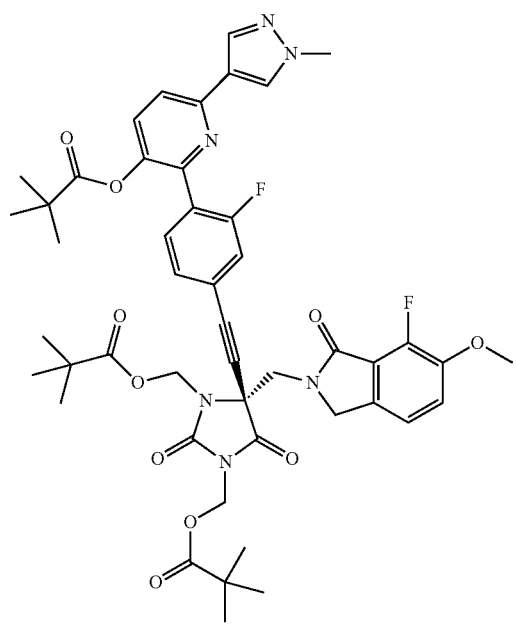
79
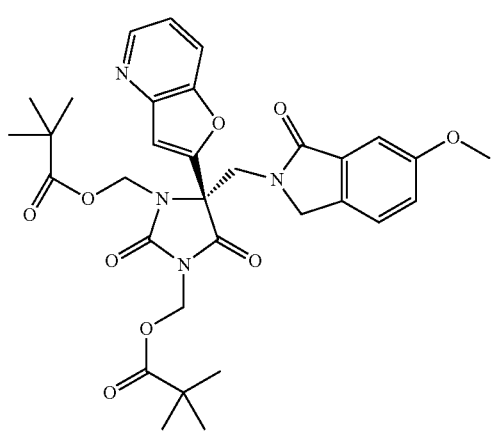
80
232
-continued
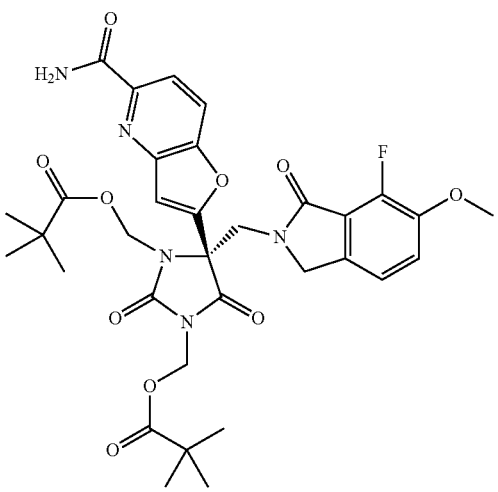
81
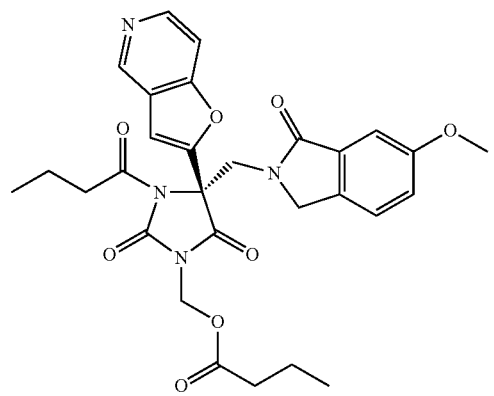
82
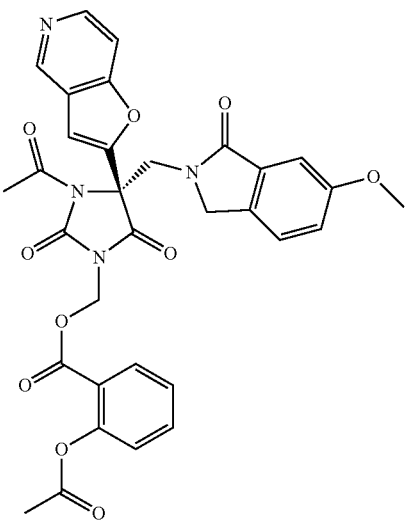
83

233
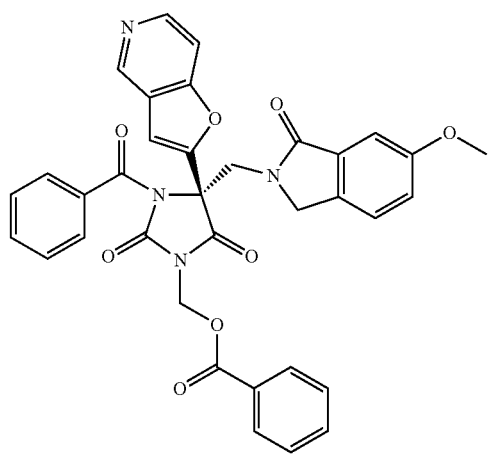
84
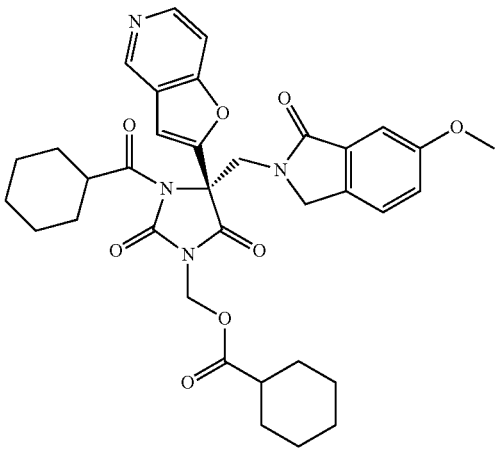
85
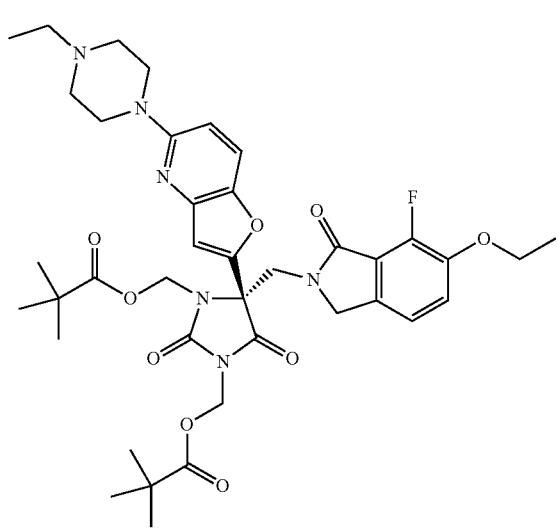
86
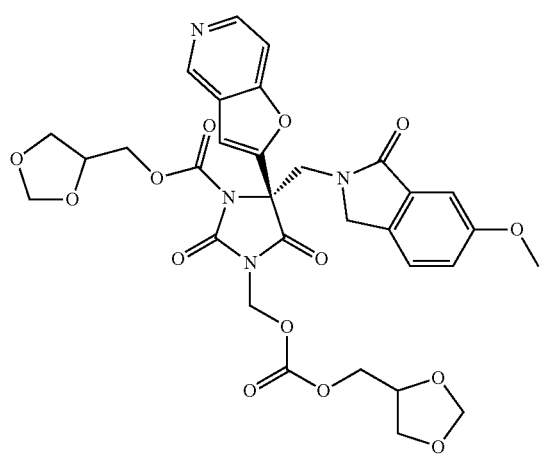
234
87
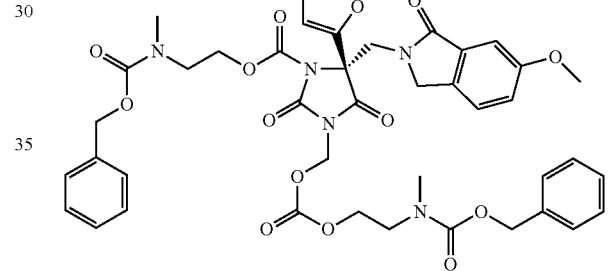
89
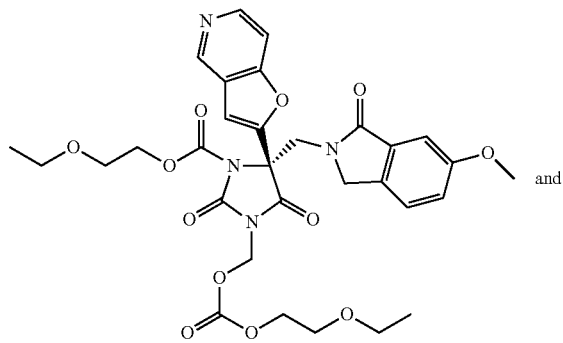
89.1
and
or a pharmaceutically acceptable salt thereof.

15. The compound of claim 1, selected from the group consisting of:
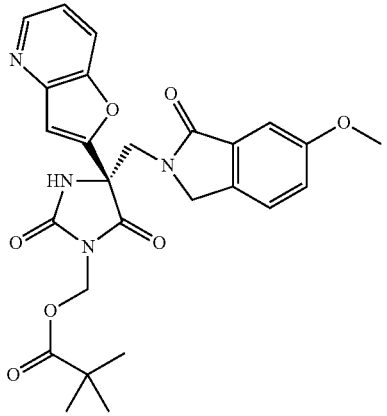
1
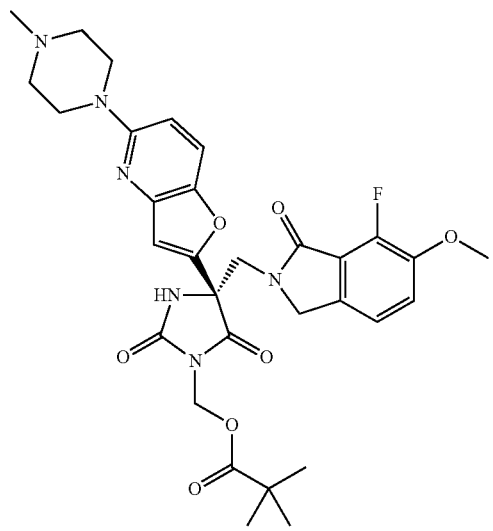
4
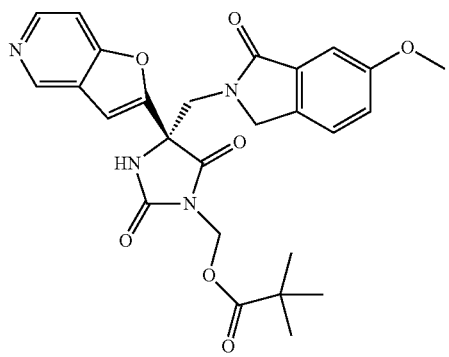
2
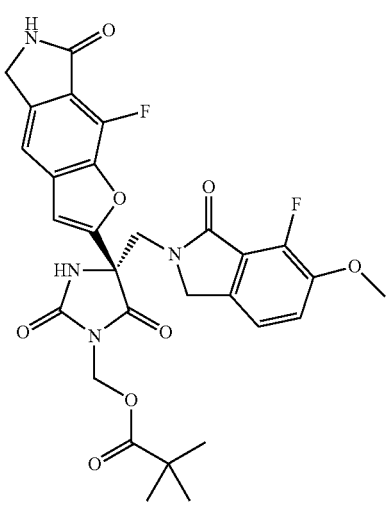
7
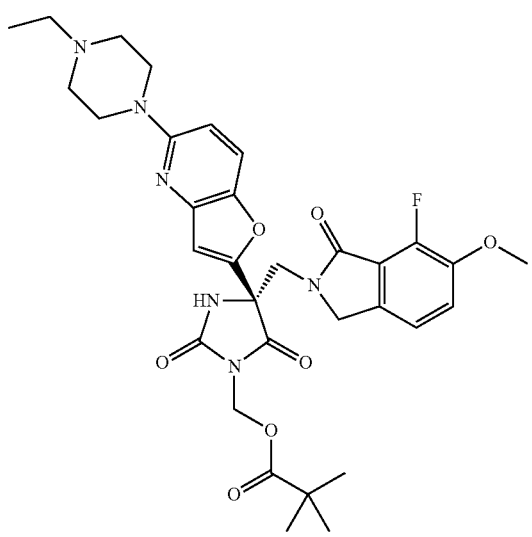
3
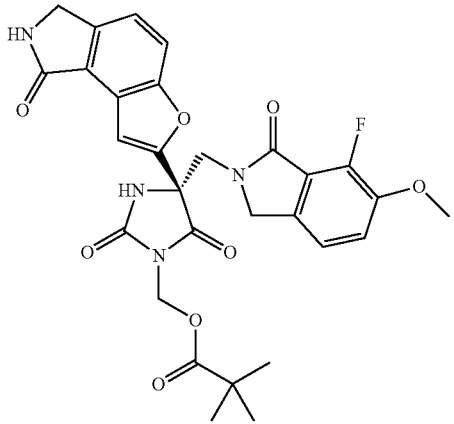
8

237 -continued
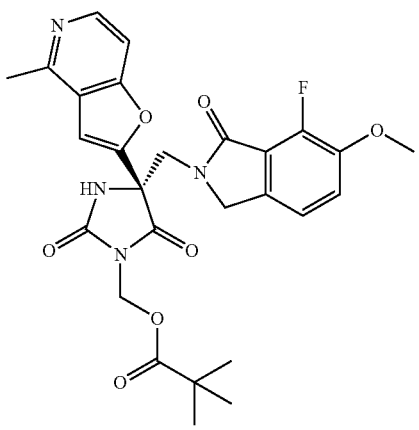
11
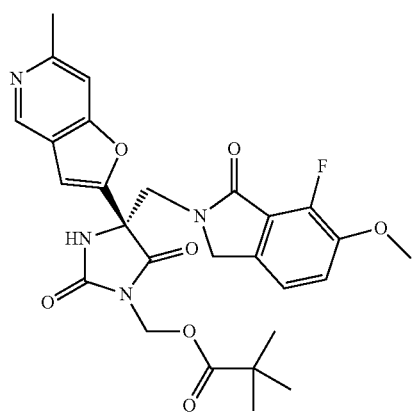
12
21
238 -continued
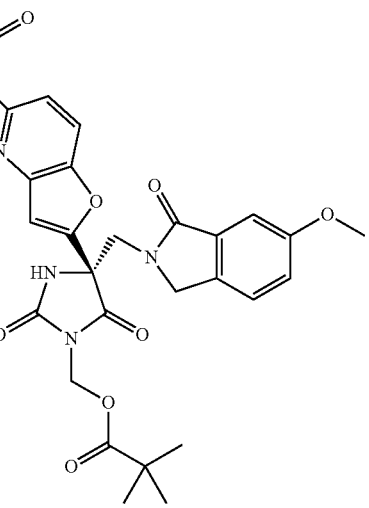
23
35.4
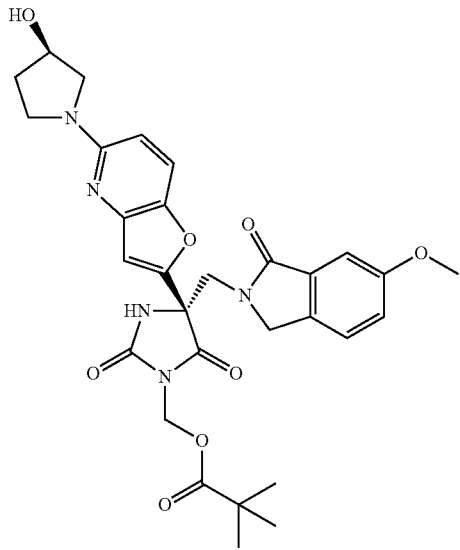
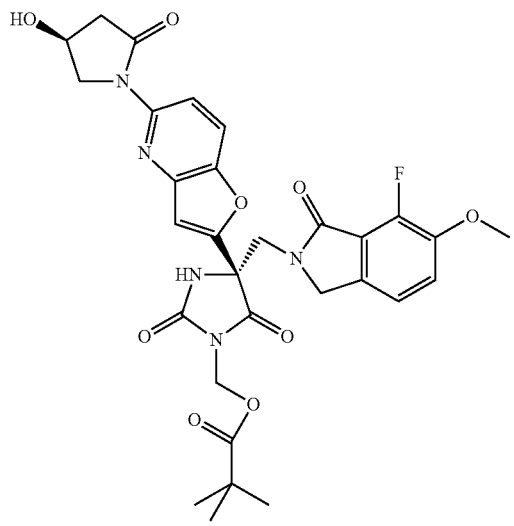
38

57
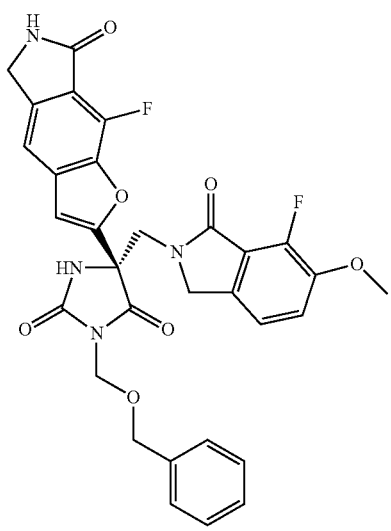
64
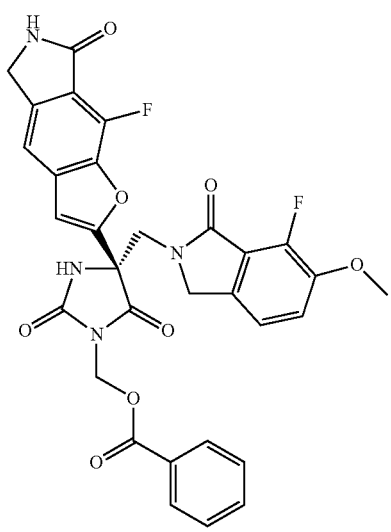
65
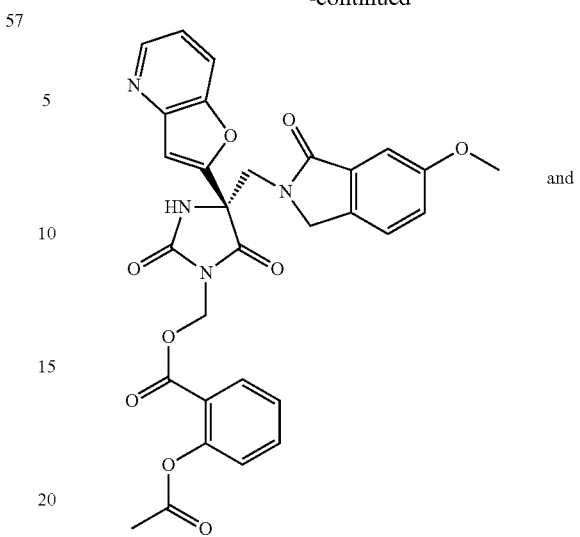
and
66.1
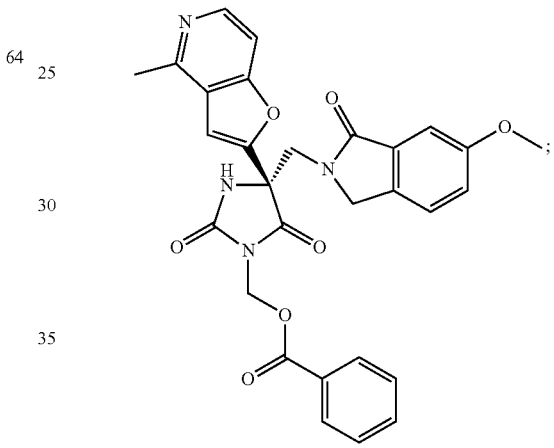
or a pharmaceutically acceptable salt thereof.
16. A pharmaceutical composition comprising the compound of claim 1 or a pharmaceutically acceptable salt thereof, and at least one pharmaceutically acceptable carrier.
* * * * *